US00RE48140E

(19) United States
(12) Reissued Patent
Irie et al.

(10) Patent Number: US RE48,140 E
(45) Date of Reissued Patent: *Aug. 4, 2020

(54) FURANONE DERIVATIVE

(71) Applicant: Carna Biosciences, Inc., Kobe (JP)

(72) Inventors: Takayuki Irie, Kobe (JP); Ayako Sawa, Osaka (JP); Masaaki Sawa, Ibaraki (JP); Tokiko Asami, Kobe (JP); Yoko Funakoshi, Tokyo (JP); Chika Tanaka, Tokyo (JP)

(73) Assignee: CARNA BIOSCIENCES, INC., Hyogo (JP)

( * ) Notice: This patent is subject to a terminal disclaimer.

(21) Appl. No.: 15/967,323

(22) Filed: Apr. 30, 2018

Related U.S. Patent Documents

Reissue of:
(64) Patent No.: 8,742,113
Issued: Jun. 3, 2014
Appl. No.: 14/008,488
PCT Filed: Mar. 30, 2012
PCT No.: PCT/JP2012/058636
§ 371 (c)(1),
(2) Date: Sep. 27, 2013
PCT Pub. No.: WO2012/113802
PCT Pub. Date: Oct. 4, 2012

U.S. Applications:
(63) Continuation of application No. 15/172,021, filed on Jun. 2, 2016, now Pat. No. Re. 46,815, which is an application for the reissue of Pat. No. 8,742,113.

(30) Foreign Application Priority Data

Mar. 31, 2011 (JP) ..... 2011-080185

(51) Int. Cl.

| | |
|---|---|
| ***C07D 471/04*** | (2006.01) |
| ***A61K 31/437*** | (2006.01) |
| ***A61K 31/4375*** | (2006.01) |
| ***A61K 31/444*** | (2006.01) |
| ***A61K 31/4545*** | (2006.01) |
| ***A61K 31/4709*** | (2006.01) |
| ***A61K 31/496*** | (2006.01) |
| ***A61K 31/506*** | (2006.01) |
| ***C07D 519/00*** | (2006.01) |
| ***A61K 31/5355*** | (2006.01) |
| ***A61K 31/541*** | (2006.01) |

(52) U.S. Cl.
CPC ..... *C07D 471/04* (2013.01); *A61K 31/437* (2013.01); *A61K 31/4375* (2013.01); *A61K 31/444* (2013.01); *A61K 31/4545* (2013.01); *A61K 31/4709* (2013.01); *A61K 31/496* (2013.01); *A61K 31/506* (2013.01); *A61K 31/5355* (2013.01); *A61K 31/541* (2013.01); *C07D 519/00* (2013.01)

(58) Field of Classification Search
CPC .. C07D 471/04; C07D 519/00; A61K 31/541; A61K 31/5355; A61K 31/506; A61K 31/437; A61K 31/4709; A61K 31/4545; A61K 31/444; A61K 31/4375; A61K 31/496
See application file for complete search history.

(56) References Cited

U.S. PATENT DOCUMENTS

| | | | | |
|---|---|---|---|---|
| 6,335,342 | B1 * | 1/2002 | Longo et al. | 514/254.09 |
| 8,742,113 | B2 | 6/2014 | Irie et al. | |
| 2003/0158215 | A1 | 8/2003 | Tang | |
| 2007/0112020 | A1 | 5/2007 | Vanotti | |
| 2009/0253679 | A1 | 10/2009 | Leroy et al. | |

(Continued)

FOREIGN PATENT DOCUMENTS

| | | | |
|---|---|---|---|
| FR | 2907120 | A1 | 4/2008 |
| MX | 344474 | B | 12/2016 |

(Continued)

OTHER PUBLICATIONS

PCT International Search Report, International Application No. PCT/JP2012/058636, dated Apr. 24, 2012.

(Continued)

*Primary Examiner* — Jerry D Johnson
(74) *Attorney, Agent, or Firm* — Fenwick & West LLP

(57) ABSTRACT

To provide a novel furanone derivative, and a medicine including the same. The furanone derivative is represented by the formula (I):

(I)

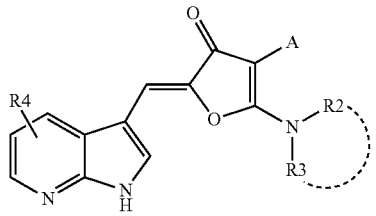

wherein A represents —COOR1 or a hydrogen atom; R1 represents a hydrogen atom, an optionally substituted hydrocarbon group, or an optionally substituted heterocycle; R2 and R3 are the same or different and each independently represent a hydrogen atom, an optionally substituted hydrocarbon group, an optionally substituted phenyl group, an optionally substituted heterocycle, an optionally substituted heterocyclic fused ring, or an optionally substituted amino group; or alternatively, R2 and R3, taken together with the nitrogen atom to which they are attached, may form an optionally substituted heterocycle or an optionally substituted heterocyclic fused ring; and R4 represents a hydrogen atom or a halogen atom; with the proviso that when A represents —COOR1, R2 and R3 are not optionally substituted amino groups at the same time, and when A represents a hydrogen atom, R3 represents a hydrogen atom.

18 Claims, No Drawings

(56) References Cited

U.S. PATENT DOCUMENTS

| | | | |
|---|---|---|---|
| 2009/0298820 | A1 | 12/2009 | Tsou et al. |
| 2012/0276093 | A1 | 11/2012 | Ballinari et al. |
| 2014/0018533 | A1 | 1/2014 | Irie et al. |
| 2015/0218138 | A1 | 8/2015 | Vanotti et al. |
| 2017/0065609 | A1 | 3/2017 | Funakoshi et al. |

FOREIGN PATENT DOCUMENTS

| | | | |
|---|---|---|---|
| WO | 01/98299 | A1 | 12/2001 |
| WO | WO 2001/098299 | A1 | 12/2001 |
| WO | WO-2004/007504 | A1 | 1/2004 |
| WO | WO 2005/009370 | A2 | 2/2005 |
| WO | WO 2005/013986 | A1 | 2/2005 |
| WO | WO 2005/014572 | A1 | 2/2005 |
| WO | WO 2006/037875 | A1 | 4/2006 |
| WO | WO 2007/054508 | A1 | 5/2007 |
| WO | WO 2008/046982 | A3 | 4/2008 |
| WO | WO 2008/109443 | A2 | 9/2008 |
| WO | WO 2009/155052 | A1 | 12/2009 |
| WO | WO 2010/030727 | A1 | 3/2010 |
| WO | WO 2011/008915 | A1 | 1/2011 |
| WO | WO 2012/002568 | A1 | 1/2012 |

OTHER PUBLICATIONS

Kim, J.M., et al., "Cdc7 kinase mediates Claspin phosphorylation in DNA replication checkpoint," Oncogene, 2008, pp. 3475-3482, vol. 27, No. 24.

Intellectual Property Australia, Examination Report, Australian Patent Application No. 2012233246, dated Apr. 4, 2016, 3 Pages.

European Patent Office, Office Action, European Patent Application No. 12763979.7, dated Jul. 1, 2016, 4 Pages.

Patani, G.A., et al., "Bioisosterism: A Rational Approach in Drug Design," Chem. Rev., 1996, pp. 3147-3176, vol. 96.

International Search Report of PCT/JP2012/058636, mailing date of Apr. 24, 2012.

Masai, Hisao et al., "Cdc7 Kinase Complex: A Key Regulator in the Initiation of DNA Replication", Journal of Cellular Physiology, 2002, vol. 190, pp. 287-296.

Bonte, Dorine et al., "Cdc7-Dbf4 Kinase Overexpression in Multiple Cancers and Tumor Cell Lines is Correlated with p53 Inactiviation", Neoplasia, 2008, vol. 10, pp. 920-931.

Rodriguez-Acebes, Sara et al., "Targeting DNA Replication before it Starts; Cdc7 as a Therapeutic Target in p53-Mutant Breast Cancers", The American Journal of Pathology, 2010, vol. 177, pp. 2034-2045.

Montagnoli, Alessia et al., "Cdc7 Inhibition Reveals a p53-Dependent Replication Checkpoint That Is Defective in Cancer Cells", Cancer Research, 2004, vol. 64, pp. 7110-7116.

Kuo, Sheng-Chu et al., "Studies on Heterocyclic Compounds, IX. Synthesis and Antiallergic Activity of Furo[2,3-b][1,8]naphthyridine-3,4(2H,9H)-diones and 4H-Furo[2,3-d]pyrido[1,2-a]-pyrimidine-3,4(2H)-diones", Chem. Pharm. Bull., 1988, vol. 36, No. 11, pp. 4403-4407.

Mack, Robert A. et al., "Drug-Induced Modifications of the Immune Response. 12. 4,5-Dihydro-4-oxo-2-(substituted amino)-3-furancarboxylic Acids and Derivatives as Novel Antiallergic Agents", J. Med. Chem., 1988, vol. 31, No. 10, pp. 1910-1918.

Iwasaki, Takanori, et al., "Transesterification of Various Methyl Esters Under Mild Conditions Catalyzed by Tetranuclear Zinc Cluster", J. Org. Chem., 2008, vol. 73, No. 13, pp. 5147-5150.

Kuo, Sheng-Chu et al., "Studies on Heterocyclic Compounds. X. Dealkoxycarbonylation of Ethyl 2-Arylamino-4-oxo-4,5-dihydrofuran-3-carboxylates", Chem. Pharm. Bull, 1990, vol. 38, No. 2, pp. 340-341.

* cited by examiner

FURANONE DERIVATIVE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*The present application is a reissue application of application Ser. No. 14/008,488, filed Mar. 30, 2012, which issued as U.S. Pat. No. 8,742,113, and adds new claims relative to U.S. Pat. No. 8,742,113. The present application is a continuation application of reissue application Ser. No. 15/172,021, filed on Jun. 2, 2016, which issued as U.S. Pat. No. RE46,815, and which is a reissue application of application Ser. No. 14/008,488, filed Mar. 30, 2012, which issued as U.S. Pat. No. 8,742,113, which is a National Stage Entry of International application No. PCT/JP2012/058636, filed Mar. 30, 2012, which claims the benefit of Japanese application No. 2011-080185, filed Mar. 31, 2011. More than one reissue application has been filed for the reissue of U.S. Pat. No. 8,742,113. The reissue applications are the present application and application Ser. No. 15/172,021, filed Jun. 2, 2016, which issued as U.S. Pat. No. RE46,815.*

TECHNICAL FIELD

The present invention relates to a medicine, particularly a novel furanone derivative having an inhibitory effect on Cdc7 or a pharmaceutically acceptable salt thereof.

BACKGROUND ART

Cancer is a group of diseases caused by uncontrolled, unlimited growth of cells within a living body. Since cancer cells usually grow faster than normal cells, cancers would be capable of being treated by controlling the replication of DNA during the cell division, particularly during the division of chromosomes. Actually, gemcitabine, which has the effect of inhibiting DNA replication, is widely used in the treatment of non-small cell lung cancer, pancreatic cancer, biliary tract cancer, bladder cancer, breast cancer, ovarian cancer, or others.

Cdc7 is a serine-threonine protein kinase and is an enzyme which is essential for the initiation of DNA replication in the cell cycle. Specifically, Cdc7 forms a complex with cofactors such as Dbf4 (ASK), and phosphorylates its substrate, MCM (mini-chromosome maintenance) proteins. It is supposed that this phosphorylation results in assembly of Cdc45 and a DNA polymerase on the DNA to form an MCM complex, thereby initiating the DNA replication (see Non Patent Literature 1). Furthermore, it has been shown in a recent study that Cdc7 plays an important role not only in the replication of DNA, but also in DNA damaging pathways (see Non Patent Literature 2).

Recently, Cdc7 has drawn attention as a target of anticancer agents, and active researches on Cdc7 have been made. For example, it was found that CDC7 is overexpressed not only in common established cell lines derived from human tumors, but also in cells taken from live tissues, such as breast cancer, colon cancer, and lung cancer (see Non Patent Literature 3). Particularly, it was shown, in more recent days, that CDC7 is overexpressed in p53-mutated triple negative (ER−/PR−/Her2−) breast cancer cells (see Non Patent Literature 4), and thus it has been expected that Cdc7 will be a promising target molecule against a triple negative type of breast cancer, which has been considered to be difficult to treat. Actually, it was observed that in experiments for suppressing the expression of Cdc7 using RNA interference techniques, the arresting of the cell cycle was induced when the expression of Cdc7 was inhibited. More importantly, the Cdc7 inhibition using RNA interference techniques suppressed the growth of human tumor cells, such as HeLa and HCT116 cells, and exhibited only limited effects on normal cells (normal human skin fibroblasts) (see Non Patent Literature 5).

Therefore, selective inhibitors of Cdc7 can be expected to have an effective therapeutic effect against various types of cancer. Although various compounds having an inhibitory effect on Cdc7 have been reported in the past, there are no reports in which novel furanone derivatives of the present invention or pharmaceutically acceptable salts thereof have an inhibitory effect on Cdc7.

CITATION LIST

Non Patent Literature

[Non Patent Literature 1]
H. Masai et al., Journal of Cellular Ohysiology, 190, 2002, 287-296
[Non Patent Literature 2]
J M. Kim et al., Oncogene, 27, 2008, 3475-3482
[Non Patent Literature 3]
D Bonte et al., Neoplasia, 10, 2008, 920-931
[Non Patent Literature 4]
S. Rodriguez-Acebes et al., The American Journal of Pathology, 177, 2010, 2034-2045
[Non Patent Literature 5]
A. Montagnoli et al., Cancer Research, 64, 2004, 7110-7116

SUMMARY OF INVENTION

Technical Problem

An object of the present invention is to provide a medicine, particularly a novel furanone derivative having an inhibitory effect on Cdc7 or a pharmaceutically acceptable salt thereof.

Solution to Problem

The present invention is achieved by the following (1) to (3):

(1) A furanone derivative or a pharmaceutically acceptable salt thereof, represented by the formula (I):

[Chemical Formula 1]

(I)

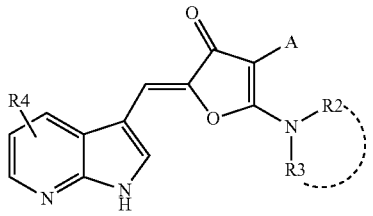

wherein A represents —COOR1 or a hydrogen atom; R1 represents a hydrogen atom, an optionally substituted hydrocarbon group, or an optionally substituted heterocycle; R2 and R3 are the same or different and each independently represent a hydrogen atom, an optionally substituted hydrocarbon group, an optionally substituted phenyl group, an optionally substituted heterocycle, an optionally substituted heterocyclic fused ring, or an optionally substituted amino group; or alternatively, R2 and R3, taken together with the nitrogen atom to which they are attached, may form an optionally substituted heterocycle or an optionally substituted heterocyclic fused ring; and R4 represents a hydrogen atom or a halogen atom; with the proviso that when A represents —COOR1, R2 and R3 are not optionally substituted amino groups at the same time, and when A represents a hydrogen atom, R3 represents a hydrogen atom;

(2) The furanone derivative or a pharmaceutically acceptable salt thereof according to (1), wherein A is —COOR1; and (3) The furanone derivative or a pharmaceutically acceptable salt thereof according to (1), wherein A is a hydrogen atom.

Advantageous Effects of Invention

The present inventors have made various studies in order to solve the above-mentioned problem, and found that novel furanone derivatives represented by the formula (I) and pharmaceutically acceptable salts thereof had excellent inhibitory effect on Cdc7, resulting in completion of the present invention. The compounds provided by the present invention are capable of controlling the growth of cells. Therefore, the compounds of the present invention having an inhibitory effect on Cdc7 will be useful as a medicine, particularly an agent for the treatment of diseases derived from abnormal growth of cells, such as cancers.

DESCRIPTION OF EMBODIMENTS

The present invention will be described in detail below.

A novel furanone derivative of the present invention is a compound represented by the formula (I):

[Chemical Formula 2]

(I)

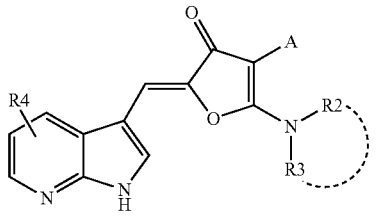

wherein A represents —COOR1 or a hydrogen atom; R1 represents a hydrogen atom, an optionally substituted hydrocarbon group, or an optionally substituted heterocycle; R2 and R3 are the same or different and each independently represent a hydrogen atom, an optionally substituted hydrocarbon group, an optionally substituted phenyl group, an optionally substituted heterocycle, an optionally substituted heterocyclic fused ring, or an optionally substituted amino group; or alternatively, R2 and R3, taken together with the nitrogen atom to which they are attached, may form an optionally substituted heterocycle or an optionally substituted heterocyclic fused ring; and R4 represents a hydrogen atom or a halogen atom; with the proviso that when A represents —COOR1, R2 and R3 are not optionally substituted amino groups at the same time, and when A represents a hydrogen atom, R3 represents a hydrogen atom.

In the formula (I), an optionally substituted hydrocarbon group includes, for example, a) a linear or branched alkyl group having 1 to 6 carbons (for example, methyl, ethyl, isopropyl, tert-butyl, hexyl, etc.);

b) a linear or branched alkenyl group having 1 to 6 carbons (for example, vinyl, allyl, isopropenyl, 2-butenyl, etc.);

c) an alkynyl group having 2 to 6 carbons (for example, ethynyl, propargyl, 2-butynyl, etc.);

d) a cycloalkyl group having 3 to 8 carbons (for example, cyclopropyl, cyclopentyl, cyclohexyl, cycloheptyl, etc.);

e) a cycloalkenyl group having 3 to 8 carbons (for example, cyclohexenyl, cycloheptenyl, etc.);

f) an aralkyl group, the aryl moiety of which is an aryl having 6 to 14 carbons (for example, phenyl, naphthyl, indenyl, etc.) and the alkylene moiety of which has the same meaning as a group where one hydrogen atom has removed from the above-mentioned alkyl group; and others.

The heterocyclic moiety of an optionally substituted heterocycle includes an alicyclic heterocyclic group and an aromatic heterocyclic group. An alicyclic heterocyclic group is, for example, a 3- to 8-membered heterocyclic group containing at least one heteroatom selected from a nitrogen atom, a sulfur atom, and an oxygen atom. Specific examples of the alicyclic heterocyclic group include pyrrolidinyl, piperidyl, piperazinyl, morpholinyl, thiomorpholinyl, etc. An aromatic heterocyclic group is, for example, a 5- or 6-membered monocyclic aromatic heterocyclic group containing at least one heteroatom selected from a nitrogen atom, a sulfur atom, and an oxygen atom. Specific examples of the aromatic heterocyclic group include imidazolyl, pyrazolyl, thienyl, thiazolyl, pyridyl, etc.

The heterocyclic fused ring moiety of an optionally substituted heterocyclic fused ring is, for example, a fused heterocyclic group which is bicyclic by fusing 3- to 8-membered rings and which contains at least one heteroatom selected from a nitrogen atom, a sulfur atom, and an oxygen atom. Specific examples of the fused heterocyclic group include benzothiophenyl, benzimidazolyl, indazolyl, benzoxazolyl, benzothiazolyl, indolyl, isoquinolyl, phthalimide, etc.

An optionally substituted amino group is, for example, an amino group having a linear, branched, or cyclic alkyl, aryl, or heteroaryl group which is substituted or unsubstituted and containing 1 to 6 carbons, for example, an amino group to which an alkyl group, an alkylamino group, an aryl group, a heteroaryl group, a heterocyclic group, a heterocyclic fused ring group, or the like which is unsubstituted or substituted with one or more substituents may be attached. The "one or more substituents" in these groups attached to an amino group may be any one or more substituents which are the same or different, unless otherwise specified, and include, for example, a halogen atom, a substituted or unsubstituted alkyl group, a substituted or unsubstituted alkenyl group, a substituted or unsubstituted alkynyl group, a substituted or unsubstituted alkoxy group, an amino group, a nitro group, a cyano group, a hydroxy group, a substituted or unsubstituted alkylamino group, a carbamoyl group, a carboxyl group, a formyl group, an acetyl group, a benzoyl group, etc.

The "substituent(s)" in an optionally substituted hydrocarbon group, an optionally substituted heterocycle, an optionally substituted phenyl group, or an optionally substituted heterocyclic fused ring is/are be one or more substituents of any type which are allowed to be located at any chemically acceptable positions, unless otherwise specified.

When two or more substituents are present, these substituents may be the same or different and include, for example, a halogen atom, a substituted or unsubstituted alkyl group, a substituted or unsubstituted alkoxy group, a substituted or unsubstituted amino group, a nitro group, a cyano group, a hydroxy group, a substituted or unsubstituted alkylamino group, a carbamoyl group, a carboxyl group, a formyl group, an acetyl group, a benzoyl group, etc.

The heterocyclic group in the case where R2 and R3, taken together with the nitrogen atom to which they are attached, form an optionally substituted heterocycle or an optionally substituted heterocyclic fused ring is, for example, a 3- to 8-membered heterocyclic group containing at least one heteroatom selected from a nitrogen atom, a sulfur atom, and an oxygen atom, or a fused alicyclic heterocyclic group which is bicyclic by fusing 3- to 8-membered rings and which contains at least one heteroatom selected from a nitrogen atom, a sulfur atom, and an oxygen atom. Specific examples of such heterocyclic groups include pyrrolidinyl, piperidyl, morpholinyl, thiomorpholinyl, azepinyl, diazepinyl, dihydroisoquinolyl, tetrahydroisoquinolyl, tetrahydroquinolyl, isoindolinyl, indolinyl, tetrahydrobenzazepinyl, benzazepinyl, benzodiazepinyl, benzoxyazepinyl, benzothiazepinyl, etc.

A halogen atom includes, for example, fluorine, chlorine, bromine, and the like.

A compound (I) of the present invention may have isomers, for example, depending on the type of its substituents. In the specification, such a compound is sometimes described by the chemical structure of only one of its isomeric forms. However, the present invention includes all of the structurally possible isomers of such a compound (geometrical isomers, optical isomers, tautomers, etc.), and also include its individual isomers or mixtures thereof.

Also, the present invention encompasses stereoisomers of a compound of the present invention represented specifically by the formulae (I-Z) and (I-E), and mixtures thereof.

[Chemical Formula 3]

(I-Z)

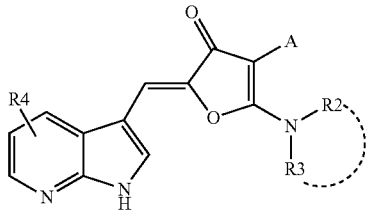

(I-E)

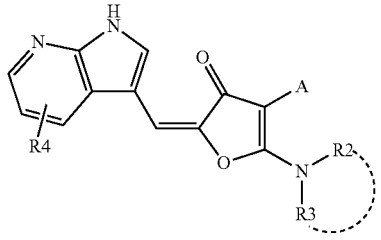

A pharmaceutically acceptable salt of a compound (I) of the present invention includes a salt with an inorganic acid, such as hydrochloric acid, sulfuric acid, carbonic acid, and phosphoric acid, and a salt with an organic acid, such as formic acid, acetic acid, fumaric acid, maleic acid, methanesulfonic acid, and p-toluenesulfonic acid. Also included in the present invention are, for example, a salt with an alkali metal, such as sodium and potassium, a salt with an alkaline earth metal, such as magnesium and calcium, a salt with an organic amine, such as a lower alkyl amine and a lower alcohol amine, and a salt with a basic amino acid, such as lysine, arginine, and ornithine, and in addition, an ammonium salt.

Compounds (I) of the present invention and pharmaceutically acceptable salts thereof can be produced, for example, by the methods mentioned below. In the production methods mentioned below, when a defined group is changed under conditions where the method is performed, or when a defined group is not suitable for performing the method, the production can be easily achieved by applying methods usually used in organic synthetic chemistry, such as procedures for protection and deprotection of functional groups [T. W. Greene, Protective Groups in Organic Synthesis, 3rd Edition, John Wiley & Sons, Inc., 1999]. In addition, the order of reaction steps, for example, those for introducing a substituent or substituents, may be changed as needed.

A compound (Ia) wherein A is —COOR1 can be produced, for example, by scheme 1:

[Scheme 1]

[Chemical Formula 4]

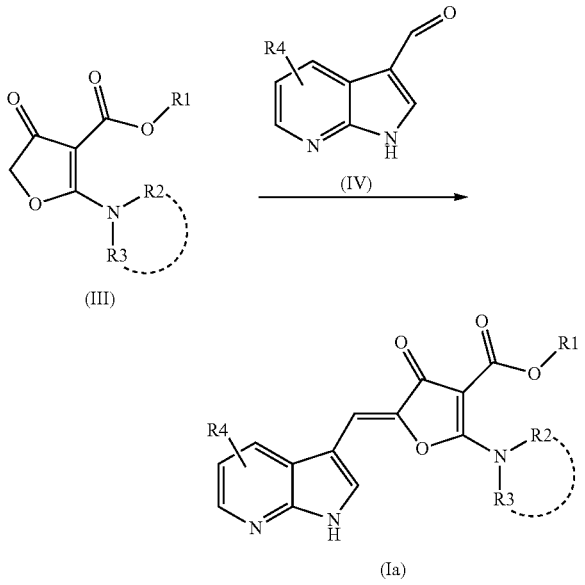

wherein R1, R2, R3 and R4 have the same meaning as mentioned above.

A compound (Ia) of the present invention can be obtained by heating and reacting a compound (III) and 1 to 5, preferably 1 to 1.5, molar equivalents of a compound (IV) in a solvent under conditions for a Knoevenagel condensation reaction, that is, in the presence of a catalytic base such as piperidine. The solvent can be any solvent which is inert in the reaction, and is not limited in particular. For example, a lower alcohol, preferably ethanol, can be used as the solvent. As the base, piperidine or proline, for example, can be used in an amount of from a catalytic amount to an equivalent amount relative to the compound (III). The reaction can be carried out in the range of from room temperature to reflux temperature and for a period of 3 hours to 2 weeks. Preferably, the reaction can be carried out for 1 to 3 days under conditions of reflux in ethanol, thereby to synthesize the compound. In addition, this reaction can also be performed under other usual conditions used in the Knoevenagel condensation reaction, for example, under acidic conditions using hydrochloric acid, acetic acid, or the like, to produce the compound.

The compound (IV) which can be used as one starting material in scheme 1 is commercially available (for example, from SIGMA-ALDRICH) or can be obtained by known methods (see, for example, Rajesh H. Bahekar et al., Bioorganic & Medicinal Chemistry, 15 (21), 6782-6795 (2007); and Seung-Jun Oh et al., Bioorganic & Medicinal Chemistry, 12 (21), 5505-5513 (2004)).

On the other hand, the compound (III) which can be used as the other starting material in scheme 1 can be produced, for example, by the procedures shown in scheme 2 or 3.

[Scheme 2]

[Chemical Formula 5]

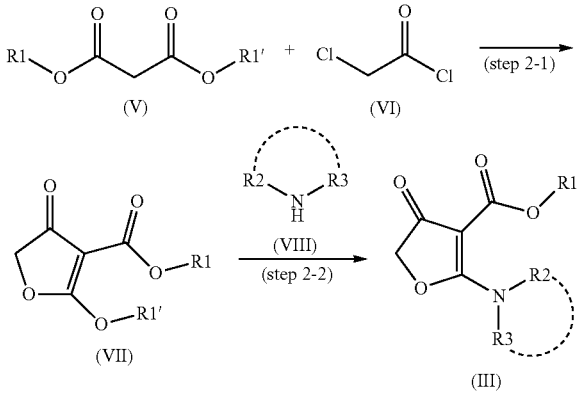

wherein R1, R2, and R3 have the same meaning as mentioned above, and R1' represents a substituted or unsubstituted lower alkyl group.

Step 2-1

A compound (VII) can be obtained by converting a malonic diester (V) to its enolate with a base, such as sodium hydride, in a solvent, such as anhydrous tetrahydrofuran, followed by reaction with chloroacetyl chloride (VI).

Step 2-2

The compound (III) can be obtained by reacting the compound (VII) obtained in the previous step and an amine (VIII) in an amount of from an equivalent amount to an excess amount, preferably in an amount of 1.2 to 3 molar equivalents, in a solvent at room temperature or at heated temperature.

The solvent can be any solvent which is inert in the reaction, and is not limited in particular. For example, tetrahydrofuran, dimethylformamide, ethanol, and the like can be used as the solvent.

The reaction is dependent on the reactivity of the amine (VIII) used, and generally is completed in a period of 1 hour to 1 day at a temperature of from room temperature to the reflux temperature of the solvent. When the reaction progresses at a significantly slow rate, the desired product can be obtained by adding a base, such as sodium hydride, sodium hydroxide, triethylamine, or the like, in an amount of from an equivalent amount to an excess amount.

Further, the compound (III) can also be produced by mean of a sequence of reactions without isolating the compound (VII), by known methods (see, for example, Sheng-Chu Kuo et al., Chem. Pharm. Bull., 36 (11), 4403-4407 (1988)) or their modified methods. That is, the compound (III) can be obtained by adding the amine (VIII) in an amount of from an equivalent amount to an excess amount, preferably in an amount of 1.2 to 3 molar equivalents, to the solution after the reaction in step 2-1, and performing the reaction at room temperature or at heated temperature.

The malonic diester (V) and the amine (VIII) which can be used as the starting materials in scheme 2 are commercially available or can be obtained by known methods.

[Scheme 3]

[Chemical Formula 6]

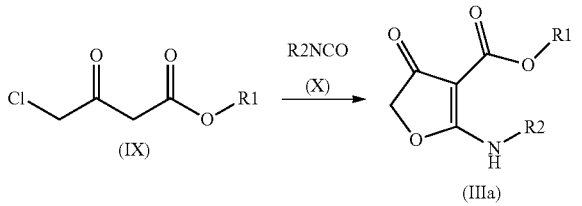

wherein R1 and R2 have the same meaning as mentioned above.

Among the compounds (III), a compound (IIIa) wherein R3 is a hydrogen atom can be produced by known methods (see, for example, Robert A. Mack et al., J. Med. Chem., 31 (10), 1910-1918 (1988)) or their modified methods. That is, the compound (IIIa) can be obtained by cyclocondensation of a compound (IX) with 1 to 5, preferably 1 to 1.5, molar equivalents of isocyanate (X) in a solvent in the presence of a base, such as triethylamine.

The solvent can be any solvent which is inert in the reaction, and is not limited in particular. For example, diethyl ether or ethyl acetate, or mixed solvents thereof can be used as the solvent.

The reaction can be carried out in the range of from ice-cooled temperature to reflux temperature and for a period of 30 minutes to 1 day. Preferably, the reaction can be carried out at room temperature for 1 to 3 hours, thereby to synthesize the compound.

The compound (IX) and isocyanate (X) that are the starting materials in scheme 3 are commercially available or can be obtained by known methods.

Further, a compound (Ia) of the present invention can also be produced by a transesterification reaction of a compound (Ia'), which is a lower alkyl ester compound, as shown in scheme 4:

[Scheme 4]

[Chemical Formula 7]

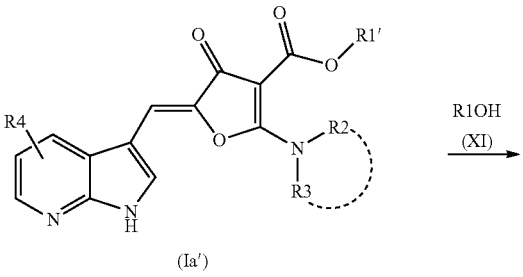

-continued

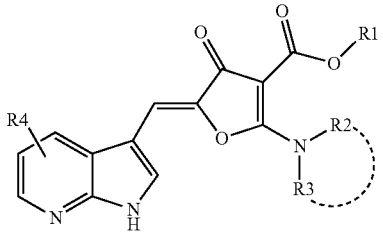

(Ia)

wherein R1, R2, R3, and R4 have the same meaning as mentioned above, and R1' represents a substituted or unsubstituted lower alkyl group.

A compound (Ia) of the present invention can be produced by a transesterification reaction of the compound (Ia') by known methods (see, for example, Takanori Iwasaki et al., J. Org. Chem., 73 (13), 5147-5150 (2008)) or their modified methods. That is, the compound (Ia) can be obtained by heating and reacting the compound (Ia') and an excess amount, preferably more than 10 molar equivalents, of an alcohol (XI) in a solvent in the presence of a tetranuclear zinc cluster catalyst. The solvent can be any solvent which is inert in the reaction, and is not limited in particular. For example, dimethylacetamide, 1,4-dioxane, diisopropyl ether, or the like can be used as the solvent. Alternatively, the alcohol (XI) may be used as the solvent. As the tetranuclear zinc cluster catalyst, catalysts which are commercially available (for example, under a product name of ZnTAC24, from STREM CHEMICALS) or are produced by the method described in the above-mentioned reference are used and added in a catalytic amount, preferably in an amount of 1 to 10% molar equivalents. Further, it is also possible that a tertiary amine, such as dimethylaminopyridine or triethylamine, is added in an amount of from a catalytic amount to 1 molar equivalent to accelerate the reaction.

The reaction can be carried out in the range of from room temperature to reflux temperature and for a period of 1 hour to 1 week. Preferably, the reaction can be carried out for 1 to 3 days under reflux conditions, thereby to synthesize the compound. Alternatively, the reaction may also be carried out using a microwave reactor, for example, for a period of from several minutes to several hours under temperature conditions of 60 to 150° C., thereby to synthesize the compound.

This reaction can also be carried out under other usual conditions used in the transesterification reaction, as shown in scheme 5, for example, under acidic or basic conditions, or under conditions using a catalyst, such as tetravalent titanium.

[Scheme 5]

[Chemical Formula 8]

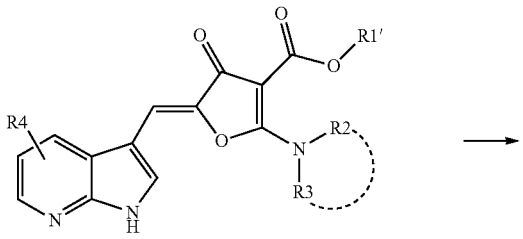

(Ia')

-continued

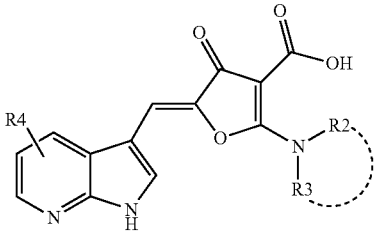

(Ib)

wherein R1', R2, R3, and R4 have the same meaning as mentioned above.

A compound (Ib) of the present invention can be obtained by hydrolysis of a compound (Ia'), which is a lower alkyl ester compound, under reaction conditions used in usual organic synthetic chemistry (using methods described in, for example, T. W. Greene, Protective Groups in Organic Synthesis, 3rd Edition, John Wiley & Sons, Inc., 1999, p. 377, or their modified methods). That is, the compound (Ib) can be obtained by reacting the compound (Ia') and a base or acid in an amount of from an equivalent amount to an excess amount in a solvent at a temperature between 0° C. and the boiling point of the solvent used.

The solvent can be any solvent which is inert in the reaction, and is not limited in particular. For example, 1,4-dioxane, tetrahydrofuran, various alcohols, or the like can be used as the solvent.

As the base or acid, use can be made of, for example, sodium hydroxide, potassium hydroxide, or hydrochloric acid.

The reaction can be carried out at a temperature between 0° C. and the boiling point of the solvent used and for a period of 1 hour to 1 week. Preferably, the reaction can be carried out for 1 hour to 1 day under reflux conditions, thereby to synthesize the compound.

Among the compounds (I) of the present invention, a compound (Ic) wherein A and R3 are hydrogen atoms can be produced, for example, as shown in scheme 6:

[Scheme 6]

[Chemical Formula 9]

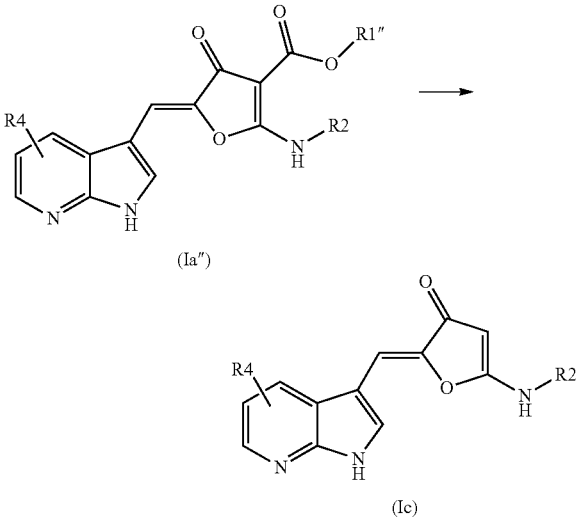

(Ia″)

(Ic)

wherein R2 and R4 have the same meaning as mentioned above, and R1" represents a hydrogen atom or a substituted or unsubstituted lower alkyl group.

A compound (Ic) of the present invention can be synthesized from a compound (Ia"), which is a compound (Ia) wherein R1 is a substituted or unsubstituted lower alkyl ester group and R3 is hydrogen, using known methods (see, for example, Sheng-Chu Kuo et al., Chem. Pharm. Bull., 38 (2), 340-341 (1990)) or their modified methods.

The reaction can be carried out by heating a solution or suspension of a compound (Ia") in N,N-dimethylformamide or N,N-dimethylacetamide at a temperature between 100° C. and the boiling point of the solvent used and for a period of 1 to 24 hours. Preferably, the reaction can be carried out for 1 to 12 hours under reflux conditions, thereby to synthesize the compound.

This reaction can also be carried out by heating and stirring in the presence of a base. For example, the reaction can be carried out by heating to reflux in an alcohol solvent, such as ethanol, in the presence of a highly-concentrated aqueous solution of potassium hydroxide, thereby to synthesize compound.

Moreover, a compound (I) of the present invention which has a desired functional group at a desired position can be obtained by combining the above-mentioned methods as appropriate and carrying out procedures usually used in organic synthetic chemistry (for example, reactions for alkylation of amino groups, reactions for oxidation of an alkylthio group to the corresponding sulfoxide or sulfone group, reactions for converting an alkoxy group to a hydroxy group or vice versa).

Compounds (I) of the present invention or pharmaceutically acceptable salts thereof can be used as medicines, particularly anti-tumor agents, in the form of conventional pharmaceutical preparations for oral administration or for parenteral administration, such as instillation.

Pharmaceutical preparations for oral administration include solid formulations, such as tablets, granules, powders, and capsules, and liquid formulations, such as syrups. These formulations can be prepared by conventional methods. Solid formulations can be prepared using conventional pharmaceutical carriers like lactose, starches such as corn starch, crystalline cellulose such as microcrystalline cellulose, hydroxypropylcellulose, calcium carboxymethylcellulose, talc, magnesium stearate, and others. Capsules can be prepared by encapsulating the granules or powders thus prepared. Syrups can be prepared by dissolving or suspending a compound (I) of the present invention or a pharmaceutically acceptable salt thereof in an aqueous solution containing sucrose, carboxymethylcellulose, or the like.

Pharmaceutical preparations for parenteral administration include formulations for injection, such as instillation. Formulations for injection can also be prepared by conventional methods, and may be incorporated in tonicity adjusting agents (for example, mannitol, sodium chloride, glucose, sorbitol, glycerol, xylitol, fructose, maltose, mannose), stabilizing agents (for example, sodium sulfite, albumin), antiseptics (for example, benzyl alcohol, methyl p-hydroxybenzoate) as appropriate.

Compounds (I) of the present invention or pharmaceutically acceptable salts thereof are effective for medicines, particularly for the treatment of tumors. Tumors include solid tumors, such as breast cancer, colon cancer, and lung cancer, and hematological cancers, such as leukemia, lymphoma, and myeloma.

The amount of dosage of a compound (I) of the present invention or a pharmaceutically acceptable salt thereof can be varied, according to the severeness of the disease, the age and body weight of the patient, its dosage form, and others, and usually is in the range of 1 mg to 1,000 mg per day for adult humans, which can be administered once, or twice or thrice by oral route or by parenteral route.

EXAMPLES

The present invention will be more specifically described below by way of Examples and Test Examples, which are not intended to limit the present invention.

The identification of compounds was performed with hydrogen nuclear magnetic resonance ($^1$H-NMR) spectra and mass spectra (MS). $^1$H-NMR spectra were measured at 400 MHz, unless otherwise specified. In the $^1$H-NMR spectra, exchangeable hydrogens are sometimes not clearly observed, depending on the compound being measured and on the measurement conditions, and br denotes a broad signal. HPLC preparative chromatography was carried out using a commercial available ODS column, and fractions were collected using a water/methanol system (containing formic acid) as an eluent in a gradient mode, unless otherwise specified.

Example 1

Ethyl 5-[(1H-pyrrolo[2,3-b]pyridin-3-yl)methylene]-4-oxo-2-(phenylamino)-4,5-dihydrofuran-3-carboxylate

[Chemical Formula 10]

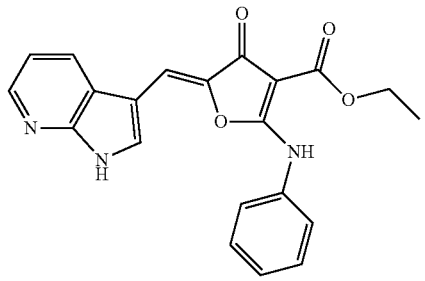

To a solution of 7-azaindole-3-carboxaldehyde (0.10 g, 0.70 mmol) and ethyl 4-oxo-2-(phenylamino)-4,5-dihydrofuran-3-carboxylate (0.18 g, 0.70 mmol) in ethanol (3.0 mL), piperidine (0.083 mL, 0.84 mmol) was added at ambient temperature. The mixture was refluxed for 12 h. Cooled to ambient temperature, the precipitate was collected by filtration, washed with cold ethanol and isopropyl ether then dried to afford the titled compound (0.13 g, y. 48%).

$^1$H NMR (DMSO-$d_6$) δ (ppm) 12.30 (br. s, 1H), 10.58 (s, 1H), 8.23 (dd, J=1.25, 4.52 Hz, 1H), 7.98 (d, J=7.28 Hz, 1H), 7.79 (d, J=2.76 Hz, 1H), 7.52-7.64 (m, 4H), 7.43-7.51

(m, 1H), 6.80-6.99 (m, 2H), 4.28 (q, J=7.03 Hz, 2H), 1.30 (t, J=7.03 Hz, 3H); LCMS (m/z): 376.0 $[M+H]^+$.

Example 2

Ethyl 5-[(1H-pyrrolo[2,3-b]pyridin-3-yl)methylene]-2-[(4-methoxyphenyl)amino]-4-oxo-4,5-dihydro-furan-3-carboxylate

[Chemical Formula 11]

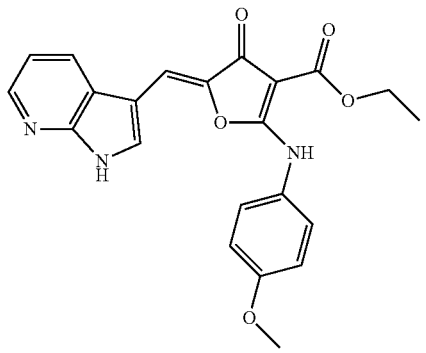

First Step

Under a nitrogen atmosphere, to a mixed solution of ethyl 4-chloroacetoacetate (0.82 mL, 6.0 mmol) and 4-methoxyphenyl isocyanate 1.1 g, 7.2 mmol) in diethyl ether/ethyl acetate (10 mL/1.0 mL) that cooled with ice bath, triethylamine (0.96 mL, 6.9 mmol) was added dropwise. The reaction mixture was stirred at ambient temperature for 1.5 h then the precipitate was collected by filtration, washed with diethyl ether, 1M hydrochloric acid solution, water and diethyl ether, and then dried to afford ethyl 2-[(4-methoxyphenyl)amino]-4-oxo-4,5-dihydrofuran-3-carboxylate as solid (1.3 g, y. 78%).

$^1$H NMR ($CDCl_3$) δ (ppm) 10.11 (br. s, 1H), 7.24-7.33 (m, 2H), 6.90-6.96 (m, 2H), 4.65 (s, 2H), 4.38 (q, J=7.07 Hz, 2H), 3.83 (s, 3H), 1.40 (t, J=7.20 Hz, 3H); LCMS (m/z): 277.9 $[M+H]^+$.

Second Step

To a solution of ethyl 2-[(4-methoxyphenyl)amino]-4-oxo-4,5-dihydrofuran-3-carboxylate (0.28 g, 1.0 mmol) and 7-azaindole-3-carboxaldehyde (0.15 g, 1.0 mmol) in ethanol (4.0 mL), piperidine (0.12 mL, 1.2 mmol) was added at ambient temperature. The mixture was refluxed for 12 h. Cooled to ambient temperature, the precipitate was collected by filtration, washed with ethanol and diisopropyl ether then dried to afford the titled compound (0.092 g, y. 22%).

$^1$H NMR (DMSO-$d_6$) δ (ppm) 12.31 (br. s, 1H), 10.47 (s, 1H), 8.24 (dd, J=1.51, 4.52 Hz, 1H), 7.94 (d, J=7.53 Hz, 1H), 7.77 (d, J=2.76 Hz, 1H), 7.50 (d, J=9.03 Hz, 2H), 7.09 (d, J=8.78 Hz, 2H), 6.81-6.92 (m, 2H), 4.26 (q, J=7.03 Hz, 2H), 3.87 (s, 3H), 1.29 (t, J=7.03 Hz, 3H); LCMS (m/z): 406.0 $[M+H]^+$.

Example 3

Ethyl 5-[(5-chloro-1H-pyrrolo[2,3-b]pyridin-3-yl)methylene]-4-oxo-2-(phenylamino)-4,5-dihydro-furan-3-carboxylate

[Chemical Formula 12]

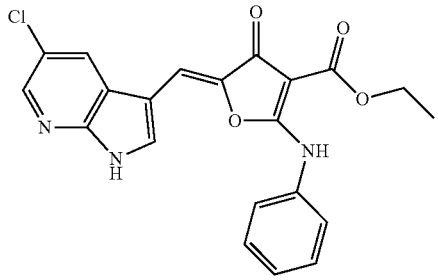

First Step

To a mixed solution of 2-amino-5-chloropyridine (2.6 g, 0.020 mol) in acetic acid/water (7.8 mL/1.8 mL) that cooled with ice bath, conc.sulfuric acid (0.26 mL, 4.9 mmol) was added dropwise, and then periodic acid (0.95 g, 4.2 mmol) and iodine (2.0 g, 8.0 mmol) were added. The reaction mixture was stirred at 80° C. for 6 h. Cooled to ambient temperature, the reaction mixture was poured into ice water, and neutralized by aqueous 5M sodium hydroxide solution. After removal of the precipitate by filtration, the filtrate was extracted with ethyl acetate. The organic layer was washed with saturated sodium thiosulfate solution, aqueous 1M sodium hydroxide solution and brine then dried over sodium sulfate and concentrated to afford 2-amino-5-chloro-3-iodopyridine as solid (4.4 g, y. 85%).

$^1$H NMR ($CDCl_3$) δ (ppm) 7.96 (s, 1H), 7.82 (s, 1H), 4.93 (s, 2H); LCMS (m/z) 255.2 $[M+H]^+$.

Second Step

Under a nitrogen atmosphere, to a solution of 2-amino-5-chloro-3-iodopyridine (4.2 g, 0.017 mol), copper(I) iodide (0.032 g, 0.17 mmol) and triethylamine (7.0 mL, 0.050 mol) in anhydrous tetrahydrofuran (10 mL), dichlorobis(triphenylphosphine)palladium(II) (0.12 g, 0.17 mmol) and ethynyl trimethylsilane (3.0 mL, 0.021 mol) were added and the mixture was stirred at ambient temperature for 2 h. The reaction mixture was diluted with diethyl ether and removed the precipitate by filtration with C elite. The filtrate was concentrated to afford 2-amino-5-chloro-3-[(trimethylsilyl)ethynyl]pyridine as solid (4.2 g).

$^1$H NMR ($CDCl_3$) δ (ppm) 7.94 (d, 1H, J=2.28 Hz), 7.49 (d, 1H, J=2.32 Hz), 5.02 (s, 2H), 0.18-0.25 (m, 9H); LCMS (m/z): 225.5 $[M+H]^+$.

Third Step

Under a nitrogen atmosphere, to a solution of potassium tert-butoxide (4.0 g, 0.036 mol) in 1-methyl-2-pyrrolidone (8.0 mL) which stirred with heating at 80° C., a solution of 2-amino-5-chloro-3-[(trimethylsilyl)ethynyl]pyridine (4.0 g, 0.018 mol) in 1-methyl-2-pyrrolidone (22 mL) was added dropwise and the mixture was stirred for 1 h. Cooled to ambient temperature, the reaction mixture was diluted with brine and stirred, then extracted with diethyl ether for 3 times. The organic layer was washed with brine, dried over sodium sulfate and concentrated to afford 5-chloro-7-azaindole as solid (2.3 g, y. 85%).

$^1$H NMR ($CDCl_3$) δ (ppm) 9.46 (s, 1H), 8.26 (s, 1H), 7.91 (d, 1H, J=1.12 Hz), 7.35 (s, 1H), 6.46 (s, 1H); LCMS (m/z): 153.2 $[M+H]^+$.

Fourth Step

To a solution of 5-chloro-7-azaindole (0.50 g, 3.3 mmol) in acetic acid (5.0 mL), hexamethylenetetramine (0.69 g, 4.9 mmol) was added at ambient temperature. The mixture was refluxed for 8 h. Cooled to ambient temperature, the reaction mixture was diluted with water, extracted with ethyl acetate for 2 times. The organic layer was washed with water and brine, dried over sodium sulfate and concentrated. The residue was purified by chromatography on silica gel (hexane/ethyl acetate) to afford 5-chloro-7-azaindole-3-carboxaldehyde as solid (0.13 g, y. 22%).

$^1$H NMR ($CDCl_3$) δ (ppm) 10.01 (s, 1H), 9.77 (br. s, 1H), 8.61 (d, 1H, J=2.04 Hz), 8.37 (d, 1H, J=2.08 Hz), 7.99 (d, 1H, J=2.64 Hz); LCMS (m/z): 181.2 $[M+H]^+$.

Fifth Step

To a solution of 5-chloro-7-azaindole-3-carboxaldehyde (0.019 g, 0.11 mmol) and ethyl 4-oxo-2-(phenylamino)-4,5-dihydrofuran-3-carboxylate (0.025 g, 0.10 mmol) in ethanol (1.0 mL), piperidine (0.012 mL, 0.12 mmol) was added at ambient temperature. The mixture was refluxed for 2 days. Cooled to ambient temperature, solvents were removed under reduced pressure then the residue was purified by preparative HPLC to afford the titled compound (0.0020 g, y. 4.6%).

$^1$H NMR (DMSO-$d_6$) δ (ppm) 12.52 (br. s, 1H), 10.58 (s, 1H), 8.42 (d, J=2.26 Hz, 1H), 8.26 (d, J=2.26 Hz, 1H), 7.71 (d, J=2.51 Hz, 1H), 7.55-7.63 (m, 2H), 7.51 (t, J=7.78 Hz, 2H), 7.35-7.44 (m, 1H), 7.00 (s, 1H), 4.28 (q, J=7.03 Hz, 2H), 1.30 (t, J=7.15 Hz, 3H); LCMS (m/z): 410.0 $[M+H]^+$.

Example 4

Ethyl 5-[(1H-pyrrolo[2,3-b]pyridin-3-yl)methylene]-4-oxo-2-piperidino-4,5-dihydrofuran-3-carboxylate

[Chemical Formula 13]

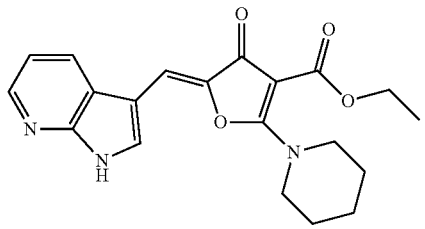

First Step

Diethyl malonate (5.0 mL, 0.033 mol) was added dropwise to a solution of sodium hydride (60% w/w in oil, 2.7 g, 0.066 mol) in anhydrous tetrahydrofuran (50 mL) that cooled with ice bath. The mixture was refluxed for 5 min. The reaction mixture was cooled with ice bath, chloroacetyl chloride (2.8 mL, 0.035 mol) was added dropwise to the reaction mixture and the mixture was stirred for 1 h then stirred at 45° C. for 1 h. The reaction mixture was cooled with ice bath again then piperidine (3.9 mL, 0.040 mol) was added dropwise and stirred at ambient temperature for further 12 h. The reaction mixture was diluted with aqueous saturated sodium bicarbonate solution, and extracted with ethyl acetate for 2 times then extracted with chloroform. The organic layer was washed with brine, dried over sodium sulfate and concentrated. The residue was purified by chromatography on silica gel(chloroform/methanol) to afford ethyl 4-oxo-2-piperidino-4,5-dihydrofuran-3-carboxylate as solid (3.5 g, y. 45%).

$^1$H NMR (DMSO-$d_6$) δ (ppm) 4.53 (s, 2H), 4.10 (q, J=7.03 Hz, 2H), 3.48-3.60 (m, 4H), 1.56-1.67 (m, 6H), 1.20 (t, J=7.03 Hz, 16H); LCMS (m/z): 240.0 $[M+H]^+$.

Second Step

To a solution of ethyl 4-oxo-2-piperidino-4,5-dihydrofuran-3-carboxylate (0.10 g, 0.42 mmol) and 7-azaindole-3-carboxaldehyde (0.061 g, 0.42 mmol) in ethanol (2.0 mL), piperidine (0.041 mL, 0.42 mmol) was added at ambient temperature. The mixture was refluxed for 24 h. Cooled to ambient temperature, the precipitate was collected by filtration, washed with ethanol and diisopropyl ether then dried to afford the titled compound (0.045 g, y. 29%).

$^1$H NMR (DMSO-$d_6$) δ (ppm) 12.29 (br. s, 1H), 8.37 (dd, J=1.25, 8.03 Hz, 1H), 8.31 (dd, J=1.51, 4.52 Hz, 1H), 7.96 (d, J=2.76 Hz, 1H), 7.19 (dd, J=4.64, 7.91 Hz, 1H), 6.84 (s, 1H), 4.16 (q, J=7.19 Hz, 2H), 3.70-3.80 (m, 4H), 1.65-1.78 (m, 6H), 1.24 (t, J=7.03 Hz, 3H); LCMS (m/z): 368.0 $[M+H]^+$.

Example 5

Ethyl 5-[(1H-pyrrolo[2,3-b]pyridin-3-yl)methylene]-2-[(3-methoxyphenyl)amino]-4-oxo-4,5-dihydrofuran-3-carboxylate

[Chemical Formula 14]

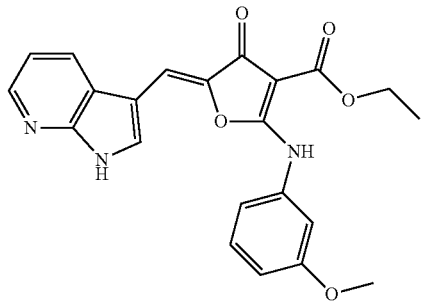

To a solution of ethyl 2-[(3-methoxyphenyl)amino]-4-oxo-4,5-dihydrofuran-3-carboxylate (0.28 g, 1.0 mmol) which similarly prepared according to the procedure described in the Example 2, First step and 7-azaindole-3-carboxaldehyde (0.15 g, 1.2 mmol) in ethanol (4.0 mL), piperidine (0.12 mL, 1.2 mmol) was added at ambient temperature. The mixture was refluxed for 2 days. Cooled to ambient temperature, the precipitate was collected by filtration, washed with ethanol and diisopropyl ether then dried to afford the titled compound (0.17 g, y. 29%).

$^1$H NMR (DMSO-$d_6$) δ (ppm) 12.34 (br. s, 1H), 10.52 (s, 1H), 8.25 (dd, J=1.38, 4.64 Hz, 1H), 8.03 (d, J=7.03 Hz, 1H), 7.84 (d, J=2.76 Hz, 1H), 7.45 (t, J=8.03 Hz, 1H), 7.13-7.26 (m, 2H), 7.04 (dd, J=2.01, 8.28 Hz, 1H), 6.86-6.95 (m, 2H), 4.27 (q, J=7.03 Hz, 2H), 3.77 (s, 3H), 1.30 (t, J=7.15 Hz, 3H); LCMS (m/z): 406.0 $[M+H]^+$.

Example 6

Ethyl 5-[(1H-pyrrolo[2,3-b]pyridin-3-yl)methylene]-4-oxo-2-(2-pyridinylamino)-4,5-dihydrofuran-3-carboxylate

[Chemical Formula 15]

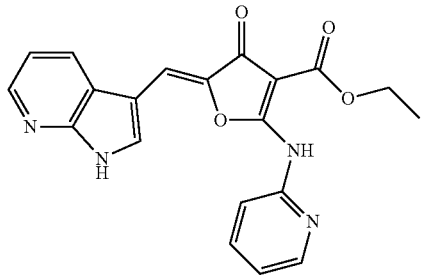

To a solution of ethyl 4-oxo-2-(2-pyridinylamino)-4,5-dihydrofuran-3-carboxylate (0.080 g, 0.32 mmol) which similarly prepared according to the procedure described in the Example 4, First step and 7-azaindole-3-carboxaldehyde (0.047 g, 0.32 mmol) in ethanol (2.0 mL), piperidine (0.038 mL, 0.39 mmol) was added at ambient temperature. The mixture was refluxed for 10 h. Cooled to ambient temperature, the precipitate was removed by filtration and the filtrate was purified by preparative HPLC to afford the titled compound as solid (0.0030 g, y. 2.5%).

$^1$H NMR (DMSO-$d_6$) δ (ppm) 12.41 (br. s, 1H), 10.74 (br. s, 1H), 8.60 (d, J=3.26 Hz, 1H), 8.35 (d, J=7.78 Hz, 1H), 8.30 (dd, J=1.38, 4.64 Hz, 1H), 8.24 (br. s, 1H), 7.97 (dt, J=1.88, 7.84 Hz, 1H), 7.61 (d, J=8.03 Hz, 1H), 7.36-7.45 (m, 1H), 7.02-7.14 (m, 2H), 4.27 (q, J=7.03 Hz, 2H), 1.29 (t, J=7.03 Hz, 3H); LCMS (m/z): 377.0 $[M+H]^+$.

Example 7

Ethyl 5-[(1H-pyrrolo[2,3-b]pyridin-3-yl)methylene]-2-[(2-methoxyphenyl)amino]-4-oxo-4,5-dihydrofuran-3-carboxylate

[Chemical Formula 16]

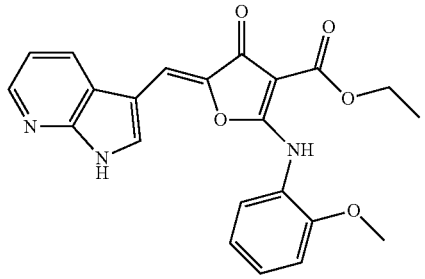

To a solution of ethyl 2-[(2-methoxyphenyl)amino]-4-oxo-4,5-dihydrofuran-3-carboxylate (0.28 g, 1.0 mmol) which similarly prepared according to the procedure described in the Example 2, First step and 7-azaindole-3-carboxaldehyde (0.15 g, 1.2 mmol) in ethanol (4.0 mL), piperidine (0.12 mL, 1.2 mmol) was added at ambient temperature. The mixture was refluxed for 2 days. Cooled to ambient temperature, the precipitate was collected by filtration, washed with ethanol and diisopropyl ether then dried to afford the titled compound (0.30 g, y. 74%).

$^1$H NMR (DMSO-$d_6$) δ (ppm) 12.34 (br. s, 1H), 10.35 (s, 1H), 8.25 (dd, J=1.38, 4.64 Hz, 1H), 8.02 (d, J=7.03 Hz, 1H), 7.85 (d, J=2.76 Hz, 1H), 7.66 (dd, J=1.38, 7.91 Hz, 1H), 7.41-7.51 (m, 1H), 7.28 (d, J=7.53 Hz, 1H), 7.12 (t, J=7.65 Hz, 1H), 6.88-6.99 (m, 2H), 4.28 (q, J=7.03 Hz, 2H), 3.85 (s, 3H), 1.30 (t, J=7.15 Hz, 3H); LCMS (m/z): 406.0 $[M+H]^+$.

Example 8

Ethyl 5-[(1H-pyrrolo[2,3-b]pyridin-3-yl)methylene]-2-[(4-chlorophenyl)amino]-4-oxo-4,5-dihydrofuran-3-carboxylate

[Chemical Formula 17]

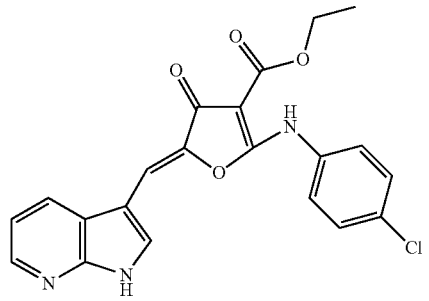

To a solution of ethyl 2-[(4-chlorophenyl)amino]-4-oxo-4,5-dihydrofuran-3-carboxylate (0.18 g, 0.61 mmol) which similarly prepared according to the procedure described in the Example 2, First step and 7-azaindole-3-carboxaldehyde (0.088 g, 0.61 mmol) in ethanol (10 mL), piperidine (0.0044 mL, 0.044 mmol) was added at ambient temperature. The mixture was refluxed for 6 days. Cooled to ambient temperature, the precipitate was collected by filtration, washed with ethanol and hexane then dried to afford the titled compound (0.061 g, y. 23%).

$^1$H NMR (DMSO-$d_6$) δ (ppm) 12.33 (br. s, 1H), 10.61 (s, 1H), 8.26 (d, J=3.26 Hz, 1H), 7.96 (d, J=7.53 Hz, 1H), 7.82 (d, J=2.76 Hz, 1H), 7.58-7.67 (m, 4H), 6.87-6.95 (m, 2H), 4.27 (q, J=7.03 Hz, 2H), 1.29 (t, J=7.03 Hz, 3H); LCMS (m/z): 409.9 $[M+H]^+$.

Example 9

Ethyl 5-[(1H-pyrrolo[2,3-b]pyridin-3-yl)methylene]-2-[(3-chlorophenyl)amino]-4-oxo-4,5-dihydrofuran-3-carboxylate

[Chemical Formula 18]

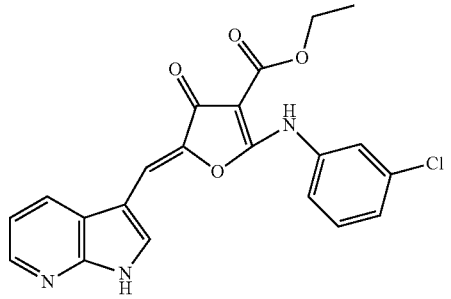

To a solution of ethyl 2-[(3-chlorophenyl)amino]-4-oxo-4,5-dihydrofuran-3-carboxylate (0.10 g, 0.36 mmol) which similarly prepared according to the procedure described in the Example 2, First step and 7-azaindole-3-carboxaldehyde (0.051 g, 0.35 mmol) in ethanol (3.0 mL), piperidine (0.0035 mL, 0.035 mmol) was added at ambient temperature. The mixture was refluxed for 6 days. Cooled to ambient temperature, the precipitate was collected by filtration, washed with ethanol then dried to afford the titled compound (0.061 g, y. 23%).

$^1$H NMR (DMSO-$d_6$) δ (ppm) 12.36 (br. s, 1H), 10.63 (s, 1H), 8.26 (dd, J=1.38, 4.64 Hz, 1H), 8.01 (d, J=7.28 Hz, 1H), 7.82 (d, J=2.76 Hz, 1H), 7.76 (s, 1H), 7.50-7.61 (m, 3H), 6.89-6.96 (m, 2H), 4.28 (q, J=7.03 Hz, 2H), 1.30 (t, J=7.03 Hz, 3H); LCMS (m/z): 409.9 $[M+H]^+$.

Example 10

Ethyl 5-[(1H-pyrrolo[2,3-b]pyridin-3-yl)methylene]-2-(benzylamino)-4-oxo-4,5-dihydrofuran-3-carboxylate hydrochloride

[Chemical Formula 19]

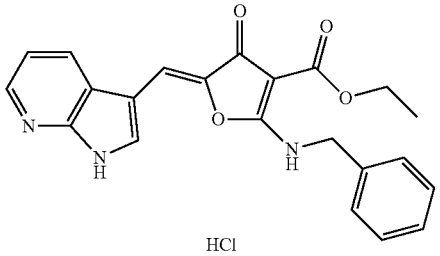

HCl

A solution of ethyl 2-(benzylamino)-4-oxo-4,5-dihydrofuran-3-carboxylate (0.026 g, 0.10 mmol) which similarly prepared according to the procedure described in the Example 2, First step and 7-azaindole-3-carboxaldehyde (0.015 g, 0.10 mmol) in 2M hydrochloric acid in ethanol (1.0 mL) was refluxed for 4 h. Cooled to ambient temperature, the precipitate was collected by filtration, washed with ethanol and diisopropyl ether then dried to afford the titled compound (0.024 g, y. 56%).

$^1$H NMR (DMSO-$d_6$) δ (ppm) 12.25-12.56 (m, 1H), 9.54 (br. s, 1H), 8.25-8.42 (m, 2H), 7.86 (s, 1H), 7.35-7.48 (m, 4H), 7.24-7.33 (m, 1H), 7.08-7.18 (m, 1H), 6.87 (s, 1H), 4.86 (d, J=6.53 Hz, 2H), 4.23 (q, J=7.19 Hz, 2H), 1.27 (t, J=7.03 Hz, 3H); LCMS (m/z): 390.0 $[M+H]^+$.

Example 11

5-[(1H-Pyrrolo[2,3-b]pyridin-3-yl)methylene]-4-oxo-2-piperidino-4,5-dihydrofuran-3-carboxylic acid

[Chemical Formula 20]

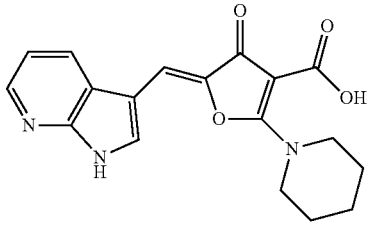

To a solution of the compound of Example 4 in dioxane (0.5 mL), 2M sodium hydroxide solution (0.50 mL, 1.0 mmol) was added at ambient temperature. The mixture was stirred at 110° C. for 1.5 h. Cooled to ambient temperature, the reaction mixture was neutralized by 2M hydrochloric acid solution then the solvent was removed under reduced pressure. The residue was purified by preparative HPLC to afford the titled compound (0.0044 g, y. 45%).

$^1$H NMR (DMSO-$d_6$) δ (ppm) 12.24 (br. s, 1H), 8.39 (d, J=8.03 Hz, 1H), 8.30 (dd, J=1.38, 4.64 Hz, 1H), 7.92 (d, J=2.26 Hz, 1H), 7.19 (dd, J=4.77, 8.03 Hz, 1H), 6.73 (s, 1H), 3.35-3.62 (m, 4H), 1.45-1.69 (m, 6H); LCMS (m/z): 339.9 $[M+H]^+$.

Example 12

Ethyl 5-[(1H-pyrrolo[2,3-b]pyridin-3-yl)methylene]-2-(ethylamino)-4-oxo-4,5-dihydrofuran-3-carboxylate hydrochloride

[Chemical Formula 21]

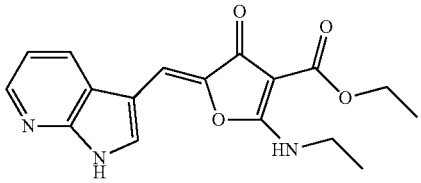

HCl

To a solution of ethyl 2-(ethylamino)-4-oxo-4,5-dihydrofuran-3-carboxylate (0.033 g, 0.17 mmol) which similarly prepared according to the procedure described in the Example 2, First step and 7-azaindole-3-carboxaldehyde (0.024 g, 0.17 mmol) in ethanol (1.5 mL), 2M hydrochloric acid in ethanol (0.17 mL, 0.34 mmol) was added at ambient temperature. The mixture was refluxed for 4 h. Cooled to ambient temperature, the precipitate was collected by filtration, washed with ethanol and diisopropyl ether then dried to afford the titled compound (0.026 g, y. 42%).

$^1$H NMR (DMSO-$d_6$) δ (ppm) 12.46 (br. s, 1H), 9.03 (t, J=6.02 Hz, 1H), 8.45-8.54 (m, 1H), 8.35 (dd, J=1.25, 4.77 Hz, 1H), 8.01 (d, J=1.25 Hz, 1H), 7.25 (dd, J=4.77, 8.03 Hz, 1H), 6.90 (s, 1H), 4.25-4.50 (m, 1H), 4.21 (q, J=7.19 Hz, 2H), 3.61-3.71 (m, 2H), 1.30 (t, J=7.15 Hz, 3H), 1.26 (t, J=7.03 Hz, 3H); LCMS (m/z): 328.0 $[M+H]^+$.

Example 13

Ethyl 5-[(1H-pyrrolo[2,3-b]pyridin-3-yl)methylene]-4-oxo-2-(phenethylamino)-4,5-dihydrofuran-3-carboxylate hydrochloride

[Chemical Formula 22]

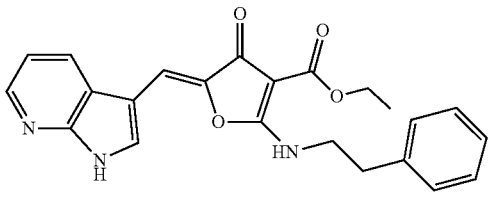

HCl

To a solution of ethyl 4-oxo-2-(phenethylamino)-4,5-dihydrofuran-3-carboxylate (0.041 g, 0.15 mmol) which similarly prepared according to the procedure described in the Example 4, First step and 7-azaindole-3-carboxaldehyde (0.022 g, 0.15 mmol) in ethanol (1.0 mL), 2M hydrochloric acid in ethanol (0.16 mL, 0.32 mmol) was added at ambient temperature. The mixture was refluxed for 3 h. Cooled to ambient temperature, the precipitate was collected by filtration, washed with ethanol and diisopropyl ether then dried to afford the titled compound (0.023 g, y. 32%).

$^1$H NMR (DMSO-$d_6$) δ (ppm) 12.45 (br. s, 1H), 9.02 (t, J=6.15 Hz, 1H), 8.40 (d, J=6.78 Hz, 1H), 8.33 (dd, J=1.38, 4.64 Hz, 1H), 7.94 (d, J=2.26 Hz, 1H), 7.23-7.33 (m, 4H), 7.11-7.22 (m, 2H), 6.84 (s, 1H), 4.21 (q, J=7.19 Hz, 2H), 3.85 (q, J=6.94 Hz, 2H), 3.00 (t, J=7.28 Hz, 2H), 1.25 (t, J=7.03 Hz, 3H); LCMS (m/z): 404.0 $[M+H]^+$.

Example 14

Ethyl 5-[(1H-pyrrolo[2,3-b]pyridin-3-yl)methylene]-4-oxo-2-pyrrolidinyl-4,5-dihydrofuran-3-carboxylate hydrochloride

[Chemical Formula 23]

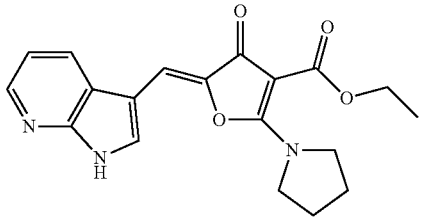

HCl

To a solution of ethyl 4-oxo-2-pyrrolidinyl-4,5-dihydrofuran-3-carboxylate (0.034 g, 0.15 mmol) which similarly prepared according to the procedure described in the Example 4, First step and 7-azaindole-3-carboxaldehyde (0.022 g, 0.15 mmol) in ethanol (1.0 mL), 2M hydrochloric acid in ethanol (0.16 mL, 0.32 mmol) was added at ambient temperature. The mixture was refluxed for 3 h. Cooled to ambient temperature, the precipitate was collected by filtration, washed with ethanol and diisopropyl ether then dried to afford the titled compound (0.038 g, y. 61%).

$^1$H NMR (DMSO-$d_6$) δ (ppm) 12.38 (br. s, 1H), 8.46 (d, J=8.03 Hz, 1H), 8.33 (dd, J=1.38, 4.64 Hz, 1H), 7.95 (d, J=2.26 Hz, 1H), 7.23 (dd, J=4.77, 7.78 Hz, 1H), 6.84 (s, 1H), 4.16 (q, J=7.03 Hz, 2H), 3.79-3.98 (m, 3H), 3.63-3.73 (m, 2H), 1.92-2.05 (m, 4H), 1.24 (t, J=7.03 Hz, 3H); LCMS (m/z): 354.0 $[M+H]^+$.

Example 15

Ethyl 5-[(1H-pyrrolo[2,3-b]pyridin-3-yl)methylene]-2-[(2-chlorophenyl)amino]-4-oxo-4,5-dihydrofuran-3-carboxylate

[Chemical Formula 24]

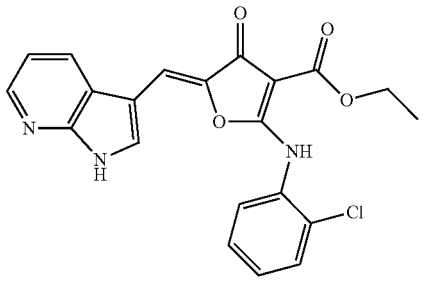

HCl

To a solution of ethyl 2[(2-chlorophenyl)amino]-4-oxo-4,5-dihydrofuran-3-carboxylate (0.14 g, 0.50 mmol) which similarly prepared according to the procedure described in the Example 2, First step and 7-azaindole-3-carboxaldehyde (0.073 g, 0.50 mmol) in ethanol (2.0 mL), piperidine (0.054 mL, 0.55 mmol) was added at ambient temperature. The mixture was refluxed for 12 h. Cooled to ambient temperature, the precipitate was collected by filtration, washed with ethanol and diisopropyl ether then dried to afford the titled compound (0.099 g, y. 48%).

$^1$H NMR (DMSO-$d_6$) δ (ppm) 12.31 (br. s, 1H), 10.65 (s, 1H), 8.22 (dd, J=1.38, 4.64 Hz, 1H), 7.70-7.83 (m, 4H), 7.51-7.64 (m, 2H), 6.92 (s, 1H), 6.81 (dd, J=4.64, 7.91 Hz, 1H), 4.29 (q, J=7.11 Hz, 2H), 1.30 (t, J=7.03 Hz, 3H); LCMS (m/z): 409.8 $[M+H]^+$.

Example 16

Ethyl 5-[(1H-pyrrolo[2,3-b]pyridin-3-yl)methylene]-2-{[4-(dimethylamino)phenyl]amino}-4-oxo-4,5-dihydrofuran-3-carboxylate hydrochloride

[Chemical Formula 25]

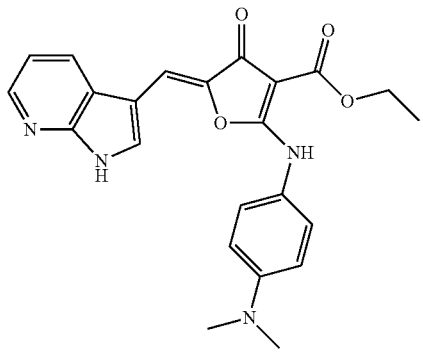

HCl

To a solution of ethyl 2-{[4-(dimethylamino)phenyl]amino}-4-oxo-4,5-dihydrofuran-3-carboxylate (0.073 g, 0.20 mmol) which similarly prepared according to the procedure described in the Example 2, First step and 7-azaindole-3-carboxaldehyde (0.029 g, 0.20 mmol) in ethanol (1.5 mL), 2M hydrochloric acid in ethanol (0.33 mL, 0.66 mmol) was added at ambient temperature. The mixture was refluxed for 1 h. Cooled to ambient temperature, the precipitate was collected by filtration, washed with ethanol and diisopropyl ether then dried to afford the titled compound (0.034 g, y. 35%).

$^1$H NMR (DMSO-$d_6$) δ (ppm) 12.51 (br. s, 1H), 10.47 (br. s, 1H), 8.23-8.33 (m, 1H), 8.10 (d, J=7.78 Hz, 1H), 7.81 (s, 1H), 7.50 (d, J=8.03 Hz, 2H), 7.16 (br. s, 2H), 6.95 (dd, J=4.77, 7.78 Hz, 1H), 6.90 (s, 1H), 4.40-5.20 (m, 1H), 4.27 (q, J=7.03 Hz, 2H), 3.08 (s, 6H), 1.29 (t, J=7.15 Hz, 3H); LCMS (m/z): 419.0 $[M+H]^+$.

Example 17

Ethyl 5-[(1H-pyrrolo[2,3-b]pyridin-3-yl)methylene]-2-(diethylamino)-4-oxo-4,5-dihydrofuran-3-carboxylate hydrochloride

[Chemical Formula 26]

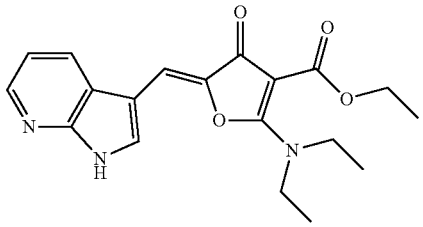

HCl

To a solution of ethyl 2-(diethylamino)-4-oxo-4,5-dihydrofuran-3-carboxylate (0.034 g, 0.15 mmol) which similarly prepared according to the procedure described in the Example 4, First step and 7-azaindole-3-carboxaldehyde (0.022 g, 0.15 mmol) in ethanol (1.0 mL), 2M hydrochloric acid in ethanol (0.16 mL, 0.32 mmol) was added at ambient temperature. The mixture was refluxed for 3 h. Cooled to ambient temperature, the precipitate was collected by filtration, washed with ethanol and diisopropyl ether then dried to afford the titled compound (0.023 g, y. 38%).

$^1$H NMR (DMSO-$d_6$) δ (ppm) 12.36 (br. s, 1H), 8.41 (d, J=7.78 Hz, 1H), 8.33 (dd, J=1.25, 4.77 Hz, 1H), 7.93 (d, J=2.26 Hz, 1H), 7.22 (dd, J=4.77, 7.78 Hz, 1H), 6.84 (s, 1H), 4.18 (q, J=7.11 Hz, 2H), 3.50-3.84 (m, 5H), 1.11-1.38 (m, 9H); LCMS (m/z): 356.0 $[M+H]^+$.

Example 18

Ethyl 5-[(1H-pyrrolo[2,3-b]pyridin-3-yl)methylene]-2-(cyclohexylamino)-4-oxo-4,5-dihydrofuran-3-carboxylate hydrochloride

[Chemical Formula 27]

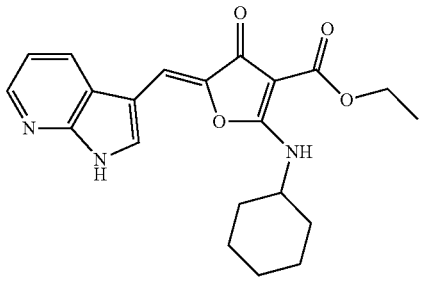

HCl

To a solution of ethyl 2-(cyclohexylamino)-4-oxo-4,5-dihydrofuran-3-carboxylate (0.019 g, 0.075 mmol) which similarly prepared according to the procedure described in the Example 2, First step and 7-azaindole-3-carboxaldehyde (0.011 g, 0.075 mmol) in ethanol (1.0 mL), 2M hydrochloric acid in ethanol (0.079 mL, 0.16 mmol) was added at ambient temperature. The mixture was refluxed for 4 h. Cooled to ambient temperature, the precipitate was collected by filtration, washed with ethanol and diisopropyl ether then dried to afford the titled compound (0.0070 g, y. 22%).

$^1$H NMR (DMSO-$d_6$) δ (ppm) 12.40 (br. s, 1H), 8.53 (d, J=8.53 Hz, 1H), 8.46 (d, J=7.78 Hz, 1H), 8.34 (dd, J=1.26, 4.52 Hz, 1H), 7.99 (d, J=2.26 Hz, 1H), 7.22 (dd, J=4.64, 7.91 Hz, 1H), 6.90 (s, 1H), 4.21 (q, J=7.03 Hz, 2H), 3.91-4.09 (m, 1H), 1.98 (d, J=9.79 Hz, 2H), 1.79 (d, J=13.05 Hz, 2H), 1.55-1.70 (m, 3H), 1.35-1.49 (m, 2H), 1.16-1.29 (m, 4H); LCMS (m/z): 382.4 $[M+H]^+$.

Example 19

Ethyl 5-[(1H-pyrrolo[2,3-b]pyridin-3-yl)methylene]-2-[(4-bromophenyl)amino]-4-oxo-4,5-dihydrofuran-3-carboxylate

[Chemical Formula 28]

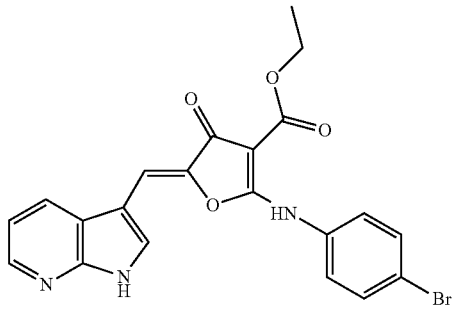

To a solution of ethyl 2-[(4-bromophenyl)amino]-4-oxo-4,5-dihydrofuran-3-carboxylate (0.15 g, 0.46 mmol) which similarly prepared according to the procedure described in the Example 4, First step and 7-azaindole-3-carboxaldehyde (0.067 g, 0.46 mmol) in ethanol (5.0 mL), piperidine (0.85 mL, 0.92 mmol) was added at ambient temperature. The mixture was refluxed for 24 h. Cooled to ambient temperature, the precipitate was collected by filtration, washed with ethanol then dried to afford the titled compound (0.075 g, y. 36%).

$^1$H NMR (DMSO-$d_6$) δ (ppm) 12.34 (br. s, 1H), 10.61 (br. s, 1H), 8.26 (d, J=3.42 Hz, 1H), 7.95 (d, J=7.34 Hz, 1H), 7.84 (br. s, 1H), 7.72 (d, J=8.31 Hz, 2H), 7.57 (d, J=8.31 Hz, 2H), 6.77-7.05 (m, 2H), 4.07-4.42 (m, 2H), 1.29 (t, J=6.85 Hz, 3H); LCMS (m/z): 382.4 $[M+H]^+$.

Example 20

Ethyl 5-[(1H-pyrrolo[2,3-b]pyridin-3-yl)methylene]-4-oxo-2-(p-tolylamino)-4,5-dihydrofuran-3-carboxylate

[Chemical Formula 29]

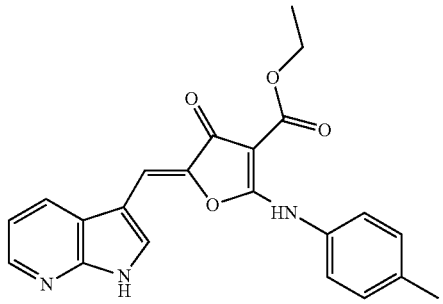

The titled compound was similarly prepared according to the procedure described in the Example 19.

$^1$H NMR (DMSO-$d_6$) δ (ppm) 12.30 (br. s, 1H), 10.51 (br. s, 1H), 8.24 (d, J=3.42 Hz, 1H), 7.97 (d, J=7.34 Hz, 1H), 7.80 (br. s, 1H), 7.46 (d, J=7.82 Hz, 2H), 7.34 (d, J=8.31 Hz, 2H), 6.74-7.02 (m, 2H), 4.14-4.37 (m, 2H), 2.44 (s, 3H), 1.29 (t, J=6.85 Hz, 3H); LCMS (m/z): 390.6 $[M+H]^+$.

Example 21

Ethyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 30]

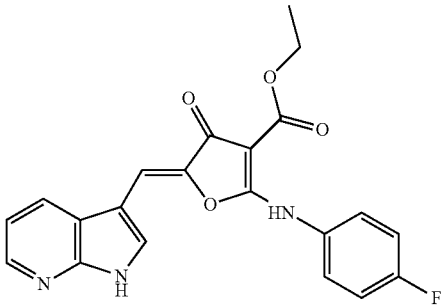

The titled compound (solid) was similarly prepared according to the procedure described in the Example 19.

$^1$H NMR (DMSO-$d_6$) δ (ppm) 12.28 (br. s, 1H), 10.57 (br. s, 1H), 8.24 (br. s, 1H), 7.95 (d, J=7.82 Hz, 1H), 7.75 (br. s, 1H), 7.60-7.68 (m, 2H), 7.38 (t, J=8.31 Hz, 2H), 6.85-6.93 (m, 2H), 4.11-4.50 (m, 2H), 1.29 (t, J=6.85 Hz, 3H); LCMS (m/z): 394.2 $[M+H]^+$.

Example 22

5-[(1H-Pyrrolo[2,3-b]pyridin-3-yl)methylene]-4-oxo-2-(phenylamino)-4,5-dihydrofuran-3-carboxylic acid

[Chemical Formula 31]

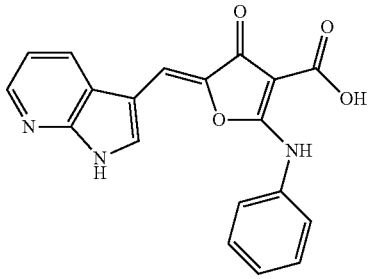

To a solution of the compound (0.050 g, 0.13 mmol) of Example 1 in ethanol (1.0 mL), 50% potassium hydroxide solution (0.5 mL, 0.13 mmol) was added at ambient temperature. The mixture was refluxed for 1 h. Cooled to ambient temperature, the precipitate was collected by filtration, washed with ethanol. The crude material was dissolved in water (0.5 mL) and tetrahydrofuran (0.5 mL), then 2M hydrochloric acid (0.023 mL, 0.046 mmol) was added and the mixture was stirred for 30 min. The precipitate was collected by filtration, washed with water and diethyl ether then dried to afford the titled compound (0.012 g, y. 26%).

$^1$H NMR (DMSO-$d_6$) δ (ppm) 12.11 (br. s, 2H), 8.21 (dd, J=1.25, 4.52 Hz, 1H), 8.06 (d, J=7.78 Hz, 1H), 7.73 (d, J=2.26 Hz, 1H), 7.38-7.49 (m, 2H), 7.32 (d, J=7.53 Hz, 2H), 7.19-7.27 (m, 1H), 6.91 (dd, J=4.64, 7.91 Hz, 1H), 6.66 (s, 1H); LCMS (m/z): 347.9 $[M+H]^+$.

Example 23

Ethyl 5-[(1H-pyrrolo[2,3-b]pyridin-3-yl)methylene]-2-[(2-hydroxyphenyl)amino]-4-oxo-4,5-dihydrofuran-3-carboxylate

[Chemical Formula 32]

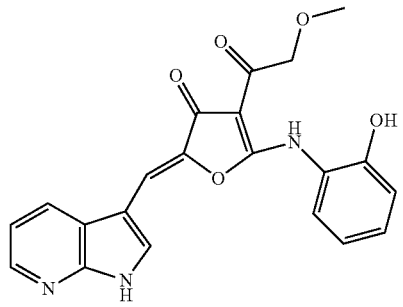

To a solution of ethyl 2-[(2-hydroxyphenyl)amino]-4-oxo-4,5-dihydrofuran-3-carboxylate (0.050 g, 0.19 mmol) which similarly prepared according to the procedure described in the Example 4 and 7-azaindole-3-carboxaldehyde (0.023 g, 0.16 mmol) in ethanol (1.0 mL), piperidine (0.0010 mL, 0.010 mmol) was added at ambient temperature. The mixture was refluxed for 2 days. The precipitate was collected by filtration, washed with hot ethanol. The solid was washed hexane then dried to afford the titled compound (0.008 g, y. 11%).

$^1$H NMR (DMSO-$d_6$) δ (ppm) 12.33 (br. s, 1H), 10.35 (s, 1H), 10.30 (s, 1H), 8.25 (dd, J=1.38, 4.64 Hz, 1H), 8.06 (d, J=7.03 Hz, 1H), 7.87 (d, J=2.76 Hz, 1H), 7.58 (d, J=7.03 Hz, 1H), 7.24-7.33 (m, 1H), 7.07 (dd, J=1.00, 8.28 Hz, 1H), 6.90-7.01 (m, 3H), 4.28 (q, J=7.03 Hz, 2H), 1.30 (t, J=7.15 Hz, 3H); LCMS (m/z): 392.0 $[M+H]^+$.

Example 24

Ethyl 5-[(1H-pyrrolo[2,3-b]pyridin-3-yl)methylene]-2-[(2,4-dimethoxyphenyl)amino]-4-oxo-4,5-dihydrofuran-3-carboxylate

[Chemical Formula 33]

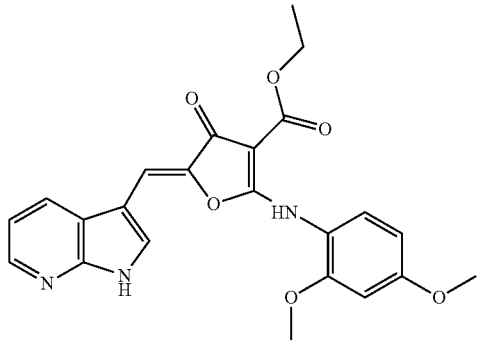

To a solution of ethyl 2-[(2,4-dimethoxyphenyl)amino]-4-oxo-4,5-dihydrofuran-3-carboxylate (0.35 g, 1.1 mmol) which similarly prepared according to the procedure described in the Example 4, First step and 7-azaindole-3-carboxaldehyde (0.12 g, 1.1 mmol) in ethanol (10 mL), piperidine (0.5 mL, 4.6 mmol) was added at ambient temperature. The mixture was refluxed for 16 h. Cooled to ambient temperature, the precipitate was collected by filtration, washed with ethanol then dried to afford the titled compound (0.13 g, y. 26%).

$^1$H NMR (DMSO-$d_6$) δ (ppm) 12.31 (br. s, 1H), 10.14 (br. s, 1H), 8.24 (br. s, 1H), 7.94 (d, J=7.82 Hz, 1H), 7.80 (br. s, 1H), 7.51 (d, J=8.80 Hz, 1H), 6.78-6.93 (m, 3H), 6.68 (d, J=8.31 Hz, 1H), 4.26 (d, J=6.85 Hz, 2H), 3.89 (s, 3H), 3.81 (s, 3H), 1.29 (t, J=6.60 Hz, 3H); LCMS (m/z): 436.2 [M+H]$^+$.

Example 25

Ethyl 5-[(1H-pyrrolo[2,3-b]pyridin-3-yl)methylene]-2-[(4-carbamoylphenyl)amino]-4-oxo-4,5-dihydrofuran-3-carboxylate

[Chemical Formula 34]

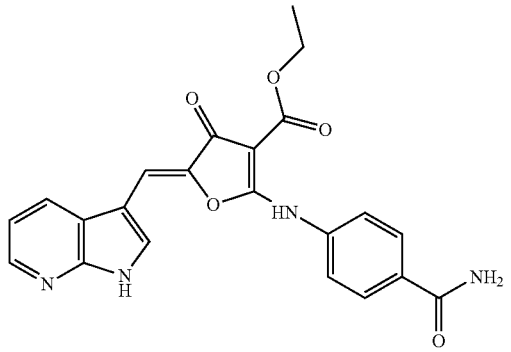

The titled compound (solid) was similarly prepared according to the procedure described in the Example 24.

$^1$H NMR (DMSO-$d_6$) δ (ppm) 12.34 (br. s, 1H), 10.67 (br. s, 1H), 8.24 (br. s, 1H), 7.95-8.13 (m, 4H), 7.84 (br. s, 1H), 7.67 (d, J=7.34 Hz, 2H), 7.49 (br. s, 1H), 6.75-7.08 (m, 2H), 4.28 (d, J=6.85 Hz, 2H), 1.30 (t, J=6.36 Hz, 3H); LCMS (m/z): 419.0 [M+H]$^+$.

Example 26

Ethyl 5-[(1H-pyrrolo[2,3-b]pyridin-3-yl)methylene]-2-[(2,4-dimethylphenyl)amino]-4-oxo-4,5-dihydrofuran-3-carboxylate

[Chemical Formula 35]

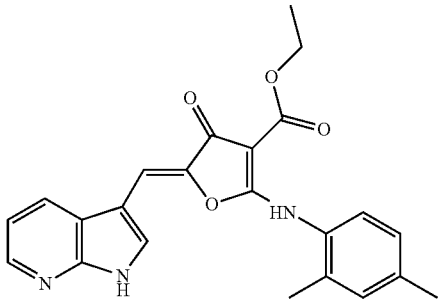

The titled compound (solid) was similarly prepared according to the procedure described in the Example 24.

$^1$H NMR (DMSO-$d_6$) δ (ppm) 12.26 (br. s, 1H), 10.35 (br. s, 1H), 8.21 (d, J=3.91 Hz, 1H), 7.65-7.80 (m, 2H), 7.39 (d, J=8.31 Hz, 1H), 7.27 (s, 1H), 7.20 (d, J=7.82 Hz, 1H), 6.84 (s, 1H), 6.73 (dd, J=4.40, 7.83 Hz, 1H), 4.27 (q, J=7.01 Hz, 2H), 2.44 (s, 3H), 2.23 (s, 3H), 1.30 (t, J=6.85 Hz, 3H); LCMS (m/z): 404.0 [M+H]$^+$.

Example 27

Ethyl 5-[(1H-pyrrolo[2,3-b]pyridin-3-yl)methylene]-4-oxo-2-(3-pyridinylamino)-4,5-dihydrofuran-3-carboxylate

[Chemical Formula 36]

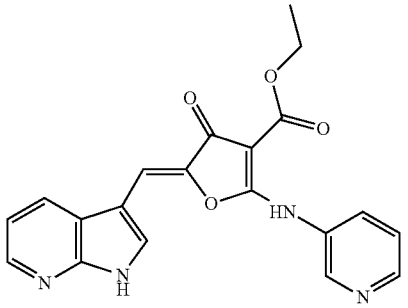

The titled compound (solid) was similarly prepared according to the procedure described in the Example 24.

$^1$H NMR (DMSO-$d_6$) δ (ppm) 12.33 (br. s, 1H), 10.72 (br. s, 1H), 8.82 (br. s, 1H), 8.65 (br. s., 1H), 8.24 (br. s, 1H), 7.90-8.11 (m, 2H), 7.73 (br. s, 1H), 7.54-7.62 (m, 1H), 6.87-6.97 (m, 2H), 4.28 (d, J=6.85 Hz, 2H), 1.30 (t, J=6.36 Hz, 3H); LCMS (m/z): 377.6 [M+H]$^+$.

Example 28

Ethyl 5-[(1H-pyrrolo[2,3-b]pyridin-3-yl)methylene]-2-[(3,4-dimethoxyphenyl)amino]-4-oxo-4,5-dihydrofuran-3-carboxylate

[Chemical Formula 37]

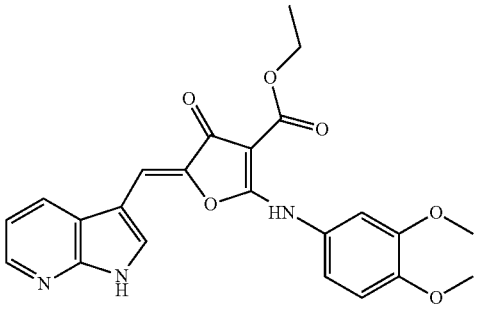

The titled compound (solid) was similarly prepared according to the procedure described in the Example 24.

$^1$H NMR (DMSO-$d_6$) δ (ppm) 12.33 (br. s, 1H), 10.44 (s, 1H), 8.24 (d, J=3.91 Hz, 1H), 7.96 (d, J=7.82 Hz, 1H), 7.82 (br. s, 1H), 7.24 (s, 1H), 7.06-7.14 (m, 2H), 6.78-6.94 (m, 2H), 4.27 (q, J=7.01 Hz, 2H), 3.87 (s, 3H), 3.71 (s, 3H), 1.29 (t, J=7.09 Hz, 3H); LCMS (m/z): 436.5 [M+H]$^+$.

Example 29

Ethyl 5-[(1H-pyrrolo[2,3-b]pyridin-3-yl)methylene]-2-{[2-(2-hydroxyethoxy)phenyl]amino}-4-oxo-4,5-dihydrofuran-3-carboxylate

[Chemical Formula 38]

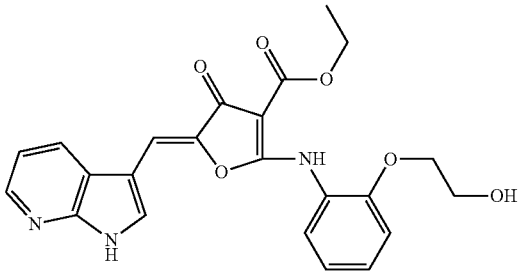

First Step

A solution of ethyl 2-[(2-hydroxyphenyl)amino]-4-oxo-4,5-dihydrofuran-3-carboxylate (0.10 g, 0.38 mmol) which similarly prepared according to the procedure described in the Example 4, First step, 2-chloroethanol (0.038 mL, 0.57 mmol) and potassium carbonate (0.11 g, 0.80 mmol) in N,N-dimethylformamide (2.0 mL) was stirred at 90° C. for 2 days. Cooled to ambient temperature, ethyl acetate was added to the reaction mixture, the organic layer was washed with aqueous 5% citric acid solution, water and brine, dried over magnesium sulfate and concentrated. To the residue, tert-butyl methyl ether was added to precipitate the product. The precipitate was collected by filtration, washed with hexane then dried to afford ethyl 2-{[2-(2-hydroxyethoxy)phenyl]amino}-4-oxo-4,5-dihydrofuran-3-carboxylate as solid (0.041 g, y. 35%).

$^1$H NMR (DMSO-$d_6$) δ (ppm) 10.40 (s, 1H), 7.66 (d, J=7.53 Hz, 1H), 7.16-7.25 (m, 2H), 6.97-7.05 (m, 1H), 4.82 (br. s, 1H), 4.75 (s, 2H), 4.24 (q, J=7.03 Hz, 2H), 4.15 (t, J=5.14 Hz, 2H), 3.72-3.80 (m, 2H), 1.26 (t, J=7.15 Hz, 3H); LCMS (m/z): 308.0 $[M+H]^+$.

Second Step

To a solution of ethyl 2-{[2-(2-hydroxyethoxy)phenyl]amino}-4-oxo-4,5-dihydrofuran-3-carboxylate (0.021 g, 0.068 mmol) and 7-azaindole-3-carboxaldehyde (0.0087 g, 0.060 mmol) in ethanol (0.5 mL), 2M hydrochloric acid in ethanol (0.030 mL, 0.059 mmol) was added at ambient temperature. The mixture was refluxed for 4 h. Cooled to ambient temperature, the precipitate was collected by filtration, washed with ethanol and hexane then dried to afford the titled compound as solid (0.021 g, y. 72%).

$^1$H NMR (DMSO-$d_6$) δ (ppm) 12.36 (br. s, 1H), 10.33 (s, 1H), 8.24-8.29 (m, 1H), 8.07 (d, J=6.78 Hz, 1H), 7.85 (s, 1H), 7.65-7.70 (m, 1H), 7.38-7.46 (m, 1H), 7.29 (d, J=7.78 Hz, 1H), 7.11 (t, J=7.65 Hz, 1H), 6.92-6.99 (m, 2H), 4.41 (br. s, 1H), 4.28 (q, J=7.20 Hz, 2H), 4.10 (t, J=5.14 Hz, 2H), 3.65 (t, J=5.02 Hz, 2H), 1.30 (t, J=7.03 Hz, 3H); LCMS (m/z): 436 $[M+H]^+$.

Example 30

Ethyl 5-[(1H-pyrrolo[2,3-b]pyridin-3-yl)methylene]-2-{[2-(2-morpholinoethoxy)phenyl]amino}-4-oxo-4,5-dihydrofuran-3-carboxylate

[Chemical Formula 39]

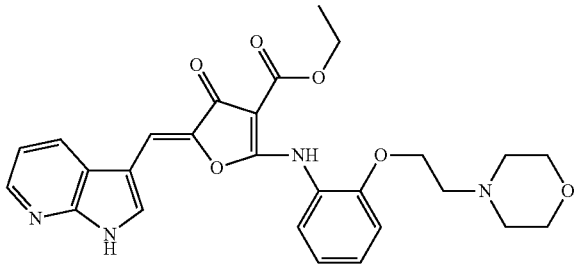

To a solution of ethyl 2-{[2-(2-morpholinoethoxy)phenyl]amino}-4-oxo-4,5-dihydrofuran-3-carboxylate (0.021 g, 0.054 mmol) which similarly prepared according to the procedure described in the Example 29, First step and 7-azaindole-3-carboxaldehyde (0.0070 g, 0.048 mmol) in ethanol (0.5 mL), 2M hydrochloric acid in ethanol (0.024 mL, 0.048 mmol) was added at ambient temperature. The mixture was refluxed for 4 h. The reaction mixture was cooled with ice bath. Aqueous 2M sodium hydroxide solution (0.024 mL, 0.048 mmol) was added dropwise to neutralize and the mixture was stirred for 1 h. The precipitate was collected by filtration then purified by preparative HPLC to afford the titled compound as solid (0.0054 g, y. 21%).

$^1$H NMR (DMSO-$d_6$) δ (ppm) 12.31 (br. s, 1H), 10.35 (br. s, 1H), 8.24 (dd, J=1.25, 4.52 Hz, 1H), 7.94 (d, J=7.78 Hz, 1H), 7.83 (d, J=2.01 Hz, 1H), 7.62 (d, J=7.03 Hz, 1H), 7.42-7.50 (m, 1H), 7.28 (d, J=7.78 Hz, 1H), 7.12 (t, J=7.28 Hz, 1H), 6.92 (s, 1H), 6.88 (dd, J=4.64, 7.91 Hz, 1H), 4.27 (q, J=7.03 Hz, 2H), 4.14 (t, J=5.14 Hz, 2H), 3.36-3.42 (m, 4H), 2.59 (t, J=5.02 Hz, 2H), 2.25-2.35 (m, 4H), 1.30 (t, J=7.03 Hz, 3H); LCMS (m/z): 505.4 $[M+H]^+$.

Example 31

Ethyl 5-[(1H-pyrrolo[2,3-b]pyridin-3-yl)methylene]-2-[(2-fluorophenyl)amino]-4-oxo-4,5-dihydrofuran-3-carboxylate

[Chemical Formula 40]

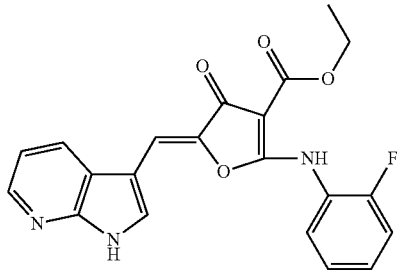

To a solution of ethyl 2-[(2-fluorophenyl)amino]-4-oxo-4,5-dihydrofuran-3-carboxylate (0.10 g, 0.38 mmol) which similarly prepared according to the procedure described in the Example 4, First step and 7-azaindole-3-carboxaldehyde (0.050 g, 0.34 mmol) in ethanol (2.0 mL), piperidine (0.0034 mL, 0.034 mmol) was added at ambient temperature. The mixture was refluxed for 36 h. The precipitate was collected by filtration, washed with hot ethanol. The solid was washed with hexane then dried to afford the titled compound as solid (0.037 g, y. 27%).

$^1$H NMR (DMSO-$d_6$) δ (ppm) 12.31 (br. s, 1H), 10.55 (s, 1H), 8.22 (dd, J=1.38, 4.64 Hz, 1H), 7.84 (d, J=7.78 Hz, 1H), 7.67-7.77 (m, 2H), 7.55-7.63 (m, 1H), 7.45-7.53 (m, 1H), 7.37-7.44 (m, 1H), 6.92 (s, 1H), 6.83 (dd, J=4.64, 7.91 Hz, 1H), 4.28 (q, J=7.03 Hz, 2H), 1.30 (t, J=7.03 Hz, 3H); LCMS (m/z): 393.9 [M+H]$^+$.

Example 32

Ethyl 5-[(1H-pyrrolo[2,3-b]pyridin-3-yl)methylene]-4-oxo-2-(o-tolylamino)-4,5-dihydrofuran-3-carboxylate

[Chemical Formula 41]

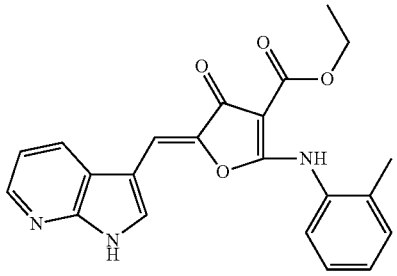

To a solution of ethyl 4-oxo-2-(o-tolylamino)-4,5-dihydrofuran-3-carboxylate (0.098 g, 0.38 mmol) which similarly prepared according to the procedure described in the Example 4, First step and 7-azaindole-3-carboxaldehyde (0.050 g, 0.34 mmol) in ethanol (2.0 mL), piperidine (0.0034 mL, 0.034 mmol) was added at ambient temperature. The mixture was refluxed for 32 h. The precipitate was collected by filtration, washed with hot ethanol. The solid was washed with hexane then dried to afford the titled compound as solid (0.019 g, y. 27%).

$^1$H NMR (DMSO-$d_6$) δ (ppm) 12.26 (br. s, 1H), 10.43 (s, 1H), 8.18-8.22 (m, 1H), 7.69-7.75 (m, 2H), 7.54 (d, J=7.78 Hz, 1H), 7.45-7.49 (m, 2H), 7.37-7.44 (m, 1H), 6.85 (s, 1H), 6.78 (dd, J=4.64, 7.91 Hz, 1H), 4.28 (q, J=7.19 Hz, 2H), 2.28 (s, 3H), 1.30 (t, J=7.03 Hz, 3H); LCMS (m/z): 390 [M+H]$^+$.

Example 33

Ethyl 5-[(1H-pyrrolo[2,3-b]pyridin-3-yl)methylene]-2-({2-[2-(dimethylamino)ethoxy]phenyl}amino)-4-oxo-4,5-dihydrofuran-3-carboxylate

[Chemical Formula 42]

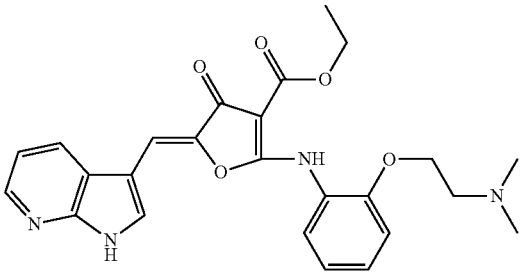

To a solution of ethyl 2-({2-[2-(dimethylamino)ethoxy]phenyl}amino)-4-oxo-4,5-dihydrofuran-3-carboxylate (0.010 g, 0.031 mmol) which similarly prepared according to the procedure described in the Example 29, First step and 7-azaindole-3-carboxaldehyde (0.0042 g, 0.029 mmol) in 2-propanol (0.3 mL), piperidine (0.00028 mL, 0.0028 mmol) was added at ambient temperature. The mixture was refluxed for 24 h. The precipitate was collected by filtration, washed with hot ethanol. The solid was washed with hexane then dried to afford the titled compound as solid (0.0029 g, y. 22%).

$^1$H NMR (DMSO-$d_6$) δ (ppm) 12.24 (br. s, 1H), 8.23 (dd, J=1.26, 4.52 Hz, 1H), 7.98 (d, J=7.53 Hz, 1H), 7.79 (s, 1H), 7.58 (d, J=7.28 Hz, 1H), 7.36-7.45 (m, 1H), 7.28 (d, J=7.53 Hz, 1H), 7.13 (t, J=7.53 Hz, 1H), 6.89 (dd, J=4.64, 7.91 Hz, 1H), 6.83 (s, 1H), 4.26 (q, J=7.19 Hz, 2H), 4.15 (t, J=5.52 Hz, 2H), 2.55-2.65 (m, 2H), 2.19 (s, 6H), 1.29 (t, J=7.03 Hz, 3H); LCMS (m/z): 463 [M+H]$^+$.

Example 34

Methyl 5-[(1H-pyrrolo[2,3-b]pyridin-3-yl)methylene]-4-oxo-2-piperidino-4,5-dihydrofuran-3-carboxylate

[Chemical Formula 43]

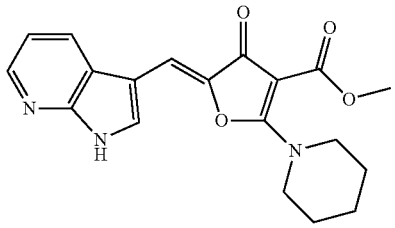

To a solution of methyl 4-oxo-2-(phenylamino)-4,5-dihydrofuran-3-carboxylate (0.047 g, 0.20 mmol) which similarly prepared according to the procedure described in the Example 2, First step using methyl 4-chloroacetoacetate and phenyl isocyanate, and 7-azaindole-3-carboxaldehyde (0.029 g, 0.20 mmol) in methanol (1.0 mL), piperidine (0.022 mL, 0.22 mmol) was added at ambient temperature. The mixture was refluxed for 5 days. Cooled to ambient temperature, the precipitate was collected by filtration, then purified by preparative HPLC, collected former fraction to afford the titled compound as solid (0.0075 g, y. 11%).

$^1$H NMR (DMSO-$d_6$) δ (ppm) 12.30 (br. s, 1H), 8.35-8.43 (m, 1H), 8.31 (dd, J=1.38, 4.64 Hz, 1H), 7.97 (d, J=2.51 Hz, 1H), 7.19 (dd, J=4.64, 7.91 Hz, 1H), 6.87 (s, 1H), 3.70-3.82 (m, 4H), 3.68 (s, 3H), 1.64-1.80 (m, 6H); LCMS (m/z): 354.0 [M+H]$^+$ Example 35

Methyl 5-[(1H-pyrrolo[2,3-b]pyridin-3-yl)methylene]-4-oxo-2-(phenylamino)-4,5-dihydrofuran-3-carboxylate

[Chemical Formula 44]

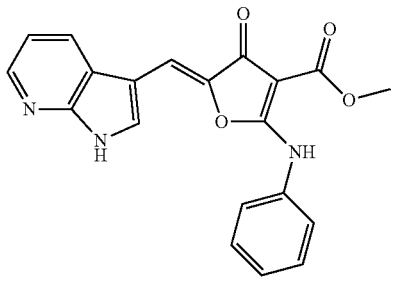

To a solution of methyl 4-oxo-2-(phenylamino)-4,5-dihydrofuran-3-carboxylate (0.047 g, 0.20 mmol) which similarly prepared according to the procedure described in the Example 2, First step using methyl 4-chloroacetoacetate and phenyl isocyanate, and 7-azaindole-3-carboxaldehyde (0.029 g, 0.20 mmol) in 2-propanol (1.0 mL), piperidine (0.022 mL, 0.22 mmol) was added at ambient temperature. The mixture was refluxed for 5 days. Cooled to ambient temperature, the precipitate was collected by filtration, washed with ethanol and diisopropyl ether then dried to afford the titled compound as solid (0.031 g, y. 43%).

$^1$H NMR (DMSO-$d_6$) δ (ppm) 12.29 (br. s, 1H), 10.59 (s, 1H), 8.23 (dd, J=1.38, 4.64 Hz, 1H), 7.98 (d, J=7.53 Hz, 1H), 7.77 (d, J=2.51 Hz, 1H), 7.52-7.64 (m, 4H), 7.44-7.51 (m, 1H), 6.93 (s, 1H), 6.89 (dd, J=4.64, 7.91 Hz, 1H), 3.77 (s, 3H); LCMS (m/z): 361.9 $[M+H]^+$.

Example 36

Ethyl 5-[(1H-pyrrolo[2,3-b]pyridin-3-yl)methylene]-2-(4-methylpiperazinyl)-4-oxo-4,5-dihydrofuran-3-carboxylate hydrochloride

[Chemical Formula 45]

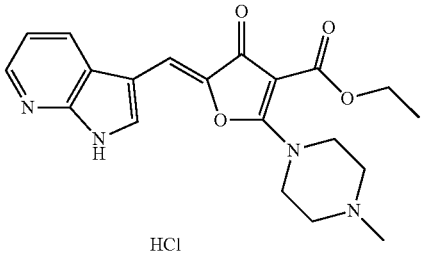

HCl

To a solution of ethyl 2-(4-methylpiperazinyl)-4-oxo-4,5-dihydrofuran-3-carboxylate (0.038 g, 0.15 mmol) which similarly prepared according to the procedure described in the Example 4, First step and 7-azaindole-3-carboxaldehyde (0.022 g, 0.15 mmol) in ethanol (1.0 mL), 2M hydrochloric acid in methanol (0.17 mL, 0.34 mmol) was added at ambient temperature. The mixture was refluxed for 40 min. Cooled to ambient temperature, the precipitate was collected by filtration, washed with ethanol then dried to afford the titled compound as solid (0.0069 g, y. 9%).

$^1$H NMR (DMSO-$d_6$) δ (ppm) 12.32-12.49 (m, 1H), 10.69 (br. s, 1H), 8.39 (d, J=8.03 Hz, 1H), 8.29-8.36 (m, 1H), 8.08 (d, J=2.76 Hz, 1H), 7.22 (dd, J=4.64, 7.91 Hz, 1H), 6.95 (s, 1H), 4.19 (q, J=7.19 Hz, 2H), 3.57-3.75 (m, 4H), 3.33-3.40 (m, 4H), 2.87 (br. s., 3H), 1.16-1.34 (m, 3H); LCMS (m/z): 383.0 $[M+H]^+$.

Example 37

Ethyl 5-[(1H-pyrrolo[2,3-b]pyridin-3-yl)methylene]-2-[(4-isopropylphenyl)amino]-4-oxo-4,5-dihydrofuran-3-carboxylate

[Chemical Formula 46]

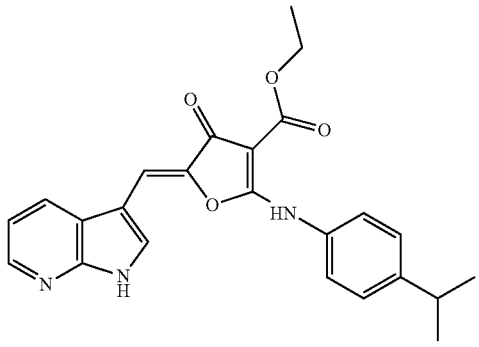

To a solution of ethyl 2-[(4-isopropylphenyl)amino]-4-oxo-4,5-dihydrofuran-3-carboxylate (0.26 g, 0.90 mmol) which similarly prepared according to the procedure described in the Example 4, First step and 7-azaindole-3-carboxaldehyde (0.13 g, 0.90 mmol) in ethanol (6.0 mL), piperidine (0.045 mL, 0.45 mmol) was added at ambient temperature. The mixture was refluxed for 16 h. Cooled to ambient temperature, the precipitate was collected by filtration, washed with ethanol then dried to afford the titled compound as solid (0.13 g, y. 35%).

$^1$H NMR (DMSO-$d_6$) δ (ppm) 12.35 (br. s, 1H), 10.50 (br. s, 1H), 8.24 (d, J=3.42 Hz, 1H), 8.04 (d, J=7.82 Hz, 1H), 7.82 (br. s, 1H), 7.33-7.58 (m, 4H), 6.82-6.96 (m, 2H), 4.08-4.44 (m, 2H), 2.86-3.17 (m, 1H), 1.31 (s, 3H), 1.29 (s, 6H); LCMS (m/z): 418.0 $[M+H]^+$.

Example 38

Ethyl 5-[(1H-pyrrolo[2,3-b]pyridin-3-yl)methylene]-4-oxo-2-(5-pyrimidinylamino)-4,5-dihydrofuran-3-carboxylate

[Chemical Formula 47]

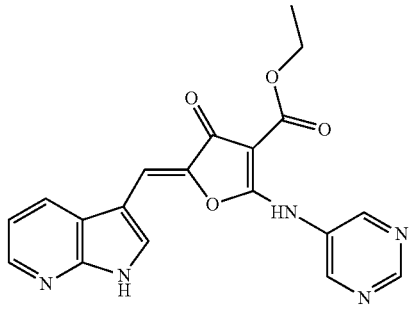

The titled compound (solid) was similarly prepared according to the procedure described in the Example 37.

$^1$H NMR (DMSO-$d_6$) δ (ppm) 12.34 (br. s, 1H), 10.80 (br. s, 1H), 9.19 (s, 1H), 9.02-9.12 (m, 2H), 8.25 (d, J=4.40 Hz, 1H), 8.03 (d, J=7.82 Hz, 1H), 7.71 (br. s, 1H), 6.86-7.00 (m, 2H), 4.28 (q, J=6.85 Hz, 2H), 1.30 (t, J=6.00 Hz, 3H); LCMS (m/z): 378.2 $[M+H]^+$.

Example 39

Ethyl 5-[(1H-pyrrolo[2,3-b]pyridin-3-yl)methylene]-2-[(1,1'-biphenyl)-4-ylamino]-4-oxo-4,5-dihydrofuran-3-carboxylate

[Chemical Formula 48]

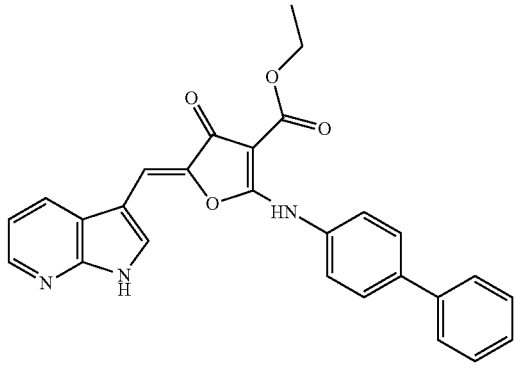

The titled compound (solid) was similarly prepared according to the procedure described in the Example 37.

$^1$H NMR (DMSO-$d_6$) δ (ppm) 12.34 (br. s, 1H), 10.63 (br. s, 1H), 8.20 (br. s, 1H), 8.09 (d, J=6.85 Hz, 1H), 7.75-7.93 (m, 5H), 7.62-7.74 (m, 2H), 7.50-7.58 (m, 2H), 7.39-7.48 (m, 1H), 6.94 (br. s, 1H), 6.83-6.91 (m, 1H), 4.29 (d, J=6.36 Hz, 2H), 1.31 (br. s, 3H); LCMS (m/z): 452.6 $[M+H]^+$.

Example 40

Ethyl 5-[(1H-pyrrolo[2,3-b]pyridin-3-yl)methylene]-2-[(4-nitrophenyl)amino]-4-oxo-4,5-dihydrofuran-3-carboxylate

[Chemical Formula 49]

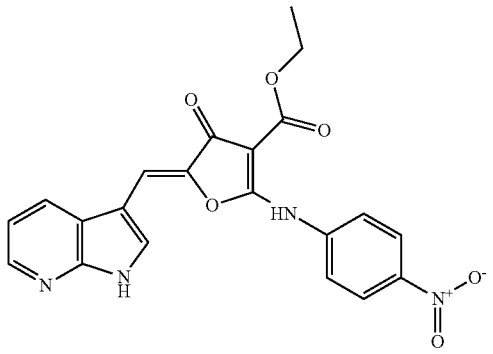

The titled compound (solid) was similarly prepared according to the procedure described in the Example 37.

$^1$H NMR (DMSO-$d_6$) δ (ppm) 12.39 (br. s, 1H), 10.89 (br. s, 1H), 8.35 (d, J=8.80 Hz, 2H), 8.27 (d, J=3.91 Hz, 1H), 8.17 (d, J=7.82 Hz, 1H), 7.88 (d, J=8.80 Hz, 2H), 7.84 (d, J=2.45 Hz, 1H), 7.03 (s, 1H), 6.98 (dd, J=4.65, 8.07 Hz, 1H), 4.28 (q, J=7.17 Hz, 2H), 1.29 (t, J=7.09 Hz, 3H); LCMS (m/z): 421.4 $[M+H]^+$.

Example 41

Ethyl 5-[(1H-pyrrolo[2,3-b]pyridin-3-yl)methylene]-2-[(4-aminophenyl)amino]-4-oxo-4,5-dihydrofuran-3-carboxylate hydrochloride

[Chemical Formula 50]

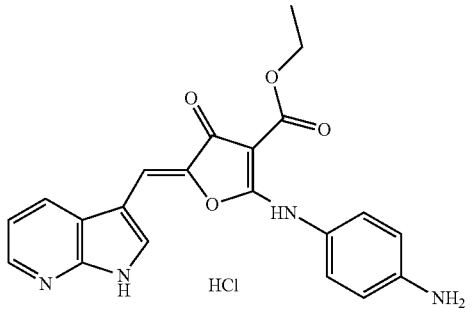

First Step

To a solution of ethyl 2-({4-[(tert-butoxycarbonyl)amino]phenyl}amino)-4-oxo-4,5-dihydrofuran-3-carboxylate (0.32 g, 0.88 mmol) which similarly prepared according to the procedure described in the Example 4, First step and 7-azaindole-3-carboxaldehyde (0.13 g, 0.88 mmol) in ethanol (5.0 mL), piperidine (0.18 mL, 1.8 mmol) was added at ambient temperature. The mixture was refluxed for 16 h. Cooled to ambient temperature, the precipitate was collected by filtration, washed with ethanol then dried to afford ethyl 5-[(1H-pyrrolo[2,3-b]pyridin-3-yl)methylene]-2-({4-[(tert-butoxycarbonyl)amino]phenyl}amino)-4-oxo-4,5-dihydrofuran-3-carboxylate as solid (0.095 g, y. 21%).

$^1$H NMR (DMSO-$d_6$) δ 12.30 (br. s, 1H), 10.44 (br. s, 1H), 9.60 (s, 1H), 8.20 (d, J=3.76 Hz, 1H), 7.91 (d, J=7.72 Hz, 1H), 7.82 (s, 1H), 7.60 (d, J=8.40 Hz, 2H), 7.45 (d, J=8.56 Hz, 2H), 6.82-6.92 (m, 2H), 4.26 (q, J=6.86 Hz, 2H), 1.53 (s, 9H), 1.29 (t, J=6.90 Hz, 3H); LCMS (m/z): 491.4 $[M+H]^+$.

Second Step

A solution of ethyl 5-[(1H-pyrrolo[2,3-b]pyridin-3-yl)methylene]-2-{[4-(tert-butoxycarbonyl)aminophenyl]amino}-4-oxo-4,5-dihydrofuran-3-carboxylate (0.090 g, 0.18 mmol) in 4M hydrochloric acid in dioxane (3.0 mL) was stirred at ambient temperature for 2 h. The solvent was removed under reduced pressure, and diethyl ether was added to precipitate the product. The precipitate was collected by filtration, washed with diethyl ether then dried to afford the titled compound as solid (0.066 g, y. 92%).

$^1$H NMR (DMSO-$d_6$) δ (ppm) 12.44 (br. s, 1H), 10.61 (br. s, 1H), 8.26 (d, J=3.91 Hz, 1H), 8.02 (d, J=7.82 Hz, 1H), 7.79 (s, 1H), 7.61 (d, J=8.31 Hz, 2H), 7.40 (d, J=7.34 Hz, 2H), 7.01 (dd, J=4.89, 7.83 Hz, 1H), 6.92 (s, 1H), 4.68 (br. s, 3H), 4.27 (q, J=7.01 Hz, 2H), 1.29 (t, J=6.85 Hz, 3H); LCMS (m/z): 391.2 $[M+H]^+$.

Example 42

Ethyl 5-[(1H-pyrrolo[2,3-b]pyridin-3-yl)methylene]-2-[(4-morpholinophenyl)amino]-4-oxo-4,5-dihydrofuran-3-carboxylate

[Chemical Formula 51]

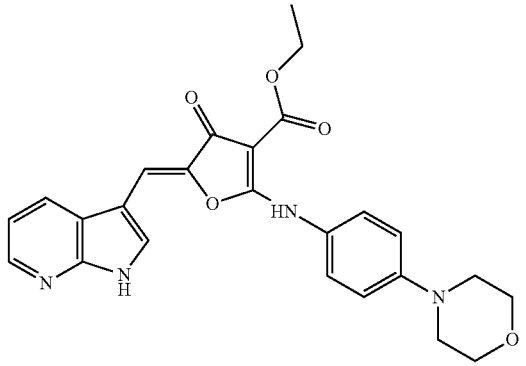

The titled compound (solid) was similarly prepared according to the procedure described in the Example 41, First step.

$^1$H NMR (DMSO-$d_6$) δ (ppm) 12.31 (br. s, 1H), 10.39 (br. s, 1H), 8.24 (br. s, 1H), 7.99 (d, J=7.34 Hz, 1H), 7.79 (br. s, 1H), 7.42 (d, J=8.31 Hz, 2H), 7.07 (d, J=8.31 Hz, 2H), 6.81-6.96 (m, 2H), 4.26 (d, J=6.85 Hz, 2H), 3.28-3.40 (m, 4H), 3.15-3.28 (m, 4H), 1.29 (t, J=6.85 Hz, 3H); LCMS (m/z): 461.4 $[M+H]^+$.

Example 43

Ethyl 5-[(1H-pyrrolo[2,3-b]pyridin-3-yl)methylene]-4-oxo-2-(4-pyridinylamino)-4,5-dihydrofuran-3-carboxylate

[Chemical Formula 52]

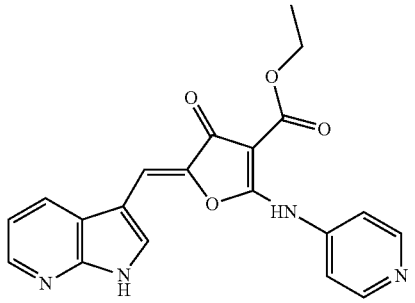

The titled compound (solid) was similarly prepared according to the procedure described in the Example 41, First step.

$^1$H NMR (DMSO-$d_6$) δ (ppm) 12.30 (br. s, 1H), 11.18 (br. s, 1H), 8.59 (d, J=3.91 Hz, 2H), 8.28 (d, J=3.91 Hz, 1H), 8.19 (d, J=7.34 Hz, 1H), 7.88 (br. s, 1H), 7.55 (br. s, 2H), 7.02 (dd, J=4.40, 7.83 Hz, 1H), 6.93 (br. s, 1H), 4.23 (d, J=6.85 Hz, 2H), 1.26 (t, J=6.85 Hz, 3H); LCMS (m/z): 377.6 $[M+H]^+$.

Example 44

Ethyl 5-[(1H-pyrrolo[2,3-b]pyridin-3-yl)methylene]-4-oxo-2-(6-quinolinylamino)-4,5-dihydrofuran-3-carboxylate

[Chemical Formula 53]

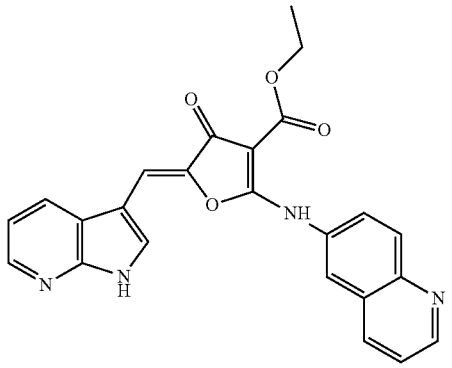

The titled compound (solid) was similarly prepared according to the procedure described in the Example 41, First step.

$^1$H NMR (DMSO-$d_6$) δ (ppm) 12.29 (br. s, 1H), 10.82 (s, 1H), 9.01 (d, J=3.42 Hz, 1H), 8.39 (d, J=8.31 Hz, 1H), 8.23 (br. s, 1H), 8.17 (d, J=8.80 Hz, 1H), 8.11 (d, J=3.91 Hz, 1H), 8.00 (d, J=8.80 Hz, 1H), 7.88 (d, J=7.34 Hz, 1H), 7.83 (br. s, 1H), 7.62 (dd, J=4.16, 8.07 Hz, 1H), 6.94 (s, 1H), 6.26-6.51 (m, 1H), 4.30 (q, J=6.85 Hz, 2H), 1.32 (t, J=6.85 Hz, 3H); LCMS (m/z): 427.4 $[M+H]^+$.

Example 45

Ethyl 5-[(1H-pyrrolo[2,3-b]pyridin-3-yl)methylene]-2-[(4-fluorobenzyl)amino]-4-oxo-4,5-dihydrofuran-3-carboxylate

[Chemical Formula 54]

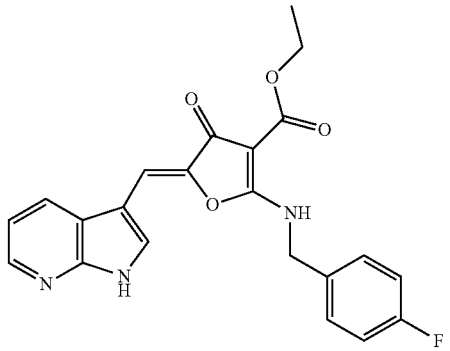

The titled compound (solid) was similarly prepared according to the procedure described in the Example 41, First step.

$^1$H NMR (DMSO-$d_6$) δ (ppm) 12.31 (br. s, 1H), 9.51 (br. s, 1H), 8.22-8.37 (m, 2H), 7.86 (br. s, 1H), 7.47 (t, J=6.30 Hz, 2H), 7.22 (t, J=8.31 Hz, 2H), 7.05-7.15 (m, 1H), 6.87 (s, 1H), 4.84 (d, J=5.87 Hz, 2H), 4.23 (q, J=6.52 Hz, 2H), 1.27 (t, J=6.85 Hz, 3H); LCMS (m/z): 408.2 $[M+H]^+$.

Example 46

Ethyl 5-[(1H-pyrrolo[2,3-b]pyridin-3-yl)methylene]-2-[(2-fluorobenzyl)amino]-4-oxo-4,5-dihydrofuran-3-carboxylate

[Chemical Formula 55]

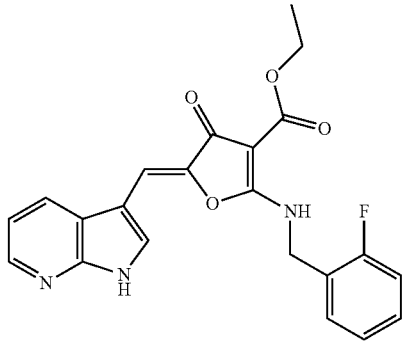

The titled compound (solid) was similarly prepared according to the procedure described in the Example 41, First step.

$^1$H NMR (DMSO-$d_6$) δ (ppm) 12.35 (br. s, 1H), 9.44 (br. s, 1H), 8.15-8.42 (m, 2H), 7.86 (s, 1H), 7.45 (t, J=7.34 Hz, 1H), 7.33-7.40 (m, 1H), 7.18-7.32 (m, 2H), 7.07 (dd, J=5.14, 7.58 Hz, 1H), 6.87 (s, 1H), 4.91 (s, 2H), 4.23 (q, J=7.17 Hz, 2H), 1.27 (t, J=6.85 Hz, 3H); LCMS (m/z): 408.0 $[M+H]^+$.

Example 47

Ethyl 5-[(1H-pyrrolo[2,3-b]pyridin-3-yl)methylene]-2-[(4-fluorophenyl)-N-methylamino]-4-oxo-4,5-dihydrofuran-3-carboxylate hydrochloride

[Chemical Formula 56]

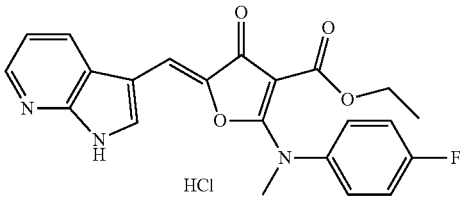

First Step

A solution of ethyl 2-[(4-fluorophenyl)amino]-4-oxo-4,5-dihydrofuran-3-carboxylate (0.10 g, 0.38 mmol) which similarly prepared according to the procedure described in the Example 4, First step, potassium carbonate (0.063 g, 0.45 mmol) and methyliodide (0.026 mL, 0.42 mmol) in anhydrous N,N-dimethylformamide (2.0 mL) was stirred at ambient temperature for 12 h. The reaction mixture was diluted with water then extracted with ethyl acetate for 3 times. The organic layer was dried over sodium sulfate and concentrated to afford ethyl 2-[(4-fluorophenyl)-N-methylamino]-4-oxo-4,5-dihydrofuran-3-carboxylate as solid (0.13 g).

$^1$H NMR (DMSO-$d_6$) δ (ppm) 7.38-7.47 (m, 2H), 7.21-7.32 (m, 2H), 4.65 (s, 2H), 3.60 (q, J=7.03 Hz, 2H), 3.43 (s, 3H), 0.96 (t, J=7.15 Hz, 3H); LCMS (m/z): 279.9 $[M+H]^+$.

Second Step

To a solution of ethyl 2-[(4-fluorophenyl)-N-methylamino]-4-oxo-4,5-dihydrofuran-3-carboxylate (0.050 g, 0.18 mmol) and 7-azaindole-3-carboxaldehyde (0.026 g, 0.18 mmol) in ethanol (1.0 mL), 2M hydrochloric acid in ethanol (0.19 mL, 0.38 mmol) was added at ambient temperature. The mixture was refluxed for 2 h. Cooled to ambient temperature, the precipitate was collected by filtration, washed with ethanol and diisopropyl ether then dried to afford the titled compound as solid (0.011 g, y. 13%).

$^1$H NMR (DMSO-$d_6$) δ (ppm) 12.38 (br. s, 1H), 8.28 (dd, J=1.25, 4.77 Hz, 1H), 8.12 (d, J=7.78 Hz, 1H), 7.81 (d, J=2.01 Hz, 1H), 7.53-7.62 (m, 2H), 7.31-7.38 (m, 2H), 7.05 (dd, J=4.77, 7.78 Hz, 1H), 6.90 (s, 1H), 3.80 (q, J=7.03 Hz, 2H), 3.63 (s, 3H), 1.01-1.10 (m, 3H); LCMS (m/z): 407.9 $[M+H]^+$.

Example 48

Ethyl 5-[(1H-pyrrolo[2,3-b]pyridin-3-yl)methylene]-2-[(2-methoxyethyl)amino]-4-oxo-4,5-dihydrofuran-3-carboxylate

[Chemical Formula 57]

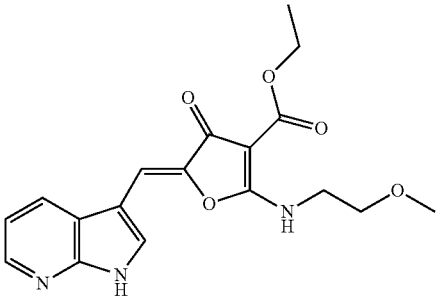

To a solution of ethyl 2-[(2-methoxyethyl)amino]-4-oxo-4,5-dihydrofuran-3-carboxylate (0.50 g, 2.2 mmol) which similarly prepared according to the procedure described in the Example 4, First step and 7-azaindole-3-carboxaldehyde (0.32 g, 2.2 mmol) in ethanol (3.0 mL), piperidine (5 drops) was added at ambient temperature. The mixture was refluxed for 16 h. Cooled to ambient temperature, the precipitate was collected by filtration, washed with ethanol then dried to afford the titled compound as solid.

$^1$H NMR (DMSO-$d_6$) δ (ppm) 12.34 (br. s, 1H), 8.89 (br. s, 1H), 8.43 (d, J=7.34 Hz, 1H), 8.31 (d, J=3.91 Hz, 1H), 8.03 (s, 1H), 7.19 (dd, J=4.40, 7.83 Hz, 1H), 6.90 (s, 1H), 4.21 (q, J=7.17 Hz, 2H), 3.79 (d, J=4.40 Hz, 2H), 3.62 (t, J=5.14 Hz, 2H), 3.28 (s, 3H), 1.26 (t, J=7.09 Hz, 3H); LCMS (m/z): 358.4 $[M+H]^+$.

Example 49

Ethyl 5-[(1H-pyrrolo[2,3-b]pyridin-3-yl)methylene]-4-oxo-2-[(2-piperidinoethyl)amino]-4,5-dihydrofuran-3-carboxylate

[Chemical Formula 58]

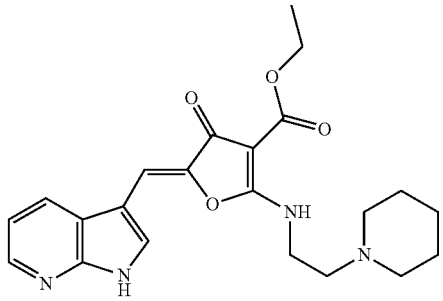

The titled compound (solid) was similarly prepared according to the procedure described in the Example 48.

$^1$H NMR (DMSO-$d_6$) δ (ppm) 12.35 (br. s, 1H), 8.83 (br. s, 1H), 8.38-8.47 (m, 1H), 8.31 (br. s, 1H), 8.02 (br. s, 1H), 7.20 (br. s, 1H), 6.88 (br. s, 1H), 4.12-4.28 (m, 2H), 3.67-3.80 (m, 2H), 2.25-2.70 (m, 6H), 1.32-1.53 (m, 6H), 1.18-1.32 (m, 3H); LCMS (m/z): 411.5 $[M+H]^+$.

Example 50

Ethyl 5-[(1H-pyrrolo[2,3-b]pyridin-3-yl)methylene]-2-(benzyl-N-methylamino)-4-oxo-4,5-dihydrofuran-3-carboxylate

[Chemical Formula 59]

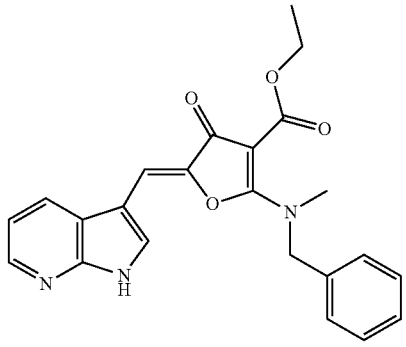

The titled compound (solid) was similarly prepared according to the procedure described in the Example 48.

$^1$H NMR (DMSO-$d_6$) δ (ppm) 12.28 (br. s, 1H), 8.24-8.39 (m, 2H), 7.88 (br. s, 1H), 7.29-7.47 (m, 5H), 7.10 (br. s, 1H), 6.87 (s, 1H), 5.01 (s, 2H), 4.14 (d, J=6.85 Hz, 2H), 3.25 (br. s, 3H), 1.19 (t, J=6.36 Hz, 3H); LCMS (m/z): 404.6 $[M+H]^+$.

Example 51

Methyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 60]

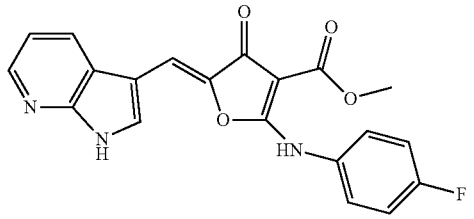

To a solution of methyl 2-[(4-fluorophenyl)amino]-4-oxo-4,5-dihydrofuran-3-carboxylate (0.25 g, 1.0 mmol) which similarly prepared according to the procedure described in the Example 2, First step using methyl 4-chloroacetoacetate and 4-fluorophenyl isocyanate, and 7-azaindole-3-carboxaldehyde (0.15 g, 1.0 mmol) in 2-propanol (5.0 mL), L-proline (0.023 g, 0.20 mmol) was added at ambient temperature. The mixture was refluxed for 2 days. Cooled to ambient temperature, the precipitate was collected by filtration, washed with ethanol and diisopropyl ether then dried to afford the titled compound as solid (0.26 g, y. 68%).

$^1$H NMR (DMSO-$d_6$) δ (ppm) 12.28 (br. s, 1H), 10.58 (s, 1H), 8.25 (dd, J=1.38, 4.64 Hz, 1H), 7.96 (d, J=8.03 Hz, 1H), 7.74 (d, J=2.51 Hz, 1H), 7.59-7.69 (m, 2H), 7.36-7.43 (m, 2H), 6.92 (s, 1H), 6.89 (dd, J=4.77, 8.03 Hz, 1H), 3.76 (s, 3H); LCMS (m/z): 379.8 $[M+H]^+$.

Example 52 n-Butyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 61]

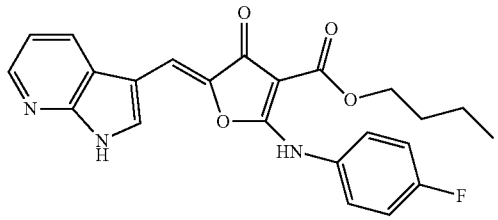

First Step

Under a nitrogen atmosphere, a solution of methyl 2-[(4-fluorophenyl)amino]-4-oxo-4,5-dihydrofuran-3-carboxylate (0.13 g, 0.50 mmol) which similarly prepared according to the procedure described in the Example 2, First step using methyl 4-chloroacetoacetate and 4-fluorophenyl isocyanate, and zinc cluster catalyst ($Zn_4(OCOCF_3)_6O$) (0.0062 g, 0.0065 mmol) in 1-butanol (2.0 mL) was stirred at 80° C. for 3 days then stirred at ambient temperature for further 3 days. The precipitate was collected by filtration, washed with 2-propanol and diisopropyl ether then dried to afford n-butyl 2-[(4-fluorophenyl)amino]-4-oxo-4,5-dihydrofuran-3-carboxylate as solid (0.078 g, y. 53%).

$^1$H NMR (DMSO-$d_6$) δ (ppm) 10.25 (s, 1H), 7.45-7.55 (m, 2H), 7.21-7.31 (m, 2H), 4.65 (s, 2H), 4.17 (t, J=6.53 Hz, 2H), 1.57-1.67 (m, 2H), 1.33-1.45 (m, 2H), 0.92 (t, J=7.40 Hz, 3H); LCMS (m/z): 293.8 $[M+H]^+$.

Second Step

To a solution of n-butyl 2-[(4-fluorophenyl)amino]-4-oxo-4,5-dihydrofuran-3-carboxylate (0.035 g, 0.12 mmol) and 7-azaindole-3-carboxaldehyde (0.018 g, 0.12 mmol) in 2-propanol (1.0 mL), L-proline (0.0028 g, 0.024 mmol) was added at ambient temperature. The mixture was refluxed for 2 days. Cooled to ambient temperature, the precipitate was collected by filtration, washed with ethanol and diisopropyl ether then dried to afford the titled compound as solid (0.019 g, y. 36%).

$^1$H NMR (DMSO-$d_6$) δ (ppm) 12.28 (br. s, 1H), 10.56 (s, 1H), 8.25 (dd, J=1.38, 4.64 Hz, 1H), 7.95 (d, J=7.78 Hz, 1H), 7.75 (d, J=2.76 Hz, 1H), 7.60-7.68 (m, 2H), 7.35-7.42 (m, 2H), 6.85-6.95 (m, 2H), 4.22 (t, J=6.65 Hz, 2H), 1.60-1.72 (m, 2H), 1.37-1.49 (m, 2H), 0.94 (t, J=7.40 Hz, 3H); LCMS (m/z): 421.9 $[M+H]^+$.

Example 53

Ethyl 5-[(1H-pyrrolo[2,3-b]pyridin-3-yl)methylene]-2-[(2,4-difluorophenyl)amino]-4-oxo-4,5-dihydrofuran-3-carboxylate

[Chemical Formula 62]

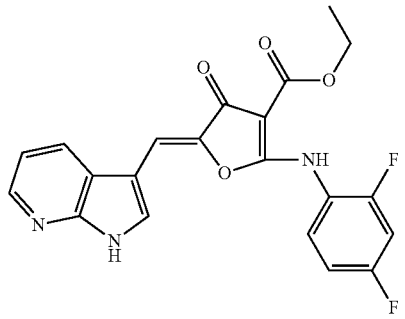

To a solution of ethyl 2-[(2,4-difluorophenyl)amino]-4-oxo-4,5-dihydrofuran-3-carboxylate (0.15 g, 0.54 mmol) which similarly prepared according to the procedure described in the Example 2, First step and 7-azaindole-3-carboxaldehyde (0.074 g, 0.50 mmol) in 2-propanol (2.5 mL), 2M hydrochloric acid in ethanol (0.25 mL, 0.50 mmol) was added at ambient temperature then refluxed for 24 h. Cooled with ice bath, aqueous 2M sodium hydroxide solution (0.024 mL, 0.048 mmol) was added dropwise to neutralize and the mixture was refluxed for 1 h. The precipitate was collected by filtration, washed with ethanol and hexane then dried to afford the titled compound as solid (0.14 g, y. 69%).

$^1$H NMR (DMSO-$d_6$) δ (ppm) 12.27 (br. s, 1H), 10.51 (s, 1H), 8.24 (dd, J=1.38, 4.64 Hz, 1H), 7.84 (d, J=7.78 Hz, 1H), 7.66-7.77 (m, 2H), 7.50-7.59 (m, 1H), 7.29 (t, J=7.78 Hz, 1H), 6.80-6.89 (m, 2H), 4.26 (q, J=7.03 Hz, 2H), 1.29 (t, J=7.03 Hz, 3H); LCMS (m/z): 411.8 $[M+H]^+$.

Example 54

Ethyl 5-[(1H-pyrrolo[2,3-b]pyridin-3-yl)methylene]-2-[(3,4-difluorophenyl)amino]-4-oxo-4,5-dihydrofuran-3-carboxylate

[Chemical Formula 63]

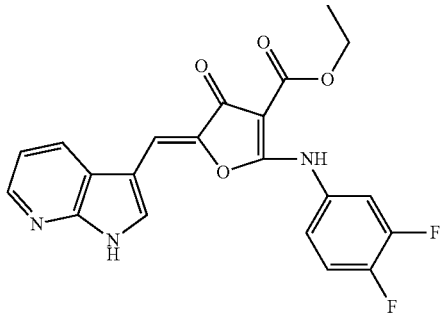

To a solution of ethyl 2-[(3,4-difluorophenyl)amino]-4-oxo-4,5-dihydrofuran-3-carboxylate (0.084 g, 0.30 mmol) which similarly prepared according to the procedure described in the Example 4, First step and 7-azaindole-3-carboxaldehyde (0.041 g, 0.28 mmol) in 2-propanol (2.0 mL), 2M hydrochloric acid in ethanol (0.14 mL, 0.28 mmol) was added at ambient temperature. The mixture was refluxed for 18 h. Cooled with ice bath, aqueous 2M sodium hydroxide solution (0.13 mL, 0.26 mmol) was added dropwise to neutralize, ethanol (5.0 mL) was added and the mixture was refluxed for 1.5 h. The precipitate was collected by filtration, washed with hot ethanol. The solid was washed with hexane then dried to afford the titled compound as solid (0.051 g, y. 44%).

$^1$H NMR (DMSO-$d_6$) δ (ppm) 12.07 (br. s, 1H), 10.63 (br. s, 1H), 8.22 (dd, J=1.38, 4.64 Hz, 1H), 8.00 (d, J=7.78 Hz, 1H), 7.65 (s, 1H), 7.33-7.51 (m, 2H), 7.13 (br. s, 1H), 6.88 (dd, J=4.64, 7.91 Hz, 1H), 6.56 (br. s, 1H), 4.16 (q, J=6.86 Hz, 2H), 1.24 (t, J=7.15 Hz, 3H); LCMS (m/z): 411.8 $[M+H]^+$.

Example 55

Ethyl 5-[(1H-pyrrolo[2,3-b]pyridin-3-yl)methylene]-4-oxo-2-{[4-(1-propoxy)phenyl]amino}-4,5-dihydrofuran-3-carboxylate

[Chemical Formula 64]

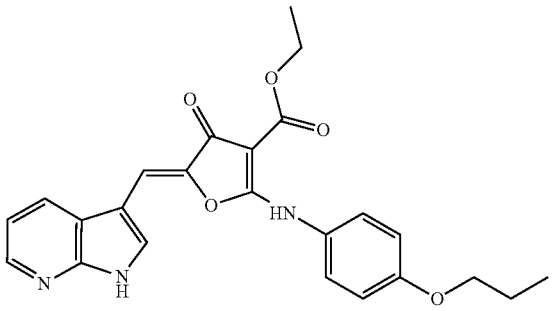

To a solution of ethyl 4-oxo-2-{[4-(1-propoxy)phenyl]amino}-4,5-dihydrofuran-3-carboxylate (0.15 g, 0.50 mmol) which similarly prepared according to the procedure described in the Example 4, First step and 7-azaindole-3-carboxaldehyde (0.072 g, 0.50 mmol) in ethanol (6.0 mL), L-proline (0.0060 g, 0.05 mmol) was added at ambient temperature. The mixture was refluxed for 16 h. Cooled to ambient temperature, the precipitate was collected by filtration, washed with ethanol then dried to afford the titled compound as solid (0.060 g, y. 28%).

$^1$H NMR (DMSO-$d_6$) δ (ppm) 12.30 (br. s, 1H), 10.44 (br. s, 1H), 8.22 (br. s, 1H), 7.85-7.99 (m, 1H), 7.79 (br. s, 1H), 7.48 (d, J=6.85 Hz, 2H), 7.07 (d, J=7.34 Hz, 2H), 6.86 (br. s, 2H), 4.18-4.37 (m, 2H), 3.93-4.11 (m, 2H), 1.70-1.90 (m, 2H), 1.22-1.38 (m, 3H), 0.98-1.12 (m, 3H); LCMS (m/z): 433.9 $[M+H]^+$.

Example 56

Ethyl 5-[(1H-pyrrolo[2,3-b]pyridin-3-yl)methylene]-2-(isopropylamino)-4-oxo-4,5-dihydrofuran-3-carboxylate

[Chemical Formula 65]

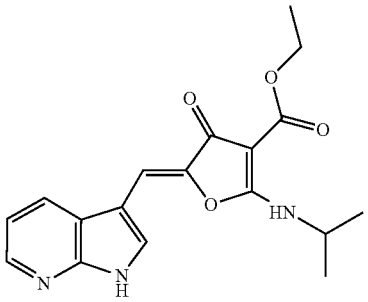

To a solution of ethyl 2-(isopropylamino)-4-oxo-4,5-dihydrofuran-3-carboxylate (0.50 g, 2.3 mmol) which similarly prepared according to the procedure described in the Example 4, First step and 7-azaindole-3-carboxaldehyde (0.34 g, 2.3 mmol) in ethanol (15 mL), L-proline (0.027 g, 0.23 mmol) was added at ambient temperature. The mixture was refluxed for 16 h. Cooled to ambient temperature, the precipitate was collected by filtration, washed with ethanol then dried to afford the titled compound as solid (0.45 g, y. 56%).

$^1$H NMR (DMSO-$d_6$) δ (ppm) 12.32 (br. s, 1H), 8.56 (br. s, 1H), 8.41 (d, J=7.82 Hz, 1H), 8.32 (d, J=3.91 Hz, 1H), 7.99 (s, 1H), 7.20 (dd, J=4.40, 7.83 Hz, 1H), 6.90 (s, 1H), 4.39 (br. s, 1H), 4.21 (q, J=7.01 Hz, 2H), 1.38 (d, J=6.36 Hz, 6H), 1.26 (t, J=6.85 Hz, 3H); LCMS (m/z): 342.3 $[M+H]^+$.

Example 57

Ethyl 5-[(1H-pyrrolo[2,3-b]pyridin-3-yl)methylene]-2-{[2-(dimethylamino)ethyl]amino}-4-oxo-4,5-dihydrofuran-3-carboxylate

[Chemical Formula 66]

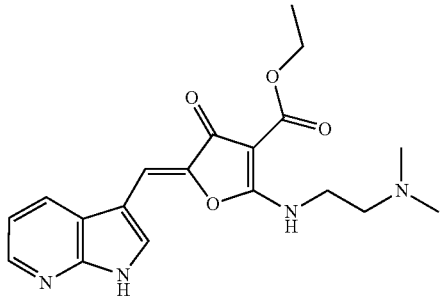

The titled compound (solid) was similarly prepared according to the procedure described in the Example 56.

$^1$H NMR (DMSO-$d_6$) δ (ppm) 12.37 (br. s, 1H), 8.82 (br. s, 1H), 8.42 (d, J=7.82 Hz, 1H), 8.31 (d, J=3.91 Hz, 1H), 8.03 (s, 1H), 7.20 (dd, J=4.89, 7.83 Hz, 1H), 6.90 (s, 1H), 4.20 (q, J=7.34 Hz, 2H), 3.68-3.80 (m, 2H), 2.38-2.65 (m, 2H), 2.23 (s, 6H), 1.26 (t, J=7.09 Hz, 3H); LCMS (m/z): 371.2 $[M+H]^+$.

Example 58

Ethyl 5-[(1H-pyrrolo[2,3-b]pyridin-3-yl)methylene]-2-[(3-fluorobenzyl)amino]-4-oxo-4,5-dihydrofuran-3-carboxylate

[Chemical Formula 67]

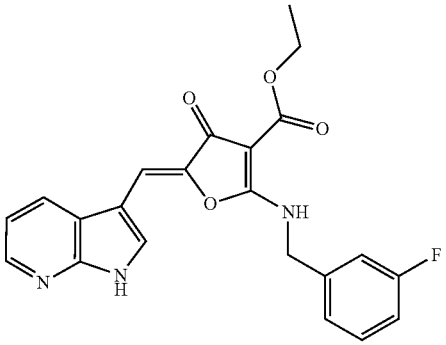

The titled compound (solid) was similarly prepared according to the procedure described in the Example 56.

$^1$H NMR (DMSO-$d_6$) δ (ppm) 12.33 (br. s, 1H), 9.54 (br. s, 1H), 8.28 (d, J=5.87 Hz, 2H), 7.88 (s, 1H), 7.44 (q, J=7.34 Hz, 1H), 7.20-7.33 (m, 2H), 7.03-7.18 (m, 2H), 6.87 (s, 1H), 4.87 (br. s, 2H), 4.23 (q, J=6.85 Hz, 2H), 1.27 (t, J=6.85 Hz, 3H); LCMS (m/z): 408.0 $[M+H]^+$.

Example 59

Ethyl 5-[(1H-pyrrolo[2,3-b]pyridin-3-yl)methylene]-2-(cycloheptylamino)-4-oxo-4,5-dihydrofuran-3-carboxylate

[Chemical Formula 68]

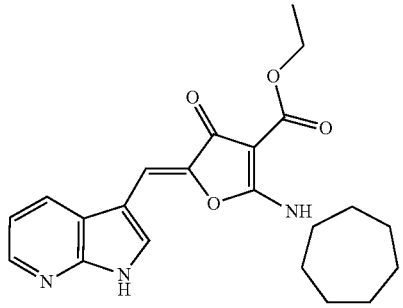

The titled compound (solid) was similarly prepared according to the procedure described in the Example 56.

$^1$H NMR (DMSO-$d_6$) δ (ppm) 12.37 (br. s, 1H), 8.56 (d, J=8.16 Hz, 1H), 8.42 (d, J=7.82 Hz, 1H), 8.32 (d, J=3.91 Hz, 1H), 7.99 (s, 1H), 7.19 (dd, J=4.89, 7.82 Hz, 1H), 6.90 (s, 1H), 4.21 (q, J=6.85 Hz, 2H), 3.39-3.50 (m, 1H), 1.94-2.08 (m, 2H), 1.77-1.91 (m, 2H), 1.48-1.76 (m, 8H), 1.26 (t, J=7.09 Hz, 3H); LCMS (m/z): 396.0 $[M+H]^+$.

Example 60

Ethyl 5-[(1H-pyrrolo[2,3-b]pyridin-3-yl)methylene]-4-oxo-2-[(2-thienylmethyl)amino]-4,5-dihydrofuran-3-carboxylate

[Chemical Formula 69]

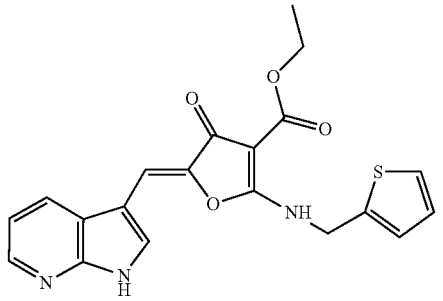

The titled compound (solid) was similarly prepared according to the procedure described in the Example 56.

$^1$H NMR (DMSO-$d_6$) δ (ppm) 12.36 (br. s, 1H), 9.55 (br. s, 1H), 8.37 (d, J=7.82 Hz, 1H), 8.30 (d, J=3.91 Hz, 1H), 8.03 (s, 1H), 7.45 (d, J=4.89 Hz, 1H), 7.09-7.22 (m, 2H), 7.00 (t, J=3.96 Hz, 1H), 6.91 (s, 1H), 5.01 (br. s, 2H), 4.22 (q, J=7.01 Hz, 2H), 1.26 (t, J=6.85 Hz, 3H); LCMS (m/z): 395.8 $[M+H]^+$.

Example 61

Ethyl 5-[(1H-pyrrolo[2,3-b]pyridin-3-yl)methylene]-2-(cyclopropylamino)-4-oxo-4,5-dihydrofuran-3-carboxylate

[Chemical Formula 70]

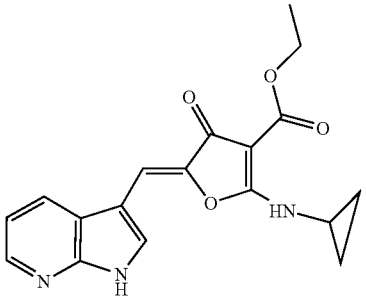

The titled compound (solid) was similarly prepared according to the procedure described in the Example 56.

$^1$H NMR (DMSO-$d_6$) δ (ppm) 12.33 (br. s, 1H), 8.86 (br. s, 1H), 8.57 (d, J=7.82 Hz, 1H), 8.31 (d, J=3.91 Hz, 1H), 8.06 (s, 1H), 7.21 (dd, J=4.89, 7.82 Hz, 1H), 6.92 (s, 1H), 4.19 (q, J=7.01 Hz, 2H), 3.08-3.20 (m, 1H), 1.24 (t, J=6.85 Hz, 3H), 0.84-1.01 (m, 4H); LCMS (m/z): 340.0 [M+H]$^+$.

Example 62

Ethyl 5-[(1H-pyrrolo[2,3-b]pyridin-3-yl)methylene]-2-(3,5-dimethylpiperidino)-4-oxo-4,5-dihydrofuran-3-carboxylate

[Chemical Formula 71]

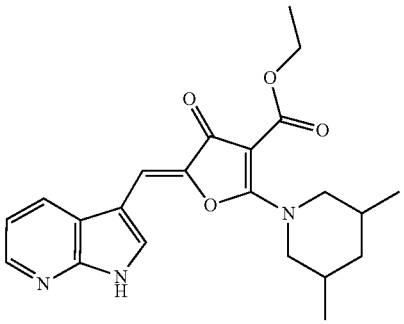

The titled compound (solid) was similarly prepared according to the procedure described in the Example 56.

$^1$H NMR (DMSO-$d_6$) δ (ppm) 12.32 (br. s, 1H), 8.38 (d, J=7.82 Hz, 1H), 8.31 (d, J=3.91 Hz, 1H), 7.96 (s, 1H), 7.11-7.26 (m, 1H), 6.84 (s, 1H), 4.00-4.25 (m, 4H), 2.81 (t, J=11.98 Hz, 2H), 1.74-1.93 (m, 3H), 1.24 (t, J=6.85 Hz, 3H), 0.82-1.02 (m, 7H); LCMS (m/z): 396.0 [M+H]$^+$.

Example 63

Ethyl 5-[(1H-pyrrolo[2,3-b]pyridin-3-yl)methylene]-2-azepinyl-4-oxo-4,5-dihydrofuran-3-carboxylate

[Chemical Formula 72]

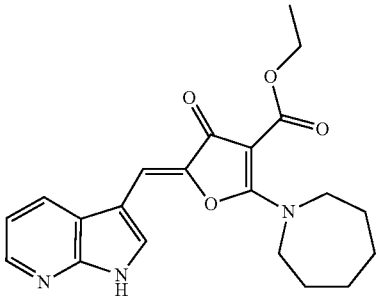

The titled compound (solid) was similarly prepared according to the procedure described in the Example 56.

$^1$H NMR (DMSO-$d_6$) δ (ppm) 12.29 (br. s, 1H), 8.38 (d, J=7.78 Hz, 1H), 8.31 (dd, J=1.51, 4.77 Hz, 1H), 7.93 (d, J=2.26 Hz, 1H), 7.19 (dd, J=4.64, 7.91 Hz, 1H), 6.84 (s, 1H), 4.17 (q, J=7.19 Hz, 2H), 3.73-3.84 (m, 4H), 1.75-1.93 (m, 4H), 1.51-1.64 (m, 4H), 1.24 (t, J=7.03 Hz, 3H); LCMS (m/z): 382.0 [M+H]$^+$.

Example 64

Ethyl 5-[(1H-pyrrolo[2,3-b]pyridin-3-yl)methylene]-2-[(cyclopropylmethyl)amino]-4-oxo-4,5-dihydro-furan-3-carboxylate

[Chemical Formula 73]

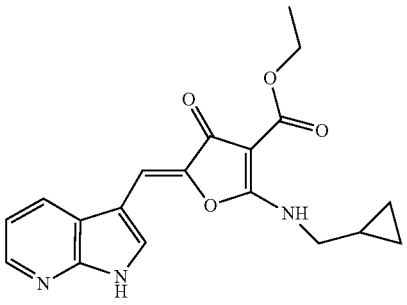

The titled compound (solid) was similarly prepared according to the procedure described in the Example 56.

$^1$H NMR (DMSO-$d_6$) δ (ppm) 12.33 (br. s, 1H), 9.06 (br. s, 1H), 8.41 (d, J=7.82 Hz, 1H), 8.31 (d, J=3.91 Hz, 1H), 8.00 (br. s, 1H), 7.19 (dd, J=4.65, 7.58 Hz, 1H), 6.89 (s, 1H), 4.22 (q, J=7.01 Hz, 2H), 3.52 (t, J=6.36 Hz, 2H), 1.15-1.35 (m, 4H), 0.52 (d, J=6.85 Hz, 2H), 0.36 (d, J=4.40 Hz, 2H); LCMS (m/z): 354.2 [M+H]$^+$.

Example 65

Ethyl 5-[(1H-pyrrolo[2,3-b]pyridin-3-yl)methylene]-2-[(1-methyl-4-piperidinyl)amino]-4-oxo-4,5-dihydrofuran-3-carboxylate

[Chemical Formula 74]

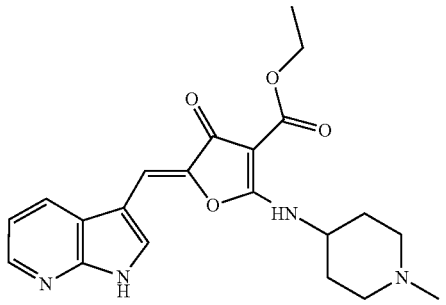

The titled compound (solid) was similarly prepared according to the procedure described in the Example 56.

$^1$H NMR (DMSO-$d_6$) δ (ppm) 12.36 (br. s, 1H), 8.58 (br. s, 1H), 8.42 (d, J=7.83 Hz, 1H), 8.33 (d, J=3.42 Hz, 1H), 7.98 (s, 1H), 7.19 (dd, J=4.65, 7.58 Hz, 1H), 6.90 (s, 1H), 4.21 (q, J=6.85 Hz, 2H), 3.90-4.07 (m, 1H), 2.79 (d, J=10.27 Hz, 2H), 2.21 (s, 3H), 2.08 (t, J=10.27 Hz, 2H), 1.80-1.99 (m, 4H), 1.26 (t, J=6.85 Hz, 3H); LCMS (m/z): 397.2 $[M+H]^+$.

Example 66

Ethyl 5-[(1H-pyrrolo[2,3-b]pyridin-3-yl)methylene]-2-(4-acetylpiperazinyl)-4-oxo-4,5-dihydrofuran-3-carboxylate

[Chemical Formula 75]

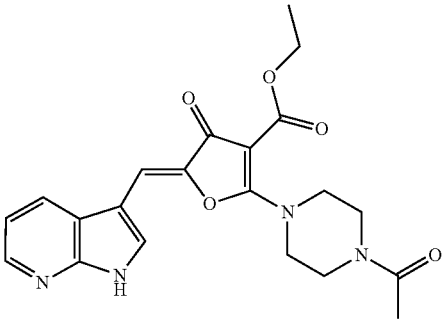

The titled compound (solid) was similarly prepared according to the procedure described in the Example 56.

$^1$H NMR (DMSO-$d_6$) δ (ppm) 12.37 (br. s, 1H), 8.38 (d, J=7.34 Hz, 1H), 8.32 (d, J=3.42 Hz, 1H), 8.01 (s, 1H), 7.21 (dd, J=4.89, 7.82 Hz, 1H), 6.89 (s, 1H), 4.18 (q, J=7.34 Hz, 2H), 3.77-3.95 (m, 4H), 3.62-3.77 (m, 4H), 2.07 (s, 3H), 1.25 (t, J=6.85 Hz, 3H); LCMS (m/z): 411.4 $[M+H]^+$.

Example 67

Ethyl 5-[(1H-pyrrolo[2,3-b]pyridin-3-yl)methylene]-2-[(3-pyrazolyl)amino]-4-oxo-4,5-dihydrofuran-3-carboxylate

[Chemical Formula 76]

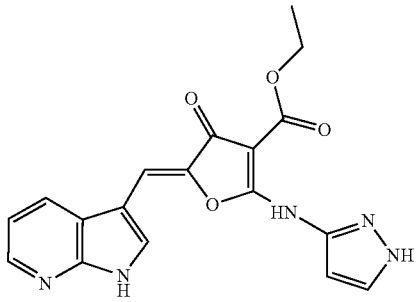

To a solution of ethyl 2-[(3-pyrazolyl)amino]-4-oxo-4,5-dihydrofuran-3-carboxylate (0.30 g, 1.3 mmol) which similarly prepared according to the procedure described in the Example 4, First step, and 7-azaindole-3-carboxaldehyde (0.19 g, 1.3 mmol) in ethanol (6.0 mL), L-proline (0.015 g, 0.13 mmol) was added at ambient temperature. The mixture was refluxed for 16 h. Cooled to ambient temperature, the precipitate was collected by filtration, washed with ethanol then dried to afford the titled compound as solid (0.20 g, y. 35%).

$^1$H NMR (DMSO-$d_6$) δ (ppm) 13.07 (br. s, 1H), 12.34 (br. s, 1H), 10.46 (br. s, 1H), 8.27 (d, J=3.91 Hz, 1H), 8.14 (d, J=7.82 Hz, 1H), 7.91-8.20 (m, 2H), 7.08 (dd, J=4.65, 7.58 Hz, 1H), 6.94 (s, 1H), 6.47 (br. s, 1H), 4.26 (q, J=6.85 Hz, 2H), 1.29 (t, J=7.09 Hz, 3H); LCMS (m/z): 366.0 $[M+H]^+$.

Example 68

Ethyl 5-[(1H-pyrrolo[2,3-b]pyridin-3-yl)methylene]-2-[(6-indazolyl)amino]-4-oxo-4,5-dihydrofuran-3-carboxylate

[Chemical Formula 77]

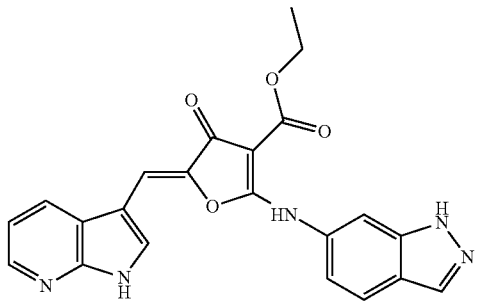

The titled compound (solid) was similarly prepared according to the procedure described in the Example 67.

$^1$H NMR (DMSO-$d_6$) δ (ppm) 13.22 (br. s, 1H), 12.24 (br. s, 1H), 10.66 (br. s, 1H), 8.22 (br. s, 1H), 8.12 (br. s, 1H), 7.91 (d, J=8.31 Hz, 1H), 7.71-7.86 (m, 3H), 7.33 (d, J=7.83

Hz, 1H), 6.89 (s, 1H), 6.33 (br. s, 1H), 4.29 (d, J=6.85 Hz, 2H), 1.31 (t, J=6.60 Hz, 3H); LCMS (m/z): 416.4 $[M+H]^+$.

Example 69

Ethyl 5-[(1H-pyrrolo[2,3-b]pyridin-3-yl)methylene]-2-[4-(hydroxymethyl)piperidino]-4-oxo-4,5-dihydrofuran-3-carboxylate

[Chemical Formula 78]

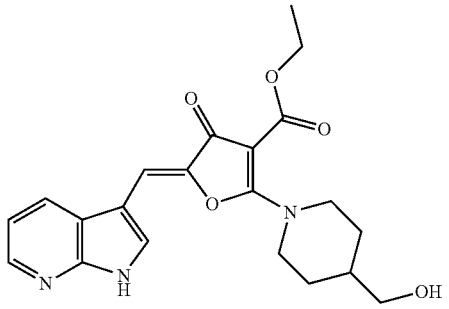

The titled compound (solid) was similarly prepared according to the procedure described in the Example 67.

$^1$H NMR (DMSO-$d_6$) δ (ppm) 12.30 (br. s, 1H), 8.37 (d, J=7.82 Hz, 1H), 8.31 (d, J=3.91 Hz, 1H), 7.97 (br. s, 1H), 7.19 (dd, J=4.40, 7.82 Hz, 1H), 6.84 (s, 1H), 4.57 (t, J=4.89 Hz, 1H), 4.08-4.32 (m, 4H), 3.22-3.40 (m, 4H), 1.70-1.95 (m, 3H), 1.37 (q, J=11.09 Hz, 2H), 1.24 (t, J=6.85 Hz, 3H); LCMS (m/z): 398.0 $[M+H]^+$.

Example 70

2-Methoxyethyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 79]

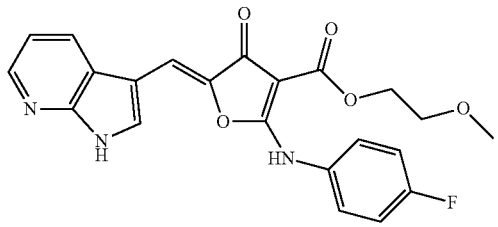

First Step

A solution of methyl 2-[(4-fluorophenyl)amino]-4-oxo-4,5-dihydrofuran-3-carboxylate (0.063 g, 0.25 mmol) which similarly prepared according to the procedure described in the Example 2, First step using methyl 4-chloroacetoacetate and 4-fluorophenyl isocyanate, 2-methoxyethanol (0.2 mL, 2.5 mmol) and zinc cluster catalyst ($Zn_4(OCOCF_3)_6O$) (0.0048 g, 0.0050 mmol) in anhydrous dioxane (1.0 mL) was stirred with the microwave synthesizer (Biotage Initiator™) at 120° C. for 1 h. Cooled to ambient temperature, the reaction mixture was concentrated under reduced pressure. The residue was purified by chromatography on silica gel (chloroform/ethyl acetate) to afford 2-methoxyethyl 2-[(4-fluorophenyl)amino]-4-oxo-4,5-dihydrofuran-3-carboxylate as solid (0.024 g, y. 33%).

$^1$H NMR (DMSO-$d_6$) δ (ppm) 10.22 (s, 1H), 7.43-7.56 (m, 2H), 7.27 (t, J=8.78 Hz, 2H), 4.66 (s, 2H), 4.22-4.37 (m, 2H), 3.52-3.66 (m, 2H), 3.30 (s, 3H); LCMS (m/z): 295.8 $[M+H]^+$ Second Step To a solution of 2-methoxyethyl 2-[(4-fluorophenyl)amino]-4-oxo-4,5-dihydrofuran-3-carboxylate (0.023 g, 0.078 mmol) and 7-azaindole-3-carboxaldehyde (0.011 g, 0.078 mmol) in 2-propanol (1.0 mL), L-proline (0.0018 g, 0.016 mmol) was added at ambient temperature. The mixture was refluxed for 2 days. Cooled to ambient temperature, the precipitate was collected by filtration. The solid was purified by preparative HPLC to afford the titled compound as solid (0.046 g, y. 14%).

$^1$H NMR (DMSO-$d_6$) δ (ppm) 12.22 (br. s, 1H), 10.65 (br. s, 1H), 8.24 (dd, J=1.25, 4.52 Hz, 1H), 7.96 (d, J=7.53 Hz, 1H), 7.72 (d, J=2.26 Hz, 1H), 7.52-7.63 (m, 2H), 7.35 (t, J=8.78 Hz, 2H), 6.89 (dd, J=4.77, 8.03 Hz, 1H), 6.82 (br. s, 1H), 4.32 (t, J=4.77 Hz, 2H), 3.54-3.72 (m, 2H), 3.33 (s, 3H); LCMS (m/z): 423.8 $[M+H]^+$.

Example 71

2-(Dimethylamino)ethyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 80]

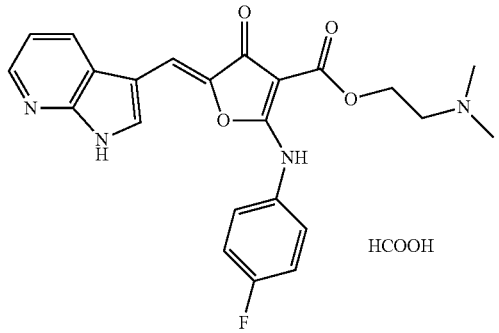

Under a nitrogen atmosphere, a solution of methyl 5-[(1H-pyrrolo[2,3-b]pyridin-3-yl)methylene]-2-[(4-fluorophenyl)amino]-4-oxo-4,5-dihydrofuran-3-carboxylate (0.038 g, 0.10 mmol) which afforded in the Example 51, 2-(dimethylamino)ethanol (0.10 mL, 1.0 mmol) and zinc cluster catalyst ($Zn_4(OCOCF_3)_6O$) (0.0019 g, 0.0020 mmol) in N,N-dimethylacetamide (0.9 mL) was stirred with the microwave synthesizer (Biotage Initiator™) at 130° C. for 1 h. Cooled to ambient temperature, the reaction mixture was purified by preparative HPLC to afford the titled compound as solid (0.016 g, y. 36%).

$^1$H NMR (DMSO-$d_6$) δ (ppm) 12.15 (br. s, 1H), 8.23 (dd, J=1.38, 4.64 Hz, 1H), 8.14 (s, 1H), 7.97 (d, J=7.53 Hz, 1H), 7.68 (d, J=2.01 Hz, 1H), 7.45 (dd, J=5.14, 8.41 Hz, 2H), 7.27-7.36 (m, 2H), 6.89 (dd, J=4.64, 7.91 Hz, 1H), 6.72 (s, 1H), 4.30 (t, J=5.77 Hz, 2H), 2.80 (t, J=5.77 Hz, 2H), 2.41 (s, 6H); LCMS (m/z): 436.9 $[M+H]^+$.

Example 72

2-Hydroxyethyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 81]

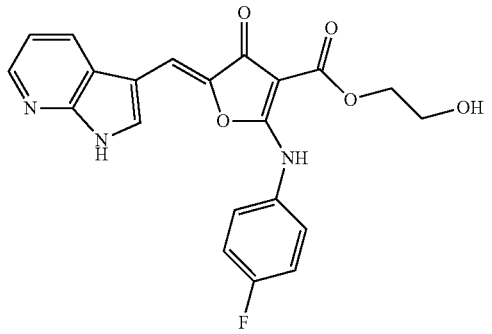

Under a nitrogen atmosphere, a solution of the compound (0.038 g, 0.10 mmol) of Example 51, ethylene glycol (0.50 mL, 9.0 mmol) and zinc cluster catalyst ($Zn_4(OCOCF_3)_6O$) (0.0019 g, 0.0020 mmol) in N,N-dimethylacetamide (0.5 mL) was stirred with the microwave synthesizer (Biotage Initiator™) at 150° C. for 1 h. Cooled to ambient temperature, the precipitate was removed by filtration. The filtrate was purified by preparative HPLC to afford the titled compound as solid (0.0040 g, y. 10%).

$^1$H NMR (DMSO-$d_6$) δ (ppm) 12.24 (br. s, 1H), 10.52 (br. s, 1H), 8.21-8.28 (m, 1H), 7.96 (d, J=7.78 Hz, 1H), 7.74 (d, J=2.40 Hz, 1H), 7.58 (br. s, 2H), 7.36 (t, J=8.66 Hz, 2H), 6.80-6.94 (m, 2H), 4.90 (br. s, 1H), 4.22 (t, J=5.27 Hz, 2H), 3.67 (t, J=5.27 Hz, 2H); LCMS (m/z): 409.8 [M+H]$^+$.

Example 73

2-Morpholinoethyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 82]

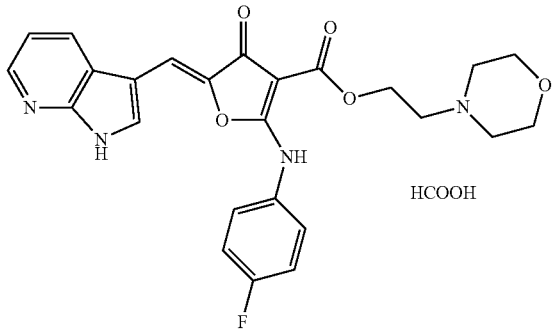

Under a nitrogen atmosphere, a solution of the compound (0.038 g, 0.10 mmol) of Example 51, N-(2-hydroxyethyl) morpholine (0.20 mL, 1.6 mmol) and zinc cluster catalyst ($Zn_4(OCOCF_3)_6O$) (0.0019 g, 0.0020 mmol) in N,N-dimethylacetamide (0.8 mL) was stirred with the microwave synthesizer (Biotage Initiator™) at 150° C. for 40 min. Cooled to ambient temperature, the precipitate was removed by filtration. The filtrate was purified by preparative HPLC to afford the titled compound as solid (0.0075 g, y. 15%).

$^1$H NMR (DMSO-$d_6$) δ (ppm) 12.25 (br. s, 1H), 8.24 (d, J=4.02 Hz, 1H), 8.15 (s, 1H), 7.95 (d, J=7.78 Hz, 1H), 7.72 (s, 1H), 7.60 (br. s, 2H), 7.33-7.43 (m, 2H), 6.84-6.93 (m, 2H), 4.31 (t, J=5.77 Hz, 2H), 3.47-3.58 (m, 4H), 2.78 (s, 2H), 2.62-2.70 (m, 2H), 2.35-2.42 (m, 2H); LCMS (m/z): 478.9 [M+H]$^+$.

Example 74

Ethyl 5-[(1H-pyrrolo[2,3-b]pyridin-3-yl)methylene]-2-{[4-(2-hydroxyethoxy)-2-methylphenyl]amino}-4-oxo-4,5-dihydrofuran-3-carboxylate

[Chemical Formula 83]

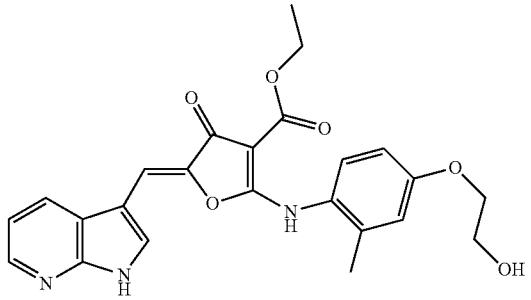

First Step

A solution of 4-nitro-m-cresol (1.4 g, 9.4 mmol), 2-bromoethanol (1.0 mL, 0.014 mol) and potassium carbonate (3.3 g, 0.024 mol) in N,N-dimethylformamide (10 mL) was stirred with heating at 70° C. for 12 h. Cooled to ambient temperature, the reaction mixture was poured into ice water and extracted with ethyl acetate. The organic layer was washed with water and brine, dried over sodium sulfate, filtered and concentrated. The residue was purified by chromatography on silica gel(hexane/ethyl acetate) to afford 2-(3-methyl-4-nitrophenoxy)ethanol as solid (1.3 g, y. 70%).

$^1$H NMR (DMSO-$d_6$) δ (ppm) 8.04 (d, J=9.08 Hz, 1H), 7.03 (br. s, 1H), 6.98 (dd, J=2.44, 9.04 Hz, 1H), 4.92 (t, J=5.42 Hz, 1H), 4.11 (t, J=4.80 Hz, 2H), 3.73 (q, J=4.99 Hz, 2H), 2.55 (s, 3H); LCMS (m/z): 198.3 [M+H]$^+$.

Second Step

Under a nitrogen atmosphere, 2-(3-methyl-4-nitrophenoxy)ethanol (1.0 g, 5.3 mmol) was dissolved in methanol/tetrahydrofuran (30 mL/30 mL) and 10% palladium on carbon (0.37 g) was added at ambient temperature. The reaction mixture was agitated under a hydrogen atmosphere for 4 h. Palladium on carbon was removed by filtration with Celite and the solvent was removed under reduced pressure to afford 4-(2-hydroxyethoxy)-2-methylaniline as solid (0.80 g, y. 90%).

$^1$H NMR DMSO-$d_6$) δ (ppm) 6.57 (br. s, 1H), 6.52 (br. s, 2H), 4.74 (t, J=5.56 Hz, 1H), 4.34 (br. s, 2H), 3.82 (t, J=5.16 Hz, 2H), 3.63 (q, J=5.30 Hz, 2H), 2.02 (s, 3H); LCMS (m/z): 168.0 [M+H]$^+$.

Third Step

Diethyl malonate (8.0 mL, 0.052 mol) was added dropwise to a solution of sodium hydride (60% w/w in oil, 4.2 g, 0.11 mol) in anhydrous tetrahydrofuran (130 mL) that cooled with ice bath. The mixture was refluxed for 7 min. The reaction mixture was cooled with ice bath, chloroacetyl chloride (4.2 mL, 0.052 mol) was added dropwise to the reaction mixture and stirred for 1 h then stirred at 45° C. for 1 h. Cooled to ambient temperature, the reaction mixture was diluted with water, and extracted with chloroform for 4 times. The organic layer was dried over magnesium sulfate and concentrated. The residue was purified by chromatography on silica gel (chloroform/methanol) to afford ethyl 2-ethoxy-4-oxo-4,5-dihydrofuran-3-carboxylate as solid (5.0 g, y. 48%).

$^1$H NMR ($CDCl_3$) δ (ppm) 4.58-4.70 (m, 4H), 4.30 (q, J=7.03 Hz, 2H), 1.53 (t, J=7.03 Hz, 3H), 1.33 (t, J=7.15 Hz, 3H)

Fourth Step

A solution of 4-(2-hydroxyethoxy)-2-methylaniline (0.69 g, 4.1 mmol) and ethyl 2-ethoxy-4-oxo-4,5-dihydrofuran-3-carboxylate (0.83 g, 4.2 mmol) in ethanol (8.3 mL) was stirred at ambient temperature for 16 h. The solvent was removed under reduced pressure, and ethanol was added to precipitate the product. The precipitate was collected by filtration then dried to afford ethyl 2-{[4-(2-hydroxyethoxy)-2-methylphenyl]amino}-4-oxo-4,5-dihydrofuran-3-carboxylate as solid (0.55 g, y. 42%).

$^1$H NMR (DMSO-$d_6$) δ (ppm) 9.99 (br. s, 1H), 7.24 (d, J=7.84 Hz, 1H), 6.89 (br. s, 1H), 6.80 (d, J=8.40 Hz, 1H), 4.83-4.91 (m, 1H), 4.56 (br. s, 2H), 4.20 (q, J=6.95 Hz, 2H), 3.97 (t, J=4.88 Hz, 2H), 3.65-3.74 (m, 2H), 2.20 (s, 3H), 1.24 (t, J=7.04 Hz, 3H); LCMS (m/z): 322.2 $[M+H]^+$.

Fifth Step

To a solution of 7-azaindole-3-carboxaldehyde (0.16 g, 1.1 mmol) and ethyl 2-{[4-(2-hydroxyethoxy)-2-methylphenyl]amino}-4-oxo-4,5-dihydrofuran-3-carboxylate (0.36 g, 1.1 mmol) in ethanol (11 mL), L-proline (0.022 g, 0.19 mmol) was added at ambient temperature. The mixture was refluxed for 2 days. Cooled to ambient temperature, the precipitate was collected by filtration, washed with diethyl ether then dried to afford the titled compound as solid (0.24 g, y. 48%).

$^1$H NMR (DMSO-$d_6$) δ (ppm) 12.27 (br. s, 1H), 10.29 (br. s, 1H), 8.19 (d, J=3.91 Hz, 1H), 7.75 (br. s, 1H), 7.68 (d, J=7.83 Hz, 1H), 7.41 (d, J=8.31 Hz, 1H), 7.03 (br. s, 1H), 6.94 (d, J=8.31 Hz, 1H), 6.72-6.86 (m, 2H), 4.97 (t, J=5.38 Hz, 1H), 4.26 (q, J=6.85 Hz, 2H), 4.09 (t, J=4.65 Hz, 2H), 3.80 (dd, J=5.14, 9.98 Hz, 2H), 2.23 (s, 3H), 1.29 (t, J=7.09 Hz, 3H); LCMS (m/z): 450.2 $[M+H]^+$.

Example 75

Ethyl 5-[(1H-pyrrolo[2,3-b]pyridin-3-yl)methylene]-2-(benzo[d]thiazol-6-ylamino)-4-oxo-4,5-dihydrofuran-3-carboxylate

[Chemical Formula 84]

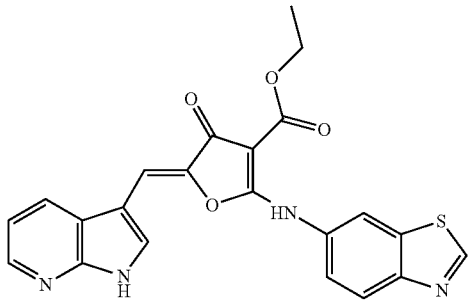

To a solution of ethyl 2-(benzo[d]thiazol-6-ylamino)-4-oxo-4,5-dihydrofuran-3-carboxylate (0.070 g, 0.23 mmol) which similarly prepared according to the procedure described in the Example 4, First step and 7-azaindole-3-carboxaldehyde (0.034 g, 0.23 mmol) in ethanol (6.0 mL), L-proline (0.0030 g, 0.023 mmol) was added at ambient temperature. The mixture was refluxed for 16 h. Cooled to ambient temperature, the precipitate was collected by filtration, washed with ethanol then dried to afford the titled compound as solid (0.045 g, y. 45%).

$^1$H NMR (DMSO-$d_6$) δ (ppm) 12.25 (br. s, 1H), 10.77 (br. s, 1H), 9.52 (s, 1H), 8.40 (s, 1H), 8.23 (d, J=8.80 Hz, 1H), 8.12 (d, J=3.42 Hz, 1H), 7.69-7.85 (m, 3H), 6.89 (s, 1H), 6.36 (t, J=5.94 Hz, 1H), 4.16-4.47 (m, 2H), 1.31 (t, J=6.85 Hz, 3H); LCMS (m/z): 433.2 $[M+H]^+$.

Example 76

Ethyl 5-[(1H-pyrrolo[2,3-b]pyridin-3-yl)methylene]-2-[4-(2-hydroxyethyl)piperazinyl]-4-oxo-4,5-dihydrofuran-3-carboxylate

[Chemical Formula 85]

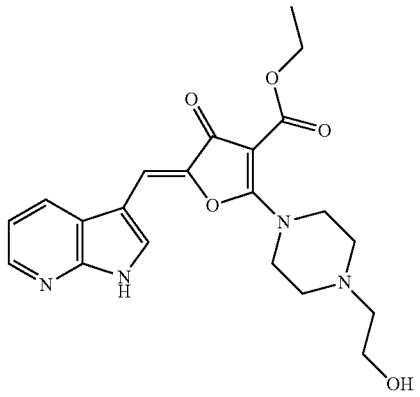

To a solution of ethyl 2-[4-(2-hydroxyethyl)piperazinyl]-4-oxo-4,5-dihydrofuran-3-carboxylate (0.35 g, 1.2 mmol) which similarly prepared according to the procedure described in the Example 74, Fourth step and 7-azaindole-3-carboxaldehyde (0.18 g, 1.2 mmol) in ethanol (6.0 mL), piperidine (0.12 mL, 1.4 mmol) was added at ambient temperature. The mixture was refluxed for 16 h. Cooled to ambient temperature, the precipitate was collected by filtration, washed with ethanol then dried to afford the titled compound as solid (0.050 g, y. 10%).

$^1$H NMR (DMSO-$d_6$) δ (ppm) 12.34 (br. s, 1H), 8.37 (d, J=7.82 Hz, 1H), 8.31 (d, J=3.91 Hz, 1H), 7.99 (s, 1H), 7.20 (dd, J=4.89, 7.82 Hz, 1H), 6.87 (s, 1H), 4.50 (br. s, 1H), 4.16 (q, J=7.34 Hz, 2H), 3.71-3.88 (m, 4H), 3.55 (t, J=5.87 Hz, 2H), 2.57-2.72 (m, 4H), 2.40-2.58 (m, 2H), 1.24 (t, J=7.09 Hz, 3H); LCMS (m/z): 413.2 $[M+H]^+$.

Example 77

Ethyl 5-[(1H-pyrrolo[2,3-b]pyridin-3-yl)methylene]-2-(4-hydroxypiperidino)-4-oxo-4,5-dihydrofuran-3-carboxylate

[Chemical Formula 86]

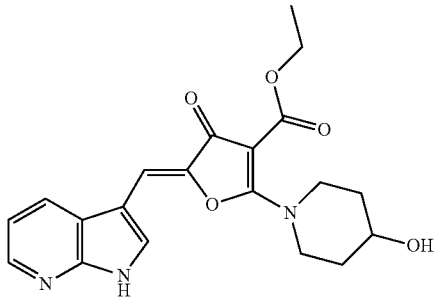

The titled compound (solid) was similarly prepared according to the procedure described in the Example 76.

$^1$H NMR (DMSO-$d_6$) δ (ppm) 12.30 (br. s, 1H), 8.37 (d, J=7.82 Hz, 1H), 8.31 (d, J=3.42 Hz, 1H), 7.98 (s, 1H), 7.19 (dd, J=4.40, 7.83 Hz, 1H), 6.85 (s, 1H), 4.92 (d, J=3.91 Hz, 1H), 4.17 (q, J=6.85 Hz, 2H), 3.92-4.02 (m, 2H), 3.80-3.90 (m, 1H), 3.58 (t, J=9.29 Hz, 2H), 1.94 (d, J=3.42 Hz, 2H), 1.52-1.69 (m, 2H), 1.24 (t, J=6.85 Hz, 3H); LCMS (m/z): 384.2 $[M+H]^+$.

Example 78

Ethyl 5-[(1H-pyrrolo[2,3-b]pyridin-3-yl)methylene]-2-(4-methylpiperidino)-4-oxo-4,5-dihydrofuran-3-carboxylate

[Chemical Formula 87]

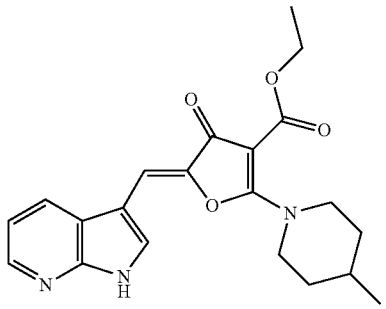

The titled compound (solid) was similarly prepared according to the procedure described in the Example 76.

$^1$H NMR (DMSO-$d_6$) δ (ppm) 12.30 (br. s, 1H), 8.37 (d, J=7.34 Hz, 1H), 8.31 (d, J=3.91 Hz, 1H), 7.97 (s, 1H), 7.19 (dd, J=4.40, 7.82 Hz, 1H), 6.84 (s, 1H), 4.08-4.29 (m, 4H), 3.22-3.40 (m, 2H), 1.68-1.92 (m, 3H), 1.28-1.42 (m, 2H), 1.24 (t, J=6.85 Hz, 3H), 0.96 (d, J=5.87 Hz, 3H); LCMS (m/z): 382.2 $[M+H]^+$.

Example 79

Ethyl 5-[(1H-pyrrolo[2,3-b]pyridin-3-yl)methylene]-2-morpholino-4-oxo-4,5-dihydrofuran-3-carboxylate

[Chemical Formula 88]

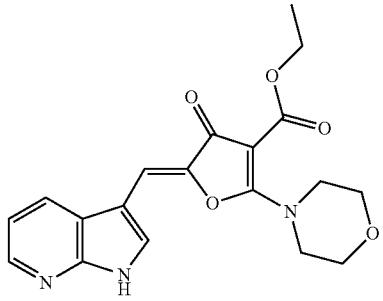

The titled compound (solid) was similarly prepared according to the procedure described in the Example 76.

$^1$H NMR (DMSO-$d_6$) δ (ppm) 12.34 (br. s, 1H), 8.37 (d, J=7.82 Hz, 1H), 8.31 (d, J=3.42 Hz, 1H), 8.00 (s, 1H), 7.20 (dd, J=4.40, 7.82 Hz, 1H), 6.89 (s, 1H), 4.16 (q, J=7.17 Hz, 2H), 3.73-3.89 (m, 8H), 1.24 (t, J=7.09 Hz, 3H); LCMS (m/z): 370.4 $[M+H]^+$.

Example 80

Ethyl 5-[(1H-pyrrolo[2,3-b]pyridin-3-yl)methylene]-2-{[2-fluoro-4-(2-methoxyethoxy)phenyl]amino}-4-oxo-4,5-dihydrofuran-3-carboxylate

[Chemical Formula 89]

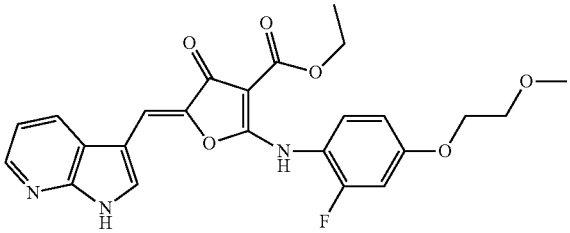

To a solution of ethyl 2-{[2-fluoro-4-(2-methoxyethoxy)phenyl]amino}-4-oxo-4,5-dihydrofuran-3-carboxylate (0.011 g, 0.032 mmol) which similarly prepared according to the procedure described in the Example 29, First step and 7-azaindole-3-carboxaldehyde (0.0045 g, 0.031 mmol) in ethanol (0.2 mL), 2M hydrochloric acid in ethanol (0.016 mL, 0.032 mmol) was added at ambient temperature. The mixture was refluxed for 4 h. Cooled with ice bath, 2M sodium hydroxide solution (0.015 mL, 0.029 mmol) was added dropwise to neutralize, and ethanol (1.5 mL) was added. The mixture was refluxed for further 30 min. The precipitate was collected by filtration, washed with hot ethanol. The solid was washed with hexane then dried to afford the titled compound as solid (0.0051 g, y. 32%).

$^1$H NMR (DMSO-$d_6$) δ (ppm) 12.34 (br. s, 1H), 10.38 (s, 1H), 8.21 (dd, J=1.38, 4.64 Hz, 1H), 7.81 (d, J=7.53 Hz, 1H), 7.75 (d, J=2.51 Hz, 1H), 7.58 (t, J=9.03 Hz, 1H), 7.13 (dd, J=2.51, 12.05 Hz, 1H), 6.98 (dd, J=2.26, 8.78 Hz, 1H), 6.89 (s, 1H), 6.82 (dd, J=4.64, 7.91 Hz, 1H), 4.20-4.31 (m, 4H), 3.71-3.77 (m, 2H), 3.37 (br. s, 3H), 1.29 (t, J=7.03 Hz, 3H); LCMS (m/z): 467.9 $[M+H]^+$.

Example 81

Ethyl 5-[(1H-pyrrolo[2,3-b]pyridin-3-yl)methylene]-2-{[2-fluoro-4-(2-hydroxyethoxy)phenyl]amino}-4-oxo-4,5-dihydrofuran-3-carboxylate

[Chemical Formula 90]

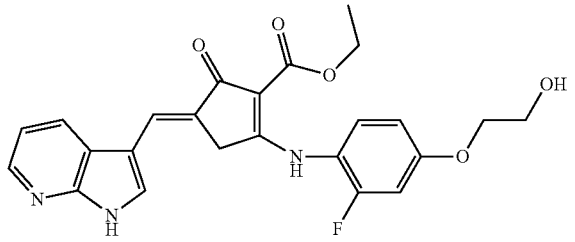

To a solution of ethyl 2-{[2-fluoro-4-(2-hydroxyethoxy)phenyl]amino}-4-oxo-4,5-dihydrofuran-3-carboxylate (0.017 g, 0.052 mmol) which similarly prepared according to the procedure described in the Example 29, First step and 7-azaindole-3-carboxaldehyde (0.0075 g, 0.051 mmol) in ethanol (0.2 mL), 2M hydrochloric acid in ethanol (0.052 mL, 0.10 mmol) was added at ambient temperature. The mixture was refluxed for 8.5 h. Cooled with ice bath, 2M sodium hydroxide solution (0.047 mL, 0.094 mmol) was added dropwise to neutralize, and ethanol (0.5 mL) was added and refluxed for further 16 min. The precipitate was collected by filtration, washed with hot ethanol. The solid was washed with hexane then dried to afford the titled compound as solid (0.014 g, y. 59%).

$^1$H NMR (DMSO-$d_6$) δ (ppm) 12.14 (br. s, 1H), 10.38 (s, 1H), 8.21 (dd, J=1.20, 4.80 Hz, 1H), 7.87 (d, J=7.20 Hz, 1H), 7.65 (br. s, 1H), 7.38 (br. s, 1H), 6.95-7.07 (m, 1H), 6.85-6.95 (m, 1H), 6.83 (dd, J=4.80, 8.00 Hz, 1H), 6.64 (br. s, 1H), 4.96 (t, J=5.40 Hz, 1H), 4.15-4.25 (m, 2H), 4.09 (t, J=4.80 Hz, 2H), 3.78 (q, J=5.07 Hz, 2H), 1.26 (t, J=7.00 Hz, 3H); LCMS (m/z): 453.8 $[M+H]^+$.

Example 82

Ethyl 5-[(1H-pyrrolo[2,3-b]pyridin-3-yl)methylene]-2-{[2-(2-methoxyethoxy)-4-methylphenyl]amino}-4-oxo-4,5-dihydrofuran-3-carboxylate

[Chemical Formula 91]

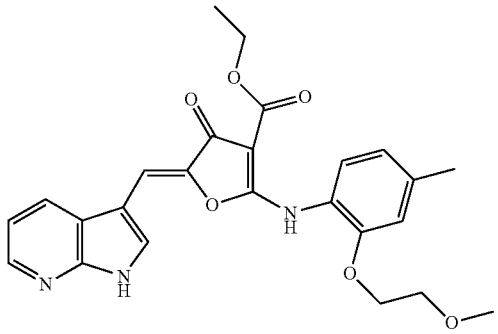

To a solution of ethyl 2-{[2-(2-methoxyethoxy)-4-methylphenyl]amino}-4-oxo-4,5-dihydrofuran-3-carboxylate (0.015 g, 0.045 mmol) which similarly prepared according to the procedure described in the Example 29, First step and 7-azaindole-3-carboxaldehyde (0.0067 g, 0.046 mmol) in ethanol (0.2 mL), 2M hydrochloric acid in ethanol (0.023 mL, 0.045 mmol) was added at ambient temperature. The mixture was refluxed for 4 h. Cooled to ambient temperature, the solvent was removed under reduced pressure. The residue was purified by preparative HPLC to afford the titled compound as solid (0.0090 g, y. 43%).

$^1$H NMR (DMSO-$d_6$) δ (ppm) 12.29 (br. s, 1H), 10.30 (br. s, 1H), 8.25 (dd, J=1.38, 4.64 Hz, 1H), 8.00 (d, J=7.03 Hz, 1H), 7.83 (s, 1H), 7.49 (d, J=7.78 Hz, 1H), 7.10 (s, 1H), 6.84-6.95 (m, 3H), 4.26 (q, J=7.03 Hz, 2H), 4.09-4.17 (m, 2H), 3.53-3.60 (m, 2H), 3.17 (s, 3H), 2.43 (s, 3H), 1.29 (t, J=7.03 Hz, 3H); LCMS (m/z): 463.9 $[M+H]^+$.

Example 83

Ethyl 5-[(1H-pyrrolo[2,3-b]pyridin-3-yl)methylene]-2-({2-[2-(dimethylamino)ethoxy]-4-methylphenyl}amino)-4-oxo-4,5-dihydrofuran-3-carboxylate

[Chemical Formula 92]

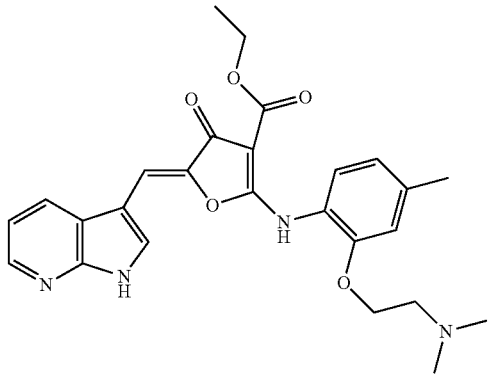

To a stirred solution of ethyl 2-({2-[2-(dimethylamino)ethoxy]-4-methylphenyl}amino)-4-oxo-4,5-dihydrofuran-3-carboxylate (0.011 g, 0.030 mmol) which similarly prepared according to the procedure described in the Example 29, First step and 7-azaindole-3-carboxaldehyde (0.0044 g, 0.030 mmol) in ethanol (0.2 mL), 2M hydrochloric acid in ethanol (0.045 mL, 0.091 mmol) was added at ambient temperature. The mixture was refluxed for 9 h. Cooled with ice bath, 2M sodium hydroxide solution (0.041 mL, 0.082 mmol) was added dropwise to neutralize, and ethanol (0.5 mL) was added. The mixture was refluxed for further 16 min. The precipitate was collected by filtration, washed with hot ethanol. The solid was washed with hexane then dried to afford the titled compound as solid (0.00079 g, y. 5%).

$^1$H NMR (DMSO-$d_6$) δ (ppm) 12.27 (br. s, 1H), 8.24 (d, J=4.52 Hz, 1H), 8.16 (s, 1H), 7.96 (d, J=8.03 Hz, 1H), 7.79-7.82 (m, 1H), 7.46 (d, J=7.53 Hz, 1H), 7.09-7.12 (m, 1H), 6.93 (d, J=7.53 Hz, 1H), 6.81-6.89 (m, 2H), 4.25 (q, J=6.94 Hz, 2H), 4.10 (t, J=4.64 Hz, 2H), 2.52-2.58 (m, 2H), 2.43 (s, 3H), 2.13 (s, 6H), 1.29 (t, J=7.03 Hz, 3H); LCMS (m/z): 477.0 $[M+H]^+$.

Example 84

Isopropyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 93]

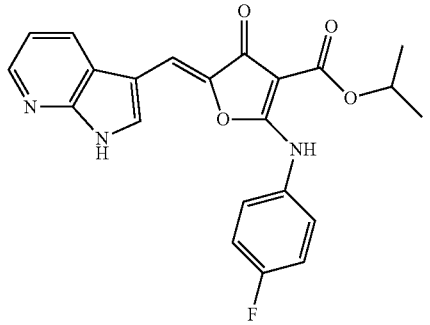

Under a nitrogen atmosphere, a solution of the compound (0.039 g, 0.10 mmol) of Example 21, 4-dimethylaniline (0.0024 g, 0.020 mmol) and zinc cluster catalyst ($Zn_4(OCOCF_3)_6O$) (0.0012 g, 0.0013 mmol) in 2-propanol (1.0 mL) and N,N-dimethylacetamide (1.0 mL) was stirred with the microwave synthesizer (Biotage Initiator™) at 150° C. for 1.5 h. Cooled to ambient temperature, the precipitate was removed by filtration. The filtrate was purified by preparative HPLC to afford the titled compound as solid (0.011 g, y. 27%).

$^1$H NMR (DMSO-$d_6$) δ (ppm) 12.29 (br. s, 1H), 10.54 (s, 1H), 8.25 (dd, J=1.51, 4.77 Hz, 1H), 7.94 (d, J=7.03 Hz, 1H), 7.76 (d, J=2.76 Hz, 1H), 7.56-7.70 (m, 2H), 7.28-7.44 (m, 2H), 6.80-6.98 (m, 2H), 5.08-5.17 (m, 1H), 1.31 (d, J=6.27 Hz, 6H); LCMS (m/z): 408.0 $[M+H]^+$.

Example 85

Cyclopropylmethyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 94]

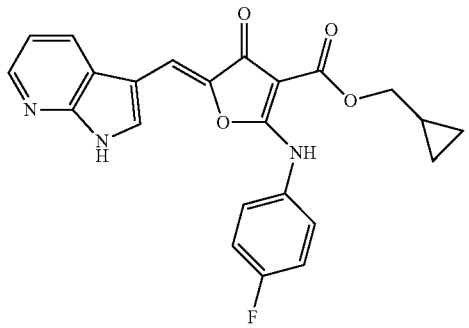

Under a nitrogen atmosphere, a solution of the compound (0.038 g, 0.10 mmol) of Example 51, cyclopropyl carbinol (0.10 mL, 1.3 mmol) and zinc cluster catalyst ($Zn_4(OCOCF_3)_6O$) (0.0019 g, 0.0020 mmol) in N,N-dimethylacetamide (0.9 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.0080 g, y. 19%).

$^1$H NMR (DMSO-$d_6$) δ (ppm) 12.29 (br. s, 1H), 10.57 (s, 1H), 8.25 (d, J=3.51 Hz, 1H), 7.95 (d, J=7.78 Hz, 1H), 7.75 (d, J=2.51 Hz, 1H), 7.60-7.69 (m, 2H), 7.34-7.43 (m, 2H), 6.85-6.95 (m, 2H), 4.08 (d, J=7.03 Hz, 2H), 1.16-1.31 (m, 1H), 0.55 (dd, J=1.51, 8.03 Hz, 2H), 0.36 (d, J=5.02 Hz, 2H); LCMS (m/z): 419.8 $[M+H]^+$.

Example 86

Methyl 5-[(1H-pyrrolo[2,3-b]pyridin-3-yl)methylene]-2-[(2,4-difluorophenyl)amino]-4-oxo-4,5-dihydrofuran-3-carboxylate

[Chemical Formula 95]

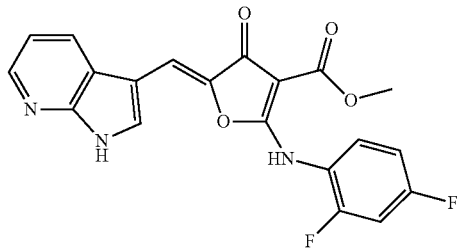

To a solution of methyl 2-[(2,4-difluorophenyl)amino]-4-oxo-4,5-dihydrofuran-3-carboxylate (0.27 g, 1.0 mmol) which similarly prepared according to the procedure described in the Example 2, First step using methyl 4-chloroacetoacetate and 2,4-difluorophenyl isocyanate, and 7-azaindole-3-carboxaldehyde (0.15 g, 1.0 mmol) in 2-propanol (5.0 mL), L-proline (0.023 g, 0.20 mmol) was added at ambient temperature. The mixture was refluxed for 12 h. Cooled to ambient temperature, the precipitate was collected by filtration, washed with ethanol and diisopropyl ether then dried to afford the titled compound as solid (0.30 g, y. 75%).

$^1$H NMR (DMSO-$d_6$) δ (ppm) 12.32 (br. s, 1H), 10.53 (s, 1H), 8.24 (dd, J=1.38, 4.64 Hz, 1H), 7.74-7.87 (m, 2H), 7.70 (d, J=2.51 Hz, 1H), 7.54-7.63 (m, 1H), 7.27-7.37 (m, 1H), 6.94 (s, 1H), 6.84 (dd, J=4.77, 8.03 Hz, 1H), 3.77 (s, 3H); LCMS (m/z): 397.9 $[M+H]^+$.

Example 87

Ethyl 5-[(1H-pyrrolo[2,3-b]pyridin-3-yl)methylene]-2-[bis(2-methoxyethyl)amino]-4-oxo-4,5-dihydrofuran-3-carboxylate

[Chemical Formula 96]

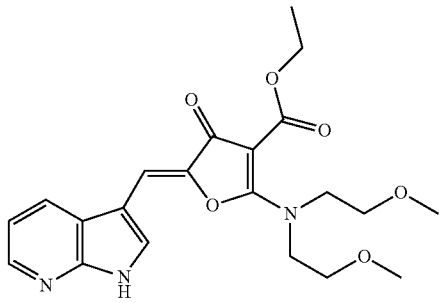

To a solution of ethyl 2-[bis(2-methoxyethyl)amino]-4-oxo-4,5-dihydrofuran-3-carboxylate (0.30 g, 1.0 mmol) which similarly prepared according to the procedure described in the Example 4, First step and 7-azaindole-3-carboxaldehyde (0.15 g, 1.0 mmol) in ethanol (5.0 mL), L-proline (0.023 g, 0.20 mmol) was added at ambient temperature. The mixture was refluxed for 2 days. Cooled to ambient temperature, the precipitate was collected by filtration, washed with ethanol then dried to afford the titled compound as solid (0.048 g, y. 11%).

$^1$H NMR (DMSO-$d_6$) δ (ppm) 12.36 (br. s, 1H), 8.38 (d, J=7.82 Hz, 1H), 8.31 (d, J=4.89 Hz, 1H), 7.98 (s, 1H), 7.19 (dd, J=4.65, 8.07 Hz, 1H), 6.85 (s, 1H), 4.16 (q, J=6.85 Hz, 2H), 3.97 (t, J=5.14 Hz, 4H), 3.57-3.67 (m, 4H), 3.25 (s, 6H), 1.24 (t, J=7.09 Hz, 3H); LCMS (m/z): 416.2 $[M+H]^+$.

Example 88

Ethyl 5-[(1H-pyrrolo[2,3-b]pyridin-3-yl)methylene]-2-{[4-(hydroxymethyl)phenyl]amino}-4-oxo-4,5-dihydrofuran-3-carboxylate

[Chemical Formula 97]

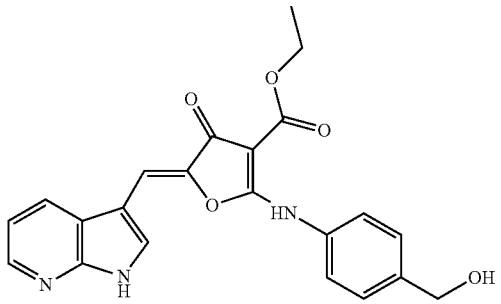

The titled compound (solid) was similarly prepared according to the procedure described in the Example 87.

$^1$H NMR (DMSO-$d_6$) δ (ppm) 12.27 (br. s, 1H), 10.66 (br. s, 1H), 8.22 (d, J=3.42 Hz, 1H), 7.97 (d, J=7.34 Hz, 1H), 7.79 (br. s, 1H), 7.42-7.55 (m, 4H), 6.86-6.94 (m, 1H), 6.84 (br. s, 1H), 5.34 (br. s, 1H), 4.62 (d, J=4.40 Hz, 2H), 4.26 (d, J=6.85 Hz, 2H), 1.29 (t, J=6.85 Hz, 3H); LCMS (m/z): 406.4 $[M+H]^+$.

Example 89

3-Hydroxypropyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 98]

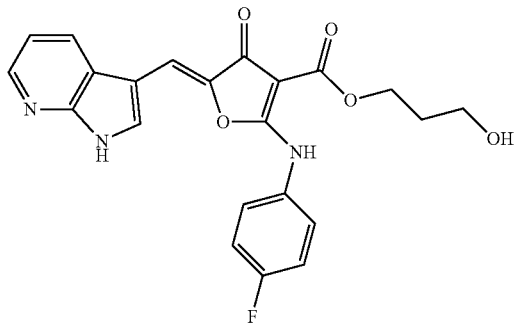

A solution of the compound of Example 51 and zinc cluster catalyst ($Zn_4(OCOCF_3)_6O$) (0.0019 g, 0.0020 mmol) in 1,3-propanediol (0.5 mL) and N,N-dimethylacetamide (0.5 mL) was stirred at 120° C. for 2 h then at 100° C. for 12 h. Cooled to ambient temperature, the reaction mixture was diluted with water, and the precipitate was collected by filtration. Ethyl acetate was added to the filtrate, and the precipitate was collected by filtration. Those precipitates were combined then purified by preparative HPLC to afford the titled compound as solid (0.0067 g, y. 16%).

$^1$H NMR (DMSO-$d_6$) δ (ppm) 12.22 (br. s, 1H), 10.72 (br. s, 1H), 8.24 (dd, J=1.38, 4.64 Hz, 1H), 7.97 (d, J=7.03 Hz, 1H), 7.72 (d, J=2.51 Hz, 1H), 7.50-7.60 (m, 2H), 7.35 (t, J=8.78 Hz, 2H), 6.89 (dd, J=4.52, 8.03 Hz, 1H), 6.81 (br. s, 1H), 4.77 (br. s, 1H), 4.25 (t, J=6.27 Hz, 2H), 3.59 (t, J=5.77 Hz, 2H), 1.79-1.87 (m, 2H); LCMS (m/z): 423.8 $[M+H]^+$.

Example 90

Isopropyl 5-[(1H-pyrrolo[2,3-b]pyridin-3-yl)methylene]-2-[(2,4-difluorophenyl)amino]-4-oxo-4,5-dihydrofuran-3-carboxylate

[Chemical Formula 99]

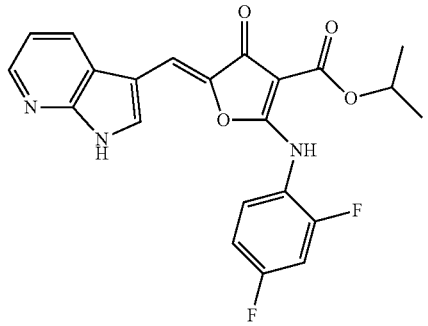

A solution of the compound (0.040 g, 0.10 mmol) of Example 86 and zinc cluster catalyst ($Zn_4(OCOCF_3)_6O$) (0.0012 g, 0.0013 mmol) in 2-propanol (0.5 mL) was stirred at 95° C. for 4 days. Cooled to ambient temperature, the reaction mixture was purified by preparative HPLC to afford the titled compound as solid (0.0061 g, y. 13%).

$^1$H NMR (DMSO-$d_6$) δ (ppm) 12.32 (br. s, 1H), 10.47 (s, 1H), 8.24 (dd, J=1.51, 4.52 Hz, 1H), 7.67-7.88 (m, 3H), 7.54-7.63 (m, 1H), 7.26-7.38 (m, 1H), 6.88 (s, 1H), 6.83 (dd, J=4.64, 7.91 Hz, 1H), 5.10-5.18 (m, 1H), 1.31 (d, J=6.27 Hz, 6H); LCMS (m/z): 426.2 $[M+H]^+$.

Example 91

2-(Dimethylamino)ethyl 5-[(1H-pyrrolo[2,3-b]pyridin-3-yl)methylene]-2-[(2,4-difluorophenyl)amino]-4-oxo-4,5-dihydrofuran-3-carboxylate

[Chemical Formula 100]

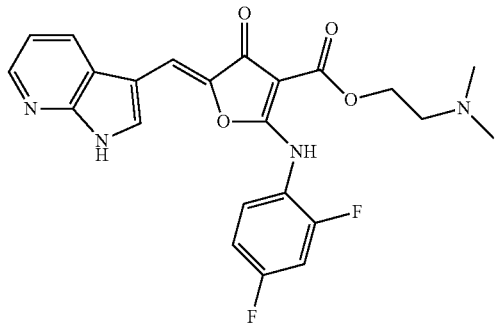

A solution of the compound (0.040 g, 0.10 mmol) of Example 86, 2-dimethylaminoethanol (0.10 mL, 1.0 mmol) and zinc cluster catalyst ($Zn_4(OCOCF_3)_6O$) (0.0019 g, 0.0020 mmol) in N,N-dimethylacetamide (0.9 mL) was stirred at 100° C. for 24 h. Cooled to ambient temperature, the precipitate was removed by filtration. The filtrate was purified by preparative HPLC to afford the titled compound as solid (0.010 g, y. 22%).

$^1$H NMR (DMSO-$d_6$) δ (ppm) 11.97 (br. s, 1H), 8.19 (dd, J=1.51, 4.52 Hz, 1H), 8.14 (s, 1H), 7.93 (d, J=7.78 Hz, 1H), 7.52 (br. s, 1H), 7.16-7.36 (m, 2H), 7.03-7.13 (m, 1H), 6.83 (dd, J=4.89, 7.91 Hz, 1H), 6.42 (s, 1H), 4.35 (t, J=5.27 Hz, 2H), 3.22 (t, J=5.27 Hz, 2H), 2.67-2.87 (m, 6H); LCMS (m/z): 455.2 $[M+H]^+$.

Example 92

5-[(1H-Pyrrolo[2,3-b]pyridin-3-yl)methylene]-2-[(2,4-difluorophenyl)amino]-4-oxo-4,5-dihydrofuran-3-carboxylic acid

[Chemical Formula 101]

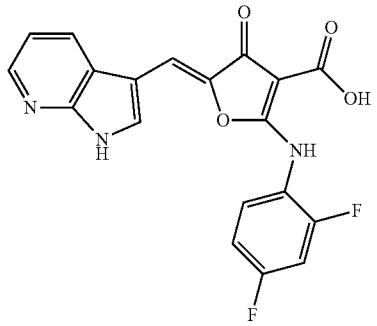

To a solution of the compound (0.20 g, 0.45 mmol) of Example 53 in ethanol (2.0 mL), aqueous 50% w/v potassium hydroxide solution (0.5 mL) was added at ambient temperature. The mixture was stirred at 95° C. for 3 h. Cooled to ambient temperature, diluted with water and conc. hydrochloric acid was added dropwise to neutralize. The precipitate was collected by filtration, washed with ethanol and diisopropyl ether then dried to afford the titled compound as solid (0.19 g, y. 98%).

$^1$H NMR (DMSO-$d_6$) δ (ppm) 12.36 (br. s, 1H), 8.25 (dd, J=1.51, 4.52 Hz, 1H), 7.86 (d, J=7.03 Hz, 1H), 7.69-7.82 (m, 2H), 7.57 (ddd, J=2.76, 8.97, 10.35 Hz, 1H), 7.25-7.37 (m, 1H), 7.01 (s, 1H), 6.85 (dd, J=4.77, 8.03 Hz, 1H); LCMS (m/z): 381.9 $[M-H]^-$ Example 93

Ethyl 5-[(1H-pyrrolo[2,3-b]pyridin-3-yl)methylene]-2-{[2-(2-hydroxyethoxy)-4-methylphenyl]amino}-4-oxo-4,5-dihydrofuran-3-carboxylate

[Chemical Formula 102]

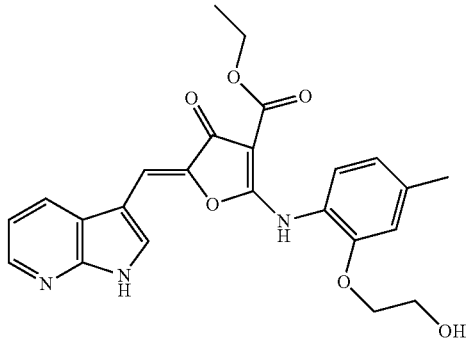

To a solution of ethyl 5-[(1H-pyrrolo[2,3-b]pyridin-3-yl)methylene]-2-[(2,4-difluorophenyl)amino]-4-oxo-4,5-dihydrofuran-3-carboxylate (0.017 g, 0.052 mmol) which similarly prepared according to the procedure described in the Example 29, First step and 7-azaindole-3-carboxaldehyde (0.0075 g, 0.051 mmol) in ethanol (0.2 mL), 2M hydrochloric acid in ethanol (0.052 mL, 0.10 mmol) was added at ambient temperature. The mixture was refluxed for 8.5 h. Cooled with ice bath, 2M sodium hydroxide solution (0.047 mL, 0.094 mmol) was added dropwise to neutralize then the solvent was removed under reduced pressure. The residue was purified by preparative HPLC to afford the titled compound as solid (0.0066 g, y. 28%).

$^1$H NMR (DMSO-$d_6$) δ (ppm) 12.30 (br. s, 1H), 10.22 (br. s, 1H), 8.25 (d, J=3.51 Hz, 1H), 8.03 (d, J=7.78 Hz, 1H), 7.83 (br. s, 1H), 7.43-7.56 (m, 1H), 7.10 (s, 1H), 6.85-6.95 (m, 3H), 4.79 (br. s, 1H), 4.26 (q, J=7.19 Hz, 2H), 4.06 (t, J=5.14 Hz, 2H), 3.62 (t, J=5.20 Hz, 2H), 2.42 (s, 3H), 1.29 (t, J=7.15 Hz, 3H); LCMS (m/z): 449.5 $[M+H]^+$.

Example 94

Methyl 5-[(1H-pyrrolo[2,3-b]pyridin-3-yl)methylene]-2-(cyclopropylamino)-4-oxo-4,5-dihydrofuran-3-carboxylate

[Chemical Formula 103]

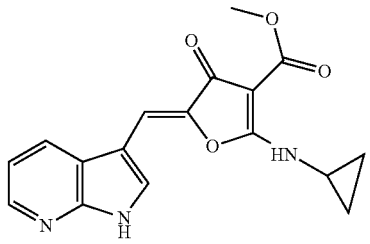

To a solution of methyl 2-(cyclopropylamino)-4-oxo-4,5-dihydrofuran-3-carboxylate (0.50 g, 2.5 mmol) which similarly prepared according to the procedure described in the Example 4, First step using dimethyl malonate, chloroacetyl chloride and cyclopropylamine, and 7-azaindole-3-carboxaldehyde (0.37 g, 2.5 mmol) in ethanol (6.0 mL), L-proline (0.029 g, 0.25 mmol) was added at ambient temperature. The mixture was refluxed for 16 h. Cooled to ambient temperature, the precipitate was collected by filtration, washed with methanol then dried to afford the titled compound as solid (0.012 g, y. 30%).

$^1$H NMR (DMSO-$d_6$) δ (ppm) 12.33 (br. s, 1H), 8.88 (br. s, 1H), 8.57 (d, J=7.82 Hz, 1H), 8.31 (d, J=3.91 Hz, 1H), 8.06 (s, 1H), 7.20 (dd, J=4.89, 7.82 Hz, 1H), 6.94 (s, 1H), 3.69 (s, 3H), 3.08-3.20 (m, 1H), 0.84-1.00 (m, 4H); LCMS (m/z): 326.0 $[M+H]^+$.

Example 95

Ethyl 5-[(1H-pyrrolo[2,3-b]pyridin-3-yl)methylene]-2-[(2-hydroxy-4-methylphenyl)amino]-4-oxo-4,5-dihydrofuran-3-carboxylate

[Chemical Formula 104]

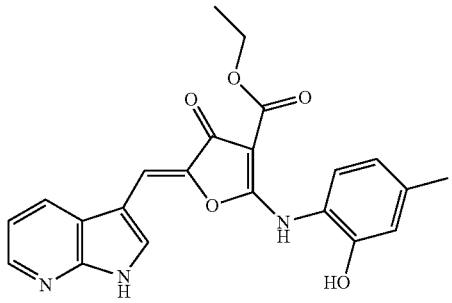

To a solution of ethyl 2-[(2-hydroxy-4-methylphenyl)amino]-4-oxo-4,5-dihydrofuran-3-carboxylate (0.10 g, 0.36 mmol) which similarly prepared according to the procedure described in the Example 74, Fourth step and 7-azaindole-3-carboxaldehyde (0.061 g, 0.42 mmol) in ethanol (2.5 mL), 2M hydrochloric acid in ethanol (0.56 mL, 1.1 mmol) was added at ambient temperature. The mixture was refluxed for 19 h. Cooled with ice bath, 2M sodium hydroxide solution (0.49 mL, 0.97 mmol) was added dropwise to neutralize, and ethanol (8.0 mL) was added and the mixture was refluxed for 30 min. The precipitate was collected by filtration, washed with hot ethanol. The solid was washed with hexane then dried to afford the titled compound as solid (0.027 g, y. 18%).

$^1$H NMR (DMSO-$d_6$) δ (ppm) 12.32 (br. s, 1H), 10.21 (s, 1H), 10.19 (s, 1H), 8.22-8.30 (m, 1H), 8.04 (d, J=7.53 Hz, 1H), 7.87 (d, J=2.26 Hz, 1H), 7.44 (d, J=8.03 Hz, 1H), 6.84-6.94 (m, 3H), 6.77 (d, J=8.03 Hz, 1H), 4.27 (q, J=7.03 Hz, 2H), 2.35 (s, 3H), 1.30 (t, J=7.03 Hz, 3H); LCMS (m/z): 405.9 $[M+H]^+$.

Example 96

Ethyl 5-[(1H-pyrrolo[2,3-b]pyridin-3-yl)methylene]-2-[(4-hydroxy-2-methylphenyl)amino]-4-oxo-4,5-dihydrofuran-3-carboxylate

[Chemical Formula 105]

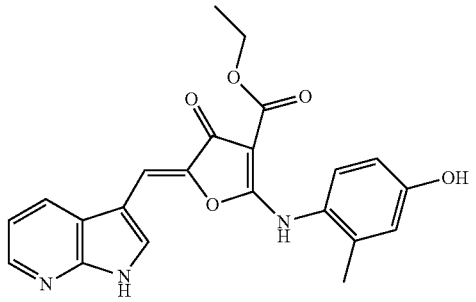

To a solution of ethyl 2-[(4-hydroxy-2-methylphenyl)amino]-4-oxo-4,5-dihydrofuran-3-carboxylate (0.10 g, 0.37 mmol) which similarly prepared according to the procedure described in the Example 74, Fourth step and 7-azaindole-3-carboxaldehyde (0.063 g, 0.43 mmol) in ethanol (2.5 mL), 2M hydrochloric acid in ethanol (0.46 mL, 0.92 mmol) was added at ambient temperature. The mixture was refluxed for 2.5 days. Cooled with ice bath, 2M sodium hydroxide solution (0.46 mL, 0.92 mmol) was added dropwise to neutralize, and ethanol (11 mL) was added and the mixture was refluxed for further 40 min. The precipitate was collected by filtration, washed with hot ethanol. The solid was washed with hexane then dried to afford the titled compound as solid (0.10 g, y. 70%).

$^1$H NMR (DMSO-$d_6$) δ (ppm) 12.27 (br. s, 1H), 10.20 (s, 1H), 9.76 (s, 1H), 8.20 (dd, J=1.25, 4.52 Hz, 1H), 7.81 (d, J=2.51 Hz, 1H), 7.64 (d, J=7.53 Hz, 1H), 7.28 (d, J=8.28 Hz, 1H), 6.72-6.87 (m, 4H), 4.26 (q, J=7.03 Hz, 2H), 2.16 (s, 3H), 1.29 (t, J=7.03 Hz, 3H); LCMS (m/z): 405.8 $[M+H]^+$.

Example 97

Ethyl 5-[(1H-pyrrolo[2,3-b]pyridin-3-yl)methylene]-2-[(4-fluoro-2-methylphenyl)amino]-4-oxo-4,5-dihydrofuran-3-carboxylate

[Chemical Formula 106]

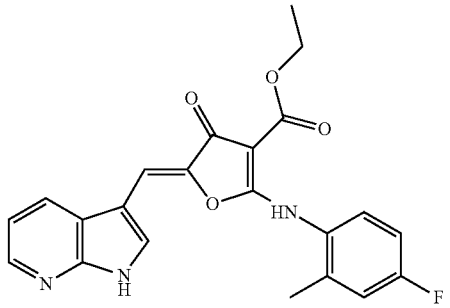

To a solution of ethyl 2-[(4-fluoro-2-methylphenyl)amino]-4-oxo-4,5-dihydrofuran-3-carboxylate (0.30 g, 1.1 mmol) which similarly prepared according to the procedure described in the Example 4, First step and 7-azaindole-3-carboxaldehyde (0.16 g, 1.1 mmol) in ethanol (7.0 mL), L-proline (0.013 g, 0.10 mmol) was added at ambient temperature. The mixture was refluxed for 3 days. Cooled to ambient temperature, the precipitate was collected by filtration, washed with methanol then dried to afford the titled compound as solid (0.25 g, y. 58%).

$^1$H NMR (DMSO-$d_6$) δ (ppm) 12.28 (br. s, 1H), 10.40 (s, 1H), 8.22 (d, J=3.91 Hz, 1H), 7.66-7.76 (m, 2H), 7.59 (dd, J=5.62, 8.56 Hz, 1H), 7.36 (dd, J=2.45, 9.78 Hz, 1H), 7.18-7.28 (m, 1H), 6.85 (s, 1H), 6.78 (dd, J=4.89, 7.83 Hz, 1H), 4.27 (q, J=7.01 Hz, 2H), 2.27 (s, 3H), 1.30 (t, J=7.09 Hz, 3H); LCMS (m/z): 408.4 [M+H]$^+$.

Example 98

Methyl 5-[(1H-pyrrolo[2,3-b]pyridin-3-yl)methylene]-2-[(2-methoxyethyl)amino]-4-oxo-4,5-dihydrofuran-3-carboxylate

[Chemical Formula 107]

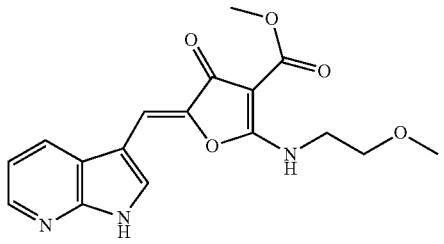

The titled compound (solid) was similarly prepared according to the procedure described in the Example 97.

$^1$H NMR (DMSO-$d_6$) δ (ppm) 12.36 (br. s, 1H), 8.94 (br. s, 1H), 8.44 (d, J=7.83 Hz, 1H), 8.31 (d, J=4.40 Hz, 1H), 8.03 (s, 1H), 7.19 (dd, J=4.40, 7.82 Hz, 1H), 6.92 (s, 1H), 3.76-3.84 (m, 2H), 3.71 (s, 3H), 3.62 (t, J=5.14 Hz, 2H), 3.31 (br. s, 3H); LCMS (m/z): 344.2 [M+H]$^+$.

Example 99

Ethyl 5-[(1H-pyrrolo[2,3-b]pyridin-3-yl)methylene]-2-{[4-(2-methoxyethoxy)-2-methylphenyl]amino}-4-oxo-4,5-dihydrofuran-3-carboxylate

[Chemical Formula 108]

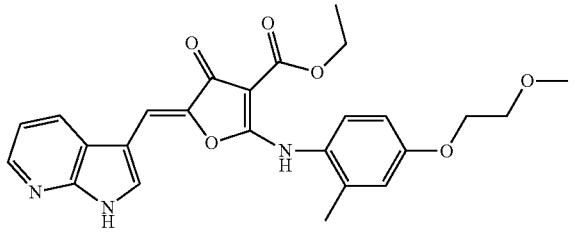

First Step

To a solution of ethyl 2-[(4-hydroxy-2-methylphenyl)amino]-4-oxo-4,5-dihydrofuran-3-carboxylate (0.10 g, 0.36 mmol) which similarly prepared according to the procedure described in the Example 74, Fourth step, 2-methoxyethanol (0.051 mL, 0.65 mmol) and triphenylphosphine (0.19 g, 0.72 mmol) in dichloromethane (2.0 mL) that cooled with ice bath, 2.2M diethyl azodicarboxylate (40% in toluene, 0.33 mL, 0.73 mmol) was added dropwise then the mixture was stirred at ambient temperature for 24 h. The reaction mixture was diluted with water, and extracted with chloroform. The organic layer was washed with 1M sodium hydroxide solution and brine, dried over magnesium sulfate and concentrated to afford ethyl 2-{[4-(2-methoxyethoxy)-2-methylphenyl]amino}-4-oxo-4,5-dihydrofuran-3-carboxylate as oil (0.30 g, crude material).

Second Step

To a solution of ethyl 2-{[4-(2-methoxyethoxy)-2-methylphenyl]amino}-4-oxo-4,5-dihydrofuran-3-carboxylate (0.12 g, 0.36 mmol, crude material) which afforded in the previous step and 7-azaindole-3-carboxaldehyde (0.043 g, 0.30 mmol) in ethanol (4.0 mL), 2M hydrochloric acid in ethanol (0.30 mL, 0.60 mmol) was added at ambient temperature. The mixture was refluxed for 24 h. Cooled with ice bath, 2M sodium hydroxide solution (0.30 mL, 0.60 mmol) was added dropwise to neutralize, and the solvent was removed under reduced pressure. The residue was suspended in chloroform, then the precipitate was collected by filtration, washed with water, ethanol and hexane then dried to afford the titled compound as solid (0.028 g, y. 12%).

$^1$H NMR (DMSO-$d_6$) δ (ppm) 11.78 (br. s, 1H), 8.13 (d, J=3.51 Hz, 1H), 7.89 (d, J=7.53 Hz, 1H), 7.47 (s, 1H), 6.77-6.90 (m, 3H), 6.72 (d, J=8.28 Hz, 1H), 6.12 (s, 1H), 4.05-4.14 (m, 2H), 3.66-3.74 (m, 2H), 3.36 (s, 3H), 3.28-3.35 (m, 2H), 2.08 (s, 3H), 1.22 (t, J=7.03 Hz, 3H); LCMS (m/z): 464.0 [M+H]$^+$.

Example 100

Ethyl 5-[(1H-pyrrolo[2,3-b]pyridin-3-yl)methylene]-2-{[2-methyl-4-(2-morpholinoethoxy)phenyl]amino}-4-oxo-4,5-dihydrofuran-3-carboxylate

[Chemical Formula 109]

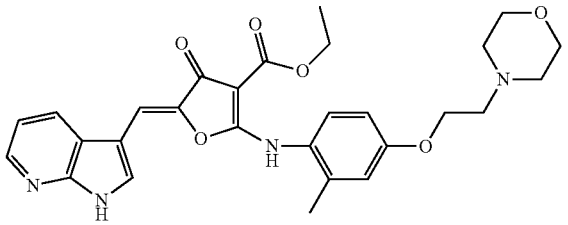

To a stirred solution of ethyl 2-({2-methyl-4-[2-(N-morpholino)ethoxy]phenyl}amino)-4-oxo-4,5-dihydrofuran-3-carboxylate (0.14 g, 0.36 mmol) which similarly prepared according to the procedure described in the Example 99, First step and 7-azaindole-3-carboxaldehyde (0.038 g, 0.26 mmol) in ethanol (4.0 mL), 2M hydrochloric acid in ethanol (0.60 mL, 1.2 mmol) was added at ambient temperature. The mixture was refluxed for 2 days. Cooled with ice bath, 2M sodium hydroxide solution (0.57 mL, 1.1 mmol) was added dropwise to neutralize and refluxed for further 10 min. Then the solvent was removed under reduced pressure. The precipitate was collected by filtration, washed with water and ethyl acetate then dried to afford the titled compound as solid (0.010 g, y. 5%).

$^1$H NMR (DMSO-$d_6$) δ (ppm) 12.28 (br. s, 1H), 10.29 (s, 1H), 8.19 (dd, J=1.26, 4.52 Hz, 1H), 7.77 (s, 1H), 7.67 (d, J=7.78 Hz, 1H), 7.42 (d, J=8.53 Hz, 1H), 7.05 (br. s, 1H), 6.95 (d, J=8.28 Hz, 1H), 6.83 (s, 1H), 6.74 (dd, J=4.77, 7.78 Hz, 1H), 4.27 (q, J=7.03 Hz, 2H), 4.15-4.23 (m, 2H), 3.58-3.68 (m, 4H), 2.74-2.82 (m, 2H), 2.50-2.60 (m, 4H), 2.23 (s, 3H), 1.30 (t, J=7.03 Hz, 3H); LCMS (m/z): 519.0 [M+H]$^+$.

Example 101

Methyl 5-[(1H-pyrrolo[2,3-b]pyridin-3-yl)methylene]-2-[(2-fluorobenzyl)amino]-4-oxo-4,5-dihydrofuran-3-carboxylate

[Chemical Formula 110]

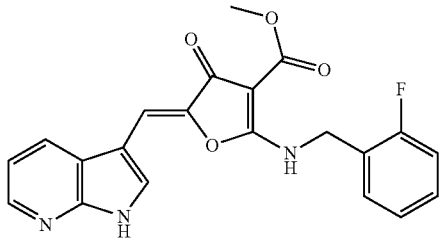

To a solution of methyl 2-[(2-fluorobenzyl)amino]-4-oxo-4,5-dihydrofuran-3-carboxylate (0.35 g, 1.5 mmol) which similarly prepared according to the procedure described in the Example 4, First step using dimethyl malonate, chloroacetyl chloride and 2-fluorobenzylamine, and 7-azaindole-3-carboxaldehyde (0.22 g, 1.5 mmol) in ethanol (10 mL), L-proline (0.018 g, 0.15 mmol) was added at ambient temperature. The mixture was refluxed for 3 days. Cooled to ambient temperature, the precipitate was collected by filtration, washed with methanol then dried to afford the titled compound as solid (0.13 g, y. 24%).

$^1$H NMR (DMSO-$d_6$) δ (ppm) 12.36 (br. s, 1H), 9.49 (br. s, 1H), 8.28 (br. s, 2H), 7.86 (br. s, 1H), 7.16-7.53 (m, 4H), 7.07 (br. s, 1H), 6.90 (br. s, 1H), 4.91 (br. s, 2H), 3.73 (br. s, 3H); LCMS (m/z): 394.4 [M+H]$^+$.

Example 102

Ethyl 5-[(1H-pyrrolo[2,3-b]pyridin-3-yl)methylene]-2-(3,4-dihydroisoquinolin-2(1H)-yl)-4-oxo-4,5-dihydrofuran-3-carboxylate

[Chemical Formula 111]

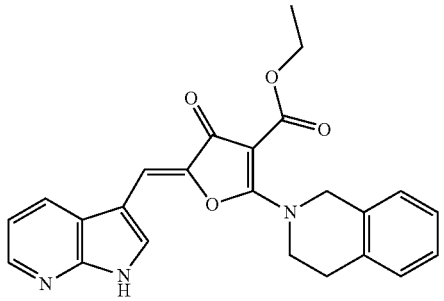

To a solution of ethyl 2-(3,4-dihydroisoquinolin-2(1H-)yl)-4-oxo-4,5-dihydrofuran-3-carboxylate (0.15 g, 0.60 mmol) which similarly prepared according to the procedure described in the Example 4, First step and 7-azaindole-3-carboxaldehyde (0.091 g, 0.60 mmol) in ethanol (5.0 mL), L-proline (0.0070 g, 0.060 mmol) was added at ambient temperature. The mixture was refluxed for 3 days. Cooled to ambient temperature, the precipitate was collected by filtration, washed with methanol then dried to afford the titled compound as solid (0.037 g, y. 14%).

$^1$H NMR (DMSO-$d_6$) δ (ppm) 12.36 (br. s, 1H), 8.42 (d, J=7.82 Hz, 1H), 8.33 (d, J=3.91 Hz, 1H), 8.07 (s, 1H), 7.17-7.37 (m, 5H), 6.90 (s, 1H), 4.98 (br. s, 2H), 4.21 (q, J=6.85 Hz, 2H), 3.97 (br. s, 2H), 3.09 (t, J=5.62 Hz, 2H), 1.27 (t, J=7.09 Hz, 3H); LCMS (m/z): 416.2 [M+H]$^+$.

Example 103

Ethyl 5-[(1H-pyrrolo[2,3-b]pyridin-3-yl)methylene]-2-(cyclopentylamino)-4-oxo-4,5-dihydrofuran-3-carboxylate

[Chemical Formula 112]

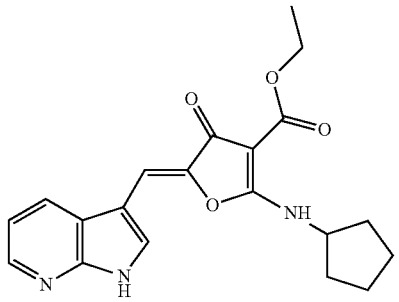

The titled compound (solid) was similarly prepared according to the procedure described in the Example 102.

$^1$H NMR (DMSO-$d_6$) δ (ppm) 12.32 (br. s, 1H), 8.53 (br. s, 1H), 8.42 (d, J=7.82 Hz, 1H), 8.32 (d, J=4.40 Hz, 1H), 8.01 (s, 1H), 7.20 (dd, J=4.40, 7.83 Hz, 1H), 6.90 (s, 1H), 4.50 (br. s, 1H), 4.21 (q, J=6.85 Hz, 2H), 2.02-2.15 (m, 2H), 1.57-1.71 (m, 6H), 1.26 (t, J=7.09 Hz, 3H); LCMS (m/z): 368.0 [M+H]$^+$.

Example 104

Methyl 5-[(1H-pyrrolo[2,3-b]pyridin-3-yl)methylene]-2-[(cyclopropylmethyl)amino]-4-oxo-4,5-dihydrofuran-3-carboxylate

[Chemical Formula 113]

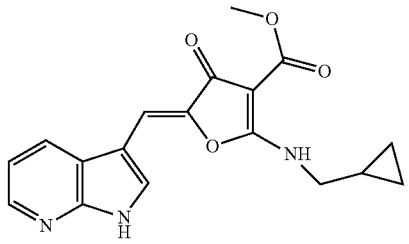

To a solution of methyl 2-[(cyclopropylmethyl)amino]-4-oxo-4,5-dihydrofuran-3-carboxylate (0.30 g, 1.4 mmol) which similarly prepared according to the procedure described in the Example 4, First step using dimethyl malonate, chloroacetyl chloride and cyclopropylmethylamine, and 7-azaindole-3-carboxaldehyde (0.21 g, 1.4 mmol) in ethanol (10 mL), L-proline (0.016 g, 0.14 mmol) was added at ambient temperature. The mixture was refluxed for 3 days. Cooled to ambient temperature, the precipitate was collected by filtration, washed with methanol then dried to afford the titled compound as solid (0.065 g, y. 14%).

$^1$H NMR (DMSO-$d_6$) δ (ppm) 12.33 (br. s, 1H), 9.08 (br. s, 1H), 8.42 (d, J=7.82 Hz, 1H), 8.31 (d, J=3.42 Hz, 1H), 8.00 (s, 1H), 7.19 (dd, J=4.40, 7.34 Hz, 1H), 6.92 (s, 1H), 3.72 (s, 3H), 3.52 (d, J=6.36 Hz, 2H), 1.23 (br. s, 1H), 0.52 (d, J=7.34 Hz, 2H), 0.37 (d, J=3.91 Hz, 2H); LCMS (m/z): 340.4 [M+H]$^+$.

Example 105

Ethyl 5-[(1H-pyrrolo[2,3-b]pyridin-3-yl)methylene]-2-isoindolinyl-4-oxo-4,5-dihydrofuran-3-carboxylate

[Chemical Formula 114]

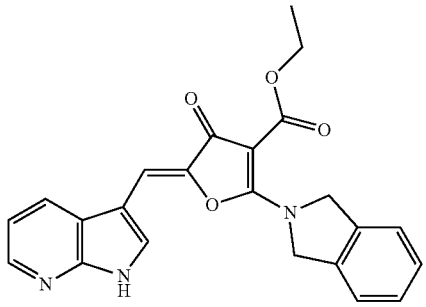

To a solution of ethyl 2-isoindolinyl-4-oxo-4,5-dihydrofuran-3-carboxylate (0.20 g, 0.70 mmol) which similarly prepared according to the procedure described in the Example 4, First step and 7-azaindole-3-carboxaldehyde (0.11 g, 0.70 mmol) in ethanol (10 mL), L-proline (0.0080 g, 0.070 mmol) was added at ambient temperature. The mixture was refluxed for 3 days. Cooled to ambient temperature, the precipitate was collected by filtration, washed with methanol then dried to afford the titled compound as solid (0.080 g, y. 27%).

$^1$H NMR (DMSO-$d_6$) δ (ppm) 12.39 (br. s, 1H), 8.44 (d, J=7.34 Hz, 1H), 8.33 (d, J=3.91 Hz, 1H), 8.08 (s, 1H), 7.43-7.53 (m, 2H), 7.33-7.43 (m, 2H), 7.23 (dd, J=4.89, 7.82 Hz, 1H), 6.91 (s, 1H), 5.37 (br. s, 2H), 5.17 (br. s, 2H), 4.23 (q, J=7.34 Hz, 2H), 1.29 (t, J=7.09 Hz, 3H); LCMS (m/z): 402.0 [M+H]$^+$.

Example 106

Ethyl 5-[(1H-pyrrolo[2,3-b]pyridin-3-yl)methylene]-4-oxo-2-[(1-phenylethyl)amino]-4,5-dihydrofuran-3-carboxylate

[Chemical Formula 115]

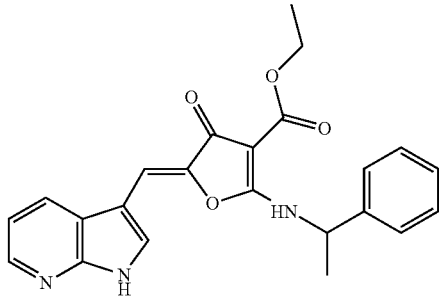

To a solution of ethyl 4-oxo-2-[(1-phenylethyl)amino]-4,5-dihydrofuran-3-carboxylate (0.40 g, 1.5 mmol) which similarly prepared according to the procedure described in the Example 4, First step and 7-azaindole-3-carboxaldehyde (0.21 g, 1.5 mmol) in ethanol (20 mL), L-proline (0.017 g, 0.15 mmol) was added at ambient temperature. The mixture was refluxed for 3 days. Cooled to ambient temperature, the precipitate was collected by filtration, washed with methanol then dried to afford the titled compound as solid (0.20 g, y. 34%).

$^1$H NMR (DMSO-$d_6$) δ (ppm) 12.35 (br. s, 1H), 8.97 (br. s, 1H), 8.25-8.34 (m, 2H), 7.82 (br. s, 1H), 7.49-7.57 (m, 2H), 7.38-7.45 (m, 2H), 7.24-7.33 (m, 1H), 7.12-7.19 (m, 1H), 6.86 (s, 1H), 5.41 (br. s, 1H), 4.24 (q, J=6.68 Hz, 2H), 1.70 (d, J=6.36 Hz, 3H), 1.27 (t, J=6.85 Hz, 3H); LCMS (m/z): 403.8 [M+H]$^+$.

Example 107

Ethyl 5-[(1H-pyrrolo[2,3-b]pyridin-3-yl)methylene]-2-[3-(2,6-dimethylpyridinyl)amino]-4-oxo-4,5-dihydrofuran-3-carboxylate

[Chemical Formula 116]

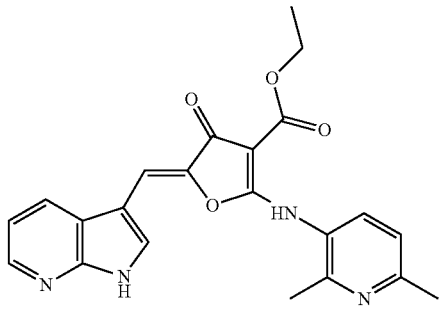

The titled compound (solid) was similarly prepared according to the procedure described in the Example 106.

$^1$H NMR (DMSO-$d_6$) δ (ppm) 12.27 (br. s, 1H), 10.47 (s, 1H), 8.21 (d, J=3.91 Hz, 1H), 7.81 (d, J=7.82 Hz, 1H), 7.64-7.76 (m, 2H), 7.27 (d, J=7.83 Hz, 1H), 6.84 (s, 1H), 6.74 (dd, J=4.65, 7.58 Hz, 1H), 4.26 (q, J=7.17 Hz, 2H), 2.57 (s, 3H), 2.41 (s, 3H), 1.29 (t, J=7.09 Hz, 3H); LCMS (m/z): 405.0 $[M+H]^+$.

Example 108

Ethyl 5-[(1H-pyrrolo[2,3-b]pyridin-3-yl)methylene]-2-[N-methyl-N-(2-thienylmethyl)amino]-4-oxo-4,5-dihydrofuran-3-carboxylate

[Chemical Formula 117]

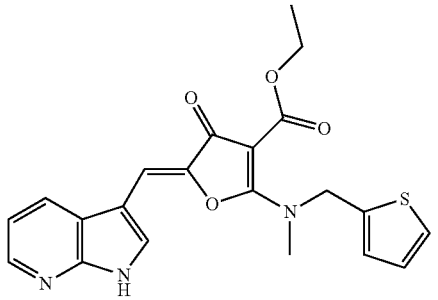

The titled compound (solid) was similarly prepared according to the procedure described in the Example 106.

$^1$H NMR (DMSO-$d_6$) δ (ppm) 12.33 (br. s, 1H), 8.37 (d, J=7.82 Hz, 1H), 8.30 (d, J=3.91 Hz, 1H), 8.03 (s, 1H), 7.53 (d, J=4.89 Hz, 1H), 7.14-7.23 (m, 2H), 7.01-7.07 (m, 1H), 6.91 (s, 1H), 5.20 (s, 2H), 4.18 (q, J=7.34 Hz, 2H), 3.26 (br. s, 3H), 1.23 (t, J=7.09 Hz, 3H); LCMS (m/z): 409.8 $[M+H]^+$.

Example 109

Ethyl 5-[(1H-pyrrolo[2,3-b]pyridin-3-yl)methylene]-4-oxo-2-thiomorpholino-4,5-dihydrofuran-3-carboxylate

[Chemical Formula 118]

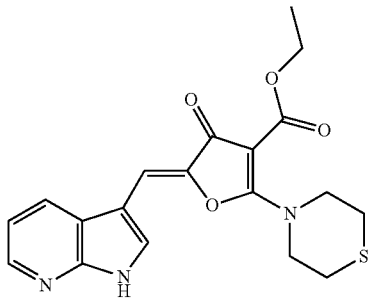

The titled compound (solid) was similarly prepared according to the procedure described in the Example 106.

$^1$H NMR (DMSO-$d_6$) δ (ppm) 12.33 (br. s, 1H), 8.27-8.45 (m, 2H), 7.94-8.04 (m, 1H), 7.20 (dd, J=4.65, 7.58 Hz, 1H), 6.88 (s, 1H), 4.17 (q, J=6.85 Hz, 2H), 4.02 (br. s, 4H), 2.89 (br. s, 4H), 1.25 (t, J=7.09 Hz, 3H); LCMS (m/z): 386.2 $[M+H]^+$.

Example 110

Ethyl 5-[(1H-pyrrolo[2,3-b]pyridin-3-yl)methylene]-2-(3-hydroxypiperidino)-4-oxo-4,5-dihydrofuran-3-carboxylate

[Chemical Formula 119]

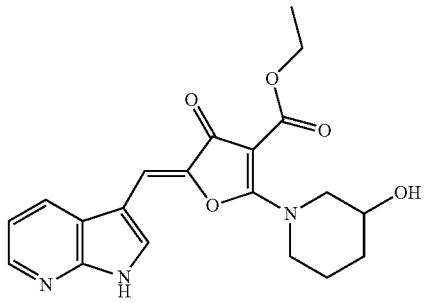

The titled compound (solid) was similarly prepared according to the procedure described in the Example 106.

$^1$H NMR (DMSO-$d_6$) δ (ppm) 12.32 (br. s, 1H), 8.39 (d, J=7.82 Hz, 1H), 8.31 (d, J=3.91 Hz, 1H), 7.93-8.00 (m, 1H), 7.20 (dd, J=4.40, 7.83 Hz, 1H), 6.85 (s, 1H), 5.11 (br. s, 1H), 4.17 (q, J=6.85 Hz, 2H), 3.85-3.94 (m, 1H), 3.72-3.84 (m, 2H), 3.54-3.65 (m, 1H), 3.41-3.53 (m, 1H), 1.83-2.02 (m, 2H), 1.51-1.69 (m, 2H), 1.25 (t, J=7.09 Hz, 3H); LCMS (m/z): 384.0 $[M+H]^+$.

Example 111

Ethyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3-carboxylate formate

[Chemical Formula 120]

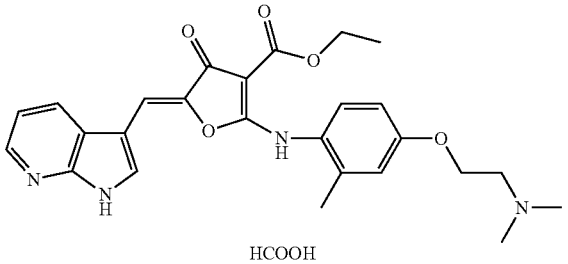

HCOOH

To a solution of ethyl 2-({4-[2-(dimethylamino)ethoxy]-2-methylphenyl}amino)-4-oxo-4,5-dihydrofuran-3-carboxylate (0.070 g, 0.20 mmol) which similarly prepared according to the procedure described in the Example 74, Fourth step and 7-azaindole-3-carboxaldehyde (0.029 g, 0.20 mmol) in ethanol (2.0 mL), piperidine (0.020 mL, 0.20 mmol) was added at ambient temperature. The mixture was refluxed for 5 days. Cooled to ambient temperature, the precipitate was collected by filtration then purified by preparative HPLC to afford the titled compound as solid (0.016 g, y. 16%).

$^1$H NMR (DMSO-$d_6$) δ (ppm) 12.28 (br. s, 1H), 10.53 (br. s, 1H), 8.18 (dd, J=1.63, 4.64 Hz, 1H), 8.16 (s, 1H), 7.76 (s, 1H), 7.67 (d, J=7.28 Hz, 1H), 7.41 (d, J=8.78 Hz, 1H), 7.04

(d, J=3.01 Hz, 1H), 6.94 (dd, J=2.89, 8.66 Hz, 1H), 6.82 (s, 1H), 6.75 (dd, J=4.77, 8.03 Hz, 1H), 4.26 (q, J=7.03 Hz, 2H), 4.16 (t, J=5.77 Hz, 2H), 2.74 (t, J=5.65 Hz, 2H), 2.30 (s, 6H), 2.28 (s, 3H), 1.29 (t, J=7.03 Hz, 3H); LCMS (m/z): 477.1 $[M+H]^+$.

Example 112

Ethyl 5-[(1H-pyrrolo[2,3-b]pyridin-3-yl)methylene]-4-oxo-2-[(2-phenyl-2-propinyl)amino]-4,5-dihydro-furan-3-carboxylate

[Chemical Formula 121]

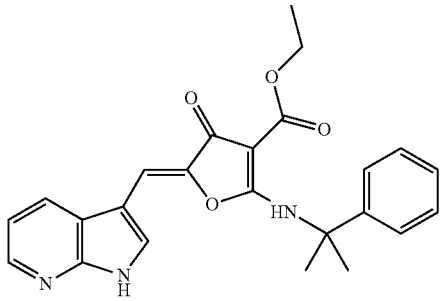

To a solution of ethyl 4-oxo-2-[(2-phenyl-2-propinyl) amino]-4,5-dihydrofuran-3-carboxylate (0.40 g, 1.4 mmol) which similarly prepared according to the procedure described in the Example 4, First step and 7-azaindole-3-carboxaldehyde (0.20 g, 1.4 mmol) in ethanol (10 mL), L-proline (0.016 g, 0.14 mmol) was added at ambient temperature. The mixture was refluxed for 3 days. Cooled to ambient temperature, the precipitate was collected by filtration, washed with methanol then dried to afford the titled compound as solid (0.15 g, y. 26%).

$^1$H NMR (DMSO-$d_6$) δ (ppm) 12.22 (br. s, 1H), 8.92 (br. s, 1H), 8.25 (d, J=3.42 Hz, 1H), 8.10 (d, J=7.82 Hz, 1H), 7.58 (d, J=7.34 Hz, 2H), 7.44-7.53 (m, 2H), 7.23-7.33 (m, 1H), 7.06 (dd, J=4.65, 7.09 Hz, 1H), 6.90 (br. s, 1H), 6.78 (br. s, 1H), 4.27 (q, J=6.52 Hz, 2H), 1.85 (br. s, 6H), 1.29 (t, J=6.85 Hz, 3H); LCMS (m/z): 418.0 $[M+H]^+$.

Example 113

Ethyl 5-[(1H-pyrrolo[2,3-b]pyridin-3-yl)methylene]-2-(2-adamantylamino)-4-oxo-4,5-dihydrofuran-3-carboxylate

[Chemical Formula 122]

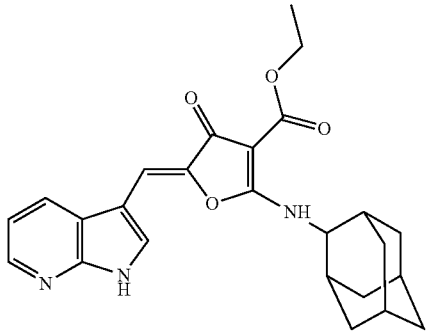

The titled compound (solid) was similarly prepared according to the procedure described in the Example 112.

$^1$H NMR (DMSO-$d_6$) δ (ppm) 12.37 (br. s, 1H), 8.71 (d, J=6.85 Hz, 1H), 8.42 (d, J=7.82 Hz, 1H), 8.32 (d, J=3.91 Hz, 1H), 7.99 (s, 1H), 7.20 (dd, J=4.89, 7.83 Hz, 1H), 6.92 (s, 1H), 4.30-4.40 (m, 1H), 4.24 (q, J=7.01 Hz, 2H), 2.10-2.19 (m, 2H), 1.81-1.99 (m, 8H), 1.67-1.80 (m, 4H), 1.27 (t, J=7.09 Hz, 3H); LCMS (m/z): 433.8 $[M+H]^+$.

Example 114

Ethyl 5-[(1H-pyrrolo[2,3-b]pyridin-3-yl)methylene]-2-[3-(6-methylpyridinyl)amino]-4-oxo-4,5-dihydro-furan-3-carboxylate

[Chemical Formula 123]

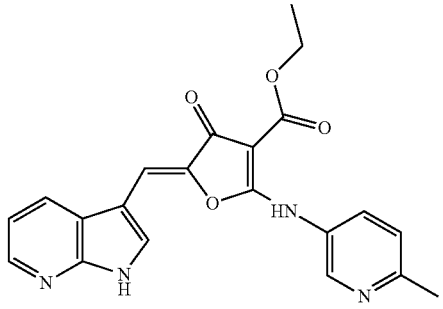

The titled compound (solid) was similarly prepared according to the procedure described in the Example 112.

$^1$H NMR (DMSO-$d_6$) δ (ppm) 12.23 (br. s, 1H), 8.41-8.61 (m, 2H), 8.25 (d, J=4.40 Hz, 1H), 8.02 (br. s, 1H), 7.79 (d, J=1.96 Hz, 1H), 7.50 (br. s, 1H), 6.89-7.00 (m, 1H), 6.78-6.89 (m, 1H), 4.08-4.28 (m, 2H), 2.27 (s, 3H), 1.18-1.30 (m, 3H); LCMS (m/z): 391.4 $[M+H]^+$.

Example 115

Ethyl 5-[(1H-pyrrolo[2,3-b]pyridin-3-yl)methylene]-2-[4-(3-methylpyridinyl)amino]-4-oxo-4,5-dihydro-furan-3-carboxylate

[Chemical Formula 124]

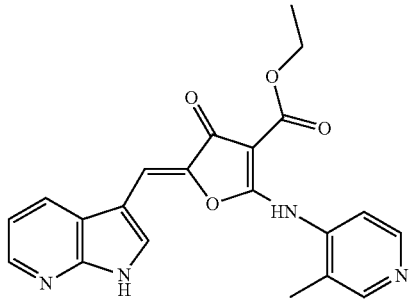

The titled compound (solid) was similarly prepared according to the procedure described in the Example 112.

$^1$H NMR (DMSO-$d_6$) δ (ppm) 12.23 (br. s, 1H), 8.41-8.61 (m, 2H), 8.25 (d, J=4.40 Hz, 1H), 8.02 (br. s, 1H), 7.79 (d, J=1.96 Hz, 1H), 7.50 (br. s, 1H), 6.89-7.00 (m, 1H), 6.83 (br. s, 1H), 4.19 (br. s, 2H), 2.27 (s, 3H), 1.24 (br. s, 3H); LCMS (m/z): 391.4 $[M+H]^+$.

Example 116

Ethyl 5-[(1H-pyrrolo[2,3-b]pyridin-3-yl)methylene]-2-[(trans-4-hydroxycyclohexyl)amino]-4-oxo-4,5-dihydrofuran-3-carboxylate

[Chemical Formula 125]

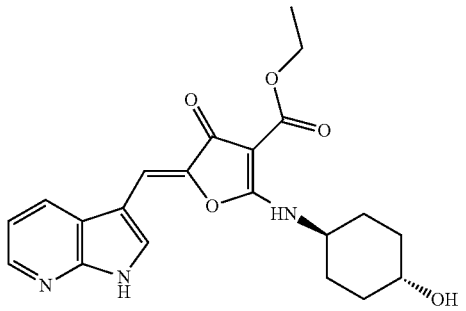

To a solution of ethyl 2-[(trans-4-hydroxycyclohexyl)amino]-4-oxo-4,5-dihydrofuran-3-carboxylate (0.30 g, 1.1 mmol) which similarly prepared according to the procedure described in the Example 4, First step and 7-azaindole-3-carboxaldehyde (0.16 g, 1.1 mmol) in ethanol (20 mL), L-proline (0.013 g, 0.11 mmol) was added at ambient temperature. The mixture was refluxed for 2 days. Cooled to ambient temperature, the precipitate was collected by filtration, washed with methanol then dried to afford the titled compound as solid (0.14 g, y. 40%).

$^1$H NMR (DMSO-$d_6$) δ (ppm) 12.36 (br. s, 1H), 8.39-8.54 (m, 2H), 8.33 (d, J=4.40 Hz, 1H), 7.99 (s, 1H), 7.20 (dd, J=4.89, 7.83 Hz, 1H), 6.89 (s, 1H), 4.69 (d, J=3.91 Hz, 1H), 4.20 (q, J=7.34 Hz, 2H), 3.97 (br. s, 1H), 3.41-3.53 (m, 1H), 1.86-2.03 (m, 4H), 1.61-1.76 (m, 2H), 1.29-1.42 (m, 2H), 1.25 (t, J=7.09 Hz, 3H); LCMS (m/z): 398.1 $[M+H]^+$.

Example 117

Ethyl 5-[(1H-pyrrolo[2,3-b]pyridin-3-yl)methylene]-2-[4-(2-fluoropyridinyl)amino]-4-oxo-4,5-dihydrofuran-3-carboxylate

[Chemical Formula 126]

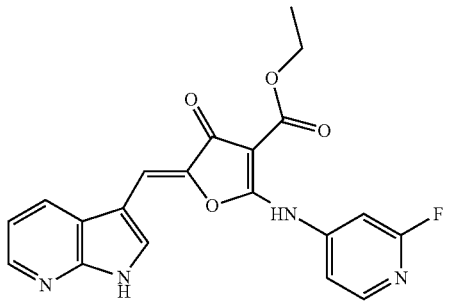

The titled compound (solid) was similarly prepared according to the procedure described in the Example 116.

$^1$H NMR (DMSO-$d_6$) δ (ppm) 12.44 (br. s, 1H), 10.86 (br. s, 1H), 8.30 (d, J=5.38 Hz, 2H), 8.21 (d, J=7.82 Hz, 1H), 7.94 (d, J=1.96 Hz, 1H), 7.63 (d, J=5.38 Hz, 1H), 7.44 (s, 1H), 7.00-7.09 (m, 2H), 4.29 (q, J=7.01 Hz, 2H), 1.30 (t, J=7.09 Hz, 3H); LCMS (m/z): 395.0 $[M+H]^+$.

Example 118

Ethyl 5-[(1H-pyrrolo[2,3-b]pyridin-3-yl)methylene]-2-[(5-indazolyl)amino]-4-oxo-4,5-dihydrofuran-3-carboxylate

[Chemical Formula 127]

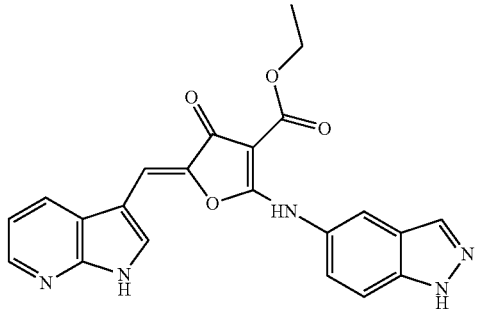

The titled compound (solid) was similarly prepared according to the procedure described in the Example 116.

$^1$H NMR (DMSO-$d_6$) δ (ppm) 13.36 (s, 1H), 12.25 (br. s, 1H), 10.62 (br. s, 1H), 8.17 (s, 1H), 8.09 (d, J=3.91 Hz, 1H), 7.99 (s, 1H), 7.78 (d, J=1.96 Hz, 1H), 7.63-7.72 (m, 2H), 7.52 (d, J=7.82 Hz, 1H), 6.85 (s, 1H), 6.12-6.27 (m, 1H), 4.28 (q, J=7.01 Hz, 2H), 1.30 (t, J=6.85 Hz, 3H); LCMS (m/z): 416.2 $[M+H]^+$.

Example 119

Ethyl 5-[(1H-pyrrolo[2,3-b]pyridin-3-yl)methylene]-2-[(5-benzimidazolyl)amino]-4-oxo-4,5-dihydrofuran-3-carboxylate

[Chemical Formula 128]

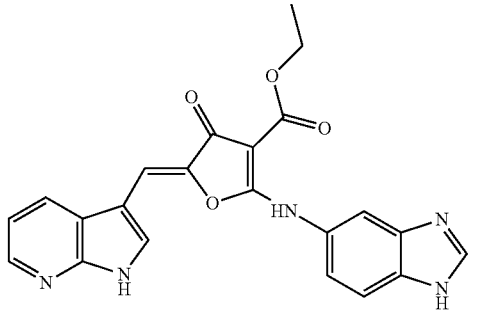

To a solution of ethyl 2-[(5-benzimidazolyl)amino]-4-oxo-4,5-dihydrofuran-3-carboxylate (0.30 g, 1.0 mmol) which similarly prepared according to the procedure described in the Example 74, Fourth step and 7-azaindole-3-carboxaldehyde (0.15 g, 1.0 mmol) in ethanol (5.0 mL), piperidine (0.20 mL, 3.1 mmol) was added at ambient temperature. The mixture was refluxed for 24 h. Cooled to ambient temperature, the precipitate was collected by filtration, washed with methanol then dried to afford the titled compound as solid (0.015 g, y. 4%).

$^1$H NMR (DMSO-$d_6$) δ (ppm) 12.28 (br. s, 1H), 10.82 (s, 1H), 9.55 (s, 1H), 8.16 (d, J=3.91 Hz, 1H), 8.08 (s, 1H), 7.98 (d, J=8.80 Hz, 1H), 7.87 (d, J=7.34 Hz, 1H), 7.59-7.89 (m, 1H), 7.74 (s, 1H), 6.93 (s, 1H), 6.53 (dd, J=4.89, 7.34 Hz, 1H), 4.30 (q, J=7.34 Hz, 2H), 1.31 (t, J=7.09 Hz, 3H); LCMS (m/z): 416.2 [M+H]$^+$.

Example 120

Ethyl 5-[(1H-pyrrolo[2,3-b]pyridin-3-yl)methylene]-2-indolinyl-4-oxo-4,5-dihydrofuran-3-carboxylate

[Chemical Formula 129]

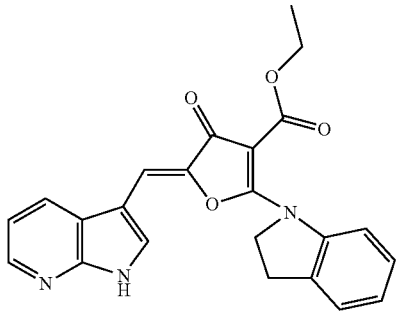

First Step

To a solution of potassium tert-butoxide (0.56 g, 5.0 mmol) in tetrahydrofuran (5.0 mL) that cooled with ice bath, a solution of indoline (0.36 g, 3.0 mmol) in tetrahydrofuran (5.0 mL) was added dropwise. The mixture was stirred at ambient temperature for 30 min. Then the reaction mixture was cooled with ice bath, a solution of ethyl 2-ethoxy-4-oxo-4,5-dihydrofuran-3-carboxylate (0.50 g, 2.5 mmol) which afforded in the Example 74, Third step dissolved in tetrahydrofuran (5.0 mL) was added dropwise. The mixture was stirred at ambient temperature for further 16 h. The reaction mixture was poured into ice water, extracted with ethyl acetate for 3 times. The combined organic layer was dried over sodium sulfate and concentrated. The residue was purified by chromatography on silica gel. Eluted with hexane/ethyl acetate to afford 2-indolinyl-4-oxo-4,5-dihydrofuran-3-carboxylate as solid (0.095 g, y. 8%).

$^1$H NMR (DMSO-$d_6$) δ (ppm) 7.49 (d, J=8.00 Hz, 1H), 7.35 (d, J=7.60 Hz, 1H), 7.24 (t, J=7.46 Hz, 1H), 7.13 (t, J=7.46 Hz, 1H), 4.73 (s, 2H), 4.05-4.20 (m, 4H), 3.20 (t, J=8.12 Hz, 2H), 1.21 (t, J=7.08 Hz, 3H); LCMS (m/z): 274.0 [M+H]$^+$.

Second Step

To a solution of 2-indolinyl-4-oxo-4,5-dihydrofuran-3-carboxylate (0.090 g, 0.32 mmol) and 7-azaindole-3-carboxaldehyde (0.048 g, 0.32 mmol) in ethanol (5.0 mL), L-proline (0.0040 g, 0.030 mmol) was added at ambient temperature. The mixture was refluxed for 2 days. Cooled to ambient temperature, the precipitate was collected by filtration, washed with ethanol then dried to afford the titled compound as solid (0.076 g, y. 58%).

$^1$H NMR (DMSO-$d_6$) δ (ppm) 12.40 (br. s, 1H), 8.36 (d, J=6.85 Hz, 1H), 8.31 (d, J=3.91 Hz, 1H), 8.01 (s, 1H), 7.56-7.63 (m, 1H), 7.44 (d, J=7.34 Hz, 1H), 7.33 (t, J=7.58 Hz, 1H), 7.21-7.27 (m, 1H), 7.12 (dd, J=4.89, 7.83 Hz, 1H), 7.00 (s, 1H), 4.26 (t, J=7.82 Hz, 2H), 4.19 (q, J=7.17 Hz, 2H), 3.24-3.28 (m, 2H), 1.22 (t, J=7.09 Hz, 3H); LCMS (m/z): 402.0 [M+H]$^+$.

Example 121

Ethyl 5-[(1H-pyrrolo[2,3-b]pyridin-3-yl)methylene]-2-(1,1-dioxidothiomorpholino)-4-oxo-4,5-dihydrofuran-3-carboxylate

[Chemical Formula 130]

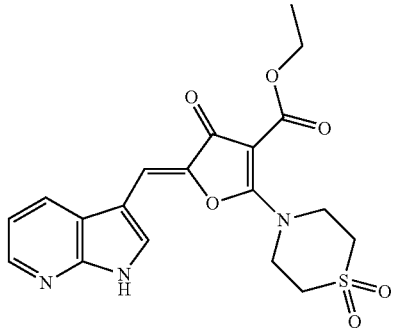

To a solution of ethyl 2-(1,1-dioxidothiomorpholino)-4-oxo-4,5-dihydrofuran-3-carboxylate (0.027 g, 0.092 mmol) which similarly prepared according to the procedure described in the Example 74, Fourth step and 7-azaindole-3-carboxaldehyde (0.014 g, 0.092 mmol) in ethanol (0.5 mL), piperidine (0.00092 mL, 0.0093 mmol) was added at ambient temperature. The mixture was refluxed for 2 days. The precipitate was collected by filtration, washed with hot ethanol. The solid was washed with hexane then dried to afford the titled compound as solid (0.037 g, y. 47%).

$^1$H NMR (DMSO-$d_6$) δ (ppm) 12.40 (br. s, 1H), 8.38 (d, J=8.03 Hz, 1H), 8.32 (dd, J=1.51, 4.77 Hz, 1H), 8.03 (d, J=2.51 Hz, 1H), 7.22 (dd, J=4.64, 7.91 Hz, 1H), 6.94 (s, 1H), 4.12-4.25 (m, 6H), 3.47-3.55 (m, 4H), 1.25 (t, J=7.03 Hz, 3H); LCMS (m/z): 418.0 [M+H]$^+$.

Example 122

Ethyl 5-[(1H-pyrrolo[2,3-b]pyridin-3-yl)methylene]-2-[3-(hydroxymethyl)piperidino]-4-oxo-4,5-dihydrofuran-3-carboxylate

[Chemical Formula 131]

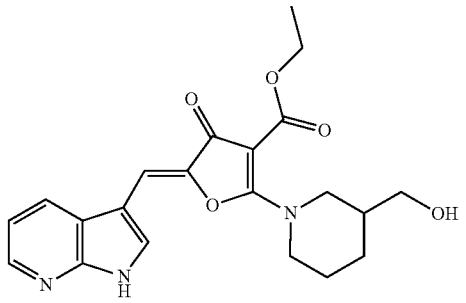

To a solution of ethyl 2-[(3-hydroxymethyl)piperidino]-4-oxo-4,5-dihydrofuran-3-carboxylate (0.30 g, 1.0 mmol) which similarly prepared according to the procedure described in the Example 74, Fourth step and 7-azaindole-3-carboxaldehyde (0.16 g, 1.0 mmol) in ethanol (5.0 mL), L-proline (0.0040 g, 0.030 mmol) was added at ambient temperature. The mixture was refluxed for 2 days. Cooled to ambient temperature, the precipitate was collected by filtration, washed with ethanol then dried to afford the titled compound as solid (0.045 g, y. 10%).

$^1$H NMR (DMSO-$d_6$) δ (ppm) 12.33 (br. s, 1H), 8.38 (d, J=7.82 Hz, 1H), 8.31 (d, J=4.40 Hz, 1H), 7.98 (s, 1H), 7.19 (dd, J=4.89, 7.82 Hz, 1H), 6.84 (s, 1H), 4.72 (br. s, 1H), 4.12-4.24 (m, 2H), 3.24-3.50 (m, 4H), 3.17 (t, J=11.74 Hz, 2H), 1.74-1.91 (m, 2H), 1.60-1.72 (m, 2H), 1.29-1.41 (m, 1H), 1.24 (t, J=6.85 Hz, 3H); LCMS (m/z): 398.2 $[M+H]^+$.

Example 123

2-(Dimethylamino)ethyl 5-[(1H-pyrrolo[2,3-b]pyridin-3-yl)methylene]-2-azepinyl-4-oxo-4,5-dihydrofuran-3-carboxylate formate

[Chemical Formula 132]

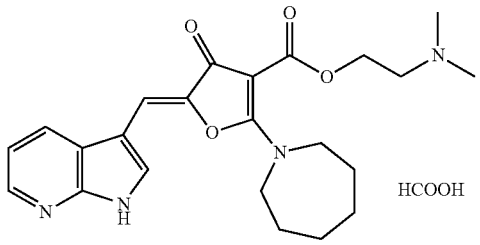

A solution of the compound (0.052 g, 0.14 mmol) of Example 63, 2-dimethylaminoethanol (0.14 mL, 1.4 mmol), zinc cluster catalyst ($Zn_4(OCOCF_3)_6O$) (0.0019 g, 0.0020 mmol) and 4-dimethylaminopyridine (0.0049 g, 0.040 mmol) in N,N-dimethylacetamide (1.0 mL) was stirred with the microwave synthesizer (Biotage Initiator™) at 150° C. for 1 h. The reaction mixture was purified by preparative HPLC to afford the titled compound as solid (0.018 g, y. 24%).

$^1$H NMR (DMSO-$d_6$) δ (ppm) 12.31 (br. s, 1H), 8.39 (dd, J=1.25, 7.78 Hz, 1H), 8.31 (dd, J=1.38, 4.64 Hz, 1H), 8.16 (s, 1H), 7.94 (d, J=1.76 Hz, 1H), 7.20 (dd, J=4.77, 7.78 Hz, 1H), 6.86 (s, 1H), 4.22 (t, J=5.77 Hz, 2H), 3.72-3.92 (m, 4H), 2.54-2.60 (m, 2H), 2.24 (s, 6H), 1.78-1.90 (m, 4H), 1.52-1.63 (m, 4H); LCMS (m/z): 425.1 $[M+H]^+$.

Example 124

Ethyl 5-[(1H-pyrrolo[2,3-b]pyridin-3-yl)methylene]-2-{[2-(3-methylthienyl)methyl]amino}-4-oxo-4,5-dihydrofuran-3-carboxylate

[Chemical Formula 133]

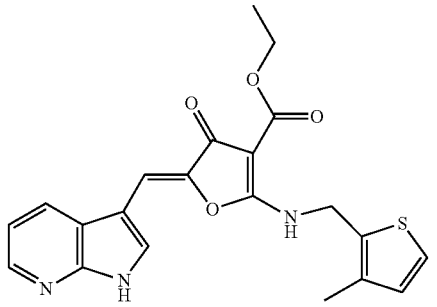

To a solution of ethyl 2-{[2-(3-methylthienyl)methyl]amino}-4-oxo-4,5-dihydrofuran-3-carboxylate (0.38 g, 1.4 mmol) which similarly prepared according to the procedure described in the Example 74, Fourth step and 7-azaindole-3-carboxaldehyde (0.20 g, 1.4 mmol) in ethanol (4.0 mL), piperidine (0.014 mL, 0.14 mmol) was added at ambient temperature. The mixture was refluxed for 5 days. The precipitate was collected by filtration, washed with hot ethanol. The solid was washed with hexane then dried to afford the titled compound as solid (0.12 g, y. 21%).

$^1$H NMR (DMSO-$d_6$) δ (ppm) 12.38 (br. s, 1H), 9.47 (t, J=6.27 Hz, 1H), 8.35 (d, J=8.03 Hz, 1H), 8.30 (dd, J=1.38, 4.64 Hz, 1H), 7.97 (d, J=2.26 Hz, 1H), 7.32 (d, J=5.02 Hz, 1H), 7.15 (dd, J=4.64, 7.91 Hz, 1H), 6.92 (s, 1H), 6.88 (d, J=5.02 Hz, 1H), 4.95 (d, J=6.27 Hz, 2H), 4.22 (q, J=7.03 Hz, 2H), 2.28 (s, 3H), 1.26 (t, J=7.03 Hz, 3H); LCMS (m/z): 410.0 $[M+H]^+$.

Example 125

Ethyl 5-[(1H-pyrrolo[2,3-b]pyridin-3-yl)methylene]-2-({4-[(2-hydroxyethyl)-N-methylamino]-2-methylphenyl}amino)-4-oxo-4,5-dihydrofuran-3-carboxylate

[Chemical Formula 134]

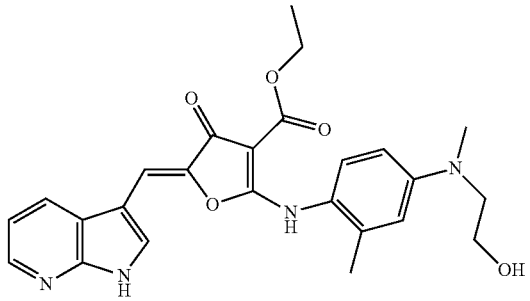

First Step

A solution of 5-fluoro-2-nitrotoluene (1.5 g, 9.6 mmol), N-methylethanolamine (0.90 mL, 0.012 mol) and triethylamine (1.6 mL, 0.012 mol) in N-methyl-2-pyrrolidone (15 mL) was stirred at 60° C. for 12 h. Cooled to ambient temperature, the reaction mixture was poured into ice water, extracted with ethyl acetate. The organic layer was washed with water and brine, dried over sodium sulfate and concentrated to afford 2-[(3-methyl-4-nitrophenyl)-N-methylamino]ethanol as solid (2.0 g, y. 98%).

$^1$H NMR (DMSO-$d_6$) δ (ppm) 7.99 (d, J=9.32 Hz, 1H), 6.58-6.71 (m, 2H), 4.78 (t, J=5.22 Hz, 1H), 3.46-3.63 (m, 4H), 3.06 (s, 3H), 2.56 (s, 3H); LCMS (m/z): 211.2 [M+H]$^+$.

Second Step

2-[(3-Methyl-4-nitrophenyl)-N-methylamino]ethanol (0.70 g, 3.3 mmol) was dissolved in ethanol (10 mL) and 10% palladium on carbon (0.050 g) was added at ambient temperature. The reaction mixture was agitated under a hydrogen atmosphere at ambient temperature for 4 h. Palladium on carbon was removed by filtration with Celite and the solvent was removed under reduced pressure to afford 2-[(4-amino-3-methylphenyl)-N-methylamino]ethanol as solid (0.58 g, y. 97%).

$^1$H NMR (DMSO-$d_6$) δ (ppm) 6.49 (d, J=8.44 Hz, 1H), 6.43 (d, J=2.60 Hz, 1H), 6.38 (q, J=6.13 Hz, 1H), 4.50 (t, J=5.38 Hz, 1H), 4.12 (br. s, 2H), 3.48 (dd, J=6.38, 12.00 Hz, 2H), 3.16 (t, J=6.58 Hz, 2H), 2.73 (s, 3H), 2.02 (s, 3H); LCMS (m/z): 181.1 [M+H]$^+$.

Third Step

A solution of ethyl 2-ethoxy-4-oxo-4,5-dihydrofuran-3-carboxylate (0.70 g, 3.5 mmol) which afforded in the Example 74, Third step and 2-[(4-amino-3-methylphenyl)-N-methylamino]ethanol (0.60 g, 3.5 mmol) in ethanol (8.3 mL) was stirred at ambient temperature for 16 h. The solvent was removed under reduced pressure, and ethanol was added to precipitate the product. The precipitate was collected by filtration, washed with ethanol then dried to afford 2-({4-[(2-hydroxyethyl)-N-methylamino]-2-methylphenyl}amino)-4-oxo-4,5-dihydrofuran-3-carboxylate as solid (0.60 g, y. 60%).

$^1$H NMR (DMSO-$d_6$) δ (ppm) 9.86 (br. s, 1H), 7.12 (d, J=8.76 Hz, 1H), 6.60 (d, J=2.60 Hz, 1H), 5.54 (dd, J=2.74, 8.80 Hz, 1H), 4.65 (br. s, 1H), 4.57 (s, 2H), 4.20 (q, J=7.06 Hz, 2H), 3.53 (t, J=6.14 Hz, 2H), 3.38 (t, J=6.22 Hz, 2H), 2.92 (s, 3H), 2.17 (s, 3H); LCMS (m/z): 335.0 [M+H]$^+$.

Fourth Step

To a solution of 2-({4-[(2-hydroxyethyl)-N-methylamino]-2-methylphenyl}amino)-4-oxo-4,5-dihydrofuran-3-carboxylate (0.20 g, 0.60 mmol) and 7-azaindole-3-carboxaldehyde (0.097 g, 0.60 mmol) in ethanol (11 mL), piperidine (0.10 mL, 1.0 mmol) was added at ambient temperature. The mixture was refluxed for 2 days. Cooled to ambient temperature, the precipitate was collected by filtration, washed with diethyl ether then dried to afford the titled compound as solid (0.055 g, y. 19%).

$^1$H NMR DMSO-$d_6$) δ (ppm) 12.22 (br. s, 1H), 10.12 (br. s, 1H), 8.15 (d, J=4.40 Hz, 1H), 7.77 (br. s, 1H), 7.68 (d, J=7.82 Hz, 1H), 7.22 (d, J=8.80 Hz, 1H), 6.77 (s, 1H), 6.67-6.73 (m, 2H), 6.63 (d, J=8.31 Hz, 1H), 4.69 (t, J=5.14 Hz, 1H), 4.23 (q, J=6.85 Hz, 2H), 3.55-3.63 (m, 2H), 3.43-3.50 (m, 2H), 3.01 (s, 3H), 2.15 (s, 3H), 1.26 (t, J=6.85 Hz, 3H); LCMS (m/z): 463.2 [M+H]$^+$.

Example 126

Ethyl 5-[(1H-pyrrolo[2,3-b]pyridin-3-yl)methylene]-2-({4-[(2-hydroxyethyl)amino]-2-methylphenyl}amino)-4-oxo-4,5-dihydrofuran-3-carboxylate

[Chemical Formula 135]

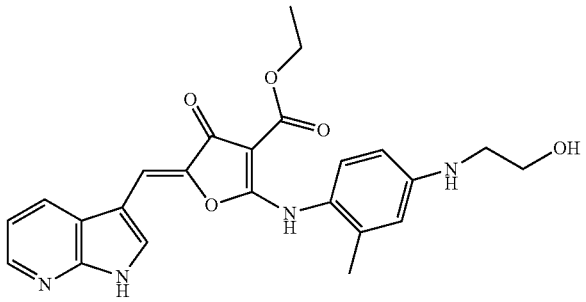

The titled compound (solid) was similarly prepared according to the procedure described in the Example 125.

$^1$H NMR (DMSO-$d_6$) δ (ppm) 12.25 (br. s, 1H), 10.11 (s 1H), 8.18 (d, J=4.40 Hz, 1H), 7.81-7.87 (m, 1H), 7.70 (d, J=7.83 Hz, 1H), 7.16 (d, J=8.31 Hz, 1H), 6.75-6.87 (m, 2H), 6.53-6.67 (m, 2H), 5.85 (t, J=5.38 Hz, 1H), 4.75 (t, J=5.38 Hz, 1H), 4.26 (q, J=6.85 Hz, 2H), 3.63 (q, J=5.87 Hz, 2H), 3.20 (q, J=5.71 Hz, 2H), 2.13 (s, 3H), 1.29 (t, J=7.09 Hz, 3H); LCMS (m/z): 449.2 [M+H]$^+$.

Example 127

Ethyl 5-[(1H-pyrrolo[2,3-b]pyridin-3-yl)methylene]-2-{[4-(2,3-dihydroxypropoxy)-2-methylphenyl]amino}-4-oxo-4,5-dihydrofuran-3-carboxylate

[Chemical Formula 136]

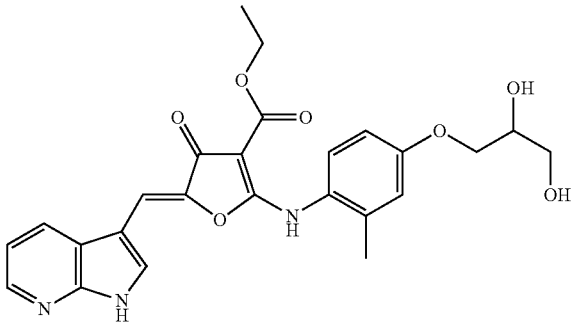

To a stirred solution of ethyl 2-{[4-(2,3-dihydroxypropoxy)-2-methylphenyl]amino}-4-oxo-4,5-dihydrofuran-3-carboxylate (0.17 g, 0.50 mmol) which similarly prepared according to the procedure described in the Example 74, First step to Fourth step and 7-azaindole-3-carboxaldehyde (0.070 g, 0.50 mmol) in ethanol (5.0 mL), piperidine (0.10 mL, 1.0 mmol) was added at ambient temperature. The mixture was refluxed for 2 days. Cooled to ambient temperature, the precipitate was collected by filtration, washed with diethyl ether then dried to afford the titled compound as solid (0.054 g, y. 23%).

$^1$H NMR (DMSO-$d_6$) δ (ppm) 12.28 (br. s, 1H), 10.30 (br. s, 1H), 8.18 (d, J=2.93 Hz, 1H), 7.78 (br. s, 1H), 7.64 (d, J=7.34 Hz, 1H), 7.41 (d, J=8.31 Hz, 1H), 7.03 (br. s, 1H), 6.94 (d, J=7.34 Hz, 1H), 6.82 (s, 1H), 6.70-6.79 (m, 1H), 5.06 (d, J=4.40 Hz, 1H), 4.76 (t, J=5.04 Hz, 1H), 4.20-4.32 (m, 2H), 4.05-4.15 (m, 1H), 3.93-4.02 (m, 1H), 3.83-3.92 (m, 1H), 3.47-3.57 (m, 2H), 2.22 (br. s, 3H), 1.29 (t, J=6.60 Hz, 3H); LCMS (m/z): 480.2 [M+H]$^+$.

Example 128

Ethyl 5-[(1H-pyrrolo[2,3-b]pyridin-3-yl)methylene]-2-({2-methyl-4-[2-(methylthio)ethoxy]phenyl}amino)-4-oxo-4,5-dihydrofuran-3-carboxylate

[Chemical Formula 137]

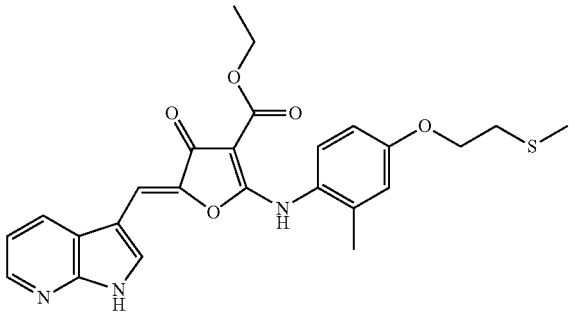

The titled compound (solid) was similarly prepared according to the procedure described in the Example 127.

$^1$H NMR (DMSO-$d_6$) δ (ppm) 12.28 (br. s, 1H), 10.30 (br. s, 1H), 8.19 (d, J=4.40 Hz, 1H), 7.77 (s, 1H), 7.65 (d, J=7.82 Hz, 1H), 7.42 (d, J=8.80 Hz, 1H), 7.05 (br. s, 1H), 6.95 (dd, J=2.69, 8.56 Hz, 1H), 6.82 (br. s, 1H), 6.76 (dd, J=4.40, 7.83 Hz, 1H), 4.21-4.32 (m, 4H), 2.94 (t, J=6.36 Hz, 2H), 2.23 (s, 3H), 2.22 (s, 3H), 1.29 (t, J=7.09 Hz, 3H); LCMS (m/z): 480.2 [M+H]$^+$.

Example 129

Ethyl 5-[(1H-pyrrolo[2,3-b]pyridin-3-yl)methylene]-2-({4-[(dimethylamino)methyl]-2-methylphenyl}amino)-4-oxo-4,5-dihydrofuran-3-carboxylate

[Chemical Formula 138]

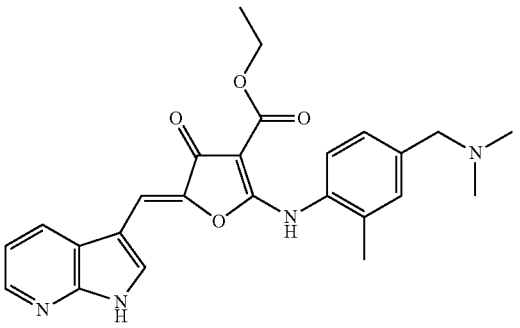

First Step

A solution of 3-methyl-4-nitrobenzyl bromide (1.0 g, 4.3 mmol), anhydrous dimethylamine (0.34 mL, 5.1 mmol) and potassium carbonate (1.5 g, 0.011 mol) in N,N-dimethylformamide (4.5 mL) was stirred at 70° C. for 12 h. Cooled to ambient temperature, the reaction mixture was poured into ice water, extracted with ethyl acetate. The organic layer was washed with water and brine, dried over sodium sulfate and concentrated to afford N,N-dimethyl-1-(3-methyl-4-nitrophenyl)methanamine as oil (0.80 g, y. 95%).

$^1$H NMR (DMSO-$d_6$) δ (ppm) 7.65 (d, J=8.32 Hz, 1H), 7.41 (s, 1H), 7.36 (d, J=8.36 Hz, 1H), 3.44 (s, 2H), 2.52 (s, 3H), 2.15 (s, 6H); LCMS (m/z): 195.4 [M+H]$^+$.

Second Step

N,N-Dimethyl-1-(3-methyl-4-nitrophenyl)methanamine (0.80 g, 4.1 mmol) was dissolved in ethanol (5.0 mL) and 10% palladium on carbon (0.18 g) was added at ambient temperature. The reaction mixture was agitated under a hydrogen atmosphere at ambient temperature for 4 h. Palladium on carbon was removed by filtration with Celite and the solvent was removed under reduced pressure to afford 4-[(dimethylamino)methyl]-2-methylaniline (0.65 g, y. 96%).

$^1$H NMR (DMSO-$d_6$) δ (ppm) 6.81 (s, 1H), 6.77 (d, J=7.92 Hz, 1H), 6.52 (d, J=7.96 Hz, 1H), 4.68 (s, 2H), 3.16 (s, 2H), 2.07 (s, 6H), 2.02 (s, 3H).

Third Step

A solution of ethyl 2-ethoxy-4-oxo-4,5-dihydrofuran-3-carboxylate (0.47 g, 2.3 mmol) which afforded in the Example 74, Third step and 4-[(dimethylamino)methyl]-2-methylaniline (0.35 g, 2.1 mmol) in ethanol (10 mL) was stirred at ambient temperature for 16 h. The solvent was removed under reduced pressure, and ethanol was added to precipitate the product. The precipitate was collected by filtration to afford ethyl 2-({4-[(dimethylamino)methyl]-2-methylphenyl}amino)-4-oxo-4,5-dihydrofuran-3-carboxylate (0.26 g, crude material) as solid.

$^1$H NMR (DMSO-$d_6$) δ (ppm) 10.18 (br. s, 1H), 7.48 (d, J=6.96 Hz, 1H), 7.25-7.40 (m, 2H), 4.65 (s, 2H), 4.23 (q, J=7.04 Hz, 2H), 2.40-2.60 (m, 9H), 1.26 (t, J=7.04 Hz, 3H); LCMS (m/z): 319.2 [M+H]$^+$.

Fourth Step

To a solution of ethyl 2-({4-[(dimethylamino)methyl]-2-methylphenyl}amino)-4-oxo-4,5-dihydrofuran-3-carboxylate (0.26 g, 0.82 mmol) and 7-azaindole-3-carboxaldehyde (0.12 g, 0.82 mmol) in ethanol (5.0 mL), piperidine (0.16 mL, 1.6 mmol) was added at ambient temperature. The mixture was refluxed for 2 days. Cooled to ambient temperature, the precipitate was collected by filtration, washed with diethyl ether then dried to afford the titled compound as solid (0.015 g, y. 4%).

$^1$H NMR (DMSO-$d_6$) δ (ppm) 12.26 (br. s, 1H), 8.20 (d, J=3.91 Hz, 1H), 8.15 (s, 1H), 7.82 (d, J=7.34 Hz, 1H), 7.72 (s, 1H), 7.47 (d, J=7.83 Hz, 1H), 7.37 (s, 1H), 7.30 (d, J=8.31 Hz, 1H), 6.83 (s, 1H), 6.79 (dd, J=4.89, 7.82 Hz, 1H), 4.26 (q, J=7.17 Hz, 2H), 3.54 (s, 2H), 2.22-2.29 (m, 9H), 1.29 (t, J=6.85 Hz, 3H); LCMS (m/z): 447.4 [M+H]$^+$ Example 130

Ethyl 5-[(1H-pyrrolo[2,3-b]pyridin-3-yl)methylene]-4-oxo-2-{[(1R,2S)-2-phenylcyclopropyl]amino}-4,5-dihydrofuran-3-carboxylate

[Chemical Formula 139]

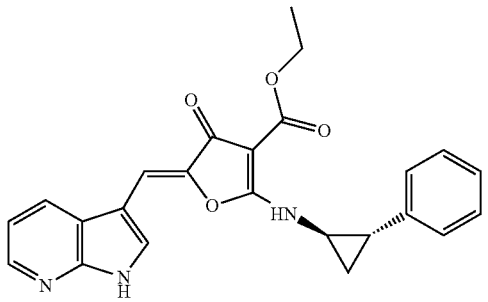

To a solution of ethyl 4-oxo-2-{[(1R,2S)-2-phenylcyclopropyl]amino}-4,5-dihydrofuran-3-carboxylate (0.090 g, 0.31 mmol) which similarly prepared according to the procedure described in the Example 74, Fourth step and 7-azaindole-3-carboxaldehyde (0.045 g, 0.30 mmol) in ethanol (5.0 mL), L-proline (0.0035 g, 0.031 mmol) was added at ambient temperature. The mixture was refluxed for 2 days. Cooled to ambient temperature, the solvent was removed under reduced pressure then the residue was purified by preparative HPLC to afford the titled compound as solid (0.018 g, y. 14%).

$^1$H NMR (DMSO-$d_6$) δ (ppm) 12.11 (br. s, 1H), 9.10 (br. s, 1H), 8.41 (d, J=7.34 Hz, 1H), 8.26 (d, J=3.91 Hz, 1H), 7.81 (s, 1H), 7.28-7.36 (m, 2H), 7.19-7.27 (m, 3H), 7.03 (dd, J=4.40, 7.82 Hz, 1H), 6.88 (s, 1H), 4.21 (q, J=6.85 Hz, 2H), 3.40-3.48 (m, 1H), 2.88-3.10 (m, 1H), 1.63-1.72 (m, 1H), 1.35-1.43 (m, 1H), 1.26 (t, J=7.08 Hz, 3H); LCMS (m/z): 415.8 [M+H]$^+$.

Example 131

Ethyl 5-[(1H-pyrrolo[2,3-b]pyridin-3-yl)methylene]-2-({4-[2-(2-hydroxyethoxy)ethoxy]-2-methylphenyl}amino)-4-oxo-4,5-dihydrofuran-3-carboxylate

[Chemical Formula 140]

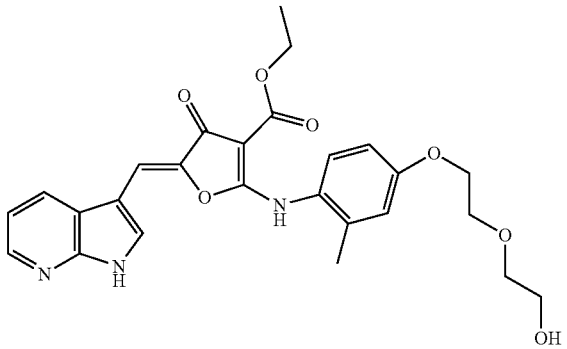

To a solution of ethyl 2-({4-[2-(2-hydroxyethoxy)ethoxy]-2-methylphenyl}amino)-4-oxo-4,5-dihydrofuran-3-carboxylate (0.15 g, 0.50 mmol) which similarly prepared according to the procedure described in the Example 74, First step to Fourth step and 7-azaindole-3-carboxaldehyde (0.070 g, 0.50 mmol) in ethanol (10 mL), L-proline (0.010 g, 0.087 mmol) was added at ambient temperature. The mixture was refluxed for 2 days. Cooled to ambient temperature, the precipitate was collected by filtration, washed with diethyl ether then dried to afford the titled compound (0.031 g, y. 15%) as solid.

$^1$H NMR (DMSO-$d_6$) δ (ppm) 12.28 (br. s, 1H), 10.29 (br. s, 1H), 8.20 (d, J=3.91 Hz, 1H), 7.75 (br. s, 1H), 7.68 (d, J=7.82 Hz, 1H), 7.42 (d, J=8.80 Hz, 1H), 7.05 (br. s, 1H), 6.95 (dd, J=2.40, 8.60 Hz, 1H), 6.83 (s, 1H), 6.77 (dd, J=4.40, 7.83 Hz, 1H), 4.64-4.70 (m, 1H), 4.26 (q, J=6.85 Hz, 2H), 4.17-4.23 (m, 2H), 3.79-3.87 (m, 2H), 3.52-3.62 (m, 4H), 2.23 (s, 3H), 1.29 (t, J=6.85 Hz, 3H); LCMS (m/z): 494.0 [M+H]$^+$.

Example 132

Ethyl 5-[(1H-pyrrolo[2,3-b]pyridin-3-yl)methylene]-2-{[4-(3-hydroxypropoxy)-2-methylphenyl]amino}-4-oxo-4,5-dihydrofuran-3-carboxylate

[Chemical Formula 141]

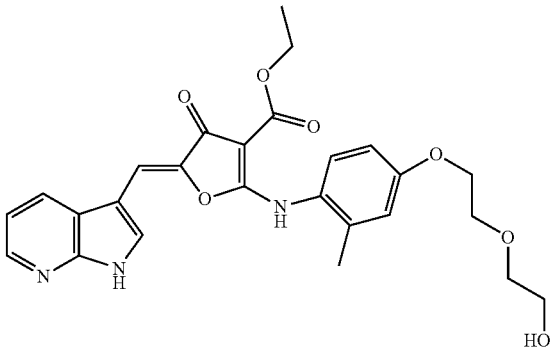

The titled compound (solid) was similarly prepared according to the procedure described in the Example 131.

$^1$H NMR (DMSO-$d_6$) δ (ppm) 12.25 (br. s, 1H), 8.19 (d, J=4.40 Hz, 1H), 7.74 (s, 1H), 7.67 (d, J=7.82 Hz, 1H), 7.36 (d, J=8.80 Hz, 1H), 7.00 (d, J=2.4 Hz, 1H), 6.91 (d, J=8.31 Hz, 1H), 6.71-6.79 (m, 2H), 4.59-4.65 (m, 1H), 4.25 (q, J=6.85 Hz, 2H), 4.14 (t, J=6.11 Hz, 2H), 3.60-3.67 (m, J=5.38 Hz, 2H), 2.21 (s, 3H), 1.94 (t, J=6.11 Hz, 2H), 1.28 (t, J=7.06 Hz, 3H); LCMS (m/z): 464.2 [M+H]$^+$.

Example 133

Ethyl 2-({4-[2-(1H-pyrrol-1-yl)ethoxy]-2-methylphenyl}amino)-5-[(1H-pyrrolo[2,3-b]pyridin-3-yl)methylene]-4-oxo-4,5-dihydrofuran-3-carboxylate

[Chemical Formula 142]

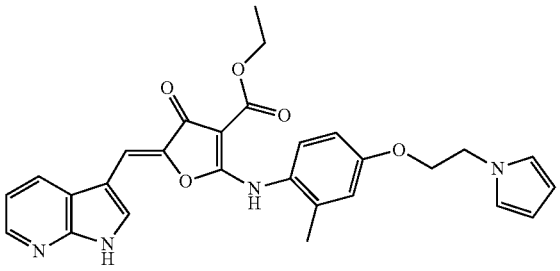

The titled compound (solid) was similarly prepared according to the procedure described in the Example 131.

$^1$H NMR (DMSO-$d_6$) δ (ppm) 12.04 (br. s, 1H), 8.08 (d, J=3.91 Hz, 1H), 7.60-7.76 (m, 2H), 7.16 (br. s, 1H), 6.88-6.94 (m, 3H), 6.84 (d, J=7.82 Hz, 1H), 6.60-6.68 (m, 1H), 6.48-6.57 (m, 1H), 6.02-6.07 (m, 2H), 4.22-4.37 (m, 4H), 4.13-4.22 (m, 2H), 2.14 (s, 3H), 1.25 (t, J=6.85 Hz, 3H); LCMS (m/z): 499.2 $[M+H]^+$.

Example 134

Ethyl 5-[(1H-pyrrolo[2,3-b]pyridin-3-yl)methylene]-2-{[2-methyl-4-(1-pyrrolidinylmethyl)phenyl]amino}-4-oxo-4,5-dihydrofuran-3-carboxylate

[Chemical Formula 143]

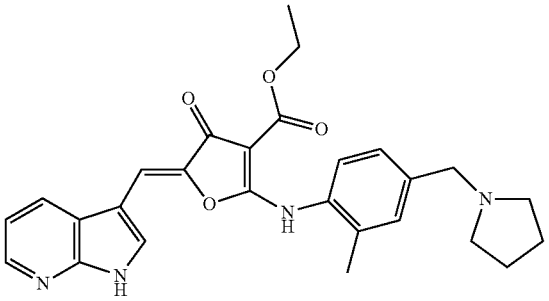

To a solution of 2-{[2-methyl-4-(1-pyrrolidinylmethyl)phenyl]amino}-4-oxo-4,5-dihydrofuran-3-carboxylate (0.25 g, 0.70 mmol) which similarly prepared according to the procedure described in the Example 129, First step to Third step and 7-azaindole-3-carboxaldehyde (0.10 g, 0.70 mmol) in ethanol (10 mL), piperidine (0.014 mL, 0.14 mmol) was added at ambient temperature. The mixture was refluxed for 2 days. Cooled to ambient temperature then the reaction mixture was purified by preparative HPLC to afford the titled compound as solid (0.035 g, y. 10%).

$^1$H NMR (DMSO-$d_6$) δ (ppm) 12.27 (br. s, 1H), 8.20 (d, J=3.91 Hz, 1H), 8.14 (s, 1H), 7.72-7.82 (m, 2H), 7.48 (d, J=7.83 Hz, 1H), 7.41 (s, 1H), 7.34 (d, J=7.34 Hz, 1H), 6.76-6.86 (m, 2H), 4.26 (q, J=6.85 Hz, 2H), 3.81 (br. s, 2H), 2.57-2.69 (m, 4H), 2.27 (s, 3H), 1.70-1.85 (m, 4H), 1.29 (t, J=6.85 Hz, 3H); LCMS (m/z): 473.2 $[M+H]^+$.

Example 135

Ethyl 5-[(1H-pyrrolo[2,3-b]pyridin-3-yl)methylene]-2-({2-methyl-4-[(4-methylpiperazinyl)methyl]phenyl}amino)-4-oxo-4,5-dihydrofuran-3-carboxylate

[Chemical Formula 144]

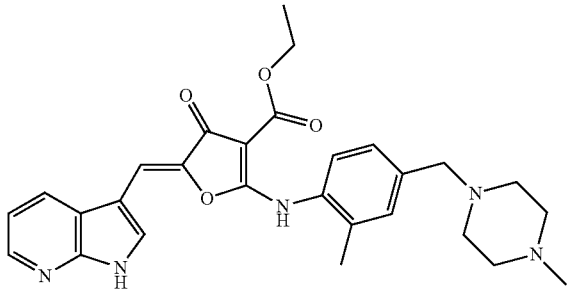

The titled compound (solid) was similarly prepared according to the procedure described in the Example 134.

$^1$H NMR (DMSO-$d_6$) δ (ppm) 12.43 (br. s, 1H), 8.18 (br. s, 1H), 8.01 (br. s, 1H), 7.41 (br. s, 1H), 6.99-7.17 (m, 3H), 6.87 (br. s, 2H), 6.40 (d, J=12.72 Hz, 1H), 4.26 (br. s, 2H), 3.57 (br. s, 2H), 2.42 (br. s, 8H), 2.28 (br. s, 3H), 2.08 (br. s, 3H), 1.12-1.39 (m, 3H); LCMS (m/z): 502.4 $[M+H]^+$.

Example 136

Ethyl 5-[(1H-pyrrolo[2,3-b]pyridin-3-yl)methylene]-2-{[2-methyl-4-(morpholinomethyl)phenyl]amino}-4-oxo-4,5-dihydrofuran-3-carboxylate

[Chemical Formula 145]

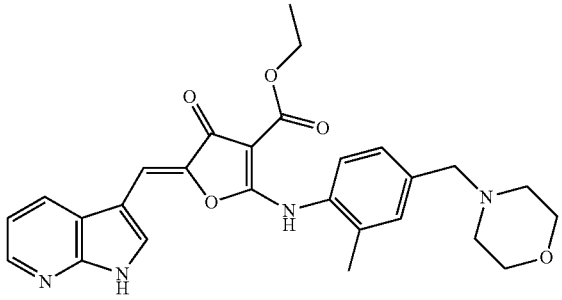

The titled compound (solid) was similarly prepared according to the procedure described in the Example 134.

$^1$H NMR (DMSO-$d_6$) δ (ppm) 12.29 (br. s, 1H), 10.38 (br. s, 1H), 8.21 (d, J=4.40 Hz, 1H), 7.72-7.83 (m, 2H), 7.46-7.54 (m, 1H), 7.28-7.44 (m, 2H), 6.86 (s, 1H), 6.75-6.81 (m, 1H), 4.27 (q, J=7.17 Hz, 2H), 3.51-3.74 (m, 6H), 2.35-2.59 (m, 4H), 2.27 (s, 3H), 1.30 (t, J=7.09 Hz, 3H); LCMS (m/z): 489.2 $[M+H]^+$.

Example 137

Ethyl 5-[(1H-pyrrolo[2,3-b]pyridin-3-yl)methylene]-2-[(4-{[2-(dimethylamino)ethyl]amino}-2-methylphenyl)amino]-4-oxo-4,5-dihydrofuran-3-carboxylate formate

[Chemical Formula 146]

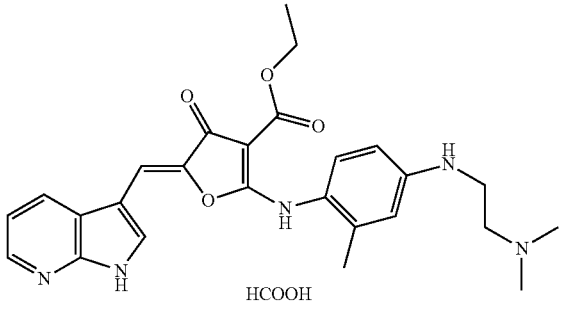

To a solution of ethyl 2-[(4-{[2-(dimethylamino)ethyl]amino}-2-methylphenyl)amino]-4-oxo-4,5-dihydrofuran-3-carboxylate (0.27 g, 0.70 mmol) which similarly prepared according to the procedure described in the Example 125, First step to Third step and 7-azaindole-3-carboxaldehyde (0.11 g, 0.70 mmol) in ethanol (5.0 mL), piperidine (0.10 mL, 1.0 mmol) was added at ambient temperature. The mixture was refluxed for 16 h. Cooled to ambient temperature, the solvent was removed under reduced pressure then the residue was purified by preparative HPLC to afford the titled compound as solid (0.015 g, y. 8%).

$^1$H NMR (DMSO-$d_6$) δ (ppm) 12.29 (br. s, 1H), 10.12 (br. s, 1H), 8.11-8.23 (m, 2H), 7.86 (s, 1H), 7.67 (d, J=7.82 Hz, 1H), 7.17 (d, J=8.31 Hz, 1H), 6.75-6.83 (m, 2H), 6.51-6.69 (m, 2H), 5.79 (br. s, 1H), 4.25 (q, J=6.85 Hz, 2H), 3.16-3.28 (m, 2H), 2.58 (t, J=6.11 Hz, 2H), 2.29 (s, 6H), 2.13 (s, 3H), 1.29 (t, J=6.85 Hz, 3H); LCMS (m/z): 476.0 [M+H]$^+$.

Example 138

2-Methoxyethyl 5-[(1H-pyrrolo[2,3-b]pyridin-3-yl) methylene]-2-azepinyl-4-oxo-4,5-dihydrofuran-3-carboxylate

[Chemical Formula 147]

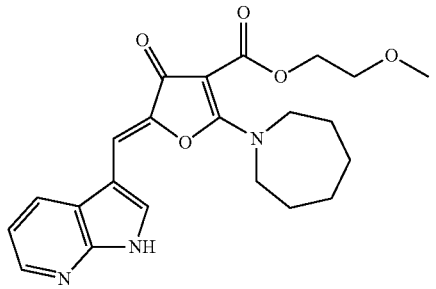

First Step

A solution of ethyl malonyl chloride (0.10 mL, 0.78 mmol) and 2-methoxyethanol (0.061 mL, 0.78 mmol) in dichloromethane (1.5 mL) was cooled with ice bath. To this solution, triethylamine (0.13 mL, 0.94 mmol) was added and stirred at ambient temperature for 1.5 h. The reaction mixture was diluted with water, extracted with dichloromethane. The organic layer was washed with brine, dried over magnesium sulfate and concentrated. The residue was purified by chromatography on silica gel(hexane/ethyl acetate) to afford ethyl 2-methoxyethyl malonate (0.10 g, y. 69%) as oil.

$^1$H NMR ($CDCl_3$) δ (ppm) 4.28-4.34 (m, 2H), 4.21 (q, J=7.11 Hz, 2H), 3.59-3.64 (m, 2H), 3.42 (s, 2H), 3.39 (s, 3H), 1.29 (t, J=7.15 Hz, 3H)

Second Step

A solution of ethyl 2-methoxyethyl malonate (0.10 g, 0.53 mmol) in anhydrous tetrahydrofuran (1.5 mL) was added dropwise to a solution of sodium hydride (60% w/w in oil, 0.043 g, 1.1 mmol) in anhydrous tetrahydrofuran (2.0 mL) that cooled with ice bath. The mixture was refluxed for 5 min. The reaction mixture was cooled with ice bath, chloroacetyl chloride (0.042 mL, 0.53 mmol) was added dropwise to the reaction mixture and the mixture was stirred for 1 h then stirred with heating at 45° C. for 1 h. The reaction mixture was cooled to ambient temperature then hexamethyleneimine (0.071 mL, 0.63 mmol) was added dropwise and the mixture was stirred at ambient temperature for further 1 h. The reaction mixture was diluted with water, and extracted with chloroform. The organic layer was dried over magnesium sulfate and concentrated. The residue was purified by chromatography on silica gel, eluted with chloroform/methanol to afford 2-methoxyethyl 2-azepinyl-4-oxo-4,5-dihydrofuran-3-carboxylate as oil (0.065 g, y. 43%).

$^1$H NMR ($CDCl_3$) δ (ppm) 4.51 (s, 2H), 4.35-4.39 (m, 2H), 3.56-3.75 (m, 6H), 3.40 (s, 3H), 1.80 (br. s, 4H), 1.61 (br. s, 4H); LCMS (m/z): 284.1 [M+H]$^+$.

Third Step

To a solution of 2-methoxyethyl 2-azepinyl-4-oxo-4,5-dihydrofuran-3-carboxylate (0.065 g, 0.23 mmol) and 7-azaindole-3-carboxaldehyde (0.033 g, 0.23 mmol) in ethanol (0.5 mL), hexamethyleneimine (0.026 mL, 0.023 mmol) was added at ambient temperature. The mixture was refluxed for 3 days. Cooled to ambient temperature, the precipitate was collected by filtration, washed with ethanol and hexane then dried to afford the titled compound as solid (0.019 g, y. 20%).

$^1$H NMR (DMSO-$d_6$) δ (ppm) 12.31 (br. s, 1H), 8.39 (dd, J=1.38, 7.91 Hz, 1H), 8.31 (dd, J=1.38, 4.64 Hz, 1H), 7.94 (s, 1H), 7.20 (dd, J=4.64, 7.91 Hz, 1H), 6.85 (s, 1H), 4.21-4.28 (m, 2H), 3.70-3.90 (m, 4H), 3.54-3.62 (m, 2H), 3.29 (s, 3H), 1.78-1.91 (m, 4H), 1.51-1.63 (m, 4H); LCMS (m/z): 412.1 [M+H]$^+$.

Example 139

Isopropyl 5-[(1H-pyrrolo[2,3-b]pyridin-3-yl)methylene]-2-azepinyl-4-oxo-4,5-dihydrofuran-3-carboxylate

[Chemical Formula 148]

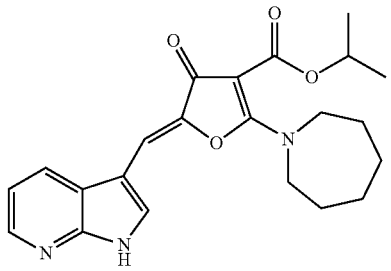

To a stirred solution of isopropyl 2-azepinyl-4-oxo-4,5-dihydrofuran-3-carboxylate (0.033 g, 0.12 mmol) which similarly prepared according to the procedure described in the Example 4, First step and 7-azaindole-3-carboxaldehyde (0.019 g, 0.13 mmol) in 2-propanol (1.0 mL), hexamethyleneimine (0.0014 mL, 0.012 mmol) was added at ambient temperature. The mixture was refluxed for 12 days. Cooled to ambient temperature, the reaction mixture was purified by preparative HPLC to afford the titled compound as solid (0.024 g, y. 49%).

$^1$H NMR (DMSO-$d_6$) δ (ppm) 12.30 (br. s, 1H), 8.37 (dd, J=1.38, 7.91 Hz, 1H), 8.31 (dd, J=1.38, 4.64 Hz, 1H), 7.93 (s, 1H), 7.20 (dd, J=4.77, 7.78 Hz, 1H), 6.81 (s, 1H), 4.94-5.05 (m, 1H), 3.70-3.90 (m, 4H), 1.75-1.91 (m, 4H), 1.52-1.62 (m, 4H), 1.25 (d, J=6.27 Hz, 6H); LCMS (m/z): 396.1 [M+H]$^+$.

Example 140

Ethyl 5-[(1H-pyrrolo[2,3-b]pyridin-3-yl)methylene]-2-{[2-methyl-4-(2-pyridinylmethoxy)phenyl]amino}-4-oxo-4,5-dihydrofuran-3-carboxylate

[Chemical Formula 149]

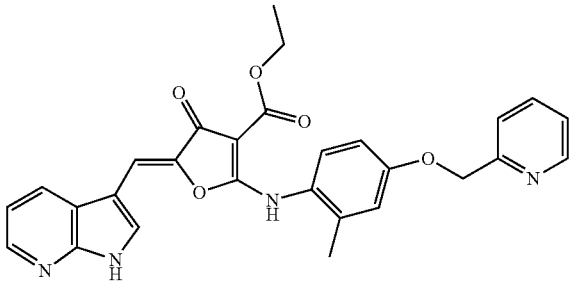

The titled compound was similarly prepared as solid according to the procedure described in the Example 1, using ethyl 2-{[2-methyl-4-(2-pyridinylmethoxy)phenyl]amino}-4-oxo-4,5-dihydrofuran-3-carboxylate which similarly prepared according to the procedure described in the Example 74, First step to Fourth step and 7-azaindole-3-carboxaldehyde as starting materials.

$^1$H NMR (DMSO-$d_6$) δ (ppm) 12.29 (br. s, 1H), 10.30 (br. s, 1H), 8.63 (d, J=3.91 Hz, 1H), 8.17 (d, J=3.91 Hz, 1H), 7.89 (t, J=7.09 Hz, 1H), 7.67-7.79 (m, 2H), 7.62 (d, J=7.34 Hz, 1H), 7.34-7.49 (m, 2H), 7.16 (br. s, 1H), 7.04 (d, J=8.31 Hz, 1H), 6.83 (s, 1H), 6.70-6.77 (m, 1H), 5.29 (s, 2H), 4.26 (q, J=6.85 Hz, 2H), 2.23 (s, 3H), 1.29 (t, J=7.09 Hz, 3H); LCMS (m/z): 497.0 [M+H]$^+$.

Example 141

Ethyl 5-[(1H-pyrrolo[2,3-b]pyridin-3-yl)methylene]-2-{[2-methyl-4-(3-pyridinylmethoxy)phenyl]amino}-4-oxo-4,5-dihydrofuran-3-carboxylate

[Chemical Formula 150]

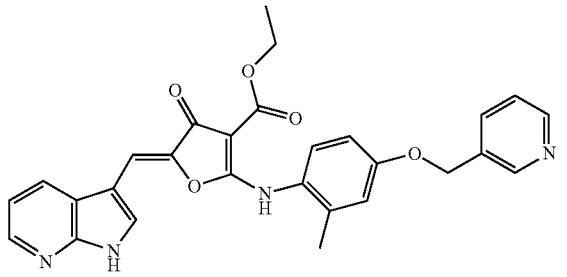

To a solution of ethyl 2-{[2-methyl-4-(3-pyridinylmethoxy)phenyl]amino}-4-oxo-4,5-dihydrofuran-3-carboxylate (0.080 g, 0.20 mmol) which similarly prepared according to the procedure described in the Example 74, First step to Fourth step and 7-azaindole-3-carboxaldehyde (0.032 g, 0.20 mmol) in ethanol (5.0 mL), L-proline (0.0050 g, 0.043 mmol) was added at ambient temperature. The mixture was refluxed for 2 days. Cooled to ambient temperature, the reaction mixture was purified by preparative HPLC to afford the titled compound as solid (0.010 g, y. 9%).

$^1$H NMR (DMSO-$d_6$) δ (ppm) 12.25 (br. s, 1H), 10.25 (br. s, 1H), 8.76 (s, 1H), 8.59 (d, J=3.42 Hz, 1H), 8.18 (d, J=4.40 Hz, 1H), 7.96 (d, J=7.83 Hz, 1H), 7.69-7.79 (m, 2H), 7.45-7.53 (m, 1H), 7.41 (d, J=8.80 Hz, 1H), 7.14 (br. s, 1H), 7.04 (d, J=8.31 Hz, 1H), 6.79 (br. s, 1H), 6.68-6.76 (m, 1H), 5.27 (s, 2H), 4.20-4.30 (m, 2H), 2.23 (s, 3H), 1.29 (t, J=7.09 Hz, 3H); LCMS (m/z): 497.4 [M+H]$^+$.

Example 142

Ethyl 5-[(1H-pyrrolo[2,3-b]pyridin-3-yl)methylene]-2-(morpholinoamino)-4-oxo-4,5-dihydrofuran-3-carboxylate

[Chemical Formula 151]

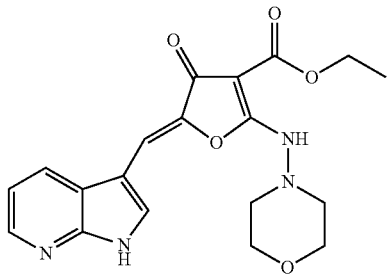

A solution of ethyl 2-ethoxy-4-oxo-4,5-dihydrofuran-3-carboxylate (0.10 g, 0.50 mmol) which afforded in the Example 74, Third step and 4-aminomorpholine (0.046 mL, 0.48 mmol) in ethanol (2.0 mL) was stirred at ambient temperature for 15 h. To this reaction mixture, 7-azaindole-3-carboxaldehyde (0.061 g, 0.42 mmol) and piperidine (0.0048 mL, 0.048 mmol) were added. The mixture was refluxed for 3 days. The precipitate was collected by filtration, washed with hot ethanol. The solid was washed with hexane then dried to afford the titled compound (0.045 g, y. 24%) as solid.

$^1$H NMR (DMSO-$d_6$) δ (ppm) 12.34 (br. s, 1H), 10.07 (s, 1H), 8.93 (d, J=7.78 Hz, 1H), 8.33 (d, J=3.51 Hz, 1H), 8.12 (br. s, 1H), 7.20-7.26 (m, 1H), 6.88 (s, 1H), 4.21 (q, J=6.78 Hz, 2H), 3.74-3.88 (m, 4H), 3.02-3.14 (br. s, 4H), 1.26 (t, J=6.90 Hz, 3H); LCMS (m/z): 385.1 [M+H]$^+$.

Example 143

Ethyl 5-[(1H-pyrrolo[2,3-b]pyridin-3-yl)methylene]-2-{[2-methyl-4-(4-pyridinylmethoxy)phenyl]amino}-4-oxo-4,5-dihydrofuran-3-carboxylate

[Chemical Formula 152]

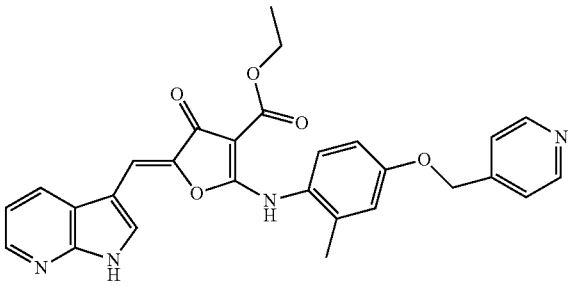

The titled compound (solid) was similarly prepared according to the procedure described in the Example 141.

$^1$H NMR (DMSO-$d_6$) δ (ppm) 12.28 (br. s, 1H), 10.30 (br. s, 1H), 8.62 (d, J=4.40 Hz, 2H), 8.17 (d, J=4.40 Hz, 1H), 7.67-7.79 (m, 2H), 7.52 (d, J=4.89 Hz, 2H), 7.45 (d, J=8.31 Hz, 1H), 7.15 (br. s, 1H), 7.03 (d, J=8.31 Hz, 1H), 6.83 (s, 1H), 6.68-6.75 (m, 1H), 5.31 (s, 2H), 4.26 (q, J=7.17 Hz, 2H), 2.23 (s, 3H), 1.29 (t, J=6.85 Hz, 3H); LCMS (m/z): 496.8 [M+H]$^+$.

Example 144

Ethyl 5-[(1H-pyrrolo[2,3-b]pyridin-3-yl)methylene]-2-({4-[2-(diethylamino)ethoxy]-2-methylphenyl}amino)-4-oxo-4,5-dihydrofuran-3-carboxylate Acetate

[Chemical Formula 153]

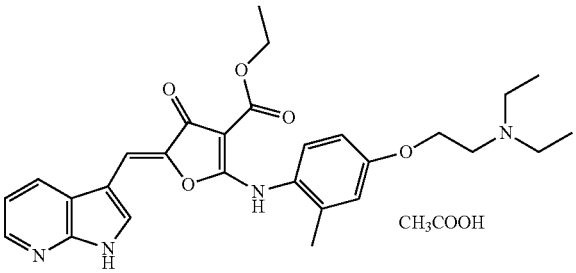

The crude material, which similarly prepared according to the procedure described in the Example 141, was purified by preparative HPLC (aqueous ammonium acetate/acetonitrile) to afford the titled compound (solid).

$^1$H NMR (DMSO-$d_6$) δ (ppm) 12.17 (br. s, 1H), 8.16 (d, J=3.91 Hz, 1H), 7.75 (s, 1H), 7.68 (d, J=7.34 Hz, 1H), 7.34 (d, J=8.31 Hz, 1H), 7.00 (br. s, 1H), 6.91 (d, J=8.80 Hz, 1H), 6.70-6.79 (m, 2H), 4.19-4.30 (m, 2H), 4.10 (t, J=5.87 Hz, 2H), 2.86 (t, J=5.87 Hz, 2H), 2.61 (q, J=6.85 Hz, 4H), 2.20 (s, 3H), 1.90 (s, 3H), 1.28 (t, J=6.85 Hz, 3H), 1.02 (t, J=7.09 Hz, 6H); LCMS (m/z): 505.6 [M+H]$^+$.

Example 145

Ethyl 5-[(1H-pyrrolo[2,3-b]pyridin-3-yl)methylene]-2-({2-methyl-4-[2-(4-methylpiperazinyl)ethoxy]phenyl}amino)-4-oxo-4,5-dihydrofuran-3-carboxylate acetate

[Chemical Formula 154]

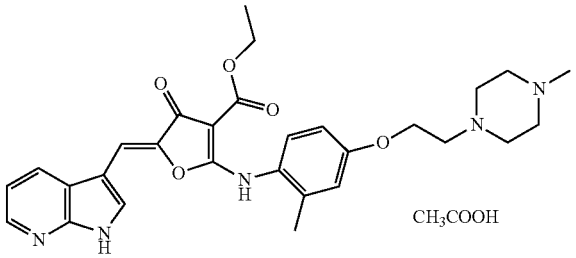

First Step

A solution of 4-nitro-m-cresol (2.0 g, 0.013 mol), 1-bromo-2-chloroethane (1.7 mL, 0.020 mol) and potassium carbonate (4.7 g, 0.034 mol) in N,N-dimethylformamide (21 mL) was stirred at 70° C. for 18 h. Cooled to ambient temperature, the reaction mixture was poured into ice water, extracted with ethyl acetate. The organic layer was washed with water and brine, dried over sodium sulfate and concentrated. The residue was purified by chromatography on silica gel(hexane/ethyl acetate) to afford 4-(2-chloroethoxy)-2-methyl-1-nitrobenzene as solid (2.1 g, y. 73%).

$^1$H NMR (DMSO-$d_6$) δ (ppm) 8.05 (d, J=9.12 Hz, 1H), 7.08 (d, J=2.48 Hz, 1H), 7.01 (dd, J=2.72, 9.08 Hz, 1H), 4.38 (t, J=5.04 Hz, 2H), 3.98 (t, J=5.08 Hz, 2H), 2.55 (s, 3H); LCMS (m/z): 216.2 [M+H]$^+$.

Second Step

A solution of 4-(2-chloroethoxy)-2-methyl-1-nitrobenzene (2.1 g, 9.7 mmol), N-methylpiperazine (1.5 g, 15 mmol) and potassium carbonate (3.4 g, 0.025 mol) in N,N-dimethylformamide (15 mL) was stirred with heating at 70° C. for 18 h. Cooled to ambient temperature, the reaction mixture was poured into ice water, extracted with ethyl acetate. The organic layer was washed with water and brine, dried over sodium sulfate and concentrated. The residue was purified by chromatography on silica gel(dichloromethane/methanol) to afford 1-methyl-4-[2-(3-methyl-4-nitrophenoxy)ethyl]piperazine as solid (1.8 g, y. 64%).

$^1$H NMR (DMSO-$d_6$) δ (ppm) 8.03 (d, J=9.12 Hz, 1H), 7.05 (d, J=2.68 Hz, 1H), 6.98 (dd, J=2.76, 9.08 Hz, 1H), 4.18 (t, J=5.78 Hz, 2H), 2.69 (t, J=5.74 Hz, 2H), 2.54 (s, 3H), 2.39-2.52 (m, 4H), 2.22-2.37 (m, 4H), 2.14 (s, 3H); LCMS (m/z): 280.2 [M+H]$^+$.

Third Step

1-Methyl-4-[2-(3-methyl-4-nitrophenoxy)ethyl]piperazine (0.69 g, 2.5 mmol) was dissolved in ethanol (10 mL) and 10% wt palladium on carbon (0.055 g) was added at ambient temperature. The reaction mixture was agitated under a hydrogen atmosphere at ambient temperature for 4 h. Palladium on carbon was removed by filtration with Celite and the solvent was removed under reduced pressure to afford 2-methyl-4-[2-(4-methylpiperazinyl)ethoxy]aniline as oil (0.60 g, y. 97%).

$^1$H NMR (DMSO-$d_6$) δ (ppm) 6.57 (br. s, 1H), 6.51 (br. s, 2H), 4.35 (br. s, 2H), 3.90 (t, J=5.90 Hz, 2H), 3.17 (br. s, 3H), 2.60 (t, J=5.88 Hz, 2H), 2.38-2.54 (m, 4H), 2.30 (br. s, 4H), 2.14 (s, 3H); LCMS (m/z): 250.4 [M+H]$^+$.

Fourth Step

A solution of ethyl 2-ethoxy-4-oxo-4,5-dihydrofuran-3-carboxylate (0.32 g, 1.6 mmol) which afforded in the Example 74, Third step and 2-methyl-4-[2-(4-methylpiperazinyl)ethoxy]aniline (0.40 g, 1.6 mmol) in ethanol (5.0 mL) was stirred at 60° C. for 30 min. The solvent was removed under reduced pressure, then the residue was purified by chromatography on silica gel(dichloromethane/methanol) to afford 2-({2-methyl-4-[2-(4-methylpiperazinyl)ethoxy]phenyl}amino)-4-oxo-4,5-dihydrofuran-3-carboxylate as solid (0.30 g, y. 46%).

$^1$H NMR (DMSO-$d_6$) δ (ppm) 9.99 (br. s, 1H), 7.26 (d, J=8.56 Hz, 1H), 6.91 (d, J=2.28 Hz, 1H), 6.78-6.86 (m, 1H), 4.58 (s, 2H), 4.21 (q, J=7.04 Hz, 2H), 4.03-4.12 (m, 2H), 3.31 (s, 3H), 2.27-2.80 (m, 10H), 2.20 (s, 3H), 1.25 (t, J=7.04 Hz, 3H); LCMS (m/z): 404.2 [M+H]$^+$.

Fifth Step

To a solution of 2-({2-methyl-4-[2-(4-methylpiperazinyl)ethoxy]phenyl}amino)-4-oxo-4,5-dihydrofuran-3-carboxylate (0.22 g, 0.55 mmol) and 7-azaindole-3-carboxaldehyde (0.080 g, 0.55 mmol) in ethanol (14 mL), L-proline (0.014 g, 0.12 mmol) was added at ambient temperature. The mixture was refluxed for 2 days. The solvent was removed under reduced pressure, and then the residue was purified by preparative HPLC (aqueous ammonium acetate/acetonitrile) to afford the titled compound as solid. (0.032 g, y. 11%).

$^1$H NMR (DMSO-$d_6$) δ (ppm) 12.16 (br. s, 1H), 8.17 (d, J=4.40 Hz, 1H), 7.64-7.79 (m, 2H), 7.31 (d, J=8.31 Hz, 1H), 7.00 (br. s, 1H), 6.90 (d, J=8.31 Hz, 1H), 6.65-6.80 (m, 2H), 4.10-4.30 (m, 4H), 2.76 (t, J=5.62 Hz, 2H), 2.25-2.65 (m, 9H), 2.19-2.21 (m, 5H), 1.86 (s, 3H), 1.28 (t, J=6.85 Hz, 3H); LCMS (m/z): 532.3 $[M+H]^+$.

Example 146

Ethyl 5-[(1H-pyrrolo[2,3-b]pyridin-3-yl)methylene]-2-{[4-(2-hydroxy-2-methylpropoxy)-2-methylphenyl]amino}-4-oxo-4,5-dihydrofuran-3-carboxylate

[Chemical Formula 155]

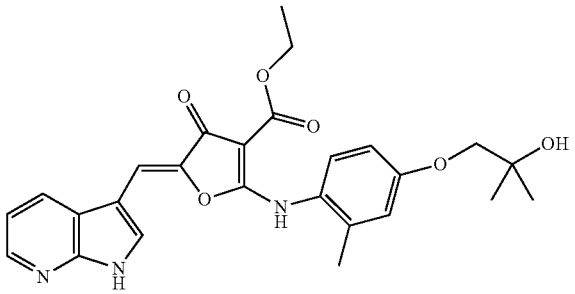

The titled compound (solid) was similarly prepared according to the procedure described in the Example 141.

$^1$H (DMSO-$d_6$) δ (ppm) 12.28 (br. s, 1H), 10.30 (br. s, 1H), 8.16 (d, J=3.91 Hz, 1H), 7.80 (s, 1H), 7.60 (d, J=7.82 Hz, 1H), 7.40 (d, J=8.31 Hz, 1H), 7.03 (br. s, 1H), 6.94 (d, J=8.31 Hz, 1H), 6.81 (s, 1H), 6.73 (dd, J=4.40, 7.82 Hz, 1H), 4.72 (s, 1H), 4.27 (q, J=7.17 Hz, 2H), 3.81 (s, 2H), 2.22 (s, 3H), 1.25-1.33 (m, 9H); LCMS (m/z): 478.2 $[M+H]^+$.

Example 147

Ethyl 5-[(1H-pyrrolo[2,3-b]pyridin-3-yl)methylene]-2-[(2-methyl-4-{[2-(pyrrolidino)ethyl]amino}phenyl)amino]-4-oxo-4,5-dihydrofuran-3-carboxylate acetate

[Chemical Formula 156]

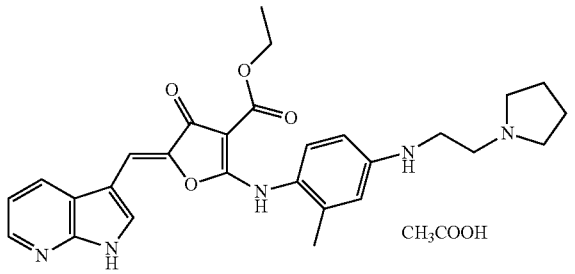

To a solution of 2-[(2-methyl-4-{[2-(pyrrolidino)ethyl]amino}phenyl)amino]-4-oxo-4,5-dihydrofuran-3-carboxylate (0.32 g, 0.85 mmol) which similarly prepared according to the procedure described in the Example 125, First step to Third step and 7-azaindole-3-carboxaldehyde (0.13 g, 0.85 mmol) in ethanol (5.0 mL), piperidine (0.10 mL, 1.0 mmol) was added at ambient temperature. The mixture was refluxed for 24 h. Cooled to ambient temperature, the reaction mixture was purified by preparative HPLC (aqueous ammonium acetate/acetonitrile) to afford the titled compound as solid (0.010 g, y. 3%).

$^1$H NMR (DMSO-$d_6$) δ (ppm) 12.05 (br. s, 1H), 8.11-8.20 (m, 1H), 7.71-7.84 (m, 2H), 7.01-7.10 (m, 1H), 6.77-6.85 (m, 1H), 6.49-6.68 (m, 3H), 5.57 (br. s, 1H), 4.15-4.25 (m, 2H), 3.21 (br. s, 2H), 2.63-2.73 (m, 2H), 2.52-2.61 (m, 4H), 2.10 (s, 3H), 1.85 (s, 3H), 1.65-1.78 (m, 4H), 1.27 (t, J=6.85 Hz, 3H); LCMS (m/z): 502.4 $[M+H]^+$.

Example 148

Isopropyl 5-[(1H-pyrrolo[2,3-b]pyridin-3-yl)methylene]-2-[N-methyl-N-(2-thienylmethyl)amino]-4-oxo-4,5-dihydrofuran-3-carboxylate

[Chemical Formula 157]

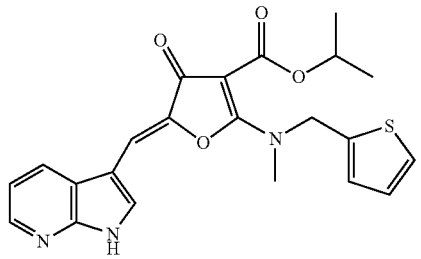

A solution of isopropyl 2-isopropoxy-4-oxo-4,5-dihydrofuran-3-carboxylate (0.10 g, 0.44 mmol) which similarly prepared according to the procedure described in the Example 74, Third step using diisopropyl malonate and chloroacetyl chloride, N-methyl-N-(2-thienylmethyl)amine (0.061 mg, 0.048 mmol) and triethylamine (0.18 mL, 1.3 mmol) in 2-propanol (2.0 mL) was stirred for 7 days then refluxed for further 24 h. To this reaction mixture, 7-azaindole-3-carboxaldehyde (0.065 g, 0.44 mmol) was added then the mixture was refluxed for 24 h. Cooled to ambient temperature, the reaction mixture was purified by preparative HPLC to afford the titled compound as solid (0.0038 g, y. 2%).

$^1$H NMR (DMSO-$d_6$) δ (ppm) 12.33 (br. s, 1H), 8.35 (d, J=8.03 Hz, 1H), 8.28-8.32 (m, 1H), 8.02 (s, 1H), 7.53 (dd, J=1.13, 5.14 Hz, 1H), 7.14-7.22 (m, 2H), 7.04 (dd, J=3.51, 5.02 Hz, 1H), 6.88 (s, 1H), 5.19 (s, 2H), 4.97-5.05 (m, 1H), 3.26 (s, 3H), 1.24 (d, J=6.27 Hz, 6H); LCMS (m/z): 424.1 $[M+H]^+$.

Example 149

Isopropyl 5-[(1H-pyrrolo[2,3-b]pyridin-3-yl)methylene]-2-(cyclohexylamino)-4-oxo-4,5-dihydrofuran-3-carboxylate

[Chemical Formula 158]

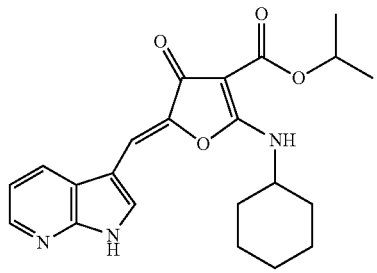

A solution of isopropyl 2-isopropoxy-4-oxo-4,5-dihydrofuran-3-carboxylate (0.10 g, 0.44 mmol) which similarly prepared according to the procedure described in the Example 74, Third step using diisopropyl malonate and chloroacetyl chloride, and cyclohexylamine (0.055 mL, 0.48 mmol) in 2-propanol (2.0 mL) was stirred at ambient temperature for 14 h. To this reaction mixture, 7-azaindole-3-carboxaldehyde (0.065 g, 0.44 mmol) and piperidine (0.0044 mL, 0.044 mmol) were added then the mixture was refluxed for further 8 days. Cooled to ambient temperature, the reaction mixture was purified by preparative HPLC to afford the titled compound as solid (0.0079 g, y. 4%).

$^1$H NMR (DMSO-$d_6$) δ (ppm) 12.35 (br. s, 1H), 8.51 (d, J=8.28 Hz, 1H), 8.41 (d, J=7.78 Hz, 1H), 8.32 (dd, J=1.38, 4.64 Hz, 1H), 7.99 (d, J=2.51 Hz, 1H), 7.20 (dd, J=4.64, 7.91 Hz, 1H), 6.86 (s, 1H), 5.00-5.12 (m, 1H), 3.96-4.05 (m, 1H), 1.93-2.04 (m, 2H), 1.72-1.84 (m, 2H), 1.54-1.69 (m, 3H), 1.35-1.49 (m, 2H), 1.18-1.31 (m, 7H); LCMS (m/z): 396.2 $[M+H]^+$.

Example 150

Isopropyl 5-[(1H-pyrrolo[2,3-b]pyridin-3-yl)methylene]-2-[(cyclohexylmethyl)amino]-4-oxo-4,5-dihydrofuran-3-carboxylate

[Chemical Formula 159]

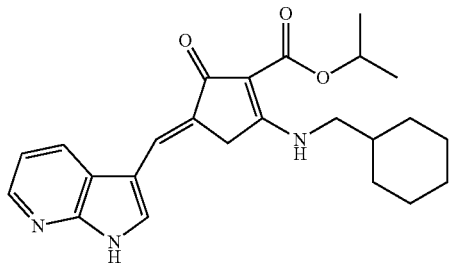

A solution of isopropyl 2-isopropoxy-4-oxo-4,5-dihydrofuran-3-carboxylate (0.10 g, 0.44 mmol) which similarly prepared according to the procedure described in the Example 74, Third step using diisopropyl malonate and chloroacetyl chloride, and aminomethylcyclohexane (0.063 mL, 0.48 mmol) in 2-propanol (2.0 mL) was stirred at ambient temperature for 14 h. To this reaction mixture, 7-azaindole-3-carboxaldehyde (0.065 g, 0.44 mmol) and piperidine (0.0044 mL, 0.044 mmol) were added then the mixture was refluxed for further 8 days. Cooled to ambient temperature, the reaction mixture was purified by preparative HPLC to afford the titled compound as solid (0.036 g, y. 19%).

$^1$H NMR (DMSO-$d_6$) δ (ppm) 12.35 (br. s, 1H), 8.90-8.98 (m, 1H), 8.41 (d, J=6.78 Hz, 1H), 8.32 (dd, J=1.38, 4.64 Hz, 1H), 7.99 (s, 1H), 7.19 (dd, J=4.77, 8.03 Hz, 1H), 6.84 (s, 1H), 5.00-5.13 (m, 1H), 3.45-3.53 (m, 2H), 1.56-1.81 (m, 5H), 1.27 (d, J=6.27 Hz, 6H), 1.08-1.24 (m, 4H), 0.94-1.07 (m, 2H); LCMS (m/z): 410.2 $[M+H]^+$.

Example 151

Isopropyl 5-[(1H-pyrrolo[2,3-b]pyridin-3-yl)methylene]-2-[(trans-4-hydroxycyclohexyl)amino]-4-oxo-4,5-dihydrofuran-3-carboxylate

[Chemical Formula 160]

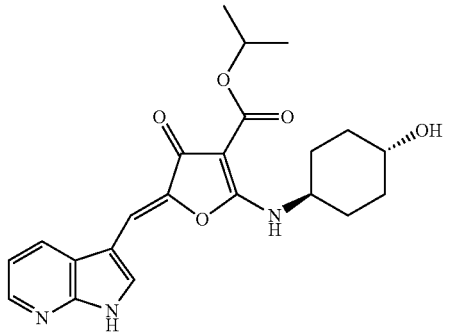

A solution of isopropyl 2-[(trans-4-hydroxycyclohexyl)amino]-4-oxo-4,5-dihydrofuran-3-carboxylate (0.10 g, 0.44 mmol) which similarly prepared according to the procedure described in the Example 74, Third step using diisopropyl malonate and chloroacetyl chloride, and trans-4-aminomethylcyclohexanol (0.056 mg, 0.49 mmol) in 2-propanol (1.0 mL) was stirred at ambient temperature for 20 h. To this reaction mixture, 7-azaindole-3-carboxaldehyde (0.065 g, 0.44 mmol) and L-proline (0.0050 g, 0.044 mmol) were added then the mixture was refluxed for further 1.5 days. The precipitate was collected by filtration, washed with hot ethanol. The solid was washed with hexane then dried to afford isopropyl 5-[(1H-pyrrolo[2,3-b]pyridin-3-yl)methylene]-2-[(trans-4-hydroxycyclohexyl)amino]-4-oxo-4,5-dihydrofuran-3-carboxylate as solid (0.0076 g, y. 4%).

$^1$H NMR (DMSO-$d_6$) δ (ppm) 12.36 (br. s, 1H), 8.46 (d, J=8.28 Hz, 1H), 8.42 (d, J=7.53 Hz, 1H), 8.33 (dd, J=1.38, 4.64 Hz, 1H), 7.99 (d, J=2.51 Hz, 1H), 7.20 (dd, J=4.64, 7.91 Hz, 1H), 6.85 (s, 1H), 5.01-5.09 (m, 1H), 4.69 (d, J=4.27 Hz, 1H), 3.93-3.99 (m, 1H), 3.43-3.51 (m, 1H), 1.86-2.03 (m, 4H), 1.60-1.73 (m, 2H), 1.29-1.42 (m, 2H), 1.26 (d, J=6.27 Hz, 6H); LCMS (m/z): 412.1 $[M+H]^+$.

Example 152

Cyclopropylmethyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3-carboxylate formate

[Chemical Formula 161]

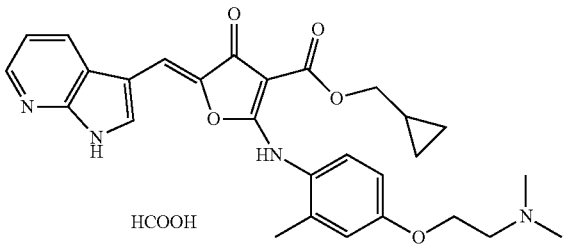

A solution of ethyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3-carboxylate (0.033 g, 0.070 mmol) which similarly prepared according to the procedure described in the Example 111, cyclopropyl carbinol (0.10 mL, 1.3 mmol) and zinc cluster catalyst ($Zn_4(OCOCF_3)_6O$) (0.0033 g, 0.0035 mmol) in N,N-dimethylacetamide (0.9 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.0029 g, y. 8%).

$^1$H NMR (DMSO-$d_6$) δ (ppm) 12.25 (br. s, 1H), 8.04-8.29 (m, 2H), 7.75 (s, 1H), 7.68 (d, J=7.78 Hz, 1H), 7.38 (d, J=8.28 Hz, 1H), 7.03 (d, J=2.51 Hz, 1H), 6.93 (d, J=8.78 Hz, 1H), 6.70-6.83 (m, 2H), 6.55 (br. s, 1H), 4.15 (t, J=5.65 Hz, 2H), 4.06 (d, J=6.78 Hz, 2H), 2.70 (t, J=5.80 Hz, 2H), 2.28 (s, 6H), 2.22 (s, 3H), 1.15-1.32 (m, 1H), 0.49-0.62 (m, 2H), 0.32-0.39 (m, 2H); LCMS (m/z): 503.2 $[M+H]^+$.

Example 153

Cyclopropylmethyl 5-[(1H-pyrrolo[2,3-b]pyridin-3-yl)methylene]-2-{[4-(2-hydroxyethoxy)-2-methylphenyl]amino}-4-oxo-4,5-dihydrofuran-3-carboxylate

[Chemical Formula 162]

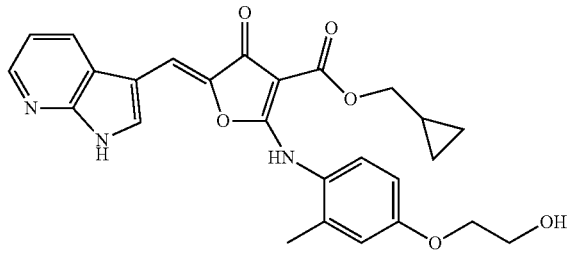

A solution of the compound (0.032 g, 0.070 mmol) of Example 74, cyclopropyl carbinol (0.10 mL, 1.3 mmol) and zinc cluster catalyst ($Zn_4(OCOCF_3)_6O$) (0.0033 g, 0.0035 mmol) in N,N-dimethylacetamide (0.9 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.0040 g, y. 11%).

$^1$H NMR (DMSO-$d_6$) δ (ppm) 12.23 (br. s, 1H), 10.36 (br. s, 1H), 8.19 (d, J=3.51 Hz, 1H), 7.65-7.80 (m, 2H), 7.38 (d, J=8.53 Hz, 1H), 7.01 (d, J=2.26 Hz, 1H), 6.92 (dd, J=2.51, 8.53 Hz, 1H), 6.72-6.84 (m, 2H), 4.95 (t, J=5.40 Hz, 1H), 4.01-4.12 (m, 4H), 3.79 (q, J=5.02 Hz, 2H), 2.22 (s, 3H), 1.14-1.26 (m, 1H), 0.51-0.58 (m, 2H), 0.31-0.39 (m, 2H); LCMS (m/z): 476.1 $[M+H]^+$.

Example 154

Isopropyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3-carboxylate formate

[Chemical Formula 163]

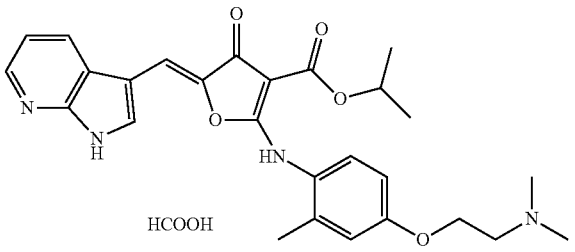

A solution of ethyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3-carboxylate (0.033 g, 0.070 mmol) which similarly prepared according to the procedure described in the Example 111, and zinc cluster catalyst ($Zn_4(OCOCF_3)_6O$) (0.0033 g, 0.0035 mmol) in 2-propanol (0.5 mL) and N,N-dimethylacetamide (0.5 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.0046 g, y. 11%).

$^1$H NMR (DMSO-$d_6$) δ (ppm) 12.28 (br. s, 1H), 10.20 (br. s, 1H), 8.18 (dd, J=1.60, 4.40 Hz, 1H), 8.14 (s, 1H), 7.78 (s, 1H), 7.67 (d, J=8.03 Hz, 1H), 7.42 (d, J=8.53 Hz, 1H), 7.04 (d, J=2.51 Hz, 1H), 6.94 (dd, J=2.76, 8.78 Hz, 1H), 6.72-6.81 (m, 2H), 5.10-5.17 (m, 1H), 4.16 (t, J=5.65 Hz, 2H), 2.75 (t, J=5.52 Hz, 2H), 2.31 (s, 6H), 2.23 (s, 3H), 1.31 (d, J=6.27 Hz, 6H); LCMS (m/z): 491.2 $[M+H]^+$.

Example 155 n-Butyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3carboxylate formate

[Chemical Formula 164]

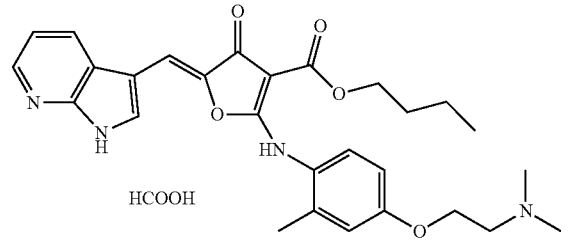

A solution of ethyl 5-[(1H-pyrrolo[2,3-b]pyridin-3-yl)methylene]-2-({4-[2-(dimethylamino)ethoxy]-2-methylphenyl}amino)-4-oxo-4,5-dihydrofuran-3-carboxylate (0.033 g, 0.070 mmol) which similarly prepared according to the procedure described in the Example 111, and zinc cluster catalyst ($Zn_4(OCOCF_3)_6O$) (0.0033 g, 0.0035 mmol) in n-butanol (0.5 mL) and N,N-dimethylacetamide (0.5 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.011 g, y. 31%).

$^1$H NMR (DMSO-$d_6$) δ (ppm) 12.28 (br. s, 1H), 10.32 (br. s, 1H), 8.18 (dd, J=1.38, 4.64 Hz, 1H), 8.15 (s, 1H), 7.76 (s, 1H), 7.67 (d, J=7.78 Hz, 1H), 7.41 (d, J=8.78 Hz, 1H), 7.04 (d, J=2.51 Hz, 1H), 6.94 (dd, J=2.76, 8.78 Hz, 1H), 6.81 (s, 1H), 6.75 (dd, J=4.77, 8.03 Hz, 1H), 4.22 (t, J=6.78 Hz, 2H), 4.16 (t, J=5.65 Hz, 2H), 2.74 (t, J=5.65 Hz, 2H), 2.30 (s, 6H), 2.22 (s, 3H), 1.60-1.72 (m, 2H), 1.34-1.51 (m, 2H), 0.94 (t, J=7.40 Hz, 3H); LCMS (m/z): 505.2 $[M+H]^+$.

Example 156 n-Butyl 5-[(1H-pyrrolo[2,3-b]pyridin-3-yl)methylene]-2-{[4-(2-hydroxyethoxy)-2-methylphenyl]amino}-4-oxo-4,5-dihydrofuran-3-carboxylate

[Chemical Formula 165]

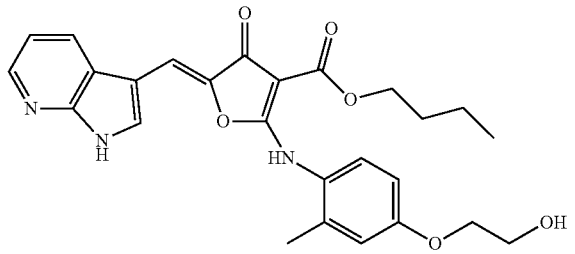

A solution of the compound (0.032 g, 0.070 mmol) of Example 74, and zinc cluster catalyst ($Zn_4(OCOCF_3)_6O$) (0.0033 g, 0.0035 mmol) in n-butanol (0.5 mL) and N,N-dimethylacetamide (0.5 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.015 g, y. 44%).

$^1$H NMR (DMSO-$d_6$) δ (ppm) 12.27 (br. s, 1H), 10.27 (s, 1H), 8.19 (dd, J=1.13, 4.64 Hz, 1H), 7.74 (d, J=2.26 Hz, 1H), 7.69 (d, J=7.78 Hz, 1H), 7.42 (d, J=8.78 Hz, 1H), 7.03 (d, J=2.76 Hz, 1H), 6.94 (dd, J=2.64, 8.66 Hz, 1H), 6.74-6.85 (m, 2H), 4.88-5.05 (m, 1H), 4.22 (t, J=6.65 Hz, 2H), 4.09 (t, J=4.89 Hz, 2H), 3.75-3.85 (m, 2H), 2.23 (s, 3H), 1.59-1.73 (m, 2H), 1.36-1.49 (m, 2H), 0.94 (t, J=7.40 Hz, 3H); LCMS (m/z): 478.2 $[M+H]^+$.

Example 157

Isopropyl 5-[(1H-pyrrolo[2,3-b]pyridin-3-yl)methylene]-2-{[4-(2-hydroxyethoxy)-2-methylphenyl]amino}-4-oxo-4,5-dihydrofuran-3-carboxylate

[Chemical Formula 166]

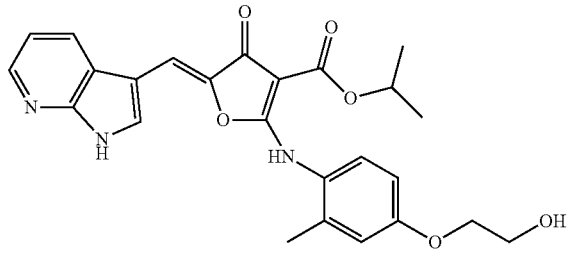

A solution of the compound (0.032 g, 0.070 mmol) of Example 74, and zinc cluster catalyst ($Zn_4(OCOCF_3)_6O$) (0.0033 g, 0.0035 mmol) in 2-propanol (0.5 mL) and N,N-dimethylacetamide (0.5 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.010 g, y. 28%).

$^1$H NMR (DMSO-$d_6$) δ (ppm) 12.27 (br. s, 1H), 10.22 (s, 1H), 8.19 (dd, J=1.26, 4.77 Hz, 1H), 7.76 (d, J=2.51 Hz, 1H), 7.69 (d, J=7.78 Hz, 1H), 7.42 (d, J=8.53 Hz, 1H), 7.03 (d, J=2.51 Hz, 1H), 6.94 (dd, J=2.76, 8.78 Hz, 1H), 6.73-6.84 (m, 2H), 5.08-5.18 (m, 1H), 4.95 (t, J=5.40 Hz, 1H), 4.09 (t, J=4.89 Hz, 2H), 3.80 (q, J=5.27 Hz, 2H), 2.23 (s, 3H), 1.31 (d, J=6.27 Hz, 6H); LCMS (m/z): 464.1 $[M+H]^+$.

Example 158

Isopropyl 5-[(1H-pyrrolo[2,3-b]pyridin-3-yl)methylene]-2-(cyclopropylamino)-4-oxo-4,5-dihydrofuran-3-carboxylate

[Chemical Formula 167]

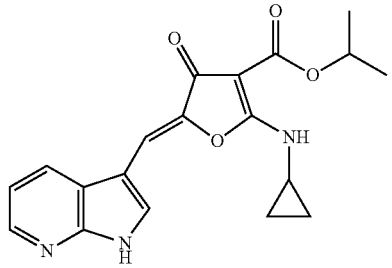

A solution of isopropyl 2-isopropoxy-4-oxo-4,5-dihydrofuran-3-carboxylate (0.10 g, 0.44 mmol) which similarly prepared according to the procedure described in the Example 74, Third step using diisopropyl malonate and chloroacetyl chloride, and cyclopropylamine (0.034 mL, 0.48 mmol) in 2-propanol (2.0 mL) was stirred at ambient temperature for 14 h. To this reaction mixture, 7-azaindole-3-carboxaldehyde (0.065 g, 0.44 mmol) and piperidine (0.0044 mL, 0.044 mmol) were added then the mixture was refluxed for further 12 days. Cooled to ambient temperature, the reaction mixture was purified by preparative HPLC to afford the titled compound as solid (0.0020 g, y. 1%).

$^1$H NMR (DMSO-$d_6$) δ (ppm) 12.33 (br. s, 1H), 8.81 (br. s, 1H), 8.56 (d, J=7.28 Hz, 1H), 8.31 (d, J=3.51 Hz, 1H), 8.06 (d, J=2.26 Hz, 1H), 7.21 (dd, J=4.64, 7.91 Hz, 1H), 6.88 (s, 1H), 4.99-5.10 (m, 1H), 3.09-3.18 (m, 1H), 1.26 (d, J=6.27 Hz, 6H), 0.89-0.97 (m, 4H); LCMS (m/z): 354.1 $[M+H]^+$.

Example 159

Ethyl 5-[(1H-pyrrolo[2,3-b]pyridin-3-yl)methylene]-2-[(cyclohexylmethyl)amino]-4-oxo-4,5-dihydrofuran-3-carboxylate

[Chemical Formula 168]

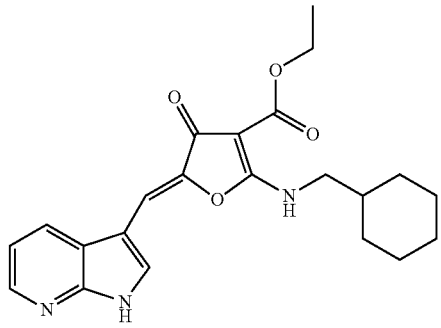

A solution of ethyl 2-ethoxy-4-oxo-4,5-dihydrofuran-3-carboxylate (0.10 g, 0.51 mmol) which afforded in the Example 74, Third step and aminomethylcyclohexane (0.072 mL, 0.55 mmol) in ethanol (2.0 mL) was stirred at ambient temperature for 1.5 h. To this reaction mixture, 7-azaindole-3-carboxaldehyde (0.073 g, 0.50 mmol) and L-proline (0.012 mg, 0.10 mmol) were added then the mixture was refluxed for further 5 days. The precipitate was collected by filtration, washed with hot ethanol. The solid was washed with hexane then dried to afford the titled compound as solid (0.024 g, y. 12%).

$^1$H NMR (DMSO-$d_6$) δ (ppm) 12.35 (br. s, 1H), 8.98 (t, J=6.27 Hz, 1H), 8.42 (d, J=7.78 Hz, 1H), 8.32 (dd, J=1.38, 4.64 Hz, 1H), 7.99 (d, J=2.51 Hz, 1H), 7.19 (dd, J=4.64, 7.91 Hz, 1H), 6.88 (s, 1H), 4.21 (q, J=7.03 Hz, 2H), 3.48 (t, J=6.40 Hz, 2H), 1.65-1.81 (m, 5H), 1.62 (d, J=9.29 Hz, 1H), 1.09-1.30 (m, 6H), 0.95-1.06 (m, 2H); LCMS (m/z): 396.2 $[M+H]^+$.

Example 160

2-Hydroxyethyl 5-[(1H-pyrrolo[2,3-b]pyridin-3-yl) methylene]-2-[N-methyl-N-(2-thienylmethyl) amino]-4-oxo-4,5-dihydrofuran-3-carboxylate

[Chemical Formula 169]

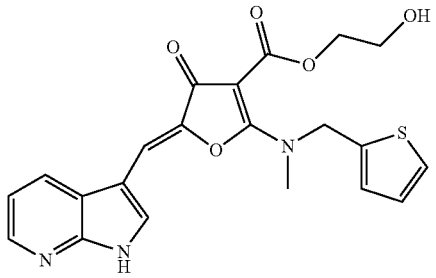

A solution of the compound (0.050 g, 0.12 mmol) of Example 108, ethylene glycol (0.20 mL, 3.6 mmol), 4-dimethylaminopyridine (0.0030 g, 0.024 mmol) and zinc cluster catalyst ($Zn_4(OCOCF_3)_6O$) (0.0058 g, 0.0061 mmol) in N,N-dimethylacetamide (0.5 mL) was stirred with the microwave synthesizer (Biotage Initiator™) at 150° C. for 30 min. Cooled to ambient temperature, the precipitate was removed by filtration. The filtrate was purified by preparative HPLC to afford the titled compound as solid (0.0061 g, y. 10%).

$^1$H NMR (DMSO-$d_6$) δ (ppm) 12.34 (br. s, 1H), 11.7 (br. s, 1H), 8.35-8.44 (m, 1H), 8.30 (dd, J=1.38, 4.64 Hz, 1H), 8.04 (s, 1H), 7.53 (dd, J=1.13, 5.14 Hz, 1H), 7.21 (d, J=3.01 Hz, 1H), 7.17 (dd, J=4.64, 7.91 Hz, 1H), 7.04 (dd, J=3.51, 5.02 Hz, 1H), 6.94 (s, 1H), 5.20 (s, 2H), 4.17 (t, J=5.14 Hz, 2H), 3.62 (q, J=5.52 Hz, 2H), 3.23-3.37 (m, 3H); LCMS (m/z): 426.1 $[M+H]^+$.

Example 161

Ethyl 5-[(1H-pyrrolo[2,3-b]pyridin-3-yl)methylene]-2-{[2-methyl-4-(2-pyrimidinylmethoxy)phenyl] amino}-4-oxo-4,5-dihydrofuran-3-carboxylate

[Chemical Formula 170]

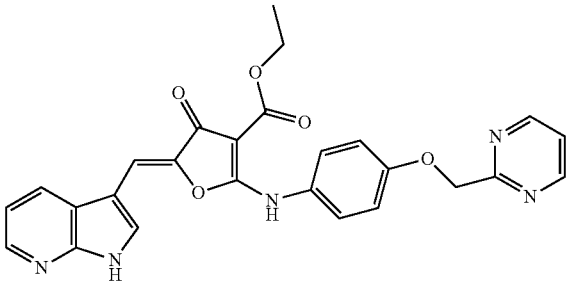

First Step

A solution of 4-nitro-m-cresol (0.25 g, 1.6 mmol), 2-(chloromethyl)pyrimidine hydrochloride (0.40 g, 2.4 mmol) and potassium carbonate (0.50 g, 4.0 mmol) in N,N-dimethylformamide (6.0 mL) was stirred at 70° C. for 18 h. Cooled to ambient temperature, the reaction mixture was poured into ice water, extracted with ethyl acetate. The organic layer was washed with water and brine, dried over sodium sulfate, filtered and concentrated to afford 2-[(3-methyl-4-nitrophenoxy)methyl]pyrimidine as crude material (0.32 g, y. 81%) as solid.

$^1$H NMR (DMSO-$d_6$) δ (ppm) 8.84 (d, J=4.92 Hz, 2H), 8.03 (d, J=9.08 Hz, 1H), 7.48 (t, J=4.90 Hz, 1H), 7.10 (d, J=2.68 Hz, 1H), 7.00 (dd, J=2.80, 9.12 Hz, 1H), 5.43 (s, 2H), 2.53 (s, 3H); LCMS (m/z): 246.4 $[M+H]^+$.

Second Step

To a solution of 2-[(3-methyl-4-nitrophenoxy)methyl]pyrimidine (0.18 g, 0.7 mmol) in ethanol (4.0 mL) and water (1.0 mL), iron (0.40 g, 7.2 mmol) and ammonium chloride (0.020 g, 0.37 mmol) were added. The mixture was refluxed for 1.5 h. Cooled to ambient temperature, the reaction mixture was filtered over Celite to remove unneeded materials and the filtrate was concentrated to afford 2-methyl-4-(2-pyrimidinylmethoxy)aniline (0.15 g, crude material) as solid.

$^1$H NMR (DMSO-$d_6$) δ (ppm) 8.82 (d, J=4.88 Hz, 2H), 7.45 (t, J=4.90 Hz, 1H), 6.62 (d, J=2.64 Hz, 1H), 6.55 (dd, J=2.74, 8.60 Hz, 1H), 6.50 (d, J=8.52 Hz, 1H), 5.08 (s, 2H), 4.40 (br. s, 2H), 2.01 (s, 3H); LCMS (m/z): 216.0 $[M+H]^+$.

Third Step

A solution of ethyl 2-ethoxy-4-oxo-4,5-dihydrofuran-3-carboxylate (0.14 g, 0.60 mmol) which afforded in the Example 74, Third step and 2-methyl-4-(2-pyrimidinylmethoxy)aniline (0.13 g, 0.6 mmol) in ethanol (5.0 mL) was stirred at 60° C. for 30 h. The solvent was removed under reduced pressure, then the residue was purified by chromatography on silica gel(hexane/ethyl acetate) to afford ethyl 2-{[2-methyl-4-(2-pyrimidinylmethoxy)phenyl]amino}-4-oxo-4,5-dihydrofuran-3-carboxylate as solid (0.035 g, y. 15%).

$^1$H NMR (DMSO-$d_6$) δ (ppm) 9.98 (br. s, 1H), 8.84 (d, J=4.88 Hz, 2H), 7.47 (t, J=4.90 Hz, 1H), 7.25 (d, J=8.76 Hz, 1H), 6.96 (d, J=2.72 Hz, 1H), 6.84 (dd, J=2.82, 8.70 Hz, 1H), 5.28 (s, 2H), 4.57 (s, 2H), 4.21 (q, J=7.07 Hz, 2H), 2.19 (s, 3H), 1.24 (t, J=7.04 Hz, 3H); LCMS (m/z): 370.0 $[M+H]^+$.

Fourth Step

To a solution of ethyl 2-{[2-methyl-4-(2-pyrimidinylmethoxy)phenyl]amino}-4-oxo-4,5-dihydrofuran-3-carboxylate (0.035 g, 0.10 mmol) and 7-azaindole-3-carboxaldehyde (0.014 g, 0.10 mmol) in ethanol (5.0 mL), piperidine (0.050 mL, 0.50 mmol) was added at ambient temperature then the mixture was refluxed for 3 days. Cooled to ambient temperature, the solvent was removed under reduced pressure. The residue was suspended in ethanol, then the precipitate was collected by filtration, washed with ethanol then dried to afford the titled compound as solid (9.0 mg, y. 19%).

$^1$H NMR (DMSO-$d_6$) δ (ppm) 12.28 (br. s, 1H), 10.27 (br. s, 1H), 8.88 (d, J=4.40 Hz, 2H), 8.19 (d, J=3.42 Hz, 1H), 7.77 (br. s, 1H), 7.68 (d, J=7.34 Hz, 1H), 7.50 (t, J=4.60 Hz, 1H), 7.42 (d, J=8.80 Hz, 1H), 7.10 (br. s, 1H), 6.98 (d, J=8.31 Hz, 1H), 6.74-6.86 (m, 2H), 5.39 (s, 2H), 4.19-4.32 (m, J=6.80 Hz, 2H), 2.22 (br. s, 3H), 1.18-1.47 (m, 3H); LCMS (m/z): 498.4 $[M+H]^+$.

Example 162

Ethyl 5-[(1H-pyrrolo[2,3-b]pyridin-3-yl)methylene]-2-({2-methyl-4-[2-(1-pyrrolidinyl)ethoxy]phenyl}amino)-4-oxo-4,5-dihydrofuran-3-carboxylate acetate

[Chemical Formula 171]

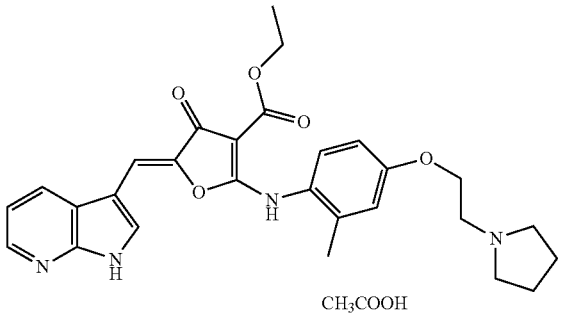

The mixture, which similarly prepared according to the procedure described in the Example 161, was purified by preparative HPLC (aqueous ammonium acetate/acetonitrile were used as eluents) to afford the titled compound (solid).

$^1$H NMR (DMSO-$d_6$) δ (ppm) 12.25 (br. s, 1H), 8.16 (d, J=3.91 Hz, 1H), 7.74 (s, 1H), 7.68 (d, J=7.82 Hz, 1H), 7.35 (d, J=7.82 Hz, 1H), 7.02 (br. s, 1H), 6.86-6.96 (m, 2H), 6.70-6.80 (m, 1H), 4.20-4.35 (m, 2H), 4.16 (t, J=5.62 Hz, 2H), 2.87 (t, J=5.62 Hz, 2H), 2.50-2.72 (m, 4H), 2.21 (s, 3H), 1.90 (s, 3H), 1.68-1.78 (m, 4H), 1.28 (t, J=7.09 Hz, 3H); LCMS (m/z): 503.2 $[M+H]^+$.

Example 163

Ethyl 5-[(1H-pyrrolo[2,3-b]pyridin-3-yl)methylene]-2-({2-methyl-4-[2-(methylsulfonyl)ethoxy]phenyl}amino)-4-oxo-4,5-dihydrofuran-3-carboxylate

[Chemical Formula 172]

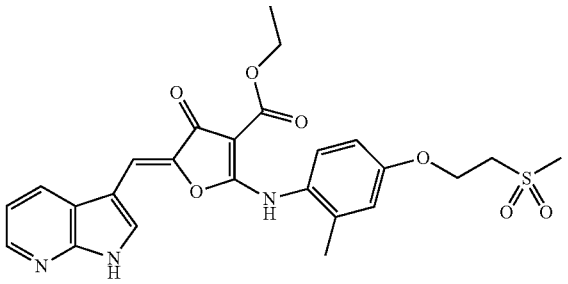

To a mixed solution of the compound (0.070 g, 0.14 mmol) of Example 128 and saturated sodium bicarbonate solution (0.80 mL) in methanol (0.4 mL) and dichloromethane (1.6 mL) that cooled with ice bath, 3-chloroperoxybenzoic acid (0.050 g, 0.28 mmol) was added at 0° C. The mixture was stirred for 1 h. The reaction mixture was extracted with dichloromethane, and the organic layer was washed with saturated sodium bicarbonate solution, dried over sodium sulfate and concentrated. The residue was purified by preparative HPLC to afford the titled compound as solid (0.010 g, y. 13%).

$^1$H NMR (DMSO-$d_6$) δ (ppm) 12.18 (br. s, 1H), 10.4 (br. s, 1H), 8.19 (d, J=4.40 Hz, 1H), 7.74 (br. s, 1H), 7.64 (d, J=7.34 Hz, 1H), 7.36 (d, J=8.31 Hz, 1H), 7.06 (br. s, 1H), 6.97 (d, J=8.31 Hz, 1H), 6.66-6.80 (m, 2H), 4.44 (t, J=5.38 Hz, 2H), 4.18-4.30 (m, J=6.80 Hz, 2H), 3.66-3.76 (m, 2H), 3.15 (s, 3H), 2.21 (s, 3H), 1.28 (t, J=7.09 Hz, 3H); LCMS (m/z): 512.2 $[M+H]^+$.

Example 164

Ethyl 5-[(1H-pyrrolo[2,3-b]pyridin-3-yl)methylene]-2-(7,8-dihydro-1,6-naphthyridin-6(5H)-yl)-4-oxo-4,5-dihydrofuran-3-carboxylate formate

[Chemical Formula 173]

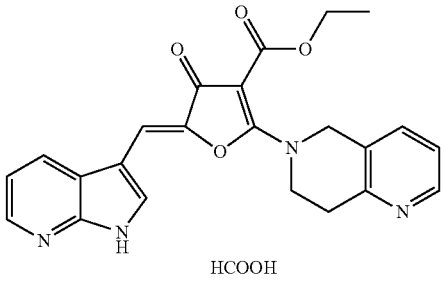

To a solution of 5,6,7,8-tetrahydro-1,6-naphthyridine dihydrochloride (0.049 g, 0.24 mmol) in ethanol (1.0 mL), 4M sodium hydroxide solution (0.13 mL, 0.52 mmol) was added at ambient temperature and the mixture was stirred for 5 min. To this reaction mixture, ethyl 2-ethoxy-4-oxo-4,5-dihydrofuran-3-carboxylate (0.049 g, 0.24 mmol), which afforded in the Example 74, Third step was added and stirred for 1 h. The solvent was removed under reduced pressure, then chloroform and water were added to the residue and two phases were separated. The organic layer was washed with brine, dried over magnesium sulfate and concentrated. To this residue, 7-azaindole-3-carboxaldehyde (0.027 g, 0.18 mmol), 5,6,7,8-tetrahydro-1,6-naphthyridine (0.0063 g, 0.047 mmol) and ethanol (1.0 mL) were added and the mixture was refluxed for further 14 days. The reaction mixture was filtered and washed with hot ethanol. The solid was purified by preparative HPLC to afford the titled compound as solid (0.0058 g, y. 5%).

$^1$H NMR (DMSO-$d_6$) δ (ppm) 12.38 (br. s, 1H), 8.46 (d, J=3.51 Hz, 1H), 8.42 (d, J=7.78 Hz, 1H), 8.33 (dd, J=1.13, 4.64 Hz, 1H), 8.10 (s, 1H), 7.71 (d, J=7.78 Hz, 1H), 7.31 (dd, J=4.77, 7.78 Hz, 1H), 7.22 (dd, J=4.64, 7.91 Hz, 1H), 6.91 (s, 1H), 5.01-5.07 (m, 2H), 4.22 (q, J=7.03 Hz, 2H), 4.07-4.13 (m, 2H), 3.19 (t, J=5.90 Hz, 2H), 1.27 (t, J=7.03 Hz, 3H); LCMS (m/z): 417.1 $[M+H]^+$.

Example 165

Ethyl 5-[(1H-pyrrolo[2,3-b]pyridin-3-yl)methylene]-2-(5,6-dihydro-1,7-naphthyridin-7(8H)-yl)-4-oxo-4,5-dihydrofuran-3-carboxylate formate

[Chemical Formula 174]

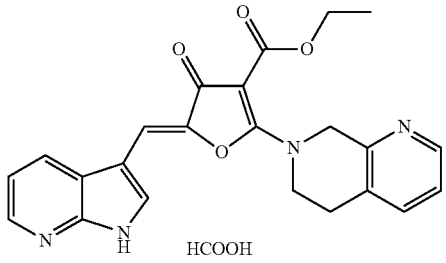

To a solution of 5,6,7,8-tetrahydro-1,7-naphthyridine dihydrochloride (0.050 g, 0.24 mmol) in ethanol (1.3 mL), 4M sodium hydroxide solution (0.13 mL, 0.52 mmol) was added at ambient temperature and the mixture was stirred for 5 min. To this reaction mixture, ethyl 2-ethoxy-4-oxo-4,5-dihydrofuran-3-carboxylate (0.049 g, 0.24 mmol), which afforded in the Example 74, Third step was added and stirred for 1 h. The solvent was removed under reduced pressure, then chloroform and water were added to the residue and two phases were separated. The organic layer was washed with brine, dried over magnesium sulfate and concentrated. To this residue, 7-azaindole-3-carboxaldehyde (0.023 g, 0.15 mmol), 5,6,7,8-tetrahydro-1,7-naphthyridine dihydrochloride (0.0056 g, 0.042 mmol) and ethanol (1.0 mL) were added and refluxed for further 14 days. Cooled to ambient temperature, the reaction mixture was purified by preparative HPLC to afford the titled compound as solid (0.0033 g, y. 3%).

$^1$H NMR (DMSO-$d_6$) δ (ppm) 12.39 (br. s, 1H), 8.39-8.49 (m, 2H), 8.33 (d, J=4.52 Hz, 1H), 8.05 (d, J=2.26 Hz, 1H), 7.70 (d, J=7.03 Hz, 1H), 7.31 (dd, J=4.77, 7.78 Hz, 1H), 7.21 (dd, J=4.77, 7.78 Hz, 1H), 6.92 (s, 1H), 5.00 (br. s, 2H), 4.22 (q, J=7.03 Hz, 2H), 4.02-4.10 (m, 2H), 3.12 (t, J=5.52 Hz, 2H), 1.27 (t, J=7.03 Hz, 3H); LCMS (m/z): 417.1 $[M+H]^+$.

Example 166

2-[(tert-Butoxycarbonyl)oxy]ethyl 5-[(1H-pyrrolo[2,3-b]pyridin-3-yl)methylene]-2-azepinyl-4-oxo-4,5-dihydrofuran-3-carboxylate

[Chemical Formula 175]

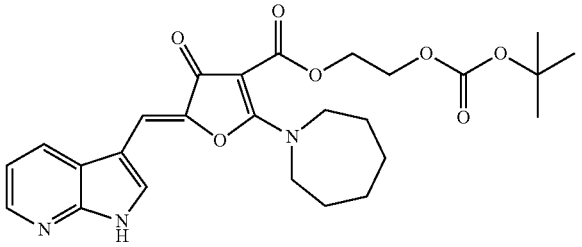

First Step

To a solution of triethylamine (0.65 mL, 4.7 mmol) in ethylene glycol (1.8 mL, 0.031 mol) that cooled with ice bath, ethyl malonyl chloride (0.40 mL, 3.1 mmol) was added dropwise and the mixture was stirred for 2.5 h. The reaction was terminated by addition of aqueous 10% citric acid solution, the reaction mixture was extracted with chloroform. The organic layer was dried over magnesium sulfate, filtered and concentrated. The residue was purified by chromatography on silica gel(chloroform/methanol) to afford ethyl (2-hydroxyethyl)malonate as oil (0.37 g, y. 66%).

$^1$H NMR ($CDCl_3$) δ (ppm) 4.28-4.35 (m, 2H), 4.22 (q, J=7.19 Hz, 2H), 3.80-3.88 (m, 2H), 3.43 (s, 2H), 2.18 (br. s, 1H), 1.29 (t, J=7.15 Hz, 3H)

Second Step

To a solution of ethyl 2-hydroxyethyl malonate (0.36 mg, 2.1 mmol) and di-tert-butyl dicarbonate (0.57 mL, 2.5 mmol) in tetrahydrofuran (2.0 mL) that cooled with ice bath, triethylamine (0.43 mL, 3.1 mmol) was added dropwise and 4-dimethylaminopyridine (0.019 mg, 0.16 mmol) was added then the mixture was stirred at ambient temperature for 2 weeks. The reaction mixture was diluted with water, and extracted with ethyl acetate. The organic layer was washed with brine, dried over magnesium sulfate and concentrated. The residue was purified by chromatography on silica gel (hexane/ethyl acetate) to afford 2-[(tert-butoxycarbonyl)oxy]ethyl ethyl malonate as oil (0.37 g, y. 43%).

$^1$H NMR ($CDCl_3$) δ (ppm) 4.33-4.39 (m, 2H), 4.26-4.31 (m, 2H), 4.21 (q, J=7.03 Hz, 2H), 3.41 (s, 2H), 1.49 (s, 9H), 1.28 (t, J=7.15 Hz, 3H)

Third Step

A solution of 2-[(tert-butoxycarbonyl)oxy]ethyl ethyl malonate (0.36 g, 1.3 mmol) in anhydrous tetrahydrofuran (1.0 mL) was added dropwise to a solution of sodium hydride (60% w/w in oil, 0.10 g, 2.6 mmol) in anhydrous tetrahydrofuran (4.0 mL) that cooled with ice bath. The mixture was refluxed for 14 min. The reaction mixture was cooled with ice bath, chloroacetyl chloride (0.11 mL, 1.3 mmol) was added dropwise to the reaction mixture and the mixture was stirred for 1 h then stirred at 45° C. for further 1 h. The reaction mixture was diluted with water, extracted with chloroform for 2 times. The organic layer was dried over magnesium sulfate and concentrated. The residue was purified by chromatography on silica gel(ethyl acetate/methanol) then concentrated. To this residue (ca. 0.11 g) in ethanol (3.0 mL), hexamethyleneimine (0.046 mL, 0.41 mmol) was added dropwise and the mixture was stirred at ambient temperature for 30 min. Then to the reaction mixture, 7-azaindole-3-carboxaldehyde (0.043 g, 0.30 mmol) was added at ambient temperature then the mixture was refluxed for further 4 days. Cooled to ambient temperature, the reaction mixture was purified by preparative HPLC to afford the titled compound as solid (0.020 g, y. 3%).

$^1$H NMR (DMSO-$d_6$) δ (ppm) 12.31 (br. s, 1H), 8.39 (d, J=8.03 Hz, 1H), 8.31 (dd, J=1.38, 4.64 Hz, 1H), 7.95 (d, J=2.51 Hz, 1H), 7.20 (dd, J=4.64, 7.91 Hz, 1H), 6.85 (s, 1H), 4.30-4.36 (m, 2H), 4.21-4.27 (m, 2H), 3.70-3.90 (m, 4H), 1.80-1.90 (m, 4H), 1.53-1.62 (m, 4H), 1.42 (s, 9H); LCMS (m/z): 498.2 $[M+H]^+$.

Example 167

2-Methoxyethyl 5-[(1H-pyrrolo[2,3-b]pyridin-3-yl) methylene]-2-[N-methyl-N-(2-thienylmethyl) amino]-4-oxo-4,5-dihydrofuran-3-carboxylate

[Chemical Formula 176]

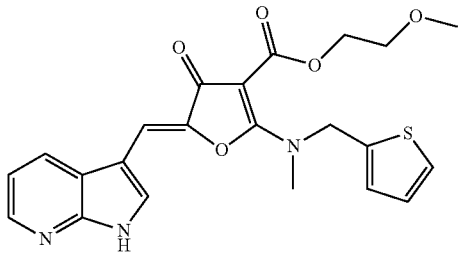

A solution of the compound (0.050 g, 0.12 mmol) of Example 108, 2-methoxyethanol (0.20 mL, 2.6 mmol), 4-dimethylaminopyridine (0.0030 g, 0.024 mmol) and zinc cluster catalyst ($Zn_4(OCOCF_3)_6O$) (0.0058 g, 0.0061 mmol) in N,N-dimethylacetamide (0.5 mL) was stirred with the microwave synthesizer (Biotage Initiator™) at 150° C. for 3.5 h. Cooled to ambient temperature, the reaction mixture was purified by preparative HPLC to afford the titled compound as solid (0.0029 g, y. 5%).

$^1$H NMR (DMSO-$d_6$) δ (ppm) 12.34 (br. s, 1H), 8.38 (d, J=8.03 Hz, 1H), 8.30 (dd, J=1.38, 4.64 Hz, 1H), 8.03 (d, J=2.26 Hz, 1H), 7.53 (dd, J=1.00, 5.02 Hz, 1H), 7.13-7.22 (m, 2H), 7.04 (dd, J=3.51, 5.02 Hz, 1H), 6.93 (s, 1H), 5.20 (s, 2H), 4.23-4.28 (m, 2H), 3.55-3.60 (m, 2H), 3.22-3.32 (m, 6H); LCMS (m/z): 440.1 $[M+H]^+$.

Example 168 n-Butyl 5-[(1H-pyrrolo[2,3-b]pyridin-3-yl)methylene]-2-[N-methyl-N-(2-thienylmethyl)amino]-4-oxo-4,5-dihydrofuran-3-carboxylate

[Chemical Formula 177]

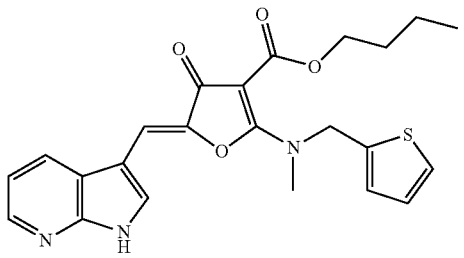

A solution of the compound (0.050 g, 0.12 mmol) of Example 108, 1-butanol (0.50 mL, 5.5 mmol), 4-dimethylaminopyridine (0.0030 g, 0.024 mmol) and zinc cluster catalyst ($Zn_4(OCOCF_3)_6O$) (0.0058 g, 0.0061 mmol) in N,N-dimethylacetamide (0.5 mL) was stirred with the microwave synthesizer (Biotage Initiator™) at 150° C. for 1.5 h. Cooled to ambient temperature, the reaction mixture was purified by preparative HPLC to afford the titled compound as solid (0.0044 g, y. 6%).

$^1$H NMR (DMSO-$d_6$) δ (ppm) 12.33 (br. s, 1H), 8.37 (d, J=7.78 Hz, 1H), 8.30 (dd, J=1.25, 4.52 Hz, 1H), 8.01-8.04 (m, 1H), 7.53 (dd, J=1.25, 5.02 Hz, 1H), 7.14-7.22 (m, 2H), 7.04 (dd, J=3.51, 5.02 Hz, 1H), 6.91 (s, 1H), 5.21 (s, 2H), 4.13 (t, J=6.53 Hz, 2H), 3.24-3.31 (m, 3H), 1.55-1.65 (m, 2H), 1.36-1.47 (m, 2H), 0.90 (t, J=7.40 Hz, 3H); LCMS (m/z): 438.1 $[M+H]^+$.

Example 169

2-Hydroxyethyl 5-[(1H-pyrrolo[2,3-b]pyridin-3-yl) methylene]-2-azepinyl-4-oxo-4,5-dihydrofuran-3-carboxylate hydrochloride

[Chemical Formula 178]

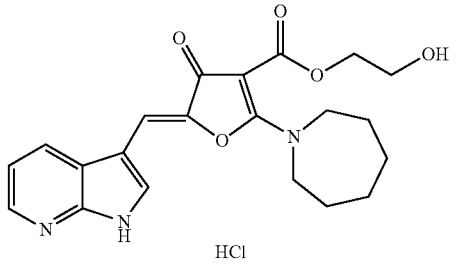

To a mixed solution of the compound (0.018 g, 0.037 mmol) of Example 166 in dioxane (0.2 mL) and chloroform (1.0 mL) that cooled with ice bath, 4M hydrochloric acid in dioxane (0.25 mL, 1.0 mmol) was added dropwise. The mixture was stirred at ambient temperature for 24 h. The precipitate was collected by filtration, washed with chloroform and hexane then dried to afford the titled compound as solid (6.3 mg, y. 37%).

$^1$H NMR (DMSO-$d_6$) δ (ppm) 12.39 (br. s, 1H), 8.44 (d, J=7.78 Hz, 1H), 8.33 (dd, J=1.38, 4.64 Hz, 1H), 7.96 (s, 1H), 7.23 (dd, J=4.77, 8.03 Hz, 1H), 6.89 (s, 1H), 4.16 (t, J=5.27 Hz, 2H), 3.67-3.95 (m, 6H), 3.62 (t, J=5.14 Hz, 2H), 1.75-1.93 (m, 4H), 1.50-1.65 (m, 4H); LCMS (m/z): 398.1 $[M+H]^+$.

Example 170

2-(Dimethylamino)ethyl 5-[(1H-pyrrolo[2,3-b]pyridin-3-yl)methylene]-2-[N-methyl-N-(2-thienylmethyl)amino]-4-oxo-4,5-dihydrofuran-3-carboxylate

[Chemical Formula 179]

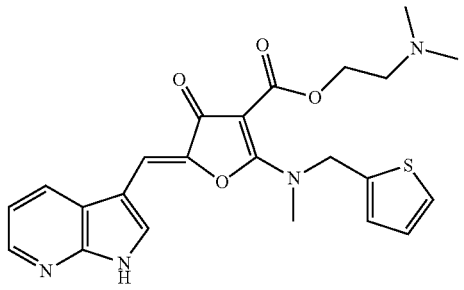

A solution of the compound (0.10 g, 0.25 mmol) of Example 108, 2-(dimethylamino)ethanol (0.40 mL, 4.0 mmol), 4-dimethylaminopyridine (0.0060 g, 0.049 mmol) and zinc cluster catalyst ($Zn_4(OCOCF_3)_6O$) (0.012 g, 0.012 mmol) in N,N-dimethylacetamide (0.5 mL) was stirred with the microwave synthesizer (Biotage Initiator™) at 150° C. for 30 min. Cooled to ambient temperature, the reaction mixture was purified by preparative HPLC to afford the titled compound as solid (0.0023 g, y. 2%).

$^1$H NMR (DMSO-$d_6$) δ (ppm) 12.33 (br. s, 1H), 8.38 (d, J=8.03 Hz, 1H), 8.28-8.32 (m, 1H), 8.03 (s, 1H), 7.53 (dd, J=1.00, 5.02 Hz, 1H), 7.14-7.22 (m, 2H), 7.04 (dd, J=3.51, 5.02 Hz, 1H), 6.92 (s, 1H), 5.20 (s, 2H), 4.21 (t, J=5.90 Hz, 2H), 3.51 (s, 3H), 3.25-3.29 (m, 2H), 2.18 (s, 6H); LCMS (m/z): 453.1 $[M+H]^+$.

Example 171

Ethyl 5-[(1H-pyrrolo[2,3-b]pyridin-3-yl)methylene]-2-({2-methyl-4-[2-(2-pyridinyl)ethoxy]phenyl}amino)-4-oxo-4,5-dihydrofuran-3-carboxylate

[Chemical Formula 180]

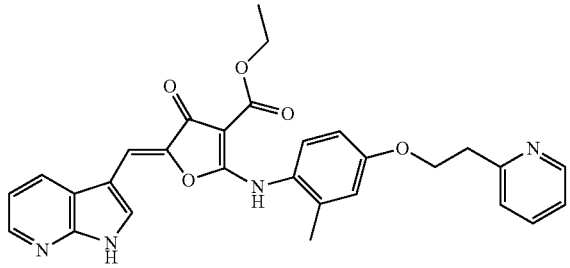

First Step

To a solution of 4-nitro-m-cresol (3.0 g, 0.020 mmol) and triphenylphosphine (7.7 g, 0.029 mmol) in tetrahydrofuran (50 mL) cooled with ice bath, diisopropyl azodicarboxylate (5.8 mL, 0.030 mmol) was added dropwise. The mixture was stirred at ambient temperature for 30 min. The reaction mixture was cooled with ice bath, and a solution of 2-pyridineethanol (2.6 mL, 0.024 mmol) in tetrahydrofuran (5.0 mL) was added dropwise to the reaction mixture then the mixture was stirred at ambient temperature for further 16 h. The solvent was removed under reduced pressure, then the residue was purified by chromatography on silica gel (hexane/ethyl acetate) to afford 2-methyl-4-[2-(2-pyridinyl)ethoxy]-1-nitrobenzene as solid (2.0 g, y. 40%).

$^1$H NMR (DMSO-$d_6$) δ (ppm) 8.43-8.59 (m, 1H), 8.03 (d, J=9.08 Hz, 1H), 7.73 (t, J=7.62 Hz, 1H), 7.37 (d, J=7.80 Hz, 1H), 7.25 (t, J=6.12 Hz, 1H), 7.03 (s, 1H), 6.98 (d, J=9.20 Hz, 1H), 4.49 (t, J=6.46 Hz, 2H), 3.22 (t, J=6.54 Hz, 2H), 2.53 (s, 3H); LCMS (m/z): 259.0 $[M+H]^+$.

Second Step

Under a nitrogen atmosphere, 2-methyl-4-[2-(2-pyridinyl)ethoxy]-1-nitrobenzene (2.0 g, 7.7 mmol) was dissolved in tetrahydrofuran (40 mL) and 10% palladium on carbon (0.20 g) was added at ambient temperature. The reaction mixture was agitated under a hydrogen atmosphere at ambient temperature for 4 h. Palladium on carbon was removed by filtration with Celite and the solvent was removed under reduced pressure to afford 2-methyl-4-[2-(2-pyridinyl)ethoxy]aniline as solid (1.4 g, y. 80%).

$^1$H NMR (DMSO-$d_6$) δ (ppm) 8.49 (d, J=4.36 Hz, 1H), 7.71 (t, J=7.64 Hz, 1H), 7.33 (d, J=7.76 Hz, 1H), 7.22 (t, J=6.10 Hz, 1H), 6.45-6.58 (m, 3H), 4.35 (br. s, 2H), 4.18 (t, J=6.66 Hz, 2H), 3.10 (t, J=6.62 Hz, 2H), 2.00 (s, 3H); LCMS (m/z): 229.4 $[M+H]^+$.

Third Step

A solution of ethyl 2-ethoxy-4-oxo-4,5-dihydrofuran-3-carboxylate (0.35 g, 1.8 mmol) which afforded in the Example 74, Third step and 2-methyl-4-[2-(2-pyridinyl)ethoxy]aniline (0.40 g, 1.8 mmol) in ethanol (5.0 mL) was stirred at ambient temperature for 1.5 days. The solvent was removed under reduced pressure, then the residue was purified by preparative HPLC to afford ethyl 2-({2-methyl-4-[2-(2-pyridinyl)ethoxy]phenyl}amino)-4-oxo-4,5-dihydrofuran-3-carboxylate as solid (0.15 g, y. 22%).

$^1$H NMR (DMSO-$d_6$) δ (ppm) 9.98 (br. s, 1H), 8.51 (d, J=4.52 Hz, 1H), 7.70-7.78 (m, 1H), 7.37 (d, J=7.92 Hz, 1H), 7.22-7.28 (m, 2H), 6.87-6.92 (m, 1H), 6.77-6.84 (m, 1H), 4.57 (s, 2H), 4.36 (t, J=6.62 Hz, 2H), 4.21 (q, J=7.06 Hz, 2H), 3.13-3.25 (m, 2H), 2.19 (s, 3H), 1.21 (s, 3H); LCMS (m/z): 383.2 $[M+H]^+$.

Fourth Step

To a stirred solution of ethyl 2-({2-methyl-4-[2-(2-pyridinyl)ethoxy]phenyl}amino)-4-oxo-4,5-dihydrofuran-3-carboxylate (0.15 g, 0.39 mmol) and 7-azaindole-3-carboxaldehyde (0.057 g, 0.39 mmol) in ethanol (5.0 mL), L-proline (5.0 mg, 0.043 mmol) was added at ambient temperature. The mixture was refluxed for 3 days. The solvent was removed under reduced pressure and the residue was purified by preparative HPLC to afford the titled compound as solid (0.015 g, y. 8%).

$^1$H NMR (DMSO-$d_6$) δ (ppm) 8.57 (d, J=3.91 Hz, 1H), 8.11 (d, J=3.91 Hz, 1H), 7.78 (t, J=7.58 Hz, 1H), 7.65-7.73 (m, 2H), 7.44 (d, J=7.82 Hz, 1H), 7.24-7.33 (m, 2H), 6.97 (br. s, 1H), 6.88 (d, J=8.31 Hz, 1H), 6.63-6.72 (m, 2H), 4.45 (t, J=6.36 Hz, 2H), 4.21 (d, J=6.85 Hz, 2H), 3.23-3.27 (m, 2H), 2.17 (s, 3H), 1.27 (t, J=6.85 Hz, 3H); LCMS (m/z): 511.2 $[M+H]^+$.

Example 172

2-Hydroxyethyl 5-[(1H-pyrrolo[2,3-b]pyridin-3-yl)methylene]-2-[(2-chlorophenyl)amino]-4-oxo-4,5-dihydrofuran-3-carboxylate

[Chemical Formula 181]

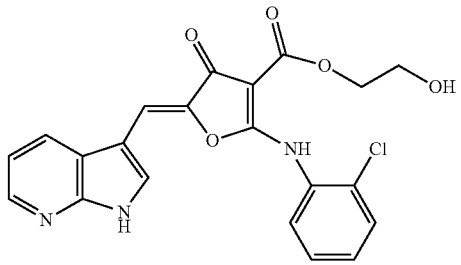

A solution of the compound (0.10 g, 0.24 mmol) of Example 15, ethylene glycol (0.14 mL, 2.5 mmol) and zinc cluster catalyst ($Zn_4(OCOCF_3)_6O$) (0.012 g, 0.012 mmol) in N,N-dimethylacetamide (2.0 mL) was stirred with the microwave synthesizer (Biotage Initiator™) at 130° C. for 1 h. Cooled to ambient temperature, the reaction mixture was purified by preparative HPLC to afford the titled compound as solid (0.030 g, y. 29%).

$^1$H NMR (DMSO-$d_6$) δ (ppm) 12.11 (br. s, 1H), 8.18 (d, J=4.24 Hz, 1H), 7.82 (d, J=7.34 Hz, 1H), 7.59-7.66 (m, 2H), 7.29-7.55 (m, 3H), 6.79 (dd, J=4.65, 7.58 Hz, 1H), 6.62 (br. s, 1H), 4.12-4.22 (m, 2H), 3.65 (t, J=4.89 Hz, 2H); LCMS (m/z): 426 $[M+H]^+$.

Example 173

2-Methoxyethyl 5-[(1H-pyrrolo[2,3-b]pyridin-3-yl) methylene]-2-[(2-chlorophenyl)amino]-4-oxo-4,5-dihydrofuran-3-carboxylate

[Chemical Formula 182]

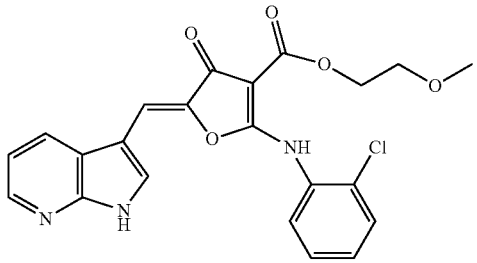

The titled compound (solid) was similarly prepared according to the procedure described in the Example 172.

$^1$H NMR (DMSO-$d_6$) δ (ppm) 12.12 (br. s, 1H), 8.18 (d, J=4.04 Hz, 1H), 7.82 (d, J=7.34 Hz, 1H), 7.58-7.67 (m, 2H), 7.32-7.54 (m, 3H), 6.79 (dd, J=4.65, 7.58 Hz, 1H), 6.63 (br. s, 1H), 4.22-4.32 (m, 2H), 3.56-3.66 (m, 2H), 3.30 (s, 3H); LCMS (m/z): 440.2 $[M+H]^+$.

Example 174

3-Hydroxypropyl 5-[(1H-pyrrolo[2,3-b]pyridin-3-yl) methylene]-2-[(2-chlorophenyl)amino]-4-oxo-4,5-dihydrofuran-3-carboxylate

[Chemical Formula 183]

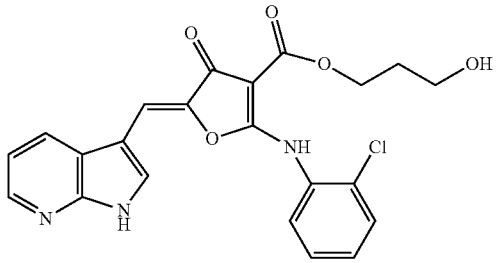

The titled compound (solid) was similarly prepared according to the procedure described in the Example 172.

$^1$H NMR (DMSO-$d_6$) δ (ppm) 12.23 (br. s, 1H), 10.70 (br. s, 1H), 8.20 (d, J=3.42 Hz, 1H), 7.62-7.85 (m, 4H), 7.43-7.58 (m, 2H), 6.73-6.83 (m, 2H), 4.72 (br. s, 1H), 4.20-4.30 (m, 2H), 3.58 (t, J=5.38 Hz, 2H), 1.75-1.89 (m, 2H); LCMS (m/z): 440.2 $[M+H]^+$.

Example 175

(1R,2S)-2-Hydroxycyclopentyl 5-[(1H-pyrrolo[2,3-b]pyridin-3-yl)methylene]-2-[(4-fluorophenyl) amino]-4-oxo-4,5-dihydrofuran-3-carboxylate

[Chemical Formula 184]

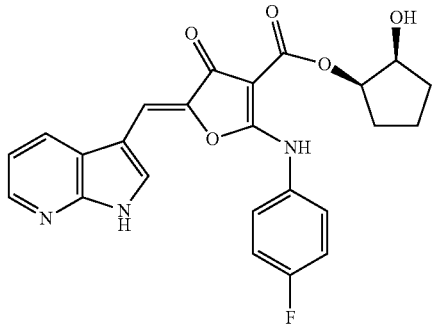

A solution of the compound (0.10 g, 0.25 mmol) of Example 21, (1R,2S)-1,2-cyclopentanediol (0.26 g, 2.5 mmol) and zinc cluster catalyst ($Zn_4(OCOCF_3)_6O$) (0.012 g, 0.012 mmol) in N,N-dimethylacetamide (1.5 mL) was stirred with the microwave synthesizer (Biotage Initiator™) at 130° C. for 2 h. Cooled to ambient temperature, the precipitate was removed by filtration. The filtrate was purified by preparative HPLC to afford the titled compound as solid (0.025 g, y. 20%).

$^1$H NMR (DMSO-$d_6$) δ (ppm) 12.26 (br. s, 1H), 10.60 (br. s, 1H), 8.26 (d, J=4.40 Hz, 1H), 8.05 (d, J=7.82 Hz, 1H), 7.77 (br. s, 1H), 7.52-7.61 (m, 2H), 7.36 (t, J=8.31 Hz, 2H), 6.94 (dd, J=4.65, 7.58 Hz, 1H), 6.87 (br. s, 1H), 5.37 (br. s, 1H), 4.88-4.98 (m, 1H), 4.09-4.18 (m, 1H), 1.94-2.06 (m, 1H), 1.70-1.90 (m, 3H), 1.43-1.69 (m, 2H); LCMS (m/z): 450.2 $[M+H]^+$.

Example 176

4-Hydroxycyclohexyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 185]

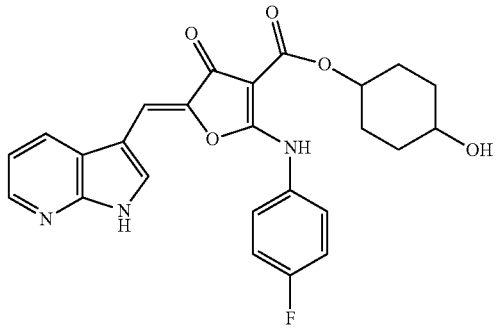

The titled compound (solid) was similarly prepared according to the procedure described in the Example 175.

$^1$H NMR (DMSO-$d_6$) δ (ppm) 12.26 (br. s, 1H), 10.65 (br. s, 1H), 8.25 (d, J=2.93 Hz, 1H), 7.95 (d, J=7.34 Hz, 1H), 7.75 (br. s, 1H), 7.55-7.65 (br. s, 2H), 7.36 (t, J=8.07 Hz, 2H), 6.87-6.94 (m, 1H), 6.82 (br. s, 1H), 4.94 (br. s, 1H), 4.53 (br. s, 1H), 3.56-3.68 (m, 1H), 1.79-1.95 (m, 2H), 1.46-1.77 (m, 6H); LCMS (m/z): 463.8 $[M+H]^+$.

Example 177

3-Hydroxy-2,2-dimethylpropyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 186]

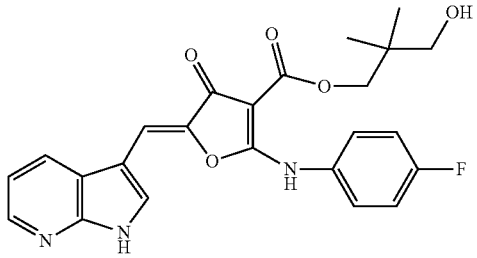

A solution of the compound (0.10 g, 0.25 mmol) of Example 21, 2,2-dimethyl-1,3-propanediol (0.40 g, 3.8 mmol) and zinc cluster catalyst ($Zn_4(OCOCF_3)_6O$) (0.018 g, 0.019 mmol) in N,N-dimethylacetamide (1.5 mL) was stirred with the microwave synthesizer (Biotage Initiator™) at 130° C. for 24 h. Cooled to ambient temperature, the precipitate was removed by filtration. The filtrate was purified by preparative HPLC to afford the titled compound as solid (0.020 g, y. 17%).

$^1$H NMR (DMSO-$d_6$) δ (ppm) 12.27 (br. s, 1H), 10.68 (br. s, 1H), 8.25 (d, J=3.91 Hz, 1H), 7.97 (d, J=7.82 Hz, 1H), 7.74 (br. s, 1H), 7.57-7.65 (m, 2H), 7.37 (t, J=8.31 Hz, 2H), 6.83-6.97 (m, 2H), 4.88 (br. s, 1H), 3.93-4.02 (m, 2H), 3.26-3.36 (m, 2H), 0.93 (s, 6H); LCMS (m/z): 452.4 $[M+H]^+$.

Example 178

2-(1-Pyrrolidinyl)ethyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 187]

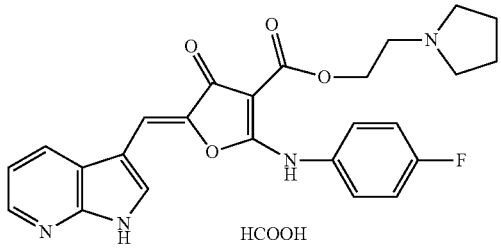

The titled compound (solid) was similarly prepared according to the procedure described in the Example 177.

$^1$H NMR (DMSO-$d_6$) δ (ppm) 12.11 (br. s, 1H), 8.21 (d, J=4.12 Hz, 1H), 8.17 (s, 1H), 7.96 (d, J=7.83 Hz, 1H), 7.65 (s, 1H), 7.34-7.43 (m, 2H), 7.24-7.33 (m, 2H), 6.87 (dd, J=4.89, 7.34 Hz, 1H), 6.65 (s, 1H), 4.25-4.38 (m, 2H), 3.03-3.12 (m, 2H), 2.87-3.00 (m, 4H), 1.65-1.80 (m, 4H); LCMS (m/z): 463.2 $[M+H]^+$.

Example 179

Ethyl 5-[(1H-pyrrolo[2,3-b]pyridin-3-yl)methylene]-2-[(4-methyl-1-piperazinyl)amino]-4-oxo-4,5-dihydrofuran-3-carboxylate

[Chemical Formula 188]

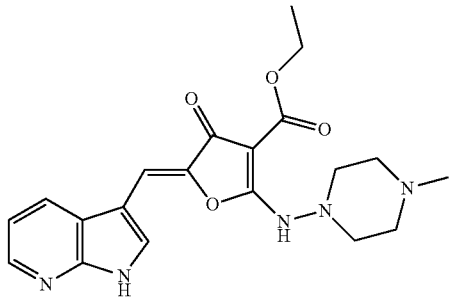

To a solution of ethyl 2-[(4-methyl-1-piperazinyl)amino]-4-oxo-4,5-dihydrofuran-3-carboxylate (0.080 g, 0.30 mmol) which similarly prepared according to the procedure described in the Example 74, Fourth step and 7-azaindole-3-carboxaldehyde (0.040 g, 0.30 mmol) in ethanol (2.0 mL), L-proline (0.020 g, 0.17 mmol) was added at ambient temperature. The mixture was refluxed for 1.5 days. Cooled to ambient temperature, the precipitate was collected by filtration, washed with ethanol and hexane then dried to afford the titled compound as solid (0.017 g, y. 14%).

$^1$H NMR (DMSO-$d_6$) δ (ppm) 12.36 (br. s, 1H), 9.95 (br. s, 1H), 8.96 (d, J=7.34 Hz, 1H), 8.35 (d, J=3.42 Hz, 1H), 8.11 (br. s, 1H), 7.23 (dd, J=4.65, 7.58 Hz, 1H), 6.85 (br. s, 1H), 4.21 (q, J=7.30 Hz, 2H), 3.06 (br. s, 3H), 2.43-2.70 (m, 6H), 2.24-2.35 (m, 2H), 1.26 (t, J=6.85 Hz, 3H); LCMS (m/z): 398.2 $[M+H]^+$.

Example 180

1-Methyl-4-piperidinyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 189]

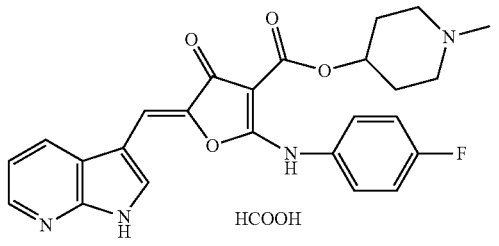

A solution of the compound (0.10 g, 0.25 mmol) (of Example 21, 4-hydroxy-1-methylpiperidine (0.44 g, 3.8 mmol) and zinc cluster catalyst ($Zn_4(OCOCF_3)_6O$) (0.018 g, 0.019 mmol) in N,N-dimethylacetamide (1.0 mL) was stirred at 180° C. for 16 h then at 130° C. for further 16 h. Cooled to ambient temperature, the precipitate was removed by filtration. The filtrate was purified by preparative HPLC to afford the titled compound as solid (0.016 g, y. 13%).

$^1$H NMR (DMSO-$d_6$) δ (ppm) 12.15 (br. s, 1H), 8.23 (d, J=3.91 Hz, 1H), 8.18 (s, 1H), 7.96 (d, J=7.82 Hz, 1H), 7.69 (s, 1H), 7.42-7.49 (m, 2H), 7.25-7.36 (m, 2H), 6.89 (dd, J=4.89, 7.83 Hz, 1H), 6.68 (s, 1H), 4.83-4.93 (m, 1H), 2.77-2.87 (m, 2H), 2.35-2.45 (m, 2H), 2.30 (s, 3H), 1.85-1.95 (m, 2H), 1.68-1.80 (m, 2H); LCMS (m/z): 463.2 $[M+H]^+$.

Example 181

Isobutyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 190]

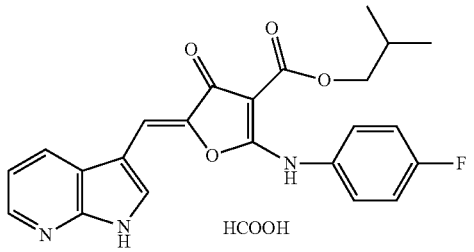

The titled compound (solid) was similarly prepared according to the procedure described in the Example 180.

$^1$H NMR (DMSO-$d_6$) δ (ppm) 12.17 (br. s, 1H), 8.23 (d, J=3.91 Hz, 1H), 8.19 (s, 1H), 7.96 (d, J=7.82 Hz, 1H), 7.70 (s, 1H), 7.43-7.54 (m, 2H), 7.31 (t, J=8.07 Hz, 2H), 6.84-6.96 (m, 1H), 6.72 (br. s, 1H), 3.96 (d, J=5.87 Hz, 2H), 1.90-2.05 (m, 1H), 0.97 (d, J=6.36 Hz, 6H); LCMS (m/z): 422.2 $[M+H]^+$.

Example 182

2-(Dimethylamino)ethyl 5-[(1H-pyrrolo[2,3-b]pyridin-3-yl)methylene]-2-[(2-chlorophenyl)amino]-4-oxo-4,5-dihydrofuran-3-carboxylate acetate

[Chemical Formula 191]

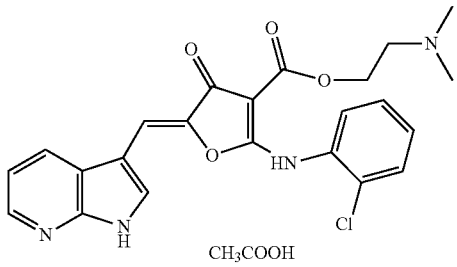

A solution of the compound (0.10 g, 0.24 mmol) of Example 15, 2-(dimethylamino)ethanol (0.40 mL, 4.0 mmol), 4-dimethylaminopyridine (0.010 g, 0.082 mmol) and zinc cluster catalyst ($Zn_4(OCOCF_3)_6O$) (0.018 g, 0.019 mmol) in N,N-dimethylacetamide (2.0 mL) was stirred at 130° C. for 24 h. Cooled to ambient temperature, the precipitate was removed by filtration. The filtrate was purified by preparative HPLC (aqueous ammonium acetate/acetonitrile as eluents) to afford the titled compound as solid (0.012 g, y. 11%).

$^1$H NMR (DMSO-$d_6$) δ (ppm) 11.92 (br. s, 1H), 8.15 (d, J=3.91 Hz, 1H), 7.86 (d, J=7.82 Hz, 1H), 7.48-7.55 (m, 2H), 7.30-7.37 (m, 1H), 7.15-7.23 (m, 2H), 6.73-6.79 (m, 1H), 6.39 (s, 1H), 4.30-4.39 (m, 2H), 3.12-3.22 (m, 2H), 2.73 (br. s, 6H), 1.91 (s, 3H); LCMS (m/z): 453.0 $[M+H]^+$.

Example 183

3-Hydroxycyclohexyl 5-[(1H-pyrrolo[2,3-b]pyridin-3-yl)methylene]-2-[(4-fluorophenyl)amino]-4-oxo-4,5-dihydrofuran-3-carboxylate

[Chemical Formula 192]

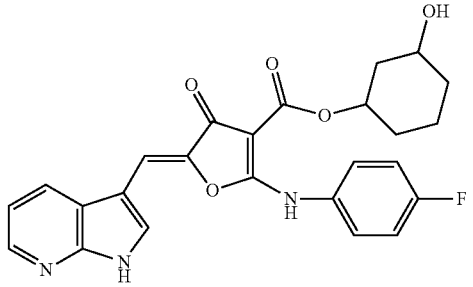

A solution of the compound (0.10 g, 0.25 mmol) of Example 21, 1,3-cyclohexanediol (0.44 g, 3.8 mmol) and zinc cluster catalyst ($Zn_4(OCOCF_3)_6O$) (0.018 g, 0.019 mmol) in N,N-dimethylacetamide (1.0 mL) was stirred at 130° C. for 1.5 days. Cooled to ambient temperature, the precipitate was removed by filtration. The filtrate was purified by preparative HPLC to afford the titled compound as solid (0.010 g, y. 13%).

$^1$H NMR (DMSO-$d_6$) δ (ppm) 12.25 (br. s, 1H), 8.24 (d, J=3.91 Hz, 1H), 7.92-8.00 (m, 1H), 7.74 (br. s, 1H), 7.55-7.65 (m, 2H), 7.31-7.42 (m, 2H), 6.90 (dd, J=4.89, 7.82 Hz, 1H), 6.78-6.86 (m, 1H), 5.19-5.28 (m, 1H), 4.92-5.02 (m, 1H), 4.55 (d, J=3.42 Hz, 1H), 1.15-2.08 (m, 8H); LCMS (m/z): 463.8 $[M+H]^+$.

Example 184

(1-Methyl-2-piperidinyl)methyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 193]

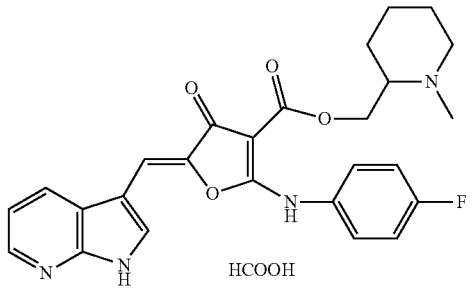

The titled compound (solid) was similarly prepared according to the procedure described in the Example 183.

$^1$H NMR (DMSO-$d_6$) δ (ppm) 12.11 (br. s, 1H), 8.22 (d, J=4.40 Hz, 1H), 8.16 (s, 1H), 7.98 (d, J=7.82 Hz, 1H), 7.66 (s, 1H), 7.34-7.42 (m, 2H), 7.25-7.33 (m, 2H), 6.88 (dd, J=4.65, 7.58 Hz, 1H), 6.65 (s, 1H), 4.23-4.35 (m, 2H), 2.90-3.00 (m, 1H), 2.62-2.72 (m, 1H), 2.46-2.56 (m, 4H), 1.18-1.83 (m, 6H); LCMS (m/z): 477.4 [M+H]$^+$.

Example 185

2-(4-Methyl-1-piperazinyl)ethyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 194]

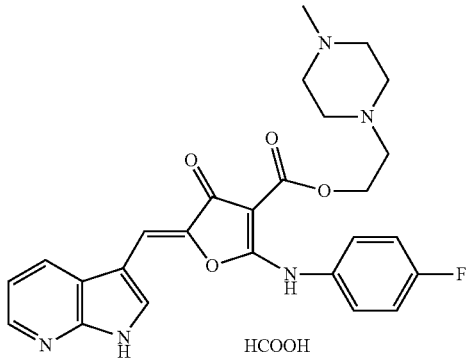

The titled compound (solid) was similarly prepared according to the procedure described in the Example 183.

$^1$H NMR (DMSO-$d_6$) δ (ppm) 12.14 (br. s, 1H), 8.16-8.25 (m, 2H), 7.95 (d, J=6.85 Hz, 1H), 7.67 (br. s, 1H), 7.38-7.48 (m, 2H), 7.25-7.36 (m, 2H), 6.84-6.91 (m, 1H), 6.68 (br. s, 1H), 4.20-4.34 (m, 2H), 2.22-2.71 (m, 10H), 2.13 (br. s, 3H); LCMS (m/z): 492.4 [M+H]$^+$.

Example 186

2-(N,N-Dimethylamino)-2-methylpropyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 195]

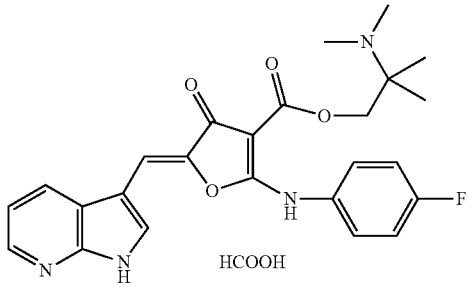

The titled compound (solid) was similarly prepared according to the procedure described in the Example 183.

$^1$H NMR (DMSO-$d_6$) δ (ppm) 12.01 (br. s, 1H), 8.15-8.29 (m, 2H), 7.98 (d, J=7.34 Hz, 1H), 7.60 (br. s, 1H), 7.05-7.33 (m, 4H), 6.83-6.93 (m, 1H), 6.47 (s, 1H), 4.20 (br. s, 2H), 2.55 (br. s, 6H), 1.22 (br. s, 6H); LCMS (m/z): 465.0 [M+H]$^+$.

Example 187

(1-Methyl-4-piperidinyl)methyl 5-[(1H-pyrrolo[2,3-b]pyridin-3-yl)methylene]-2-[(4-fluorophenyl)amino]-4-oxo-4,5-dihydrofuran-3-carboxylate formate

[Chemical Formula 196]

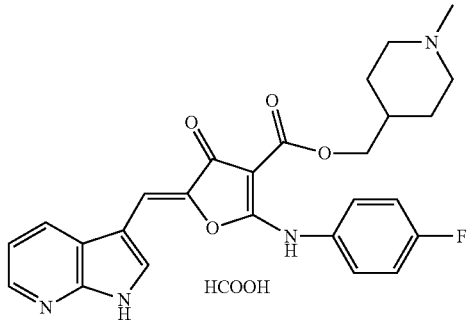

The titled compound (solid) was similarly prepared according to the procedure described in the Example 183.

$^1$H NMR (DMSO-$d_6$) δ (ppm) 12.09 (br. s, 1H), 8.18-8.24 (m, 2H), 7.96 (d, J=7.82 Hz, 1H), 7.66 (s, 1H), 7.33-7.43 (m, 2H), 7.22-7.32 (m, 2H), 6.89 (dd, J=4.89, 7.83 Hz, 2H), 6.59 (s, 1H), 4.01 (d, J=6.36 Hz, 2H), 2.88-2.96 (m, 2H), 2.29 (s, 3H), 2.03-2.15 (m, 2H), 1.62-1.82 (m, 3H), 1.26-1.41 (m, 2H); LCMS (m/z): 477.3 [M+H]$^+$.

Example 188

Ethyl 5-[(1H-pyrrolo[2,3-b]pyridin-3-yl)methylene]-2-(4-morpholinopiperidin-1-yl)-4-oxo-4,5-dihydrofuran-3-carboxylate

[Chemical Formula 197]

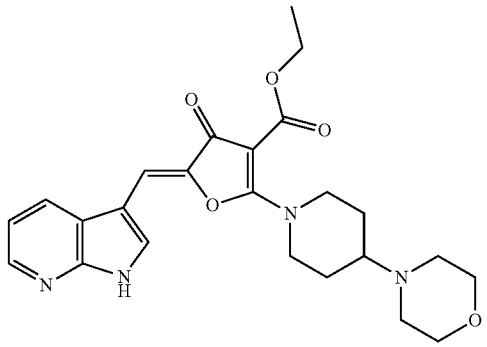

To a stirred solution of ethyl 2-(4-morpholinopiperidin-1-yl)-4-oxo-4,5-dihydrofuran-3-carboxylate (0.10 g, 0.31 mmol) which similarly prepared according to the procedure described in the Example 74, Fourth step and 7-azaindole-3-carboxaldehyde (0.045 g, 0.31 mmol) in ethanol (10 mL), piperidine (0.020 mL, 0.20 mmol) was added at ambient temperature. The mixture was refluxed for 16 h. Cooled to ambient temperature, the precipitate was collected by filtration, washed with ethanol and hexane then dried to afford the titled compound (0.018 g, y. 13%) as solid.

$^1$H NMR (DMSO-$d_6$) δ (ppm) 12.31 (br. s, 1H), 8.37 (d, J=7.34 Hz, 1H), 8.31 (d, J=3.42 Hz, 1H), 7.97 (br. s, 1H), 7.16-7.23 (m, 1H), 6.85 (s, 1H), 4.11-4.30 (m, 4H), 3.52-3.64 (m, 4H), 3.23-3.43 (m, 7H), 1.90-2.02 (m, 2H), 1.54-1.76 (m, 2H), 1.24 (t, J=6.60 Hz, 3H); LCMS (m/z): 453.2 $[M+H]^+$.

Example 189

Ethyl 5-[(1H-pyrrolo[2,3-b]pyridin-3-yl)methylene]-2-(3-carbamoylpiperidino)-4-oxo-4,5-dihydrofuran-3-carboxylate

[Chemical Formula 198]

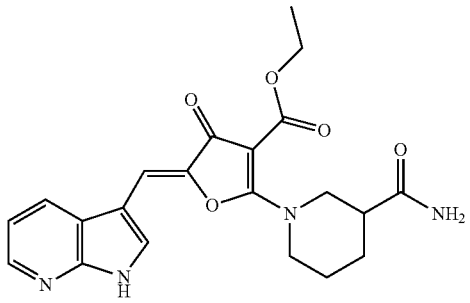

To a solution of ethyl 2-(3-carbamoylpiperidino)-4-oxo-4,5-dihydrofuran-3-carboxylate (0.15 g, 0.53 mmol) which similarly prepared according to the procedure described in the Example 74, Fourth step and 7-azaindole-3-carboxaldehyde (0.078 g, 0.53 mmol) in ethanol (10 mL), piperidine (0.020 mL, 0.20 mmol) was added at ambient temperature. The mixture was refluxed for 16 h. Cooled to ambient temperature, the precipitate was collected by filtration, washed with ethanol and hexane then dried to afford the titled compound as solid (0.018 g, y. 9%).

$^1$H NMR (DMSO-$d_6$) δ (ppm) 12.34 (br. s, 1H), 8.38 (d, J=7.52 Hz, 1H), 8.31 (d, J=3.72 Hz, 1H), 7.97 (br. s, 1H), 7.44 (br. s, 1H), 7.13-7.23 (m, 1H), 6.99 (br. s, 1H), 6.85 (s, 1H), 4.10-4.22 (m, 4H), 3.25-3.46 (m, 2H), 2.54-2.64 (m, 1H), 1.96-2.06 (m, 1H), 1.82-1.92 (m, 1H), 1.60-1.74 (m, 2H), 1.24 (t, J=6.85 Hz, 3H); LCMS (m/z): 411.4 $[M+H]^+$.

Example 190

Ethyl 5-[(1H-pyrrolo[2,3-b]pyridin-3-yl)methylene]-4-oxo-2-(3-oxopiperazino)-4,5-dihydrofuran-3-carboxylate

[Chemical Formula 199]

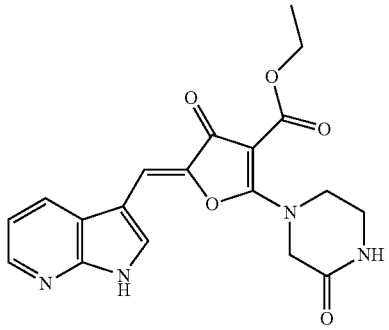

The titled compound (solid) was similarly prepared according to the procedure described in the Example 189.

$^1$H NMR (DMSO-$d_6$) δ (ppm) 12.38 (br. s, 1H), 8.29-8.44 (m, 2H), 8.01 (br. s, 1H), 7.15-7.25 (m, 1H), 6.92 (br. s, 1H), 4.30-4.40 (m, 2H), 4.11-4.23 (m, 2H), 3.92-4.04 (m, 2H), 3.41-3.49 (m, 2H), 1.18-1.31 (m, 3H); LCMS (m/z): 383.0 $[M+H]^+$.

Example 191

Ethyl 5-[(1H-pyrrolo[2,3-b]pyridin-3-yl)methylene]-2-(4-acetyl-1,4-diazepanyl)-4-oxo-4,5-dihydrofuran-3-carboxylate

[Chemical Formula 200]

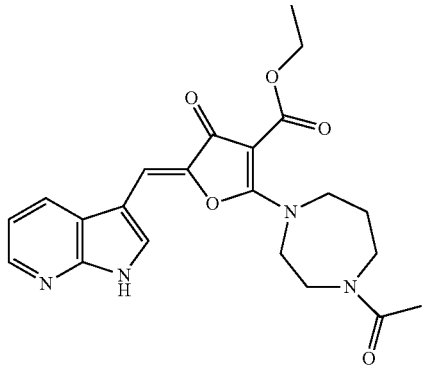

The titled compound (solid) was similarly prepared according to the procedure described in the Example 189.

$^1$H NMR (DMSO-$d_6$) δ (ppm) 12.36 (br. s, 1H), 8.41 (d, J=7.68 Hz, 1H), 8.35 (d, J=4.36 Hz, 1H), 7.99 (br. s, 1H), 7.17-7.29 (m, 1H), 6.89 (d, J=3.91 Hz, 1H), 4.15-4.27 (m, 2H), 3.92-4.10 (m, 3H), 3.73-3.90 (m, 3H), 3.51-3.64 (m, 2H), 1.83-2.08 (m, 5H), 1.28 (t, J=6.60 Hz, 3H); LCMS (m/z): 425.3 $[M+H]^+$.

Example 192

Ethyl 5-[(1H-pyrrolo[2,3-b]pyridin-3-yl)methylene]-2-(4-methyl-1,4-diazepanyl)-4-oxo-4,5-dihydrofuran-3-carboxylate acetate

[Chemical Formula 201]

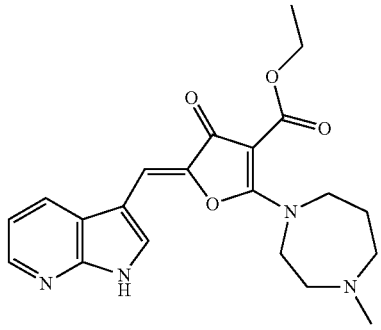

$CH_3COOH$

The titled compound (solid) was similarly prepared according to the procedure described in the Example 189. Further, preparative HPLC (aqueous ammonium acetate/acetonitrile) was used as purification procedure.

$^1$H NMR (DMSO-$d_6$) δ (ppm) 12.48 (br. s, 1H), 8.36 (d, J=7.82 Hz, 1H), 8.30 (d, J=4.40 Hz, 1H), 7.96 (s, 1H), 7.18 (dd, J=4.89, 7.82 Hz, 1H), 6.85 (s, 1H), 4.16 (q, J=7.34 Hz, 2H), 3.70-3.92 (m, 4H), 2.72-2.82 (m, 2H), 2.53-2.63 (m, 2H), 2.28 (s, 3H), 1.92-2.02 (m, 2H), 1.62 (s, 3H), 1.24 (t, J=7.09 Hz, 3H); LCMS (m/z): 397.2 $[M+H]^+$.

Example 193

Ethyl 5-[(1H-pyrrolo[2,3-b]pyridin-3-yl)methylene]-2-(2-methyl-2-phenylhydrazinyl)-4-oxo-4,5-dihydrofuran-3-carboxylate

[Chemical Formula 202]

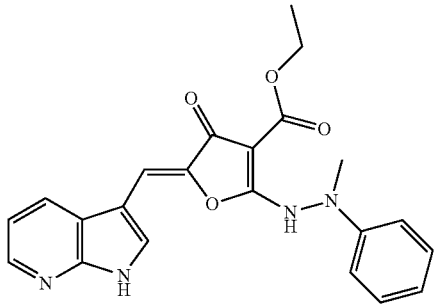

To a solution of ethyl 2-(2-methyl-2-phenylhydrazinyl)-4-oxo-4,5-dihydrofuran-3-carboxylate (0.10 g, 0.36 mmol) which similarly prepared according to the procedure described in the Example 74, Fourth step and 7-azaindole-3-carboxaldehyde (0.053 g, 0.36 mmol) in ethanol (10 mL), L-proline (0.020 g, 0.17 mmol) was added at ambient temperature. The mixture was refluxed for 2 days. Cooled to ambient temperature, the precipitate was collected by filtration, washed with ethanol and hexane then dried to afford the titled compound as solid (0.015 g, y. 10%).

$^1$H NMR (DMSO-$d_6$) δ (ppm) 12.28 (br. s, 1H), 10.79 (s, 1H), 8.48 (d, J=8.31 Hz, 1H), 8.22 (d, J=3.91 Hz, 1H), 7.90 (br. s, 1H), 7.32 (t, J=7.82 Hz, 2H), 6.83-7.05 (m, 5H), 4.25 (q, J=6.85 Hz, 2H), 3.34 (s, 3H), 1.29 (t, J=6.85 Hz, 3H); LCMS (m/z): 405.2 $[M+H]^+$.

Example 194

Ethyl 5-[(1H-pyrrolo[2,3-b]pyridin-3-yl)methylene]-2-[4-(diethylamino)piperidino]-4-oxo-4,5-dihydrofuran-3-carboxylate

[Chemical Formula 203]

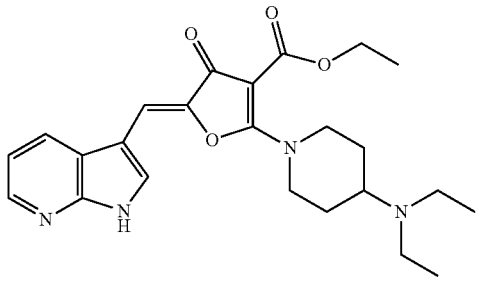

First Step

Under a nitrogen atmosphere, to a solution of tert-butyl 4-oxopiperidine-1-carboxylate (5.0 g, 0.025 mol) and diethylamine (9.1 mL, 0.090 mol) in methanol (40 mL), 10% palladium on carbon (0.50 g) was added at ambient temperature. The reaction mixture was agitated under a hydrogen atmosphere at ambient temperature for 16 h. Palladium on carbon was removed by filtration with Celite and the solvent was removed under reduced pressure, then the residue was purified by chromatography on silica gel(dichloromethane/methanol) to afford tert-butyl 4-(diethylamino)piperidine-1-carboxylate as solid (6.1 g, y. 95%).

$^1$H NMR ($CDCl_3$) δ (ppm) 4.12 (br. s, 2H), 3.76-3.89 (m, 1H), 2.45-2.72 (m, 6H), 1.30-1.53 (m, 13H), 0.90-1.10 (m, 6H)

Second Step

Cooled with ice bath, 4M hydrochloric acid in dioxane (25 mL) was added to tert-butyl 4-(N,N-diethylamino)piperidine-1-carboxylate (6.1 g, 0.024 mol) and the mixture was stirred at ambient temperature for 2 h. The solvent was removed under reduced pressure, and the residue was suspended in diethyl ether, then the precipitate was collected by filtration, washed with diethyl ether and then dried to afford 4-(diethylamino)piperidine dihydrochloride as solid (3.9 g, y. 99%).

Third Step

To a solution of 4-(diethylamino)piperidine dihydrochloride (3.0 g, 0.019 mmol) in water (20 mL), 2M sodium hydroxide solution (5.0 mL) was added at ambient temperature. The mixture was stirred for 30 min. The solvent was removed under reduced pressure, and methanol (10 mL) was added to the crude material, then the residue was removed by filtration. The filtrate was concentrated and dried to afford 4-(diethylamino)piperidine (1.7 g, y. 77%) as solid.

$^1$H NMR (DMSO-$d_6$) δ (ppm) 3.20-3.29 (m, 2H), 3.09-3.14 (m, 1H), 2.77-2.93 (m, 3H), 2.52-2.62 (m, 4H), 1.64-1.90 (m, 4H), 1.00 (t, J=7.04 Hz, 6H)

Fourth Step

A solution of 4-(diethylamino)piperidine (0.50 g, 3.2 mmol), ethyl 2-ethoxy-4-oxo-4,5-dihydrofuran-3-carboxylate (0.76 g, 3.8 mmol) which afforded in the Example 74, Third step and triethylamine (0.60 mL, 4.3 mmol) in tetrahydrofuran (10 mL) was stirred at ambient temperature for 24 h. The solvent was removed under reduced pressure, then the crude material was purified by chromatography on silica gel (dichloromethane/methanol) to afford ethyl 2-[4-(diethylamino)piperidino]-4-oxo-4,5-dihydrofuran-3-carboxylate as oil (0.29 g, y. 30%).

$^1$H NMR (DMSO-$d_6$) δ (ppm) 4.53 (s, 2H), 4.03-4.15 (m, 4H), 3.05-3.19 (m, 2H), 2.82 (br. s, 1H), 2.42-2.58 (m, 4H), 1.73-1.86 (m, 2H), 1.40-1.59 (m, 2H), 1.20 (t, J=7.08 Hz, 3H), 0.91-1.02 (m, 6H); LCMS (m/z): 311.0 $[M+H]^+$ Fifth Step To a solution of ethyl 2-[4-(diethylamino)piperidino]-4-oxo-4,5-dihydrofuran-3-carboxylate (0.10 g, 0.30 mmol) and 7-azaindole-3-carboxaldehyde (0.047 g, 0.30 mmol) in ethanol (5.0 mL), L-proline (0.0040 mg, 0.035 mmol) was added at ambient temperature. The mixture was refluxed for 16 h. Cooled to ambient temperature, the precipitate was collected by filtration, washed with ethanol and hexane then dried to afford the titled compound as solid (0.035 g, y. 25%).

$^1$H NMR (DMSO-$d_6$) δ (ppm) 12.30 (br. s, 1H), 8.37 (d, J=7.82 Hz, 1H), 8.31 (d, J=3.91 Hz, 1H), 7.97 (s, 1H), 7.19 (dd, J=4.89, 7.82 Hz, 1H), 6.84 (s, 1H), 4.11-4.33 (m, 4H), 3.27-3.37 (m, 2H), 2.82-2.92 (m, 1H), 2.41-2.60 (m, 4H), 1.82-1.92 (m, 2H), 1.56-1.71 (m, 2H), 1.24 (t, J=6.85 Hz, 3H), 0.98 (t, J=7.09 Hz, 6H); LCMS (m/z): 439.4 $[M+H]^+$.

Example 195

Ethyl 5-[(1H-pyrrolo[2,3-b]pyridin-3-yl)methylene]-4-oxo-2-(N-piperidinoamino)-4,5-dihydrofuran-3-carboxylate

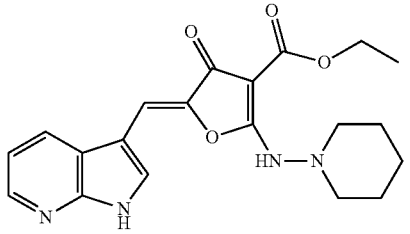

To a solution of ethyl 4-oxo-2-(N-piperidinoamino)-4,5-dihydrofuran-3-carboxylate (0.25 g, 0.98 mmol) which similarly prepared according to the procedure described in the Example 74, Fourth step and 7-azaindole-3-carboxaldehyde (0.14 g, 0.98 mmol) in ethanol (10 mL), L-proline (0.011 mg, 0.096 mmol) was added at ambient temperature. The mixture was refluxed for 2 days. Cooled to ambient temperature, the precipitate was collected by filtration, washed with ethanol and diethyl ether then dried to afford the titled compound as solid (0.015 g, y. 4%).

$^1$H NMR (DMSO-$d_6$) δ (ppm) 12.34 (br. s, 1H), 9.86 (br. s, 1H), 9.00 (d, J=7.82 Hz, 1H), 8.33 (d, J=3.91 Hz, 1H), 8.10 (d, J=2.45 Hz, 1H), 7.18 (dd, J=4.65, 8.07 Hz, 1H), 6.85 (s, 1H), 4.20 (q, J=6.85 Hz, 2H), 2.95-3.05 (m, 4H), 1.69-1.79 (m, 4H), 1.42-1.53 (m, 2H), 1.26 (t, J=6.85 Hz, 3H); LCMS (m/z): 383.2 $[M+H]^+$.

Example 196

Ethyl 5-[(1H-pyrrolo[2,3-b]pyridin-3-yl)methylene]-2-(2,2-dimethylhydrazinyl)-4-oxo-4,5-dihydrofuran-3-carboxylate

[Chemical Formula 205]

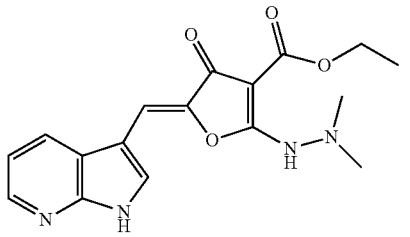

The titled compound (solid) was similarly prepared according to the procedure described in the Example 195.

$^1$H NMR (DMSO-$d_6$) δ (ppm) 11.85 (br. s, 1H), 8.52 (d, J=7.82 Hz, 1H), 8.23 (d, J=3.91 Hz, 1H), 7.83 (s, 1H), 7.10 (dd, J=4.89, 7.82 Hz, 1H), 6.14 (s, 1H), 4.02 (q, J=6.85 Hz, 2H), 1.70 (s, 6H), 1.18 (t, J=7.09 Hz, 3H); LCMS (m/z): 342.8 $[M+H]^+$.

Example 197

Ethyl 5-[(1H-pyrrolo[2,3-b]pyridin-3-yl)methylene]-2-{[2-(dimethylamino)ethyl]-N-methylamino}-4-oxo-4,5-dihydrofuran-3-carboxylate formate

[Chemical Formula 206]

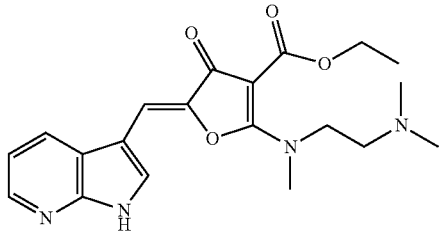

HCOOH

To a solution of ethyl 2-{[2-(dimethylamino)ethyl]-N-methylamino}-4-oxo-4,5-dihydrofuran-3-carboxylate (0.20 g, 0.78 mmol) which similarly prepared according to the procedure described in the Example 74, Fourth step and 7-azaindole-3-carboxaldehyde (0.11 g, 0.78 mmol) in ethanol (6.0 mL), L-proline (0.0093 mg, 0.078 mmol) was added at ambient temperature. The mixture was refluxed for 20 h. Cooled to ambient temperature, the reaction mixture was purified by preparative HPLC to afford the titled compound as solid (0.035 g, y. 12%).

$^1$H NMR (DMSO-$d_6$) δ (ppm) 12.35 (br. s, 1H), 8.38 (d, J=7.83 Hz, 1H), 8.27-8.34 (m, 1H), 8.18 (s, 1H), 7.98 (s, 1H), 7.16-7.22 (m, 1H), 6.85 (s, 1H), 4.17 (q, J=6.85 Hz, 2H), 3.83 (t, J=6.60 Hz, 2H), 3.29 (br. s, 3H), 2.54-2.61 (m, 2H), 2.19 (s, 6H), 1.21-1.28 (m, 3H); LCMS (m/z): 385.0 $[M+H]^+$.

Example 198

Ethyl 5-[(1H-pyrrolo[2,3-b]pyridin-3-yl)methylene]-2-(1,4-oxoazepan-4-yl)-4-oxo-4,5-dihydrofuran-3-carboxylate acetate

[Chemical Formula 207]

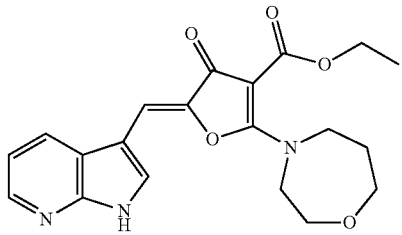

$CH_3COOH$

The titled compound (solid) was similarly prepared according to the procedure described in the Example 197. Further, preparative HPLC (aqueous ammonium acetate/acetonitrile) was used as purification procedure.

$^1$H NMR (DMSO-$d_6$) δ (ppm) 8.35 (d, J=7.82 Hz, 1H), 8.30 (d, J=4.40 Hz, 1H), 7.97 (s, 1H), 7.18 (dd, J=4.89, 7.82 Hz, 1H), 6.87 (s, 1H), 4.17 (q, J=7.17 Hz, 2H), 3.80-4.01 (m, 6H), 3.74 (t, J=5.14 Hz, 2H), 1.95-2.07 (m, 2H), 1.63 (s, 3H), 1.24 (t, J=7.09 Hz, 3H); LCMS (m/z): 383.8 $[M+H]^+$.

Example 199

Ethyl 5-[(1H-pyrrolo[2,3-b]pyridin-3-yl)methylene]-2-[(cis-4-hydroxycyclohexyl)amino]-4-oxo-4,5-dihydrofuran-3-carboxylate

[Chemical Formula 208]

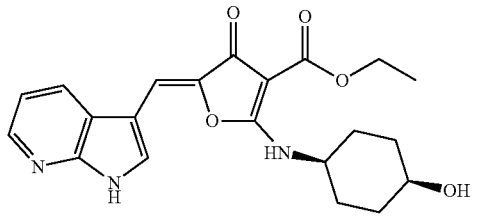

First Step

Cooled with ice bath, to a mixed solution of cyclohexanone oxime (4.0 g, 0.035 mol) in dichloromethane (40 mL) and ethanol (5.0 mL), tert-butyl hypochlorite (4.7 mL, 0.038 mol) was added dropwise and the reaction mixture was cooled to −20° C. then stirred for 30 min. To this reaction mixture, 1,3-cyclohexadiene (5.0 mL, 0.052 mol) was added dropwise and the reaction mixture was allowed to warm to 0° C. then stirred for 4 days. The reaction mixture was concentrated under reduced pressure to half the solvents, and then diethyl ether (80 mL) was added at ambient temperature then the mixture was stirred for further 1 day. To this reaction mixture, ethanol (10 mL) was added and the mixture was stirred for further 4 h, then the precipitate was collected by filtration. The solid was washed with mixed solution of diethyl ether/ethanol (10/1), diethyl ether and hexane then dried to afford 2-oxa-3-azabicyclo[2.2.2]-5-octene hydrochloride as solid (4.2 g, y. 82%).

$^1$H NMR ($CDCl_3$) δ (ppm) 12.43 (br. s, 1H), 11.29 (br. s, 1H), 6.81-6.88 (m, 1H), 6.64-6.71 (m, 1H), 4.87-4.93 (m, 1H), 4.58-4.65 (m, 1H), 2.54-2.66 (m, 1H), 2.31-2.47 (m, 1H), 1.45-1.59 (m, 2H)

Second Step

Under a nitrogen atmosphere, to a mixed solution of 2-oxa-3-azabicyclo[2.2.2]-5-octene hydrochloride (0.20 g, 1.4 mol) in ethanol (2.0 mL) and methanol (1.0 mL), platinum oxide (0.12 g, 0.53 mmol) was added at ambient temperature. The reaction mixture was agitated under a hydrogen atmosphere at ambient temperature for 6.5 h. Platinum oxide was removed by filtration with Celite, cooled this filtrate with ice bath, and 2M hydrochloric acid in ethanol (1.6 mL, 3.2 mmol) was added then the mixture was stirred for 10 min. The solvent was removed under reduced pressure, then 2-propanol (2.0 mL) and ethanol (0.20 mL) were added to the residue then the mixture was refluxed for 40 min and filtered. The filtrate was refluxed for further 10 min, stirred at ambient temperature for 14 h, then cooled with ice bath and stirred for further 30 min. The precipitate was collected by filtration, washed with ice-cold 2-propylalcohol and hexane then dried to afford cis-4-aminocyclohexanol hydrochloride as solid (0.056 g, y. 27%).

$^1$H NMR (DMSO-$d_6$) δ (ppm) 7.92 (br. s, 3H), 4.47 (br. s, 1H), 3.70-3.82 (m, 1H), 2.89-3.04 (m, 1H), 1.57-1.76 (m, 6H), 1.37-1.51 (m, 2H)

Third Step

To a solution of cis-4-aminocyclohexanol hydrochloride (0.051 g, 0.34 mmol) and ethyl 2-ethoxy-4-oxo-4,5-dihydrofuran-3-carboxylate (0.073 g, 0.37 mmol) which afforded in the Example 74, Third step in ethanol (0.8 mL), triethylamine (0.052 mL, 0.37 mmol) was added. The mixture was stirred at ambient temperature for 1 h. To this reaction mixture, 7-azaindole-3-carboxaldehyde (0.044 g, 0.30 mmol) and piperidine (0.0067 mL, 0.067 mmol) was added at ambient temperature then the mixture was refluxed for 4 days. Ethanol (2.0 mL) was added then the mixture was refluxed for further 1 h, the precipitate was collected by filtration, washed with hot ethanol. The solid was washed with hexane then dried to afford the titled compound as solid (0.013 g, y. 11%).

$^1$H NMR (DMSO-$d_6$) δ (ppm) 12.33 (br. s, 1H), 8.50 (d, J=8.03 Hz, 1H), 8.42 (d, J=7.78 Hz, 1H), 8.32 (dd, J=1.38, 4.64 Hz, 1H), 8.02 (d, J=2.51 Hz, 1H), 7.20 (dd, J=4.64, 7.91 Hz, 1H), 6.90 (s, 1H), 4.55 (d, J=3.26 Hz, 1H), 4.22 (q, J=7.03 Hz, 2H), 4.03-4.14 (m, 1H), 3.74-3.82 (m, 1H), 1.90-2.02 (m, 2H), 1.72-1.81 (m, 2H), 1.61-1.69 (m, 4H), 1.26 (t, J=7.15 Hz, 3H); LCMS (m/z): 396.1 $[M+H]^+$.

Example 200

Ethyl 5-[(1H-pyrrolo[2,3-b]pyridin-3-yl)methylene]-2-[4-(dimethylamino)piperidino]-4-oxo-4,5-dihydrofuran-3-carboxylate

[Chemical Formula 209]

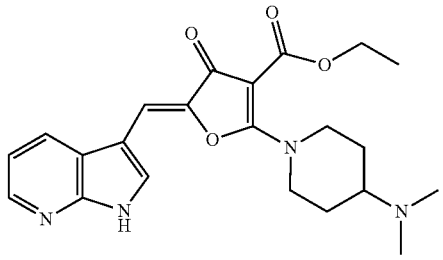

The titled compound (solid) was similarly prepared according to the procedure described in the Example 194.

$^1$H NMR (DMSO-$d_6$) δ (ppm) 12.37 (br. s, 1H), 8.39 (d, J=7.00 Hz, 1H), 8.33 (d, J=5.16 Hz, 1H), 8.01 (s, 1H), 7.21 (dd, J=5.12, 7.72 Hz, 1H), 6.89 (s, 1H), 4.35-4.45 (m, 2H), 4.13-4.23 (m, 2H), 3.88-3.98 (m, 1H), 3.61-3.71 (m, 1H), 3.51-3.61 (m, 1H), 2.50 (s, 6H), 2.18-2.28 (m, 1H), 1.95-2.05 (m, 1H), 1.80-1.95 (m, 1H), 1.25 (t, J=6.96 Hz, 3H); LCMS (m/z): 411.2 $[M+H]^+$.

Example 201

Ethyl 5-[(1H-pyrrolo[2,3-b]pyridin-3-yl)methylene]-2-({2-[(2-methoxyethoxy)methoxy]ethyl}-N-methylamino)-4-oxo-4,5-dihydrofuran-3-carboxylate

[Chemical Formula 210]

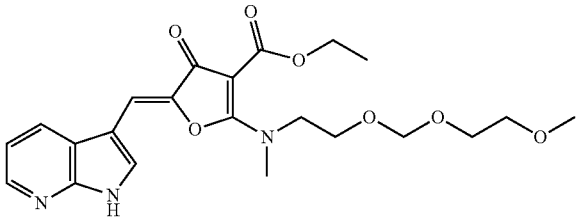

First Step

To a solution of ethyl 2-[(2-hydroxyethyl)-N-methylamino]-4-oxo-4,5-dihydrofuran-3-carboxylate (0.5 g, 2.18 mmol) which similarly prepared according to the procedure described in the Example 74, Fourth step in dichloromethane (6.0 mL) that cooled with ice bath, diisopropylethylamine (0.75 mL, 4.36 mmol) then 2-methoxyethoxymethyl chloride (0.5 mL, 4.36 mmol) were added. The reaction mixture was allowed to warm to ambient temperature and stirred for 16 h. The reaction mixture was diluted with water, extracted with ethyl acetate for 3 times. The organic layer was dried over sodium sulfate and concentrated. The residue was purified by chromatography on silica gel(hexane/ethyl acetate) to afford ethyl 2-({2-[(2-methoxyethoxy)methoxy]ethyl}-N-methylamino)-4-oxo-4,5-dihydrofuran-3-carboxylate as oil (0.31 g, y. 46%).

$^1$H NMR (DMSO-$d_6$) δ (ppm) 4.62 (s, 2H), 4.54 (s, 2H), 4.10 (q, J=7.04 Hz, 2H), 3.63-3.80 (m, 4H), 3.52-3.62 (m, 2H), 3.38-3.48 (m, 2H), 3.24 (s, 3H), 3.12 (s, 3H), 1.20 (t, J=7.04 Hz, 3H); LCMS (m/z): 230.0 $[M+H]^+$ Second Step To a solution of ethyl 2-({2-[(2-methoxyethoxy)methoxy]ethyl}-N-methylamino)-4-oxo-4,5-dihydrofuran-3-carboxylate (0.146 g, 0.46 mmol) and 7-azaindole-3-carboxaldehyde (0.067 g, 0.46 mmol) in ethanol (6.0 mL), L-proline (0.005 g, 0.046 mmol) was added at ambient temperature. The mixture was refluxed for 16 h. Cooled to ambient temperature, the reaction mixture was purified by chromatography on silica gel(hexane/ethyl acetate) to afford the titled compound as solid (0.035 g, y. 17%).

$^1$H NMR (DMSO-$d_6$) δ (ppm) 12.33 (br. s, 1H), 8.39 (d, J=7.34 Hz, 1H), 8.31 (d, J=4.40 Hz, 1H), 7.98 (s, 1H), 7.19 (dd, J=4.65, 7.58 Hz, 1H), 6.85 (s, 1H), 4.64 (s, 2H), 4.16 (q, J=7.17 Hz, 2H), 3.93-4.00 (m, 2H), 3.75-3.83 (m, 2H), 3.51-3.59 (m, 2H), 3.36-3.42 (m, 2H), 3.25-3.37 (m, 3H), 3.17 (s, 3H), 1.24 (t, J=7.09 Hz, 3H); LCMS (m/z): 446.2 $[M+H]^+$ Example 202

Ethyl 5-[(1H-pyrrolo[2,3-b]pyridin-3-yl)methylene]-2-[(2-hydroxyethyl)-N-methylamino]-4-oxo-4,5-dihydrofuran-3-carboxylate

[Chemical Formula 211]

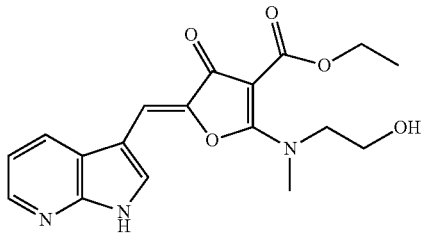

Cooled with ice bath, 4M hydrochloric acid in dioxane (4.0 mL) was added to ethyl 5-[(1H-pyrrolo[2,3-b]pyridin-3-yl)methylene]-2-({2-[(2-methoxyethoxy)methoxy]ethyl}-N-methylamino)-4-oxo-4,5-dihydrofuran-3-carboxylate (0.020 mg, 0.046 mmol) which afforded in the Example 201. The mixture was stirred at ambient temperature for 3 h. The solvent was removed under reduced pressure, and the precipitate was suspended in diethyl ether, then collected by filtration. The solid was washed with diethyl ether then dried to afford the titled compound as solid (0.012 g, y. 75%).

$^1$H NMR (DMSO-$d_6$) δ (ppm) 12.35 (br. s, 1H), 8.42 (d, J=7.82 Hz, 1H), 8.32 (d, J=3.91 Hz, 1H), 7.99 (s, 1H), 7.21 (dd, J=4.89, 7.82 Hz, 1H), 6.84 (s, 1H), 4.16 (q, J=6.85 Hz, 2H), 3.80-3.86 (m, 2H), 3.65-3.78 (m, 2H), 3.31 (br. s., 3H), 1.24 (t, J=7.09 Hz, 4H); LCMS (m/z): 358.2 $[M+H]^+$ Example 203

Ethyl 5-[(1H-pyrrolo[2,3-b]pyridin-3-yl)methylene]-2-{4-[(2-hydroxyethyl)-N-methylamino]piperidino}-4-oxo-4,5-dihydrofuran-3-carboxylate

[Chemical Formula 212]

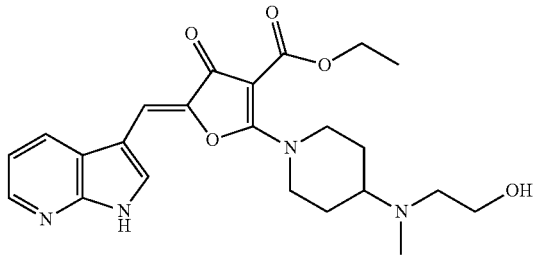

The titled compound (solid) was similarly prepared according to the procedure described in the Example 194.

$^1$H NMR (DMSO-$d_6$) δ (ppm) 12.30 (br. s, 1H), 8.37 (d, J=7.82 Hz, 1H), 8.31 (d, J=4.40 Hz, 1H), 7.97 (s, 1H), 7.20 (dd, J=4.65, 7.58 Hz, 1H), 6.85 (s, 1H), 4.22-4.38 (m, 4H), 4.17 (q, J=6.85 Hz, 2H), 3.45 (q, J=5.87 Hz, 2H), 3.25-3.40 (m, 2H), 2.69-2.81 (m, 1H), 2.23 (s, 3H), 1.85-1.95 (m, 2H), 1.58-1.72 (m, 2H), 1.25 (t, J=6.85 Hz, 3H); LCMS (m/z): 441.2 $[M+H]^+$.

Example 204

2-[(1H-Pyrrolo[2,3-b]pyridin-3-yl)methylene]-5-(phenylamino)furan-3(2H)-one

[Chemical Formula 213]

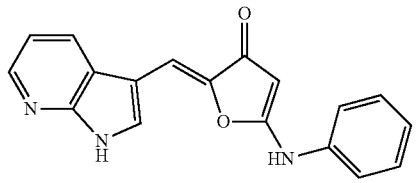

A solution of the compound (0.050 g, 0.13 mmol) of Example 1 in N,N-dimethylformamide (1.0 mL) was refluxed for 6 h. Cooled to ambient temperature, the reaction mixture was purified by preparative HPLC to afford the titled compound as solid (0.010 g, y. 25%).

$^1$H NMR (DMSO-$d_6$) δ (ppm) 12.36 (br. s, 1H), 10.74 (s, 1H), 8.42 (d, J=7.53 Hz, 1H), 8.31 (dd, J=1.25, 4.52 Hz, 1H), 8.10 (d, J=2.26 Hz, 1H), 7.41-7.49 (m, 2H), 7.34 (d, J=7.53 Hz, 2H), 7.13-7.25 (m, 2H), 6.81 (s, 1H), 5.25 (s, 1H); LCMS (m/z): 304.0 [M+H]$^+$.

Example 205

2-[(1H-Pyrrolo[2,3-b]pyridin-3-yl)methylene]-5-[(4-methoxyphenyl)amino]furan-3(2H)-one

[Chemical Formula 214]

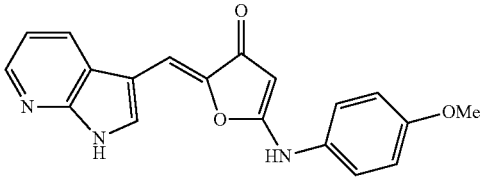

To a solution of the compound (0.31 g, 0.76 mmol) of Example 2 in ethanol (6.0 mL), 18M potassium hydroxide solution (0.41 mL, 7.4 mmol) was added at ambient temperature. The mixture was refluxed for 24 h. Cooled to ambient temperature, the precipitate was removed by filtration. The filtrate was purified by preparative HPLC to afford the titled compound as solid (0.031 g, y. 12%).

$^1$H NMR (DMSO-$d_6$) δ (ppm) 12.31 (br. s, 1H), 10.56 (s, 1H), 8.39 (d, J=7.53 Hz, 1H), 8.30 (dd, J=1.51, 4.52 Hz, 1H), 8.05 (s, 1H), 7.25-7.32 (m, 2H), 7.14 (dd, J=4.64, 7.91 Hz, 1H), 6.99-7.04 (m, 2H), 6.76 (s, 1H), 5.05 (s, 1H), 3.79 (s, 3H); LCMS (m/z): 334.0 [M+H]$^+$.

Example 206

2-[(1H-Pyrrolo[2,3-b]pyridin-3-yl)methylene]-5-[(4-chlorophenyl)amino]furan-3(2H)-one

[Chemical Formula 215]

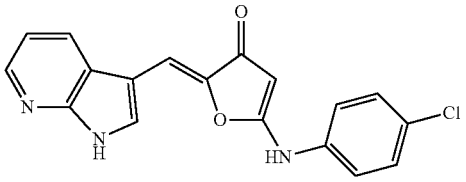

A solution of the compound (0.050 g, 0.12 mmol) of Example 8 in N,N-dimethylformamide (1.0 mL) was refluxed for 6 h. Cooled to ambient temperature, the reaction mixture was purified by preparative HPLC to afford the titled compound as solid (0.0072 g, y. 17%).

$^1$H NMR (DMSO-$d_6$) δ (ppm) 12.36 (br. s, 1H), 10.87 (br. s, 1H), 8.41 (d, J=7.28 Hz, 1H), 8.31 (dd, J=1.38, 4.64 Hz, 1H), 8.08 (d, J=2.26 Hz, 1H), 7.48 (d, J=8.78 Hz, 2H), 7.36 (d, J=8.78 Hz, 2H), 7.17 (dd, J=4.64, 7.91 Hz, 1H), 6.82 (s, 1H), 5.27 (s, 1H); LCMS (m/z): 337.9 [M+H]$^+$.

Example 207

2-[(1H-Pyrrolo[2,3-b]pyridin-3-yl)methylene]-5-[(3-chlorophenyl)amino]furan-3(2H)-one

[Chemical Formula 216]

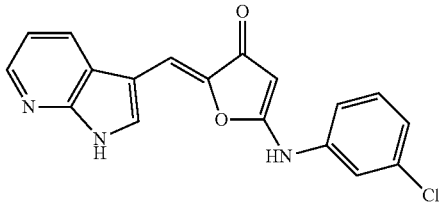

A solution of the compound (0.040 g, 0.098 mmol) of Example 9 in N,N-dimethylformamide (1.0 mL) was refluxed for 6 h. Cooled to ambient temperature, the reaction mixture was purified by preparative HPLC to afford the titled compound as solid (0.0075 g, y. 23%).

$^1$H NMR (DMSO-$d_6$) δ (ppm) 12.40 (br. s, 1H), 10.85 (s, 1H), 8.41 (d, J=7.28 Hz, 1H), 8.32 (dd, J=1.38, 4.64 Hz, 1H), 8.09 (d, J=2.76 Hz, 1H), 7.42-7.51 (m, 1H), 7.36-7.41 (m, 1H), 7.32 (d, J=8.03 Hz, 1H), 7.26 (dd, J=1.00, 8.03 Hz, 1H), 7.17 (dd, J=4.64, 7.91 Hz, 1H), 6.85 (s, 1H), 5.31 (s, 1H); LCMS (m/z): 337.9 [M+H]$^+$.

Example 208

2-[(1H-Pyrrolo[2,3-b]pyridin-3-yl)methylene]-5-[(2-chlorophenyl)amino]furan-3(2H)-one

[Chemical Formula 217]

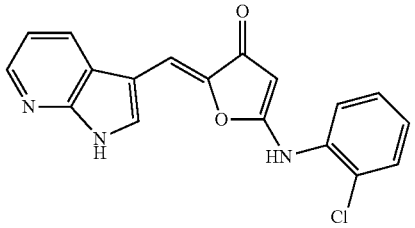

A solution of the compound (0.050 g, 0.12 mmol) of Example 15 in N,N-dimethylformamide (1.0 mL) was stirred at 150° C. for 6 h. Cooled to ambient temperature, the reaction mixture was purified by preparative HPLC to afford the titled compound as solid (0.0050 g, y. 11%).

$^1$H NMR (DMSO-$d_6$) δ (ppm) 12.29 (br. s, 1H), 10.63 (br. s, 1H), 8.21-8.32 (m, 2H), 8.01 (br. s, 1H), 7.63 (d, J=8.03 Hz, 1H), 7.57 (d, J=7.28 Hz, 1H), 7.45 (t, J=7.40 Hz, 1H), 7.32-7.39 (m, 1H), 7.06 (dd, J=4.77, 7.53 Hz, 1H), 6.75 (s, 1H), 4.89 (br. s, 1H); LCMS (m/z): 337.9 [M+H]$^+$.

Example 209

2-[(1H-Pyrrolo[2,3-b]pyridin-3-yl)methylene]-5-[(2,4-dimethoxyphenyl)amino]furan-3(2H)-one

[Chemical Formula 218]

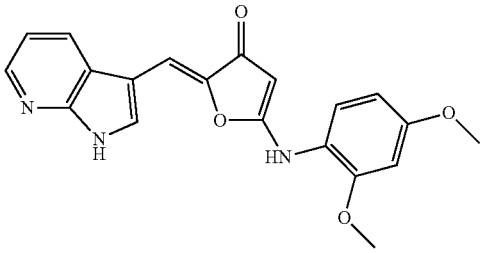

A solution of the compound (0.10 g, 0.23 mmol) of Example 24 in N,N-dimethylformamide (3.0 mL) was refluxed for 7 h. Cooled to ambient temperature, the reaction mixture was purified by preparative HPLC to afford the titled compound as solid (0.015 g, y. 18%).

$^1$H NMR (DMSO-$d_6$) δ (ppm) 12.27 (br. s, 1H), 10.11 (br. s, 1H), 8.25-8.36 (br. s, 2H), 8.03 (br. s, 1H), 7.30 (d, J=8.31 Hz, 1H), 7.08 (br. s, 1H), 6.72 (d, J=17.12 Hz, 2H), 6.60 (d, J=8.31 Hz, 1H), 4.74 (br. s, 1H), 3.75-3.92 (m, 6H); LCMS (m/z): 364.2 $[M+H]^+$.

Example 210

2-[(1H-Pyrrolo[2,3-b]pyridin-3-yl)methylene]-5-[(4-isopropylphenyl)amino]furan-3(2H)-one

[Chemical Formula 219]

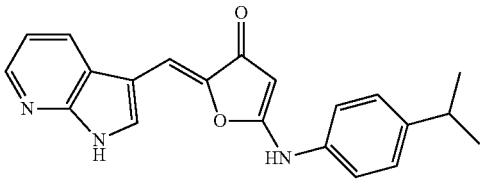

A solution of the compound (0.12 g, 0.29 mmol) of Example 37 in N,N-dimethylformamide (3.0 mL) was refluxed for 6 h. Cooled to ambient temperature, the reaction mixture was purified by preparative HPLC to afford 2-[(1H-pyrrolo[2,3-b]pyridin-3-yl)methylene]-5-[(4-isopropylphenyl)amino]furan-3(2H)-one as solid (0.0050 g, y. 5%).

$^1$H NMR (DMSO-$d_6$) δ (ppm) 12.34 (br. s, 1H), 10.68 (br. s, 1H), 8.41 (d, J=7.82 Hz, 1H), 8.30 (d, J=3.91 Hz, 1H), 8.09 (br. s, 1H), 7.21-7.37 (m, 4H), 7.15 (d, J=4.40 Hz, 1H), 6.77 (s, 1H), 5.18 (br. s, 1H), 2.84-3.00 (m, 1H), 1.22 (d, J=6.85 Hz, 6H); LCMS (m/z): 346.2 $[M+H]^+$.

Example 211

2-[(1H-Pyrrolo[2,3-b]pyridin-3-yl)methylene]-5-(3-pyridinylamino)furan-3(2H)-one

[Chemical Formula 220]

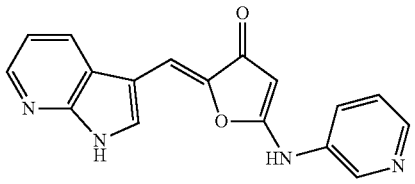

The titled compound (solid) was similarly prepared according to the procedure described in the Example 210, using the compound of Example 27.

$^1$H NMR (DMSO-$d_6$) δ (ppm) 12.35 (br. s, 1H), 10.95 (br. s, 1H), 8.58 (br. s, 1H), 8.35-8.43 (m, 2H), 8.27-8.33 (m, 1H), 8.06 (br. s, 1H), 7.76 (d, J=6.85 Hz, 1H), 7.38-7.53 (m, 1H), 7.09-7.24 (m, 1H), 6.81 (br. s, 1H), 5.27 (br. s, 1H); LCMS (m/z): 305.2 $[M+H]^+$.

Example 212

2-[(1H-Pyrrolo[2,3-b]pyridin-3-yl)methylene]-5-[(4-carbamoylphenyl)amino]furan-3(2H)-one

[Chemical Formula 221]

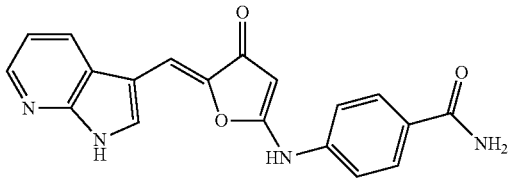

The titled compound (solid) was similarly prepared according to the procedure described in the Example 210, using the compound of Example 25.

$^1$H NMR (DMSO-$d_6$) δ (ppm) 12.37 (br. s, 1H), 8.42 (d, J=7.34 Hz, 1H), 8.32 (br. s, 1H), 8.12 (br. s, 1H), 7.85-8.04 (m, 4H), 7.28-7.44 (m, 3H), 7.14-7.21 (m, 1H), 6.83 (br. s, 1H), 5.38 (br. s, 1H); LCMS (m/z): 347.2 $[M+H]^+$.

Example 213

2-[(1H-Pyrrolo[2,3-b]pyridin-3-yl)methylene]-5-[(2,4-dimethylphenyl)amino]furan-3(2H)-one

[Chemical Formula 222]

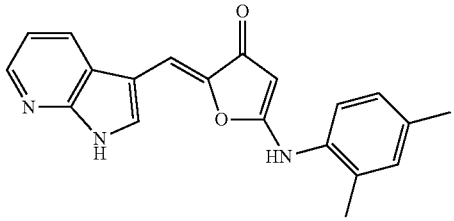

The titled compound (solid) was similarly prepared according to the procedure described in the Example 210, using the compound of Example 26.

$^1$H NMR (DMSO-$d_6$) δ (ppm) 12.22 (br. s, 1H), 10.21 (br. s, 1H), 8.11-8.34 (m, 2H), 7.94 (br. s, 1H), 7.25 (d, J=7.92 Hz, 1H), 7.17 (br. s, 1H), 6.99-7.14 (m, 2H), 6.74 (s, 1H), 4.78 (br. s, 1H), 2.31 (s, 3H), 2.22 (s, 3H); LCMS (m/z): 332.2 $[M+H]^+$.

Example 214

2-[(1H-Pyrrolo[2,3-b]pyridin-3-yl)methylene]-5-(p-tolylamino)furan-3(2H)-one

[Chemical Formula 223]

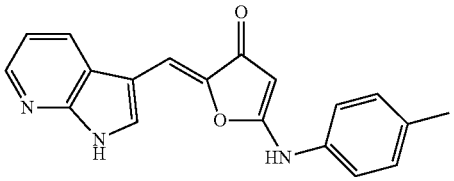

The titled compound (solid) was similarly prepared according to the procedure described in the Example 210, using the compound of Example 20.

$^1$H NMR (DMSO-$d_6$) δ (ppm) 12.32 (br. s, 1H), 8.40 (d, J=7.34 Hz, 1H), 8.30 (br. s, 1H), 8.06 (br. s, 1H), 7.10-7.36 (m, 5H), 6.74 (br. s, 1H), 5.12 (br. s, 1H), 2.32 (s, 3H); LCMS (m/z): 318.4 $[M+H]^+$.

Example 215

2-[(1H-Pyrrolo[2,3-b]pyridin-3-yl)methylene]-5-[(4-bromophenyl)amino]furan-3(2H)-one

[Chemical Formula 224]

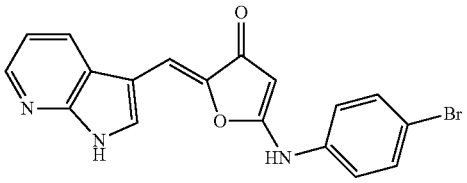

The titled compound (solid) was similarly prepared according to the procedure described in the Example 210, using the compound of Example 19.

$^1$H NMR (DMSO-$d_6$) δ (ppm) 12.31 (br. s, 1H), 8.39 (d, J=7.76 Hz, 1H), 8.23-8.35 (m, 1H), 8.05 (s, 1H), 7.58 (d, J=8.31 Hz, 2H), 7.27 (d, J=8.31 Hz, 2H), 7.18 (dd, J=4.65, 7.58 Hz, 1H), 6.80 (s, 1H), 5.20 (br. s, 1H); LCMS (m/z): 382.5 $[M+H]^+$.

Example 216

2-[(1H-Pyrrolo[2,3-b]pyridin-3-yl)methylene]-5-[(3,4-dimethoxyphenyl)amino]furan-3(2H)-one

[Chemical Formula 225]

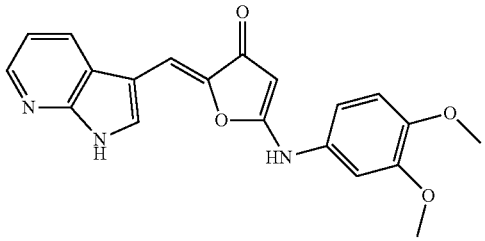

A solution of the compound (0.043 g, 0.099 mmol) of Example 28 in N,N-dimethylformamide (1.2 mL) was refluxed for 6 h. Cooled to ambient temperature, the reaction mixture was purified by preparative HPLC to afford the titled compound (0.0050 g, y. 12%).

$^1$H NMR (DMSO-$d_6$) δ (ppm) 12.35 (br. s, 1H), 10.56 (br. s, 1H), 8.40 (d, J=7.34 Hz, 1H), 8.30 (d, J=3.91 Hz, 1H), 8.06 (br. s, 1H), 7.08-7.22 (m, 1H), 7.01 (d, J=8.31 Hz, 1H), 6.92 (br. s, 1H), 6.87 (d, J=8.31 Hz, 1H), 6.77 (s, 1H), 5.12 (s, 1H), 3.78 (s, 6H); LCMS (m/z): 364.0 $[M+H]^+$.

Example 217

2-[(1H-Pyrrolo[2,3-b]pyridin-3-yl)methylene]-5-[(4-fluorophenyl)amino]furan-3(2H)-one

[Chemical Formula 226]

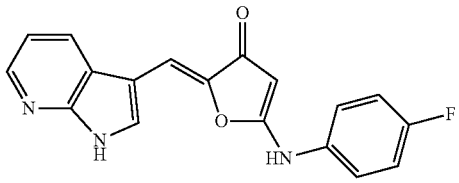

The titled compound (solid) was similarly prepared according to the procedure described in the Example 216, using the compound of Example 21.

$^1$H NMR (DMSO-$d_6$) δ (ppm) 12.34 (br. s, 1H), 10.72 (br. s, 1H), 8.40 (d, J=7.34 Hz, 1H), 8.31 (d, J=3.91 Hz, 1H), 8.06 (br. s, 1H), 7.33-7.46 (m, 2H), 7.22-7.33 (m, 2H), 7.16 (dd, J=4.65, 7.58 Hz, 1H), 6.80 (s, 1H), 5.18 (s, 1H); LCMS (m/z): 322.0 $[M+H]^+$.

Example 218

2-[(1H-Pyrrolo[2,3-b]pyridin-3-yl)methylene]-5-[(1,1'-biphenyl)-4-ylamino]furan-3(2H)-one

[Chemical Formula 227]

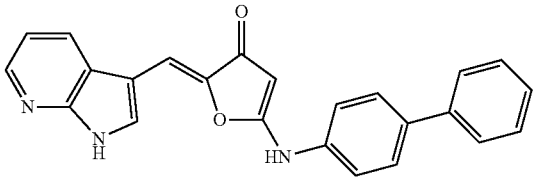

The titled compound (solid) was similarly prepared according to the procedure described in the Example 216, using the compound of Example 39.

$^1$H NMR (DMSO-$d_6$) δ (ppm) 12.29 (br. s, 1H), 8.24-8.49 (m, 3H), 8.07 (br. s, 1H), 7.70 (br. s, 3H), 7.48 (br. s, 2H), 7.38 (br. s, 3H), 7.15 (br. s, 1H), 6.72 (br. s, 1H), 5.19 (br. s, 1H); LCMS (m/z): 380.2 $[M+H]^+$.

Example 219

2-[(1H-Pyrrolo[2,3-b]pyridin-3-yl)methylene]-5-{[2-(2-hydroxyethoxy)phenyl]amino}furan-3(2H)-one

[Chemical Formula 228]

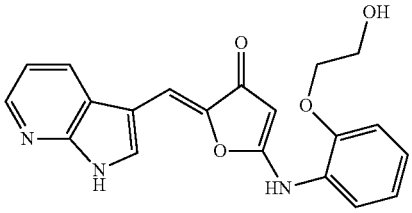

A solution of the compound (0.015 g, 0.034 mmol) of Example 29 in N,N-dimethylformamide (0.50 mL) was refluxed for 4 h. Cooled to ambient temperature, the reaction mixture was purified by preparative HPLC to afford the titled compound as solid (0.0013 g, y. 11%).

$^1$H NMR (DMSO-$d_6$) δ (ppm) 12.24 (br. s, 1H), 8.44 (br. s, 1H), 8.24-8.35 (m, 2H), 8.03 (br. s, 1H), 7.32-7.41 (m, 1H), 6.96-7.25 (m, 4H), 6.67 (br. s, 1H), 4.90 (br. s, 1H), 4.01-4.12 (m, 2H), 3.67-3.80 (m, 2H); LCMS (m/z): 363.9 $[M+H]^+$.

Example 220

2-[(1H-Pyrrolo[2,3-b]pyridin-3-yl)methylene]-5-(6-quinolinylamino)furan-3(2H)-one

[Chemical Formula 229]

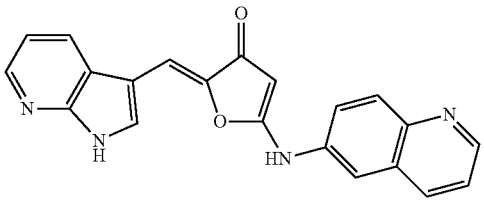

A solution of the compound (0.075 g, 0.18 mmol) of Example 44 in N,N-dimethylformamide (4.0 mL) was refluxed for 6 h. Cooled to ambient temperature, the reaction mixture was purified by preparative HPLC to afford the titled compound as solid (0.0080 g, y. 13%).

$^1$H NMR (DMSO-$d_6$) δ (ppm) 12.41 (br. s, 1H), 11.07 (br. s, 1H), 8.81-8.87 (m, 1H), 8.42 (t, J=8.56 Hz, 2H), 8.31 (d, J=3.91 Hz, 1H), 8.15 (br. s, 1H), 8.07 (d, J=8.80 Hz, 1H), 7.88 (br. s, 1H), 7.73 (d, J=8.80 Hz, 1H), 7.55 (dd, J=3.91, 7.82 Hz, 1H), 7.15 (d, J=4.40 Hz, 1H), 6.85 (br. s, 1H), 5.56 (br. s, 1H); LCMS (m/z): 355.2 $[M+H]^+$.

Example 221

2-[(1H-Pyrrolo[2,3-b]pyridin-3-yl)methylene]-5-[(2-methoxyphenyl)amino]furan-3(2H)-one

[Chemical Formula 230]

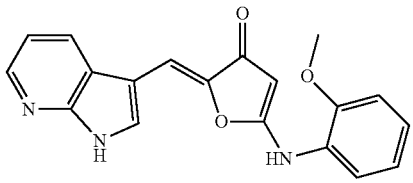

A solution of the compound (0.099 g, 0.24 mmol) of Example 7 in N,N-dimethylformamide (2.0 mL) was refluxed for 9 h. Cooled to ambient temperature, the reaction mixture was diluted with 2-butanol and washed with 4M sodium hydroxide solution. The organic layer was concentrated then purified by chromatography on silica gel(chloroform/methanol) to afford the titled compound as solid (0.0097 g, y. 12%).

$^1$H NMR (DMSO-$d_6$) δ (ppm) 12.31 (br. s, 1H), 10.29 (s, 1H), 8.33 (d, J=7.78 Hz, 1H), 8.27-8.30 (m, 1H), 8.12 (s, 1H), 7.42 (d, J=7.78 Hz, 1H), 7.26-7.33 (m, 1H), 7.18 (d, J=7.28 Hz, 1H), 7.10 (dd, J=4.77, 8.03 Hz, 1H), 7.04 (t, J=7.65 Hz, 1H), 6.75 (s, 1H), 4.90-4.94 (m, 1H), 3.88 (s, 3H); LCMS (m/z): 333.9 $[M+H]^+$.

Example 222

2-[(1H-Pyrrolo[2,3-b]pyridin-3-yl)methylene]-5-[(2,4-difluorophenyl)amino]furan-3(2H)-one

[Chemical Formula 231]

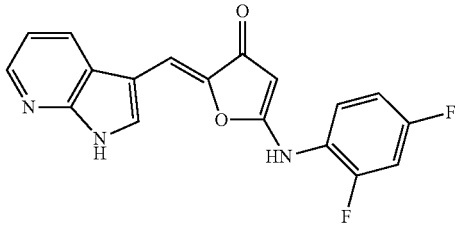

A solution of the compound (0.099 g, 0.24 mmol) of Example 53 in N,N-dimethylformamide (1.0 mL) was refluxed for 4 h. Cooled to ambient temperature, the reaction mixture was purified by preparative HPLC to afford the titled compound as solid (0.0030 g, y. 4%).

$^1$H NMR (DMSO-$d_6$) δ (ppm) 12.31 (br. s, 1H), 10.60 (br. s, 1H), 8.26-8.36 (m, 2H), 8.01 (br. s, 1H), 7.55-7.65 (m, 1H), 7.44-7.54 (m, 1H), 7.16-7.25 (m, 1H), 7.06-7.14 (m, 1H), 6.79 (br. s, 1H), 4.95 (br. s, 1H); LCMS (m/z): 339.8 $[M+H]^+$.

Example 223

2-[(1H-Pyrrolo[2,3-b]pyridin-3-yl)methylene]-5-[(4-morpholinophenyl)amino]furan-3(2H)-one

[Chemical Formula 232]

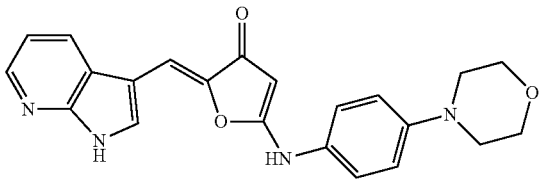

A solution of the compound (0.080 g, 0.17 mmol) of Example 42 in N,N-dimethylacetamide (3.0 mL) was stirred at 160° C. for 4 h. Cooled to ambient temperature, the reaction mixture was diluted with water and the precipitate was collected by filtration. The solid was washed with water, tetrahydrofuran and diethyl ether then dried to afford the titled compound as solid (0.015 g, y. 22%).

$^1$H NMR (DMSO-$d_6$) δ (ppm) 12.32 (br. s, 1H), 10.53 (br. s, 1H), 8.41 (d, J=8.12 Hz, 1H), 8.31 (d, J=4.28 Hz, 1H), 8.05 (br. s, 1H), 7.23 (d, J=8.31 Hz, 2H), 7.12-7.18 (m, 1H), 7.02 (d, J=8.31 Hz, 2H), 6.75 (s, 1H), 5.05 (s, 1H), 3.70-3.83 (m, 4H), 3.05-3.18 (m, 4H); LCMS (m/z): 389.4 $[M+H]^+$.

Example 224

2-[(1H-Pyrrolo[2,3-b]pyridin-3-yl)methylene]-5-[(4-fluorobenzyl)amino]furan-3(2H)-one

[Chemical Formula 233]

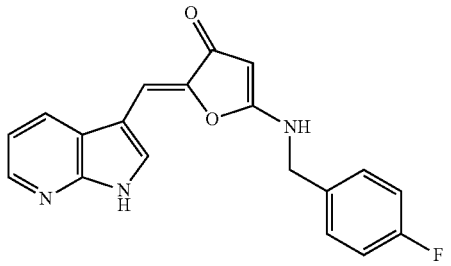

A solution of the compound (0.10 g, 0.31 mmol) of Example 45 in N,N-dimethylacetamide (3.0 mL) was refluxed for 7 h. Cooled to ambient temperature, the reaction mixture was diluted with water and the precipitate was collected by filtration. The solid was washed with water and diethyl ether then dried to afford the titled compound as solid (0.0070 g, y. 9%).

$^1$H NMR (DMSO-$d_6$) δ (ppm) 12.23 (br. s, 1H), 9.08 (s, 1H), 8.40 (br. s, 1H), 8.21-8.32 (m, 2H), 7.96 (br. s, 1H), 7.34-7.50 (m, 1H), 7.05-7.32 (m, 3H), 6.67 (s, 1H), 4.91 (s, 1H), 4.35-4.60 (m, 2H); LCMS (m/z): 336.0 $[M+H]^+$.

Example 225

2-[(1H-Pyrrolo[2,3-b]pyridin-3-yl)methylene]-5-[(2-thienylmethyl)amino]furan-3(2H)-one

[Chemical Formula 234]

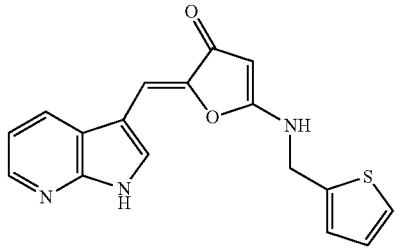

A solution of the compound (0.10 g, 0.26 mmol) of Example 60 in N,N-dimethylformamide (0.80 mL) was refluxed for 16 h. Cooled to ambient temperature, the reaction mixture was diluted with chloroform and the precipitate was collected by filtration. The solid was washed with chloroform/methanol (10/1) and hexane then dried to afford the titled compound as solid (0.019 g, y. 22%).

$^1$H NMR (DMSO-$d_6$) δ (ppm) 12.25 (br. s, 1H), 9.20 (t, J=6.02 Hz, 1H), 8.41 (d, J=7.53 Hz, 1H), 8.29 (dd, J=1.26, 4.52 Hz, 1H), 7.99 (d, J=2.01 Hz, 1H), 7.49 (dd, J=1.00, 5.02 Hz, 1H), 7.12-7.20 (m, 2H), 7.02 (dd, J=3.51, 5.02 Hz, 1H), 6.67 (s, 1H), 4.96 (br. s, 1H), 4.69 (br. s, 2H); LCMS (m/z): 324.0 $[M+H]^+$.

Example 226

2-[(1H-Pyrrolo[2,3-b]pyridin-3-yl)methylene]-5-(cycloheptylamino)furan-3(2H)-one

[Chemical Formula 235]

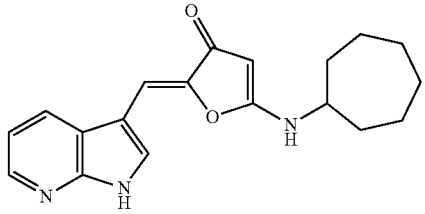

A solution of the compound (0.040 g, 0.10 mmol) of Example 59 in N,N-dimethylformamide (2.0 mL) was refluxed for 8 h. Cooled to ambient temperature, the reaction mixture was purified by preparative HPLC to afford the titled compound as solid (0.0040 g, y. 12%).

$^1$H NMR (DMSO-$d_6$) δ (ppm) 12.26 (br. s, 1H), 8.64 (d, J=7.82 Hz, 1H), 8.39 (d, J=7.34 Hz, 1H), 8.29 (d, J=3.91 Hz, 1H), 8.00 (br. s, 1H), 7.17 (dd, J=4.89, 7.82 Hz, 1H), 6.61 (s, 1H), 4.78 (br. s, 1H), 2.83-3.11 (m, 1H), 1.85-2.02 (m, 2H), 1.40-1.78 (m, 10H); LCMS (m/z): 324.2 $[M+H]^+$.

Example 227

2-[(1H-Pyrrolo[2,3-b]pyridin-3-yl)methylene]-5-(isopropylamino)furan-3(2H)-one

[Chemical Formula 236]

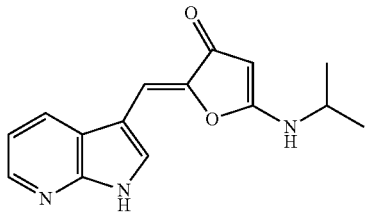

A solution of the compound (0.15 g, 0.43 mmol) of Example 56 in N,N-dimethylacetamide (1.5 mL) was refluxed for 12 h. Cooled to ambient temperature, the reaction mixture was diluted with water and the precipitate was collected by filtration. The solid was washed with diethyl ether then dried to afford the titled compound as solid (0.015 g, y. 12%).

$^1$H NMR (DMSO-$d_6$) δ (ppm) 12.24 (br. s, 1H), 8.58 (d, J=7.82 Hz, 1H), 8.38 (d, J=7.83 Hz, 1H), 8.27 (d, J=4.40 Hz, 1H), 7.97 (br. s, 1H), 7.15 (dd, J=4.89, 7.82 Hz, 1H), 6.60 (s, 1H), 4.79 (br. s, 1H), 3.53-3.69 (m, 1H), 1.22 (d, J=6.36 Hz, 6H); LCMS (m/z): 270.2 $[M+H]^+$.

Example 228

2-[(1H-Pyrrolo[2,3-b]pyridin-3-yl)methylene]-5-[(3-pyrazolyl)amino]furan-3(2H)-one

[Chemical Formula 237]

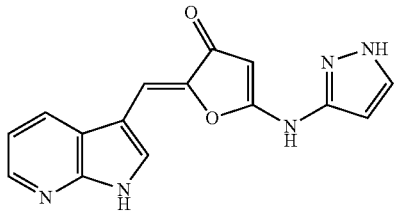

The titled compound (solid) was similarly prepared according to the procedure described in the Example 227, using the compound of Example 67.

$^1$H NMR (DMSO-$d_6$) δ (ppm) 12.52 (br. s, 2H), 11.67 (br. s, 1H), 8.45 (d, J=6.85 Hz, 1H), 8.16 (d, J=3.42 Hz, 1H), 7.72 (br. s, 2H), 7.56 (br. s, 1H), 7.13-7.25 (m, 1H), 6.98-7.09 (m, 1H), 4.69 (s, 1H); LCMS (m/z): 294.2 $[M+H]^+$.

Example 229

2-[(1H-Pyrrolo[2,3-b]pyridin-3-yl)methylene]-5-[(3-fluorobenzyl)amino]furan-3(2H)-one

[Chemical Formula 238]

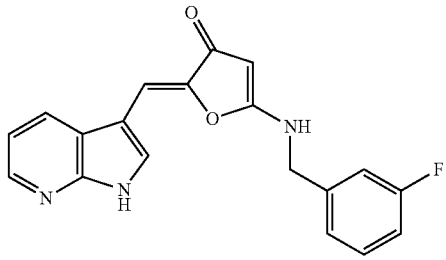

A solution of the compound (0.050 g, 0.12 mmol) of the Example 58 in N,N-dimethyacetamide (1.5 mL) was refluxed for 12 h. Cooled to ambient temperature, the reaction mixture was diluted with water and the precipitate was collected by filtration. The solid was purified by preparative HPLC to afford the titled compound as solid (0.012 g, y. 30%).

$^1$H NMR (DMSO-$d_6$) δ (ppm) 12.26 (br. s, 1H), 9.13-9.23 (m, 1H), 8.41 (br. s, 1H), 8.29 (d, J=3.91 Hz, 1H), 7.98 (br. s, 1H), 7.38-7.53 (m, 1H), 7.20-7.32 (m, 2H), 7.16 (d, J=6.36 Hz, 2H), 6.66 (s, 1H), 4.91 (br. s, 1H), 4.41-4.60 (m, 2H); LCMS (m/z): 336.0 $[M+H]^+$.

Example 230

2-[(1H-Pyrrolo[2,3-b]pyridin-3-yl)methylene]-5-(cyclopropylamino)furan-3(2H)-one

[Chemical Formula 239]

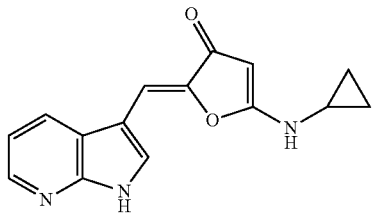

To a solution of the compound (0.25 g, 0.76 mmol) of Example 94 in ethanol (7.0 mL), 50% potassium hydroxide solution (4.0 mL, 0.071 mol) was added at ambient temperature. The mixture was refluxed for 2 h. Cooled to ambient temperature, the solvent was removed under reduced pressure. The residue was diluted with water, 1M hydrochloric acid was added to adjust pH to acidic, and then the solvent was removed under reduced pressure. The residue was purified by preparative HPLC to afford the titled compound as solid (0.0090 g, y. 4%).

$^1$H NMR (DMSO-$d_6$) δ (ppm) 12.26 (br. s, 1H), 8.88 (br. s, 1H), 8.44 (d, J=6.85 Hz, 1H), 8.22-8.34 (m, 1H), 7.97 (br. s, 1H), 7.12-7.20 (m, 1H), 6.66 (br. s, 1H), 4.87 (br. s, 1H), 2.62-2.80 (m, 1H), 0.72-0.88 (m, 2H), 0.55-0.72 (m, 2H); LCMS (m/z): 268.0 $[M+H]^+$.

Example 231

2-[(1H-Pyrrolo[2,3-b]pyridin-3-yl)methylene]-5-[(2-methoxyethyl)amino]furan-3(2H)-one

[Chemical Formula 240]

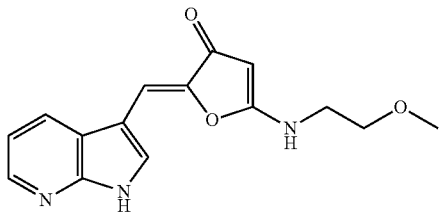

To a solution of the compound (0.070 g, 0.20 mmol) of Example 98 in ethanol (2.0 mL), 50% potassium hydroxide solution (1.0 mL, 0.018 mol) was added at ambient temperature. The mixture was refluxed for 1 h. Cooled to ambient temperature, 1M hydrochloric acid was added to adjust pH to acidic, and then the solvent was removed under reduced pressure. To this residue, ethanol (2.0 mL) and water (2.0 mL) were added then refluxed for 1 h. Cooled to ambient temperature, the solvent was removed under reduced pressure, and the residue was purified by preparative HPLC to afford the titled compound as solid (0.0060 g, y. 12%).

$^1$H NMR (DMSO-$d_6$) δ (ppm) 12.24 (br. s, 1H), 8.65-8.90 (m, 1H), 8.41 (d, J=6.85 Hz, 1H), 8.29 (br. s, 1H), 8.01 (br. s, 1H), 7.08-7.32 (m, 1H), 6.53-6.70 (m, 1H), 4.72-4.97 (m, 1H), 3.30-3.55 (m, 4H), 3.26 (br. s, 3H); LCMS (m/z): 286.2 $[M+H]^+$.

Example 232

2-[(1H-Pyrrolo[2,3-b]pyridin-3-yl)methylene]-5-[(1-methyl-4-piperidinyl)amino]furan-3(2H)-one

[Chemical Formula 241]

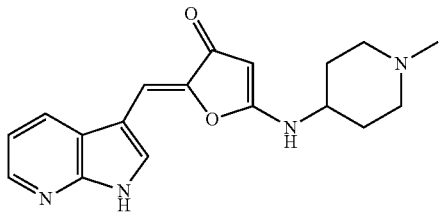

The titled compound (solid) was similarly prepared according to the procedure described in the Example 231, using the compound of Example 65.

$^1$H NMR (DMSO-$d_6$) δ (ppm) 12.25 (br. s, 1H), 8.61 (d, J=7.34 Hz, 1H), 8.39 (d, J=7.82 Hz, 1H), 8.23-8.34 (m, 1H), 8.17 (br. s, 1H), 7.99 (br. s, 1H), 7.06-7.24 (m, 1H), 6.62 (s, 1H), 4.77-4.99 (m, 1H), 2.73-2.85 (m, 2H), 2.22 (s, 3H), 2.00-2.14 (m, 2H), 1.82-1.97 (m, 2H), 1.49-1.67 (m, 2H); LCMS (m/z): 325.4 $[M+H]^+$.

Example 233

2-[(1H-Pyrrolo[2,3-b]pyridin-3-yl)methylene]-5-[(4-fluoro-2-methylphenyl)amino]furan-3(2H)-one

[Chemical Formula 242]

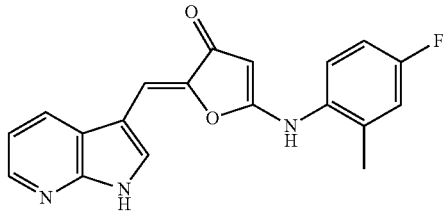

To a solution of the compound (0.15 g, 0.37 mmol) of Example 97 in ethanol (4.0 mL), 50% potassium hydroxide solution (2.0 mL, 0.036 mol) was added at ambient temperature. The mixture was refluxed for 2 h. Cooled to ambient temperature, the solvent was removed under reduced pressure. Water was added to this residue, the mixture was washed with ethyl acetate then 1M hydrochloric acid was added to adjust pH to acidic. The precipitate was collected by filtration, washed with water, diethyl ether, ethyl acetate and hexane then dried to afford the titled compound as solid (0.12 g, y. 93%).

$^1$H NMR (DMSO-$d_6$) δ (ppm) 12.28 (br. s, 1H), 10.24 (s, 1H), 8.19-8.32 (m, 2H), 7.97 (br. s, 1H), 7.43 (dd, J=5.62, 8.56 Hz, 1H), 7.26 (d, J=7.34 Hz, 1H), 7.11-7.19 (m, 1H), 7.04-7.10 (m, 1H), 6.74 (s, 1H), 4.72 (s, 1H), 2.31 (s, 3H); LCMS (m/z): 335.8 $[M+H]^+$.

Example 234

2-[(1H-Pyrrolo[2,3-b]pyridin-3-yl)methylene]-5-[(2,6-dimethyl-3-pyridinyl)amino]furan-3(2H)-one

[Chemical Formula 243]

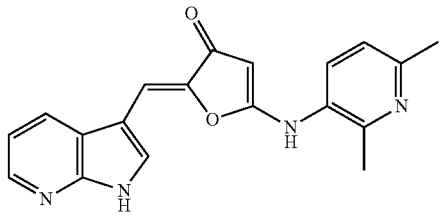

To a solution of the compound (0.090 g, 0.20 mmol) of Example 107 in ethanol (4.0 mL), 50% potassium hydroxide solution (2.0 mL, 0.036 mol) was added at ambient temperature. The mixture was refluxed for 2 h. Cooled to ambient temperature, the solvent was removed under reduced pressure. Water was added to this residue, the mixture was washed with ethyl acetate then 1M hydrochloric acid was added to adjust pH to acidic. The precipitate was collected by filtration, washed with water and diethyl ether then dried to afford the titled compound (0.037 g, y. 50%) as solid.

$^1$H NMR (DMSO-$d_6$) δ (ppm) 12.26 (br. s, 1H), 10.33 (br. s, 1H), 8.28 (d, J=4.40 Hz, 2H), 7.96 (br. s, 1H), 7.64 (d, J=8.31 Hz, 1H), 7.17 (d, J=7.82 Hz, 1H), 7.02-7.12 (m, 1H), 6.70 (br. s, 1H), 4.73 (br. s, 1H), 2.48 (br. s, 3H), 2.44 (br. s, 3H); LCMS (m/z): 333.3 $[M+H]^+$.

Example 235

2-[(1H-Pyrrolo[2,3-b]pyridin-3-yl)methylene]-5-[(2-fluorobenzyl)amino]furan-3(2H)-one

[Chemical Formula 244]

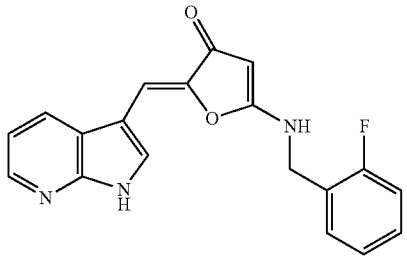

To a solution of the compound (0.10 g, 0.25 mmol) of Example 101 in ethanol (4.0 mL), 50% potassium hydroxide solution (2.0 mL, 0.036 mol) was added at ambient temperature. The mixture was refluxed for 2 h. Cooled to ambient temperature, the solvent was removed under reduced pressure. Water was added to this residue, the mixture was washed with ethyl acetate then 1M hydrochloric acid was added to adjust pH to acidic, and then extracted with ethyl acetate. The organic layer was dried over sodium sulfate and concentrate then purified by chromatography on silica gel(dichloromethane/methanol) to afford the titled compound as solid (0.012 g, y. 14%).

$^1$H NMR (DMSO-$d_6$) δ (ppm) 12.24 (br. s, 1H), 9.08-9.17 (m, 1H), 8.34-8.46 (m, 1H), 8.22-8.33 (m, 1H), 7.98 (br. s, 1H), 7.45-7.55 (m, 1H), 7.34-7.43 (m, 1H), 7.20-7.31 (m, 2H), 7.10-7.19 (m, 1H), 6.65 (s, 1H), 4.83-4.97 (m, 1H), 4.40-4.64 (m, 2H); LCMS (m/z): 335.8 $[M+H]^+$.

Example 236

2-[(1H-Pyrrolo[2,3-b]pyridin-3-yl)methylene]-5-[(2-phenyl-2-propanyl)amino]furan-3(2H)-one

[Chemical Formula 245]

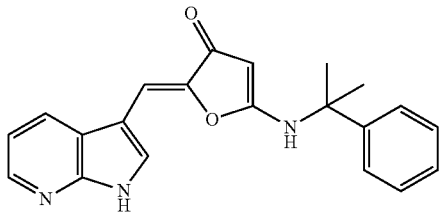

To a solution of the compound (0.060 g, 0.14 mmol) of Example 112 in ethanol (2.0 mL), 50% potassium hydroxide solution (1.0 mL, 0.018 mol) was added at ambient temperature. The mixture was refluxed for 2 h. Cooled to ambient temperature, the solvent was removed under reduced pressure. Water was added to this residue, the mixture was washed with ethyl acetate then 1M hydrochloric acid was added to adjust pH to acidic. The precipitate was collected by filtration, washed with water and diethyl ether then dried to afford the titled compound as solid (0.010 g, y. 20%).

$^1$H NMR (DMSO-$d_6$) δ (ppm) 12.26 (br. s, 1H), 9.05 (br. s, 1H), 8.24-8.38 (m, 2H), 8.0 (br, 1H), 7.36-7.50 (m, 4H), 7.25-7.32 (m, 1H), 7.12-7.18 (m, 1H), 6.57 (s, 1H), 4.06 (br. s, 1H), 1.70 (s, 6H); LCMS (m/z): 346.2 $[M+H]^+$.

Example 237

2-[(1H-Pyrrolo[2,3-b]pyridin-3-yl)methylene]-5-(2-adamantylamino)furan-3(2H)-one

[Chemical Formula 246]

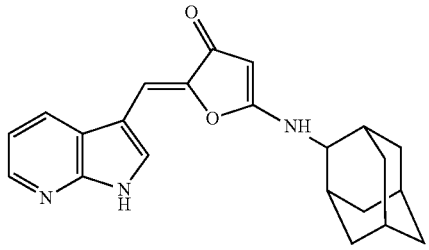

The titled compound (solid) was similarly prepared according to the procedure described in the Example 236, using the compound of Example 113.

$^1$H NMR (DMSO-$d_6$) δ (ppm) 12.29 (br. s, 1H), 8.55 (br. s, 1H), 8.37 (d, J=7.82 Hz, 1H), 8.30 (d, J=4.40 Hz, 1H), 8.14 (br. s, 1H), 7.17 (dd, J=4.89, 7.83 Hz, 1H), 6.64 (s, 1H), 4.83 (s, 1H), 3.25-3.40 (m, 1H), 1.96-2.11 (m, 4H), 1.80-1.92 (m, 4H), 1.69-1.77 (m, 2H), 1.55-1.63 (m, 2H), 1.09 (t, J=7.00 Hz, 2H); LCMS (m/z): 362.4 $[M+H]^+$.

Example 238

2-[(1H-Pyrrolo[2,3-b]pyridin-3-yl)methylene]-5-(cyclopentylamino)furan-3(2H)-one

[Chemical Formula 247]

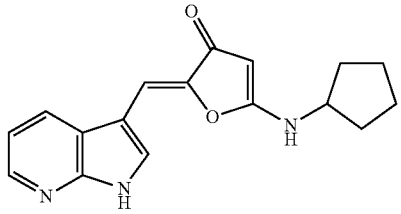

To a solution of the compound (0.10 g, 0.27 mmol) of Example 103 in ethanol (4.0 mL), 50% potassium hydroxide solution (2.0 mL, 0.036 mol) was added at ambient temperature. The mixture was refluxed for 2 h. Cooled to ambient temperature, the solvent was removed under reduced pressure. Water was added to this residue, the mixture was washed with ethyl acetate then 1M hydrochloric acid was added to adjust pH to acidic, and then the solvent was removed under reduced pressure. The residue was purified by preparative HPLC to afford the titled compound as solid (0.0015 g, y. 5%).

$^1$H NMR (DMSO-$d_6$) δ (ppm) 12.25 (br. s, 1H), 8.58-8.70 (m, 1H), 8.39 (d, J=7.83 Hz, 1H), 8.22-8.32 (m, 1H), 7.99 (br. s, 1H), 7.17 (dd, J=4.65, 7.58 Hz, 1H), 6.62 (s, 1H), 6.55 (s, 1H), 4.75-4.96 (m, 1H), 1.90-2.03 (m, 2H), 1.65-1.77 (m, 2H), 1.50-1.65 (m, 4H); LCMS (m/z): 296.2 $[M+H]^+$.

Example 239

2-[(1H-Pyrrolo[2,3-b]pyridin-3-yl)methylene]-5-[(5-indazolyl)amino]furan-3(2H)-one

[Chemical Formula 248]

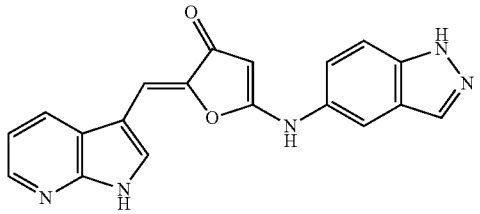

To a solution of the compound (0.14 g, 0.33 mmol) of Example 118 in ethanol (4.0 mL), 50% potassium hydroxide solution (2.2 mL, 0.039 mol) was added at ambient temperature. The mixture was refluxed for 2 h. Cooled to ambient temperature, 1M hydrochloric acid was added to adjust pH to acidic, and the solvent was removed under reduced pressure. The residue was purified by preparative HPLC to afford the titled compound as solid (0.010 g, y. 9%).

$^1$H NMR (DMSO-$d_6$) δ (ppm) 13.16 (br. s, 1H), 12.30 (br. s, 1H), 8.42 (br. s, 1H), 8.37 (d, J=7.76 Hz, 1H), 8.28 (d, J=3.91 Hz, 1H), 8.09 (br. s, 1H), 8.05 (br. s, 1H), 7.71 (s, 1H), 7.61 (d, J=8.80 Hz, 1H), 7.35 (d, J=8.80 Hz, 1H), 7.04-7.11 (m, 1H), 6.73 (s, 1H), 5.10 (s, 1H); LCMS (m/z): 344.2 $[M+H]^+$.

Example 240

2-[(1H-Pyrrolo[2,3-b]pyridin-3-yl)methylene]-5-[(5-benzimidazolyl)amino]furan-3(2H)-one

[Chemical Formula 249]

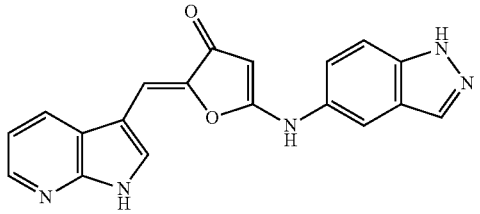

To a solution of the compound (0.055 g, 0.13 mmol) of Example 119 in ethanol (6.0 mL), 50% potassium hydroxide solution (3.0 mL, 0.053 mol) was added at ambient temperature. The mixture was refluxed for 1.5 h. Cooled to ambient temperature, 1M hydrochloric acid was added to adjust pH to acidic, and the solvent was removed under reduced pressure. The residue was purified by preparative HPLC to afford the titled compound (0.0090 g, y. 20%) as solid.

$^1$H NMR (DMSO-$d_6$) δ (ppm) 12.28 (br. s, 1H), 12.10 (br. s, 1H), 8.34 (br. s, 1H), 8.22-8.29 (m, 1H), 8.10-8.20 (m, 1H), 7.95 (br. s, 1H), 7.50-7.62 (m, 1H), 7.25-7.38 (m, 1H), 6.98-7.15 (m, 2H), 6.34-6.67 (m, 2H), 4.84 (s, 1H); LCMS (m/z): 344.0 $[M+H]^+$.

Example 241

2-[(1H-Pyrrolo[2,3-b]pyridin-3-yl)methylene]-5-[(1-phenylethyl)amino]furan-3(2H)-one

[Chemical Formula 250]

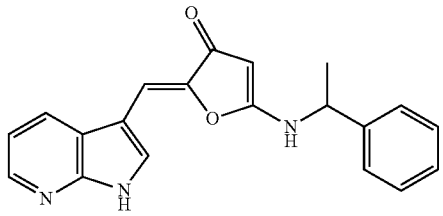

The titled compound (solid) was similarly prepared according to the procedure described in the Example 240, using the compound of Example 106.

$^1$H NMR (DMSO-$d_6$) δ (ppm) 12.29 (br. s, 1H), 9.15 (d, J=7.83 Hz, 1H), 8.23-8.43 (m, 2H), 7.80 (br. s, 1H), 7.11-7.49 (m, 6H), 6.62 (s, 1H), 5.00-5.10 (m, 1H), 4.60-4.80 (m, 1H), 1.36-1.60 (m, 3H); LCMS (m/z): 332.2 $[M+H]^+$.

Example 242

2-[(1H-Pyrrolo[2,3-b]pyridin-3-yl)methylene]-5-{[(3-methyl-2-thienyl)methyl]amino}furan-3(2H)-one

[Chemical Formula 251]

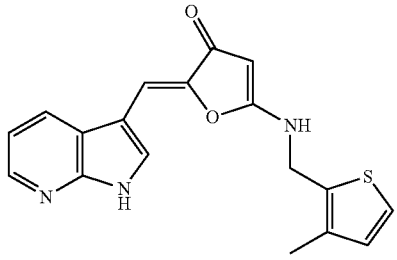

A solution of the compound (0.050 g, 0.12 mmol) of Example 124 in N,N-dimethylformamide (1.0 mL) was refluxed for 16 h. Cooled to ambient temperature, the reaction mixture was purified by preparative HPLC to afford the titled compound as solid (0.012 g, y. 28%).

$^1$H NMR (DMSO-$d_6$) δ (ppm) 12.25 (br. s, 1H), 9.09 (t, J=5.77 Hz, 1H), 8.40 (d, J=7.78 Hz, 1H), 8.29 (dd, J=1.38, 4.64 Hz, 1H), 7.99 (d, J=2.26 Hz, 1H), 7.38 (d, J=5.02 Hz, 1H), 7.15 (dd, J=4.77, 8.03 Hz, 1H), 6.90 (d, J=5.02 Hz, 1H), 6.66 (s, 1H), 4.92 (br. s, 1H), 4.59 (br. s, 2H), 2.25 (s, 3H); LCMS (m/z): 338.1 $[M+H]^+$.

Example 243

2-[(1H-Pyrrolo[2,3-b]pyridin-3-yl)methylene]-5-[(trans-4-hydroxycyclohexyl)amino]furan-3(2H)-one

[Chemical Formula 252]

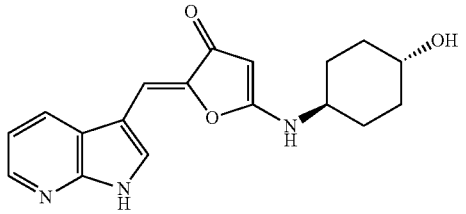

The titled compound (solid) was similarly prepared according to the procedure described in the Example 240, using the compound of Example 116.

$^1$H NMR (DMSO-$d_6$) δ (ppm) 12.23 (br. s, 1H), 8.51-8.60 (m, 1H), 8.34-8.43 (m, 1H), 8.24-8.32 (m, 1H), 7.92-8.10 (m., 1H), 7.16 (dd, J=4.64, 7.91 Hz, 1H), 6.61 (s, 1H), 4.85 (br. s, 1H), 4.40-4.72 (m, 2H), 1.69-2.07 (m, 4H), 1.02-1.54 (m, 4H); LCMS (m/z): 326.1 [M+H]$^+$.

Example 244

Ethyl 5-[(1H-pyrrolo[2,3-b]pyridin-3-yl)methylene]-2-(7-methoxy-3,4-dihydroisoquinolin-2(1H)-yl)-4-oxo-4,5-dihydrofuran-3-carboxylate

[Chemical Formula 253]

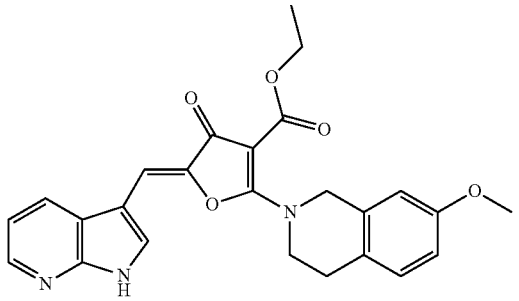

First Step

To a suspension of 7-methoxy-1,2,3,4-tetrahydroisoquinoline hydrochloride (2.10 g, 10.5 mmol) in tetrahydrofuran, triethylamine (3.48 mL, 25.0 mmol) was added at ambient temperature and the mixture was stirred for 30 min. To this reaction mixture, ethyl 2-ethoxy-4-oxo-4,5-dihydrofuran-3-carboxylate (2.00 g, 10.0 mmol), which afforded in the Example 74, Third step was added and the mixture was stirred for 5 days. Water was added to the reaction mixture, and the mixture was extracted with ethyl acetate. The organic layer was washed with brine, dried over sodium sulfate and concentrated. The residue was purified by chromatography on silica gel(chloroform/methanol) to afford ethyl 2-[7-methoxy-3,4-dihydroisoquinolin-2(1H)-yl]-4-oxo-4,5-dihydrofuran-3-carboxylate as oil (2.85 g, y. 89%).

$^1$H NMR ($CDCl_3$) δ (ppm) 7.09 (d, J=8.4 Hz, 1H), 6.80 (dd, J=8.4, 2.6 Hz, 1H), 6.64 (d, J=2.4 Hz, 1H), 4.78 (s, 2H), 4.54 (s, 2H), 4.33 (q, J=7.1 Hz, 2H), 3.89 (t, J=5.9 Hz, 2H), 3.79 (d, J=2.9 Hz, 3H), 2.86-3.04 (m, 2H), 1.38 (t, J=7.1 Hz, 3H); LCMS (m/z): 318.2 [M+H]$^+$.

Second Step

To a solution of ethyl 2-[7-methoxy-3,4-dihydroisoquinolin-2(1H)-yl]-4-oxo-4,5-dihydrofuran-3-carboxylate (2.58 g, 8.98 mmol) and 7-azaindole-3-carboxaldehyde (1.31 g, 8.98 mmol) in ethanol (12 mL), L-proline was added at ambient temperature. The mixture was refluxed for 24 h. The precipitate was collected by filtration, washed with ethanol and diisopropyl ether then dried to afford the titled compound as solid (1.20 g, y. 30%).

$^1$H NMR (DMSO-$d_6$) δ (ppm) 12.37 (s, 1H), 8.41 (dd, J=7.9, 1.5 Hz, 1H), 8.33 (dd, J=4.7, 1.5 Hz, 1H), 8.08 (s, 1H), 7.26-7.13 (m, 2H), 6.90 (s, 2H), 6.85 (dd, J=8.3, 2.6 Hz, 1H), 4.95 (br. s, 2H), 4.21 (q, J=7.1 Hz, 2H), 3.85-4.05 (m, 2H), 3.76 (s, 3H), 3.00 (t, J=5.8 Hz, 2H), 1.26 (t, J=7.1 Hz, 3H); LCMS (m/z): 446.2 [M+H]$^+$.

Example 245

Isopropyl 5-[(1H-pyrrolo[2,3-b]pyridin-3-yl)methylene]-2-(morpholinoamino)-4-oxo-4,5-dihydrofuran-3-carboxylate

[Chemical Formula 254]

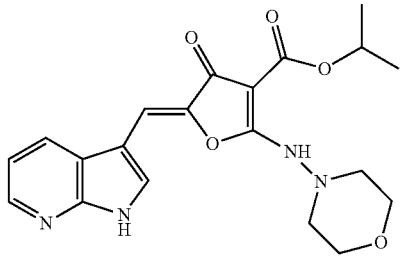

First Step

To a solution of isopropyl 2-isopropoxy-4-oxo-4,5-dihydrofuran-3-carboxylate (12.2 g, 53.6 mmol), which similarly prepared according to the procedure described in the Example 74, Third step using diisopropyl malonate and chloroacetyl chloride, in ethanol (45 mL), 4-aminomorpholine (5.7 mL, 59.2 mmol) was added at ambient temperature. The mixture was stirred for 18 h. The solvent was removed under reduced pressure, and the crude product was suspended in methyl tert-butyl ether, then the precipitate was collected by filtration, washed with methyl tert-butyl ether and hexane then dried to afford isopropyl 2-(morpholinoamino)-4-oxo-4,5-dihydrofuran-3-carboxylate as solid (11.2 g, y. 75%).

$^1$H NMR (DMSO-$d_6$) δ (ppm) 9.60 (s, 1H), 4.95-5.05 (m, 1H), 4.57 (s, 2H), 3.60-3.68 (m, 4H), 2.87-2.95 (m, 4H), 1.22 (d, J=6.40 Hz, 6H); LCMS (m/z): 271.0 [M+H]$^+$ Second Step To a stirred solution of isopropyl 2-(morpholinoamino)-4-oxo-4,5-dihydrofuran-3-carboxylate (5.00 g, 18.5 mmol) and 7-azaindole-3-carboxaldehyde (2.49 g, 17.1 mmol) in ethanol (25 mL), L-proline (0.24 g, 2.04 mmol) was added at ambient temperature. The mixture was refluxed for 3 days. The precipitate was collected by filtration, washed with hot ethanol then hexane, and then dried to afford the titled compound as solid (4.22 g, y. 62%).

$^1$H NMR (DMSO-$d_6$) δ (ppm) 12.34 (br. s, 1H), 10.07 (s, 1H), 8.94 (d, J=7.78 Hz, 1H), 8.33 (dd, J=1.38, 4.64 Hz, 1H), 8.12 (d, J=2.76 Hz, 1H), 7.22 (dd, J=4.52, 8.03 Hz, 1H), 6.84 (s, 1H), 4.99-5.12 (m, 1H), 3.75-3.86 (m, 4H), 3.03-3.13 (m, 4H), 1.27 (d, J=6.27 Hz, 6H); LCMS (m/z): 399.1 $[M+H]^+$.

Example 246

Ethyl 5-[(1H-pyrrolo[2,3-b]pyridin-3-yl)methylene]-4-oxo-2-{[4-(2,2,2-trifluoroethyl)piperazinyl]amino}-4,5-dihydrofuran-3-carboxylate

[Chemical Formula 255]

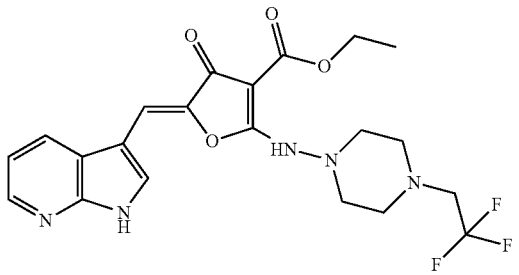

First Step

To a solution of 1-(2,2,2-trifluoroethyl)piperazine (4.88 g, 29.0 mmol) in water (4.9 mL) that cooled with ice bath, a solution of sodium nitrite (4.04 g, 58.6 mmol) in water (20 mL) and acetic acid (5.0 mL, 87.0 mmol) were added dropwise slowly, then the mixture was stirred for 1 h. The reaction mixture was all owed to warm to ambient temperature, stirred for further 2 h. The reaction mixture was adjusted to pH9 using sodium carbonate, diluted with ethyl acetate and washed with water and brine. The organic layer was dried over magnesium sulfate and concentrated to afford 1-nitrso-4-(2,2,2-trifluoroethyl)piperazine as oil (5.57 g, y. 97%).

$^1$H NMR (DMSO-$d_6$) δ (ppm) 4.18-4.22 (m, 2H), 3.72-3.76 (m, 2H), 3.32 (q, J=10.13 Hz, 2H), 2.84-2.89 (m, 2H), 2.59-2.64 (m, 2H).

Second Step

To a suspension of lithium aluminum hydride (2.22 g, 58.5 mmol) in tetrahydrofuran (100 mL) that cooled with ice bath, a solution of 1-nitroso-4-(2,2,2-trifluoroethyl)piperazine (5.43 g, 27.5 mmol) in tetrahydrofuran (10 mL) was added dropwise and the reaction mixture was allowed to warm to ambient temperature, then stirred for 5 days. The reaction mixture was cooled with ice bath, ethyl acetate was added until cease bubbling up, and water (2.1 mL) was added then the mixture was stirred for 20 min. To this mixture, 15% w/v sodium hydroxide solution (2.1 mL) and water (6.3 mL) were added, then the suspension mixture was allowed to warm to ambient temperature and then the mixture was stirred vigorously for 1 h. Magnesium sulfate was added to the mixture and stirred for a while, then the suspension was filtered. The filtrate was concentrated to afford 4-(2,2,2-trifluoroethyl)piperazine-1-amine as oil (4.72 g, y. 94%).

$^1$H NMR (DMSO-$d_6$) δ (ppm) 3.12 (br. s, 1H), 2.98 (q, J=9.6 Hz, 2H), 2.60-2.80 (m, 8H).

Third Step

To a solution of 4-(2,2,2-trifluoroethyl)piperazine-1-amine (4.72 g, 25.8 mmol) in ethanol (43 mL), ethyl 2-ethoxy-4-oxo-4,5-dihydrofuran-3-carboxylate (4.70 g, 23.5 mmol) which similarly prepared according to the procedure described in the Example 74, Third step was added at ambient temperature. The mixture was stirred for 2 h. The precipitate was collected by filtration, washed with diethyl ether and hexane then dried to afford ethyl 4-oxo-2-{[4-(2,2,2-trifluoroethyl)piperazinyl]amino}-4,5-dihydrofuran-3-carboxylate as solid (5.64 g, y. 71%).

$^1$H NMR (DMSO-$d_6$) δ (ppm) 8.94 (s, 1H), 4.61 (s, 2H), 4.32 (q, J=7.07 Hz, 2H), 3.03 (q, J=9.47 Hz, 2H), 2.95-2.99 (m, 4H), 2.85-2.90 (m, 4H), 1.37 (t, J=7.20 Hz, 3H); LCMS (m/z): 338.1 $[M+H]^+$.

Fourth Step

To a solution of ethyl 4-oxo-2-{[4-(2,2,2-trifluoroethyl)piperazinyl]amino}-4,5-dihydrofuran-3-carboxylate (3.01 g, 8.93 mmol) and 7-azaindole-3-carboxaldehyde (1.25 g, 8.55 mmol) in ethanol (25 mL), L-proline (99 mg, 0.86 mmol) was added at ambient temperature then the mixture was refluxed for 2 days. The precipitate was collected by filtration, washed with hot ethanol then hexane, and then dried to afford the titled compound a solid (2.64 g, y. 66%).

$^1$H NMR (DMSO-$d_6$) δ (ppm) 12.32 (s, 1H), 10.09 (s, 1H), 8.95 (d, J=7.6 Hz, 1H), 8.33 (d, J=4.1 Hz, 1H), 8.09 (s, 1H), 7.30-7.16 (m, 1H), 6.80 (s, 1H), 4.19 (q, J=7.1 Hz, 2H), 3.31-3.41 (m, 2H), 3.06 (s, 4H), 2.88 (s, 4H), 1.25 (t, J=7.0 Hz, 3H); LCMS (m/z): 466.0 $[M+H]^+$.

Each of the Example compounds shown in the following [Table 1-1] to [Table 1-10] were prepared according to the procedure described in the above Examples or modified procedure well known in the art of organic chemistry if needed, using appropriate starting materials (those materials which are commercially available, or which are derivatized by known methods or their modified methods from commercial compounds). The physicochemical data of each compound were shown in the following [Table 2-1] to [Table 2-6].

TABLE 1-1

| Example | Chemical Formula | Chemical Name |
|---|---|---|
| 247 | 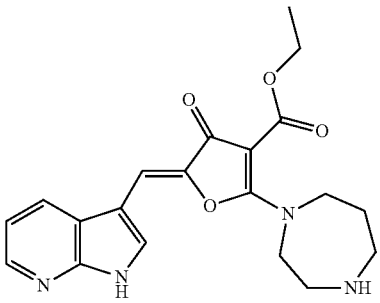 | Ethyl 5-[(1H-pyrrolo[2,3-b]pyridin-3-yl)methylene]-2-(1,4-diazepan-1-yl)-4-oxo-4,5-dihydrofuran-3-carboxylate |

TABLE 1-1-continued

| Example | Chemical Formula | Chemical Name |
|---|---|---|
| 248 | | Ethyl 5-[(1H-pyrrolo[2,3-b]pyridin-3-yl)methylene]-2-(4,5-dihydrothieno[2,3-c]pyridin-6(7H)-yl)-4-oxo-4,5-dihydrofuran-3-carboxylate |
| 249 | | Ethyl 5-[(1H-pyrrolo[2,3-b]pyridin-3-yl)methylene]-2-(4,5-dihydro-1H-benzo[c]azepin-2(3H)-yl)-4-oxo-4,5-dihydrofuran-3-carboxylate |
| 250 | | Ethyl 5-[(1H-pyrrolo[2,3-b]pyridin-3-yl)methylene]-2-(2,3-dihydrobenzo-[f][1,4]oxazepin-4(5H)-yl)-4-oxo-4,5-dihydrofuran-3-carboxylate |
| 251 | | Carbamoylmethyl 5-[(1H-pyrrolo[2,3-b]pyridin-3-yl)methylene]-2-[(4-fluorophenyl)amino]-4-oxo-4,5-dihydrofuran-3-carboxylate |
| 252 | | Ethyl 5-[(1H-pyrrolo[2,3-b]pyridin-3-yl)methylene]-2-[(1-hydroxypropan-2-yl)amino]-4-oxo-4,5-dihydrofuran-3-carboxylate |

TABLE 1-1-continued

| Example | Chemical Formula | Chemical Name |
|---|---|---|
| 253 | 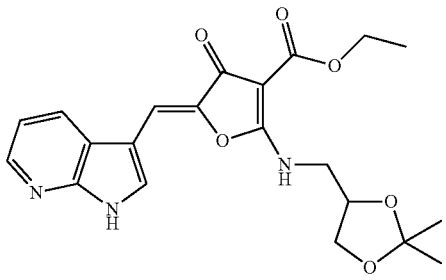 | Ethyl 5-[(1H-pyrrolo[2,3-b]pyridin-3-yl)methylene]-2-[(2,2-dimethyl-1,3-dioxolan-4-yl)methylamino]-4-oxo-4,5-dihydrofuran-3-carboxylate |
| 254 | 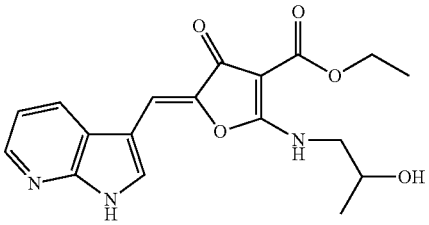 | Ethyl 5-[(1H-pyrrolo[2,3-b]pyridin-3-yl)methylene]-2-[(2-hydroxypropyl)amino]-4-oxo-4,5-dihydrofuran-3-carboxylate |
| 255 | 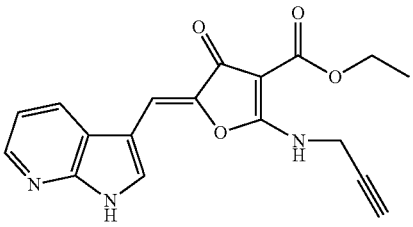 | Ethyl 5-[(1H-pyrrolo[2,3-b]pyridin-3-yl)methylene]-4-oxo-2-(prop-2-yn-1-ylamino)-4,5-dihydrofuran-3-carboxylate |
| 256 | 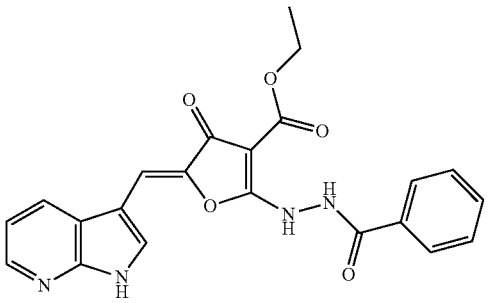 | Ethyl 5-[(1H-pyrrolo[2,3-b]pyridin-3-yl)methylene]-2-(2-benzoylhydrazinyl)-4-oxo-4,5-dihydrofuran-3-carboxylate |
| 257 | 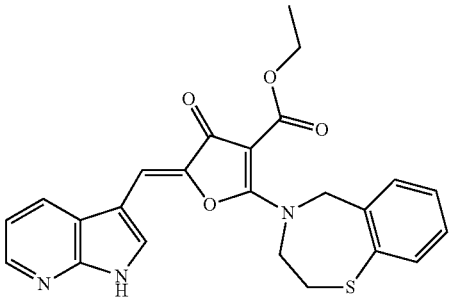 | Ethyl 5-[(1H-pyrrolo[2,3-b]pyridin-3-yl)methylene]-2-(2,3-dihydrobenzo[f][1,4]thiazepin-4(5H)-yl)-4-oxo-4,5-dihydrofuran-3-carboxylate |

TABLE 1-1-continued

| Example | Chemical Formula | Chemical Name |
|---|---|---|
| 258 | 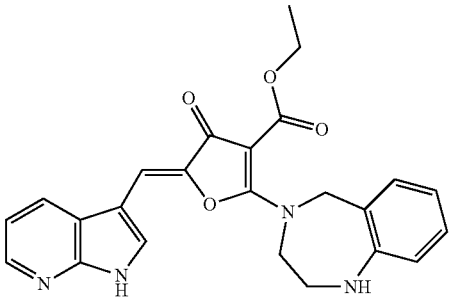 | Ethyl 5-[(1H-pyrrolo[2,3-b]pyridin-3-yl)methylene]-2-(2,3-dihydro-1H-benzo[e][1,4]diazepin-4(5H)-yl)-4-oxo-4,5-dihydrofuran-3-carboxylate |

TABLE 1-2

| | | |
|---|---|---|
| 259 | 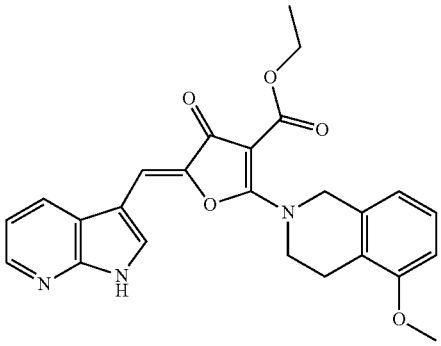 | Ethyl 5-[(1H-pyrrolo[2,3-b]pyridin-3-yl)methylene]-2-(5-methoxy-3,4-dihydroisoquinolin-2(1H)-yl)-4-oxo-4,5-dihydrofuran-3-carboxylate |
| 260 | 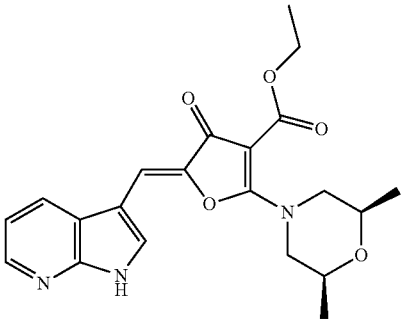 | Ethyl 5-[(1H-pyrrolo[2,3-b]pyridin-3-yl)methylene]-2-[(2S,6R)-2,6-dimethylmorpholino]-4-oxo-4,5-dihydrofuran-3-carboxylate |
| 261 | 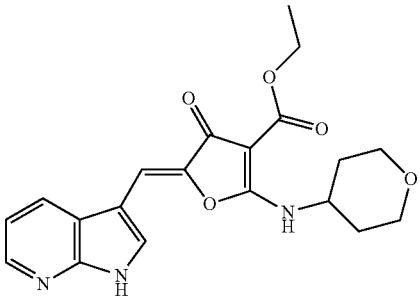 | Ethyl 5-[(1H-pyrrolo[2,3-b]pyridin-3-yl)methylene]-4-oxo-2-[(tetrahydro-2H-pyran-4-yl)amino]-4,5-dihydrofuran-3-carboxylate |

TABLE 1-2-continued

| | | |
|---|---|---|
| 262 | 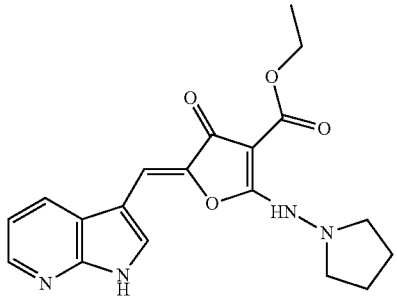 | Ethyl 5-[(1H-pyrrolo[2,3-b]pyridin-3-yl)methylene]-4-oxo-2-(pyrrolidin-1-ylamino)-4,5-dihydrofuran-3-carboxylate |
| 263 | 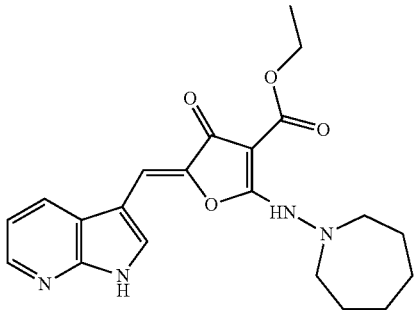 | Ethyl 5-[(1H-pyrrolo[2,3-b]pyridin-3-yl)methylene]-2-(azepan-1-4-oxo-4,5-dihydrofuran-3-carboxylate |
| 264 | 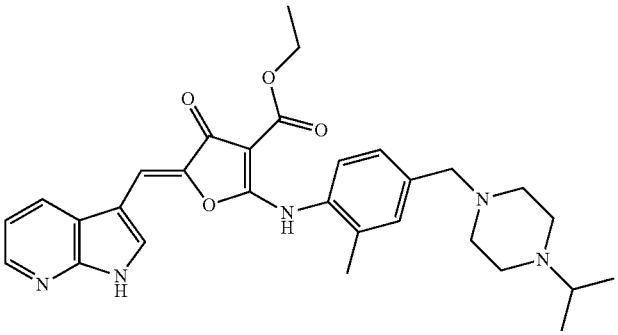 | Ethyl 5-[(1H-pyrrolo[2,3-b]pyridin-3-yl)methylene]-2-({4-[(4-isopropylpiperazinyl)methyl]-2-methylphenyl}amino)-4-oxo-4,5-dihydrofuran-3-carboxylate |
| 265 | 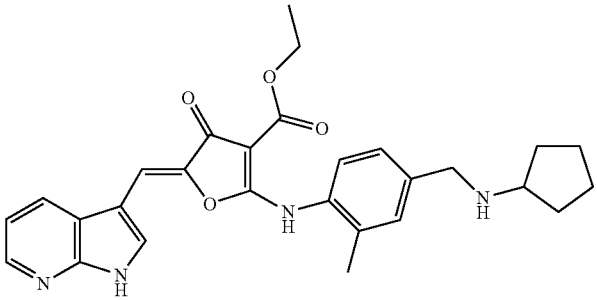 | Ethyl 5-[(1H-pyrrolo[2,3-b]pyridin-3-yl)methylene]-2-({4-[(cyclopentylamino)methyl]-2-methylphenyl}amino-4-oxo-4,5-dihydrofuran-3-carboxylate |
| 266 | 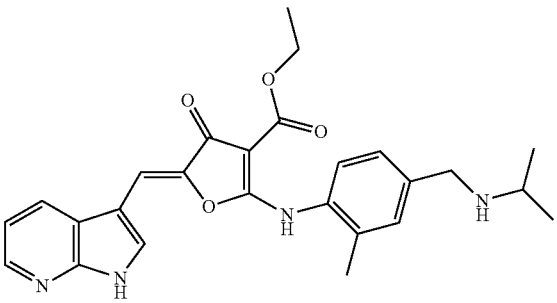 | Ethyl 5-[(1H-pyrrolo[2,3-b]pyridin-3-yl)methylene]-2-({4-[(isopropylamino)methyl]-2-methylphenyl}amino)-4-oxo-4,5-dihydrofuran-3-carboxylate |

TABLE 1-2-continued

| | | |
|---|---|---|
| 267 | 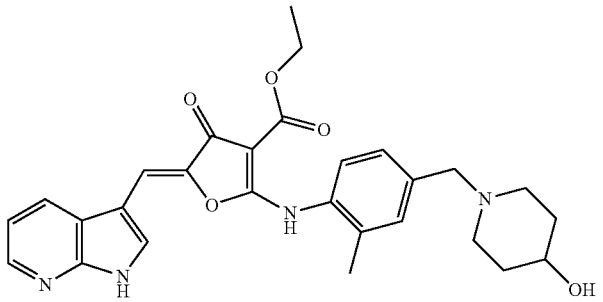 | Ethyl 5-[(1H-pyrrolo[2,3-b]pyridin-3-yl)methylene]-2-{[4-(4-hydroxypiperidinomethyl)-2-methylphenyl]amino}-4-oxo-4,5-dihydrofuran-3-carboxylate |
| 268 | 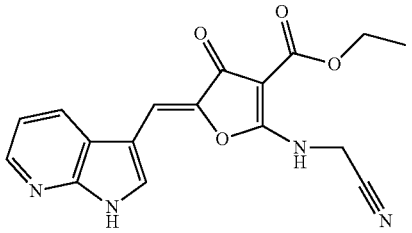 | Ethyl 5-[(1H-pyrrolo[2,3-b]pyridin-3-yl)methylene]-2-(cyanomethylamino)-4-oxo-4,5-dihydrofuran-3-carboxylate |
| 269 | 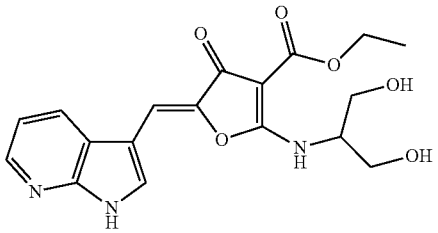 | Ethyl 5-[(1H-pyrrolo[2,3-b]pyridin-3-yl)methylene]-2-[(1,3-dihydroxypropan-2-yl)amino]-4-oxo-4,5-dihydrofuran-3-carboxylate |
| 270 | 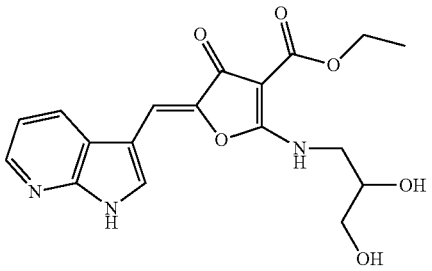 | Ethyl 5-[(1H-pyrrolo[2,3-b]pyridin-3-yl)methylene]-2-[(2,3-dihydroxypropyl)amino]-4-oxo-4,5-dihydrofuran-3-carboxylate |

TABLE 1-3

| | | |
|---|---|---|
| 271 | 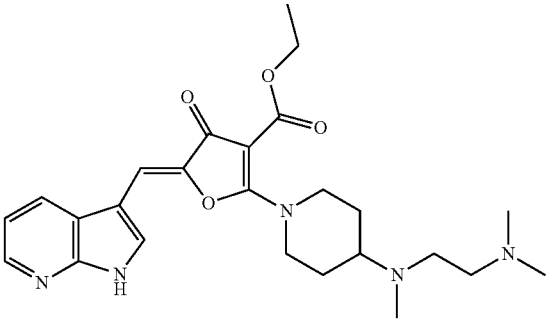 | Ethyl 5-[(1H-pyrrolo[2,3-b]pyridin-3-yl)methylene]-2-(4-{[2-(dimethylamino)ethyl](N-methyl)amino}piperidino)-4-oxo-4,5-dihydrofuran-3-carboxylate |

TABLE 1-3-continued

| | | |
|---|---|---|
| 272 | 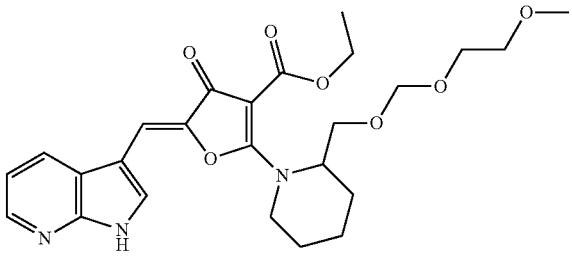 | Ethyl 5-[(1H-pyrrolo[2,3-b]pyridin-3-yl)methylene]-2-(2-{[(2-methoxyethoxy)methoxy]methyl}piperidino)-4-oxo-4,5-dihydrofuran-3-carboxylate |
| 273 | 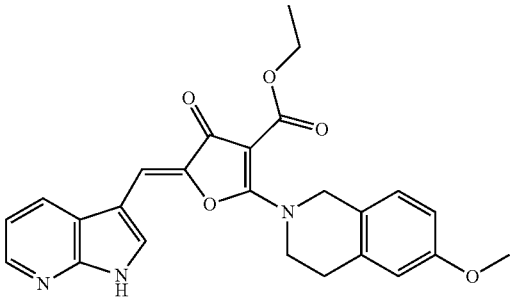 | Ethyl 5-[(1H-pyrrolo[2,3-b]pyridin-3-yl)methylene]-2-(6-methoxy-3,4-dihydroisoquinolin-2(1H)-yl)-4-oxo-4,5-dihydrofuran-3-carboxylate |
| 274 | 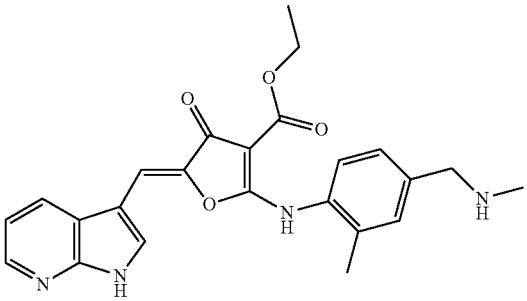 | Ethyl 5-[(1H-pyrrolo[2,3-b]pyridin-3-yl)methylene]-2-({2-methyl-4-[(methylamino)methyl]phenyl}amino)-4-oxo-4,5-dihydrofuran-3-carboxylate |
| 275 | 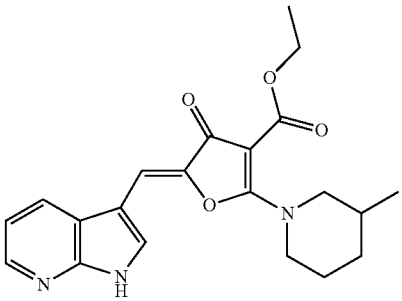 | Ethyl 5-[(1H-pyrrolo[2,3-b]pyridin-3-yl)methylene]-2-(3-methylpiperidino)-4-oxo-4,5-dihydrofuran-3-car boxylate |
| 276 | 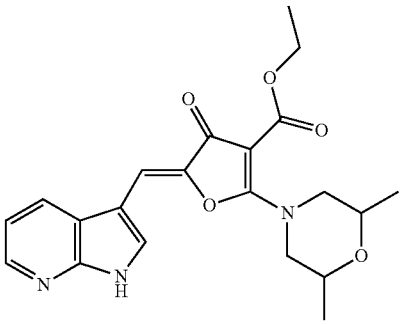 | Ethyl 5-[(1H-pyrrolo[2,3-b]pyridin-3-yl)methylene]-2-(2,6-dimethylmorpholino)-4-oxo-4,5-dihydrofuran-3-carboxylate |

TABLE 1-3-continued

| | | |
|---|---|---|
| 277 | 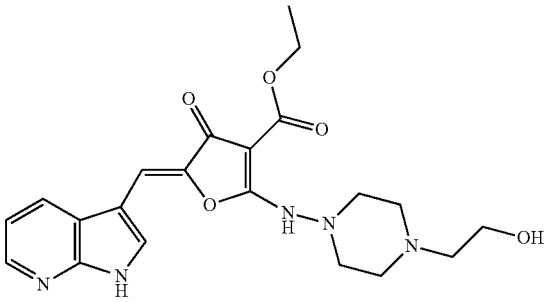 | Ethyl 5-[(1H-pyrrolo[2,3-b]pyridin-3-yl)methylene]-2-{[4-(2-hydroxyethyl)piperazinyl]amino}-4-oxo-4,5-dihydrofuran-3-carboxylate |
| 278 | 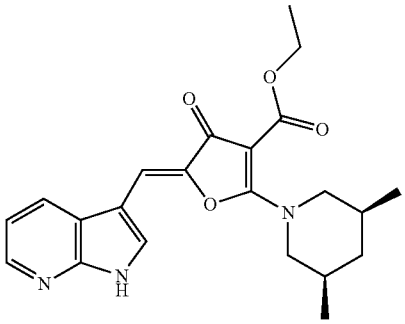 | Ethyl 5-[(1H-pyrrolo[2,3-b]pyridin-3-yl)methylene]-2-[(3R,5S)-3,5-dimethylpiperidino]-4-oxo-4,5-dihydrofuran-3-carboxylate |
| 279 | 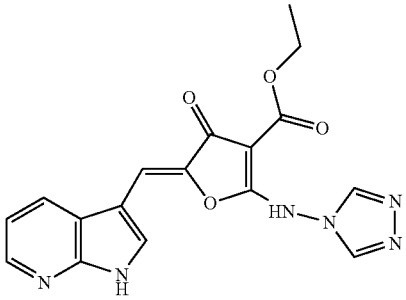 | Ethyl 5-[(1H-pyrrolo[2,3-b]pyridin-3-yl)methylene]-2-[(4H-1,2,4-triazol-4-yl)amino]-4-oxo-4,5-dihydrofuran-3-carboxylate |
| 280 | 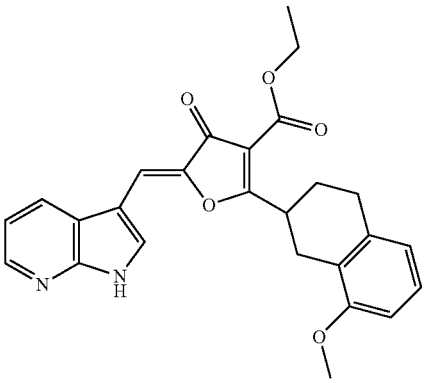 | Ethyl 5-[(1H-pyrrolo[2,3-b]pyridin-3-yl)methylene]-2-[8-methoxy-3,4-dihydroisoquinolin-2(1H)-yl]-4-oxo-4,5-dihydrofuran-3-carboxylate |

TABLE1-4

| | | |
|---|---|---|
| 281 | 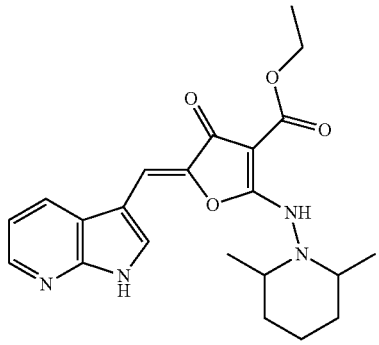 | Ethyl 5-[(1H-pyrrolo[2,3-b]pyridin-3-yl)methylene]-2-(2,6-dimethylpiperidinoamino)-4-oxo-4,5-dihydrofuran-3-carboxylate |
| 282 | 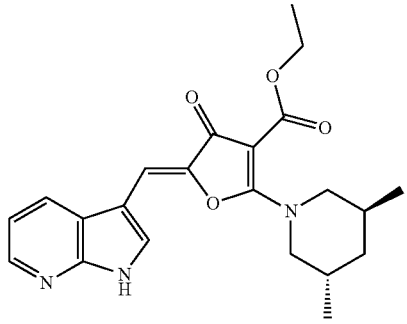 | Ethyl 5-[(1H-pyrrolo[2,3-b]pyridin-3-yl)methylene]-2-[(3S,5S)-3,5-dimethylpiperidino]-4-oxo-4,5-dihydrofuran-3-carboxylate |
| 283 | 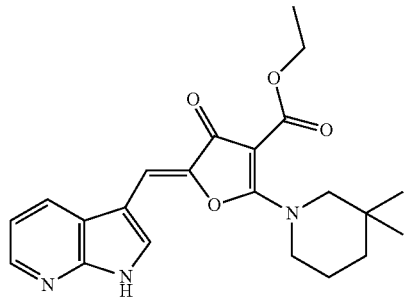 | Ethyl 5-[(1H-pyrrolo[2,3-b]pyridin-3-yl)methylene]-2-(3,3-dimethylpiperidino)-4-oxo-4,5-dihydrofuran-3-carboxylate |
| 284 | 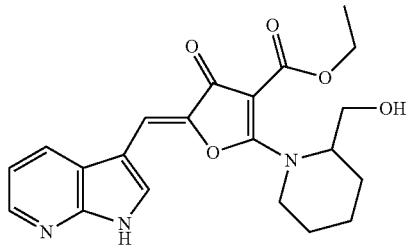 | Ethyl 5-[(1H-pyrrolo[2,3-b]pyridin-3-yl)methylene]-2-[2-(hydroxymethyl)piperidino]-4-oxo-4,5-dihydrofuran-3-carboxylate |
| 285 | 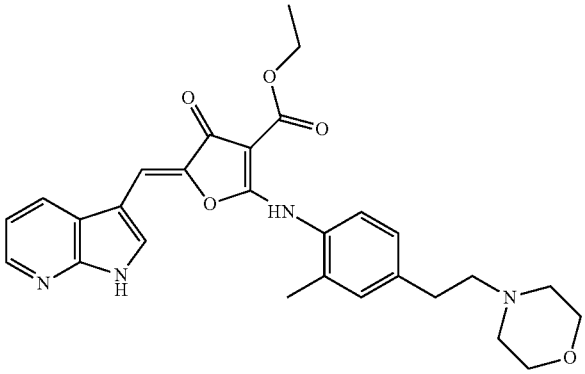 | Ethyl 5-[(1H-pyrrolo[2,3-b]pyridin-3-yl)methylene]-2-{[2-methyl-4-(2-morpholinoethyl)phenyl]aminol-4-oxo-4,5-dihydrofuran-3-carboxylate |

TABLE1-4-continued

| | | |
|---|---|---|
| 286 | 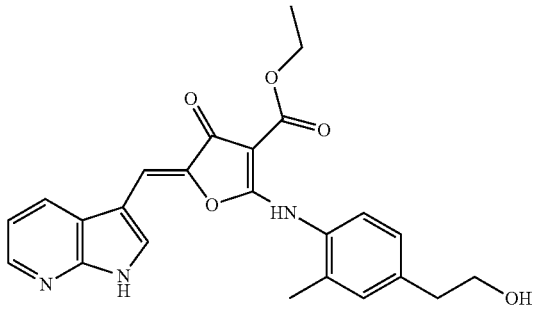 | Ethyl 5-[(1H-pyrrolo[2,3-b]pyridin-3-yl)methylene]-2-{[4-(2-hydroxyethyl)-2-methylphenyl]amino}-4-oxo-4,5-dihydrofuran-3-carboxylate |
| 287 | 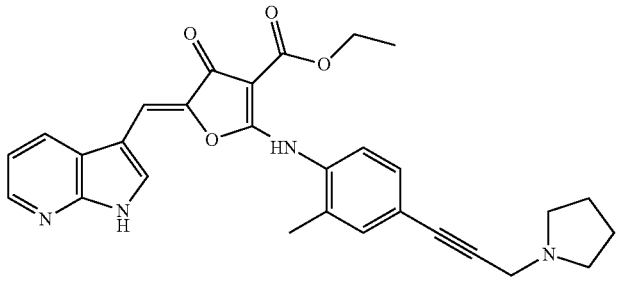 $CH_3COOH$ | Ethyl 5-[(1H-pyrrolo[2,3-b]pyridin-3-yl)methylene]-2-({2-methy1-4-[3-(pyrrolidinyl)prop-1-yn-1-yl]phenyl}amino)-4-oxo-4,5-dihydrofuran-3-carboxylate acetate |
| 288 | 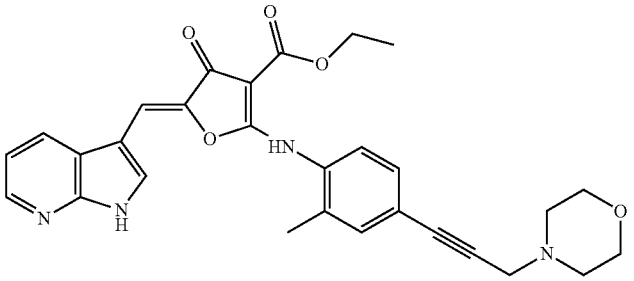 HCOOH | Ethyl 5-[(1H-pyrrolo[2,3-b]pyridin-3-yl)methylene]-2-{[2-methyl-4-(3-morpholinoprop-1-yn-1-yl)phenyl]amino}-4-oxo-4,5-dihydrofuran-3-carboxylate formate |
| 289 | 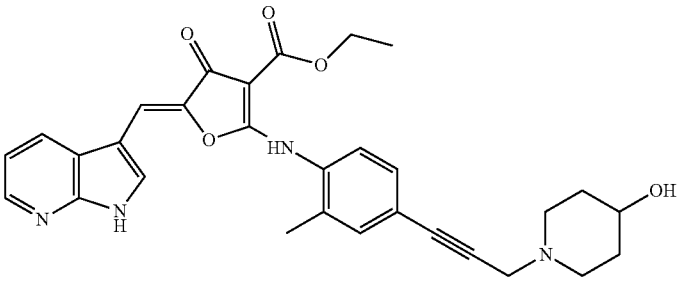 | Ethyl 5-[(1H-pyrrolo[2,3-b]pyridin-3-yl)methylene]-2-({4-[3-(4-hydroxypiperidino)prop-1-yn-1-yl]-2-methylphenyl}amino)-4-oxo-4,5-dihydrofuran-3-carboxylate |
| 290 | 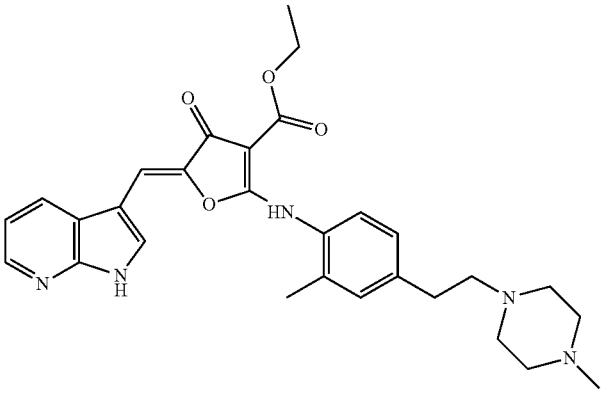 | Ethyl 5-[(1H-pyrrolo[2,3-b]pyridin-3-yl)methylene]-2-({2-methyl-4-[2-(4-methylpiperazinyl)ethyl]phenyl}amino)-4-oxo-4,5-dihydrofuran-3-carboxylate |

TABLE1-4-continued

| | | |
|---|---|---|
| 291 | 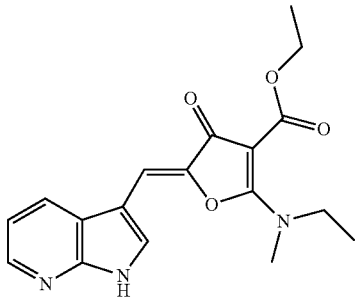 | Ethyl 5-[(1H-pyrrolo[2,3-b]pyridin-3-yl)methylene]-2-[ethyl(N-methyl)amino]-4-oxo-4,5-dihydrofuran-3-carboxylate |

TABLE 1-5

| | | |
|---|---|---|
| 292 | 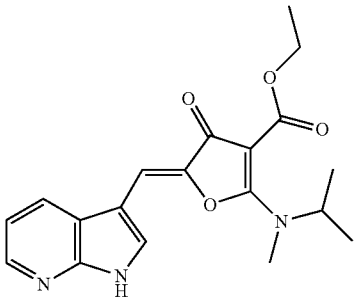 | Ethyl 5-[(1H-pyrrolo[2,3-b]pyridin-3-yl)methylene]-2-[isopropyl(N-methyl)amino]-4-oxo-4,5-dihydrofuran-3-carboxylate |
| 293 | 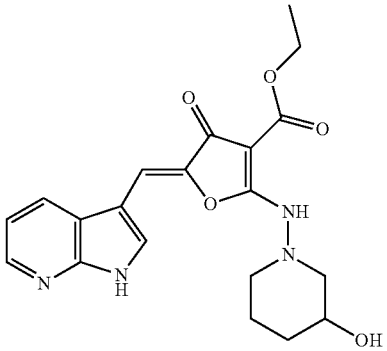 | Ethyl 5-[(1H-pyrrolo[2,3-b]pyridin-3-yl)methylene]-2-(3-hydroxypiperidinoamino)-4-oxo-4,5-dihydrofuran-3-carboxylate |
| 294 | 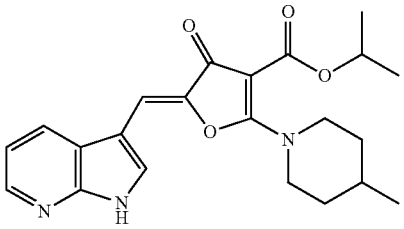 | Isopropyl 5-[(1H-pyrrolo[2,3-b]pyridin-3-yl)methylene]-2-(4-methylpiperidino)-4-oxo-4,5-dihydrofuran-3-carboxylate |
| 295 | 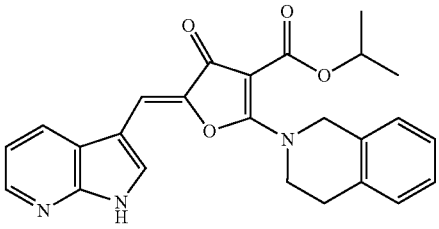 | Isopropyl 5-[(1H-pyrrolo[2,3-b]pyridin-3-yl)methylene]-2-(3,4-dihydroisoquinolin-2(1H)-yl)-4-oxo-4,5-dihydrofuran-3-carboxylate |

TABLE 1-5-continued

| | | |
|---|---|---|
| 296 | 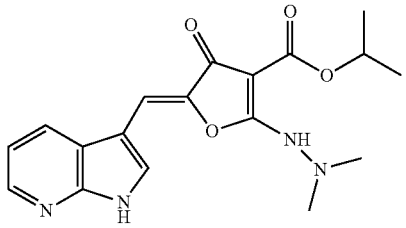 | Isopropyl 5-[(1H-pyrrolo[2,3-b]pyridin-3-yl)methylene]-2-(2,2-dimethylhydrazinyl)-4-oxo-4,5-dihydrofuran-3-carboxylate |
| 297 | 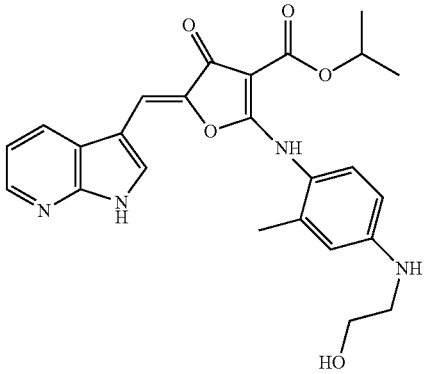 | Isopropyl 5-[(1H-pyrrolo[2,3-b]pyridin-3-yl)methylene]-2-({4-[(2-hydroxyethyl)amino]-2-methylphenyl}amino)-4-oxo-4,5-dihydrofuran-3-carboxylate |
| 298 | 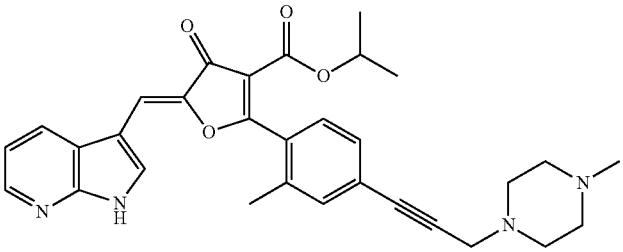 | Ethyl 5-[(1H-pyrrolo[2,3-b]pyridin-3-yl)methylene]-2-({2-methyl-4-[3-(4-methylpiperazinyl)prop-1-yn-1-yl]phenyl}amino)-4-oxo-4,5-dihydrofuran-3-carboxylate |
| 299 | 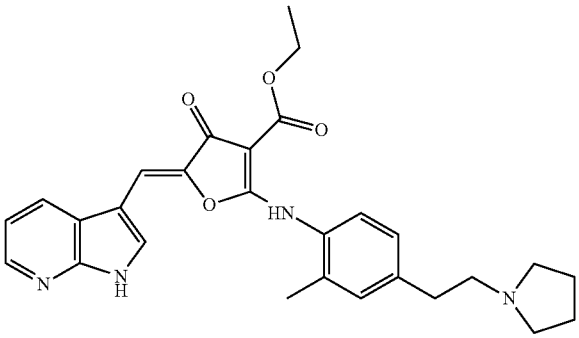 | Ethyl 5-[(1H-pyrrolo[2,3-b]pyridin-3-yl)methylene]-2-({2-methyl-4-[2-(pyrrolidinyl)ethyl]phenyl}amino)-4-oxo-4,5-dihydrofuran-3-carboxylate |
| 300 | 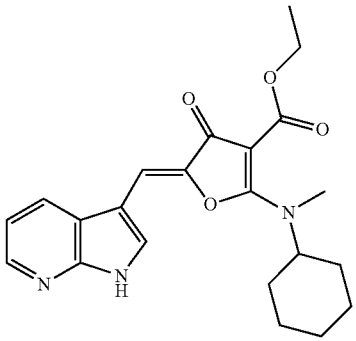 | Ethyl 5-[(1H-pyrrolo[2,3-b]pyridin-3-yl)methylene]-2-[cyclohexyl(N-methyl)amino]-4-oxo-4,5-dihydrofuran-3-carboxylate |

TABLE 1-5-continued

| | | |
|---|---|---|
| 301 | 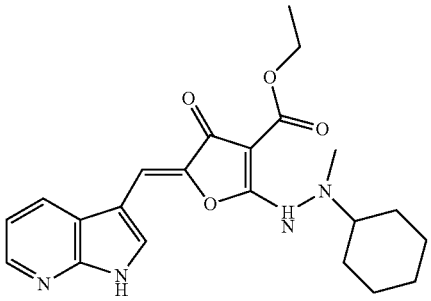 | Ethyl 5-[(1H-pyrrolo[2,3-b]pyridin-3-yl)methylene]-2-(2-cyclohexyl-2-methylhydraziny1)-4-oxo-4,5-dihydrofuran-3-carboxylate |
| 302 | 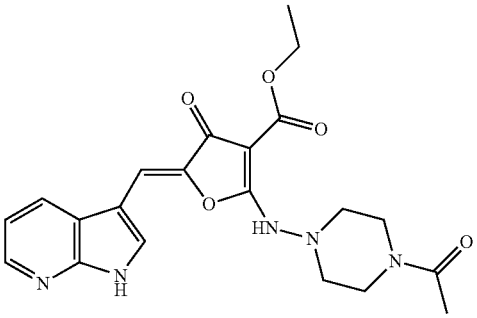 | Ethyl 5-[(1H-pyrrolo[2,3-b]pyridin-3-yl)methylene]-2-[(4-acetylpiperazinyl)amino]-4-oxo-4,5-dihydrofuran-3-carboxylate |

TABLE 1-6

| | | |
|---|---|---|
| 303 | 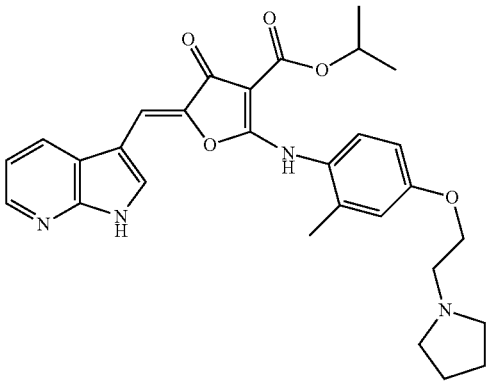 | Isopropyl 5-[(1H-pyrrolo[2,3-b]pyridin-3-yl)methylene]-2-({2-methyl-4-[2-(pyrrolidinyl)ethoxy]phenyl{amino)-4-oxo-4,5-dihydrofuran-3-carboxylate |
| 304 | 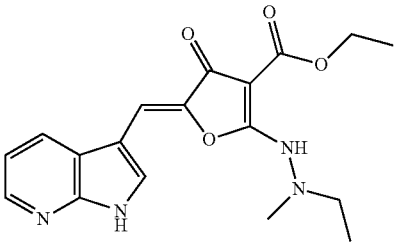 | Ethyl 5-[(1H-pyrrolo[2,3-b]pyridin-3-yl)methylene]-2-(2-ethyl-2-methylhydrazinyl)-4-oxo-4,5-dihydrofuran-3-carboxylate |
| 305 | 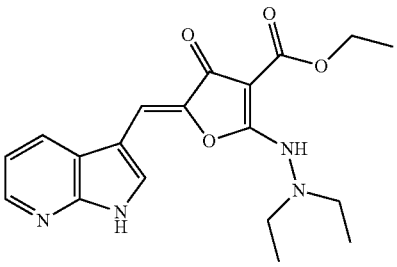 | Ethyl 5-[(1H-pyrrolo[2,3-b]pyridin-3-yl)methylene]-2-(2,2-diethylhydraziny1)-4-oxo-4,5-dihydrofuran-3-carboxylate |

TABLE 1-6-continued

| | | |
|---|---|---|
| 306 | 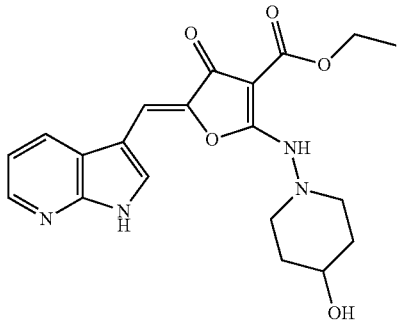 | Ethyl 5-[(1H-pyrrolo[2,3-b]pyridin-3-yl)methylene]-2-(4-hydroxypiperidinoamino)-4-oxo-4,5-dihydrofuran-3-carboxylate |
| 307 | 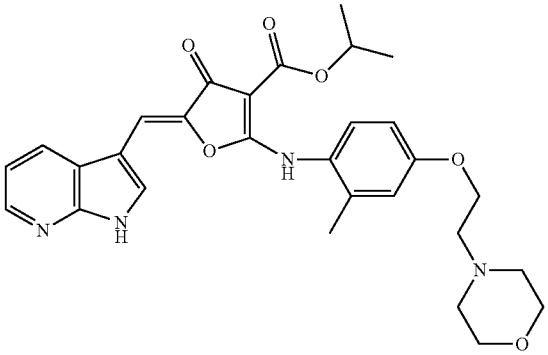 | Isopropyl 5-[(1H-pyrrolo[2,3-b]pyridin-3-yl)methylene]-2-{[2-methyl-4-(2-morpholinoethoxy)phenyl]aminol-4-oxo-4,5-dihydrofuran-3-carboxylate |
| 308 | 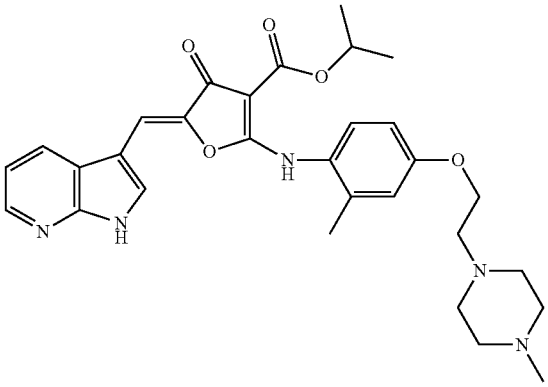 | Isopropyl 5-[(1H-pyrrolo[2,3-b]pyridin-3-yl)methylene]-2-({2-methyl-4-[2-(4-methylpiperazinyl)ethoxy]phenyl}amino)-4-oxo-4,5-dihydrofuran-3-carboxylate |
| 309 | 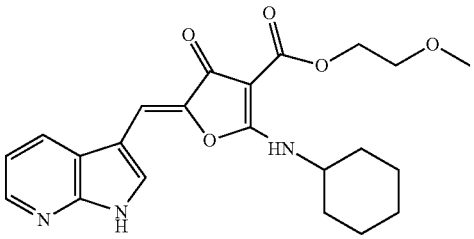 | 2-Methoxyethyl 5-[(1H-pyrrolo[2,3-b]pyridin-3-yl)methylene]-2-(cyclohexylamino)-4-oxo-4,5-dihydrofuran-3-carboxylate |
| 310 | 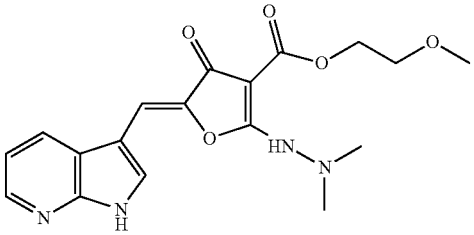 | 2-Methoxyethyl 5-[(1H-pyrrolo[2,3-b]pyridin-3-yl)methylene]-2-(2,2-dimethylhydrazinyl)-4-oxo-4,5-dihydrofuran-3-carboxylate |

TABLE 1-6-continued

| | | |
|---|---|---|
| 311 | 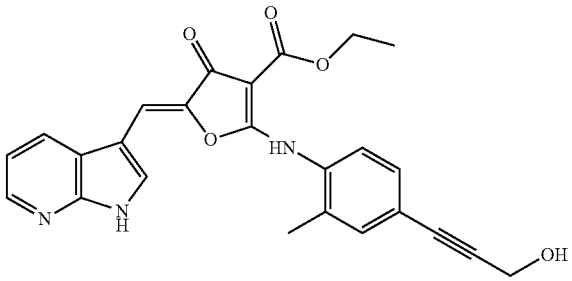 | Ethyl 5-[(1H-pyrrolo[2,3-b]pyridin-3-yl)methylene]-2-{[4-(3-hydroxyprop-1-yn-1-yl)-2-methylphenyl]amino}-4-oxo-4,5-dihydrofuran-3-carboxylate |
| 312 | 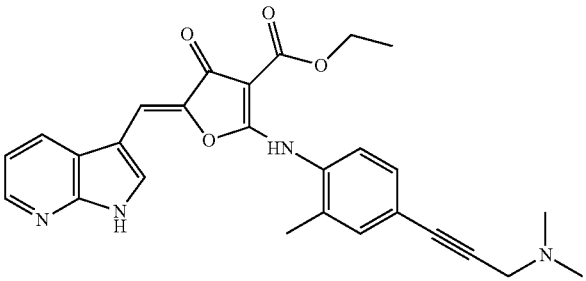 | Ethyl 5-[(1H-pyrrolo[2,3-b]pyridin-3-yl)methylene]-2-({4-[3-(dimethylamino)prop-1-yn-1-yl]-2-methylphenyl}amino)-4-oxo-4,5-dihydrofuran-3-carboxylate |
| 313 | 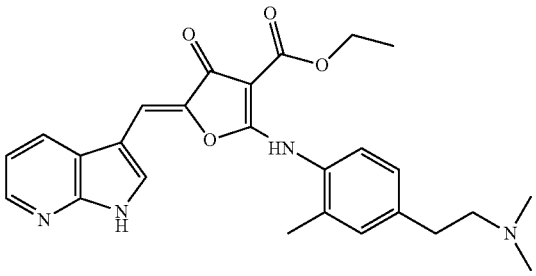 | Ethyl 5-[(1H-pyrrolo[2,3-b]pyridin-3-yl)methylene]-2-({4-[2-(dimethylamino)ethyl]-2-methylphenyl}amino)-4-oxo-4,5-dihydrofuran-3-carboxylate |

TABLE 1-7

| | | |
|---|---|---|
| 314 | 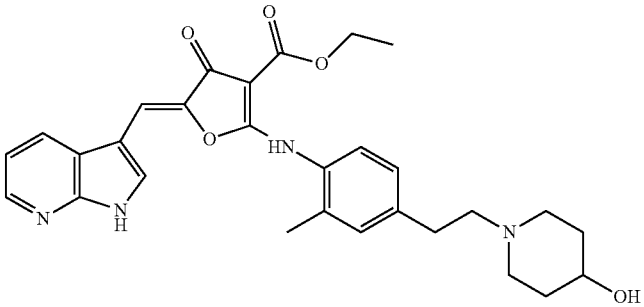 | Ethyl 5-[(1H-pyrrolo[2,3-b]pyridin-3-yl)methylene]-2-({4-[2-(4-hydroxypiperidino)ethyl]-2-methylphenyl}amino)-4-oxo-4,5-dihydrofuran-3-carboxylate |
| 315 | 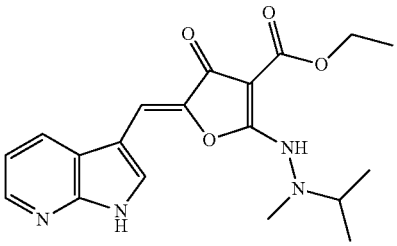 | Ethyl 5-[(1H-pyrrolo[2,3-b]pyridin-3-yl)methylene]-2-(2-isopropyl-2-methylhydrazinyl)-4-oxo-4,5-dihydrofuran-3-carboxylate |

TABLE 1-7-continued

| | | |
|---|---|---|
| 316 | 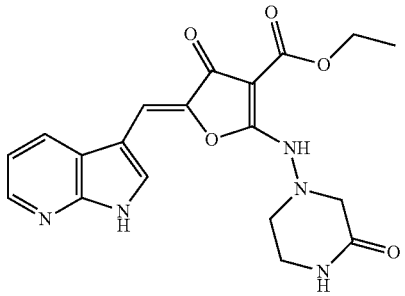 | Ethyl 5-[(1H-pyrrolo[2,3-b]pyridin-3-yl)methylene]-4-oxo-2-[(3-oxopiperazinyl)amino]-4,5-dihydrofuran-3-carboxylate |
| 317 | 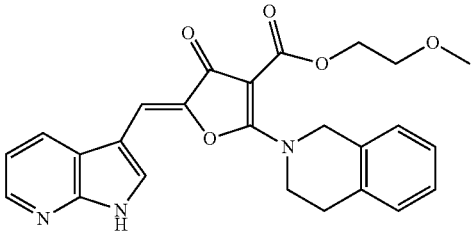 | 2-Methoxyethyl 5-[(1H-pyrrolo[2,3-b]pyridin-3-yl)methylene]-2-(3,4-dihydroisoquinolin-2 (1H)-yl)-4-oxo-4,5-dihydrofuran-3-carboxylate |
| 318 | 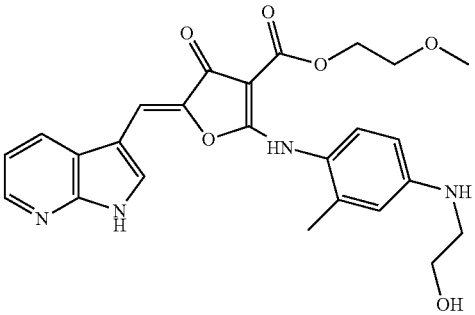 | 2-Methoxyethyl 5-[(1H-pyrrolo[2,3-b]pyridin-3-yl)methylene]-2-({4-[(2-hydroxyethyl)amino]-2-methylphenyl}amino)-4-oxo-4,5-dihydrofuran-3-carboxylate |
| 319 | 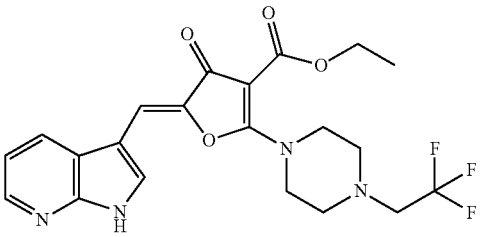 | Ethyl 5-[(1H-pyrrolo[2,3-b]pyridin-3-yl)methylene]-4-oxo-2-[4-(2,2,2-trifluoroethyl)piperazinyl]-4,5-dihydrofuran-3-carboxylate |
| 320 | 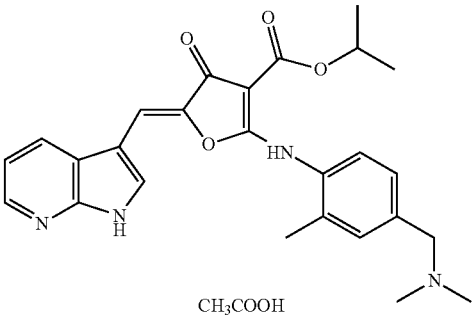 | Isopropyl 5-[(1H-pyrrolo[2,3-b]pyridin-3-yl)methylene]-2-({4-[(dimethylamino)methyl]-2-methylphenyl}amino)-4-oxo-4,5-dihydrofuran-3-carboxylate acetate |

TABLE 1-7-continued

| | | |
|---|---|---|
| 321 | 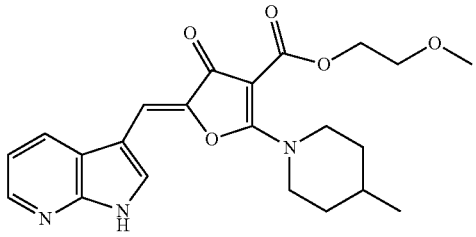 | 2-Methoxyethyl 5-[(1H-pyrrolo[2,3-b] pyridin-3-yl)methylene]-2-(4-methylpiperidino)-4-oxo-4,5-dihydrofuran-3-carboxylate |
| 322 | 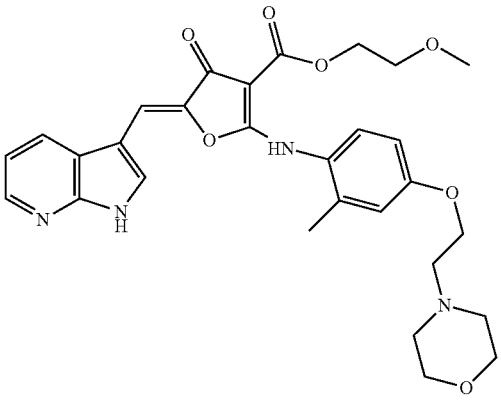 | 2-Methoxyethyl 5-[(1H-pyrrolo[2,3-b] pyridin-3-yl)methylene]-2-{[2-methyl-4-(2-morpholinoethoxy)phenyl] amino}-4-oxo-4,5-dihydrofuran-3-carboxylate |
| 323 | 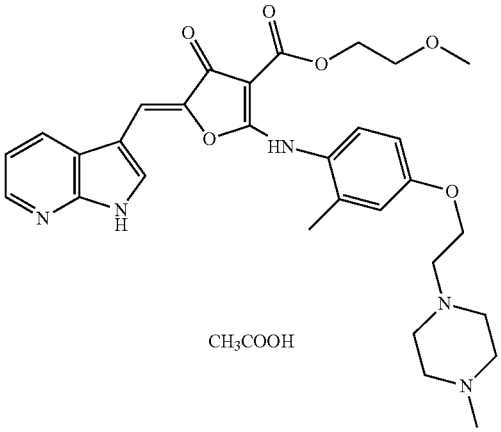 | 2-Methoxyethyl 5-[(1H-pyrrolo[2,3-b] pyridin-3-yl)methylene]-2-({2-methy1-4-[2-(4-methylpiperazinyl) ethoxy]phenyl}amino)-4-oxo-4,5-dihydrofuran-3-carboxylate acetate |
| 324 | 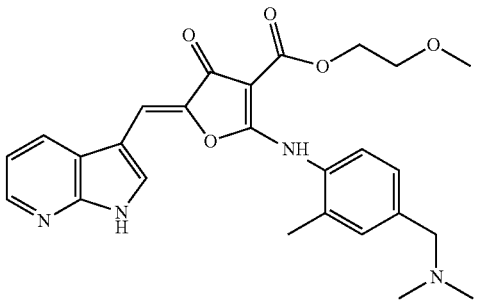 | 2-Methoxyethyl 5-[(1H-pyrrolo[2,3-b] pyridin-3-yl)methylene]-2-({4-[(dimethylamino)methyl]-2-methylphenyl}amino)-4-oxo-4,5-dihydrofuran-3-carboxylate |
| 325 | 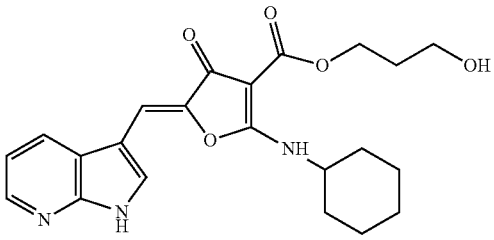 | 3-Hydroxypropyl 5-[(1H-pyrrolo[2,3-b] pyridin-3-yl)methylene]-2-(cyclohexylamino)-4-oxo-4,5-dihydrofuran-3-carboxylate |

TABLE 1-8

| | | |
|---|---|---|
| 326 | 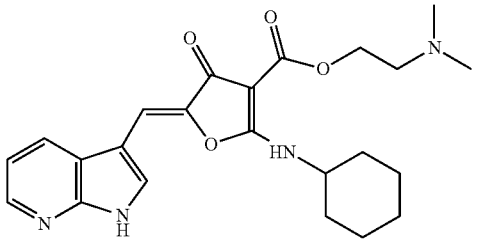 | 2-(Dimethylamino)ethyl 5-[(1H-pyrrolo[2,3-b]pyridin-3-yl)methylene]-2-(cyclohexylamino)-4-oxo-4,5-dihydrofuran-3-carboxylate |
| 327 | 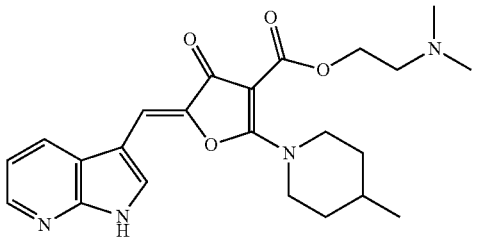 | 2-(Dimethylamino)ethyl 5-[(1H-pyrrolo[2,3-b]pyridin-3-yl)methylene]-2-(4-methylpiperidino)-4-oxo-4,5-dihydrofuran-3-carboxylate |
| 328 | 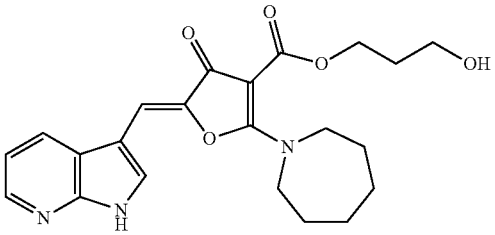 | 3-Hydroxypropyl 5-[(1H-pyrrolo[2,3-b]pyridin-3-yl)methylene]-2-azepinyl-4-oxo-4,5-dihydrofuran-3-carboxylate |
| 329 | 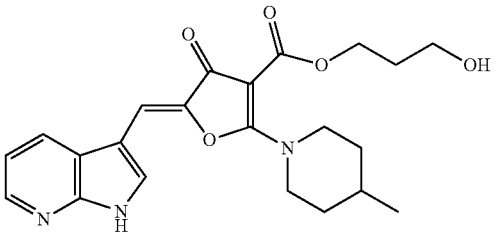 | 3-Hydroxypropyl 5-[(1H-pyrrolo[2,3-b]pyridin-3-yl)methylene]-2-(4-methylpiperidino)-4-oxo-4,5-dihydrofuran-3-carboxylate |
| 330 | 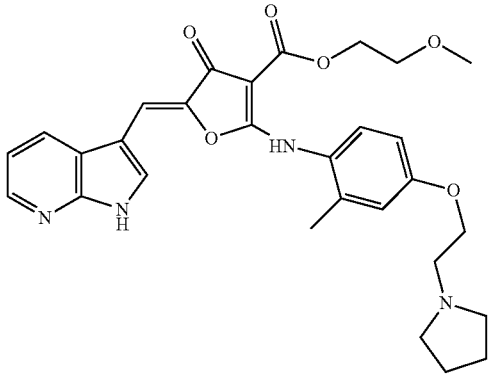 $CH_3COOH$ | 2-Methoxyethyl 5-[(1H-pyrrolo[2,3-b]pyridin-3-yl)methylene]-2-({2-methyl-4-[2-(pyrrolidinyl)ethoxy]phenyl}amino)-4-oxo-4,5-dihydrofuran-3-carboxylate acetate |
| 331 | 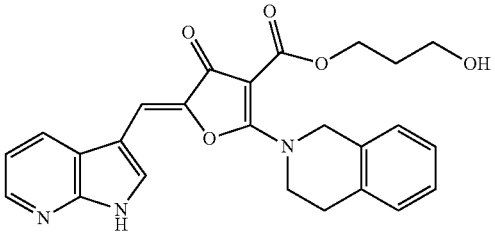 | 3-Hydroxypropyl 5-[(1H-pyrrolo[2,3-b]pyridin-3-yl)methylene]-2-(3,4-dihydroisoquinolin-2(1H)-yl)-4-oxo-4,5-dihydrofuran-3-carboxylate |

TABLE 1-8-continued

| | | |
|---|---|---|
| 332 | 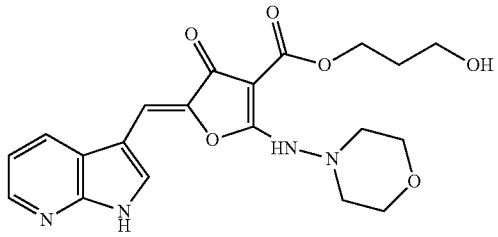 | 3-Hydroxypropyl 5-[(1H-pyrrolo[2,3-b] pyridin-3-yl)methylene]-2-(morpholinoamino)-4-oxo-4,5-dihydrofuran-3-carboxylate |
| 333 | 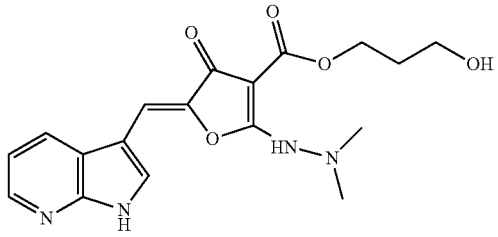 | 3-Hydroxypropyl 5-[(1H-pyrrolo[2,3-b] pyridin-3-yl)methylene]-2-(2,2-dimethylhydrazinyl)-4-oxo-4,5-dihydrofuran-3-carboxylate |
| 334 | 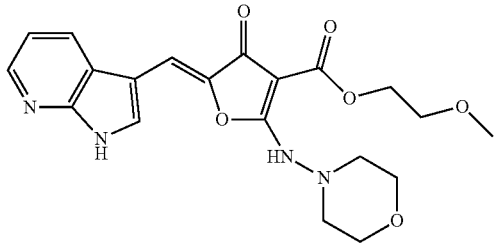 | 2-Methoxyethyl 5-[(1H-pyrrolo[2,3-b] pyridin-3-yl)methylene]-2-(morpholinoamino)-4-oxo-4,5-dihydrofuran-3-carboxylate |
| 335 | 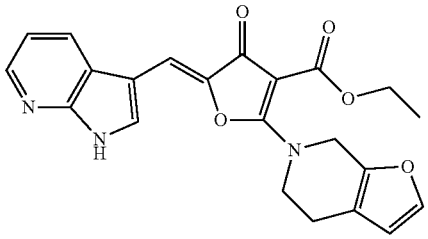 | Ethyl 5-[(1H-pyrrolo[2,3-b]pyridin-3-yl)methylene]-2-(4,5-dihydrofuro [2, 3-c] pyridin-6(7H)-yl)-4-oxo-4,5-dihydrofuran-3-carboxylate |
| 336 | 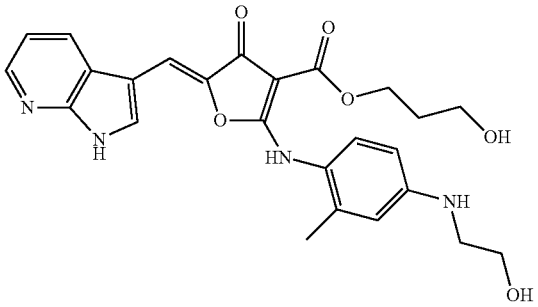 | 3-Hydroxypropyl 5-[(1H-pyrrolo[2,3-b] pyridin-3-yl)methylene]-2-({4-[(2-hydroxyethyl)amino]-2-methylphenyl}amino)-4-oxo-4,5-dihydrofuran-3-carboxylate |
| 337 | 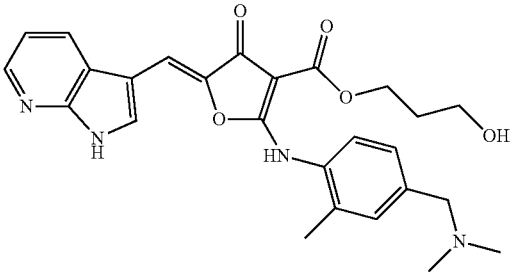 HCl | 3-Hydroxypropyl 5-[(1H-pyrrolo[2,3-b] pyridin-3-yl)methylene]-2-({4-[(dimethylamino)methyl]-2-methylphenyl}amino)-4-oxo-4,5-dihydrofuran-3-carboxylate hydrochloride |

TABLE 1-8-continued

| | | |
|---|---|---|
| 338 | 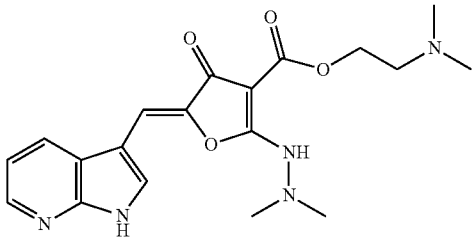 $CH_3COOH$ | 2-(Dimethylamino)ethyl 5-[(1H-pyrrolo[2,3-b]pyridin-3-yl)methylene]-2-(2,2-dimethylhydrazinyl)-4-oxo-4,5-dihydrofuran-3-carboxylate acetate |

TABLE 1-9

| | | |
|---|---|---|
| 339 | 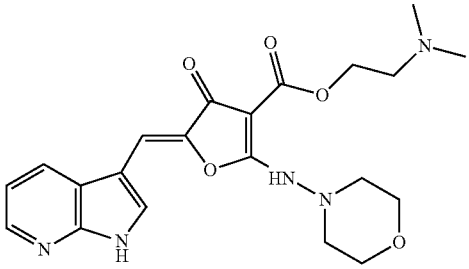 $CH_3COOH$ | 2-(Dimethylamino)ethyl 5-[(1H-pyrrolo[2,3-b]pyridin-3-yl)methylene]-2-(morpholinoamino)-4-oxo-4,5-dihydrofuran-3-carboxylate acetate |
| 340 | 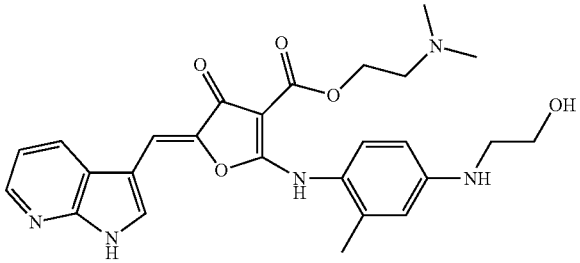 $CH_3COOH$ | 2-(Dimethylamino)ethyl 5-[(1H-pyrrolo[2,3-b]pyridin-3-yl)methylene]-2-({4-[(2-hydroxyethyl) amino]-2-methylphenyl}amino)-4-oxo-4,5-dihydrofuran-3-carboxylate acetate |
| 341 | 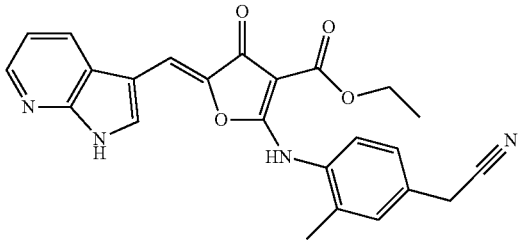 | Ethyl 5-[(1H-pyrrolo[2,3-b]pyridin-3-yl)methylene]-2-{[4-(cyanomethyl)-2-methylphenyl]amino}-4-oxo-4,5-dihydrofuran-3-carboxylate |
| 342 | 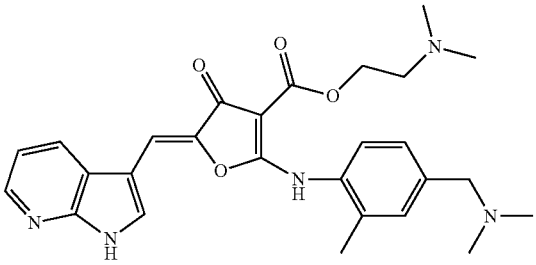 2 HCOOH | 2-(Dimethylamino)ethyl 5-[(1H-pyrrolo[2,3-b]pyridin-3-yl)methylene]-2-({4-[(dimethylamino)methyl]-2-methylphenyl}amino)-4-oxo-4,5-dihydrofuran-3-carboxylate diformate |

TABLE 1-9-continued

| | | |
|---|---|---|
| 343 | 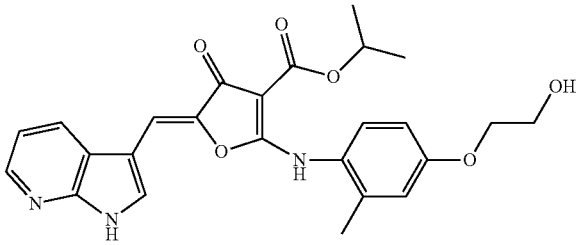 | Isopropyl 5-[(1H-pyrrolo[2,3-b]pyridin-3-yl)methylene]-2-{[4-(2-hydroxy-ethoxy)-2-methylphenyl]amino}-4-oxo-4,5-dihydrofuran-3-carboxylate |
| 344 | 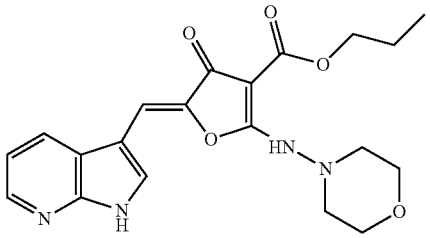 | Propyl 5-[(1H-pyrrolo[2,3-b]pyridin-3-yl)methylene]-2-(morpholinoamino)-4-oxo-4,5-dihydrofuran-3-carboxylate |
| 345 | 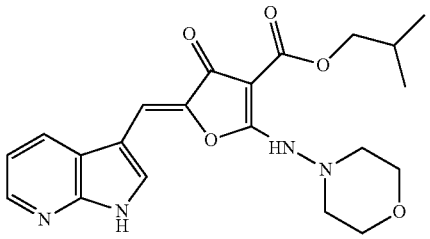 | Isobutyl 5-[(1H-pyrrolo[2,3-b]pyridin-3-yl)methylene]-2-(morpholinoamino)-4-oxo-4,5-dihydrofuran-3-carboxylate |
| 346 | 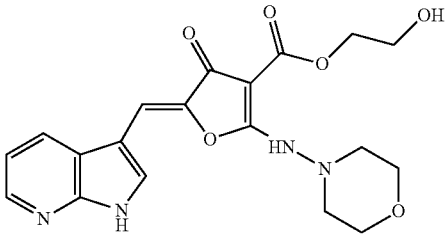 | 2-Hydroxyethyl 5-[(1H-pyrrolo[2,3-b]pyridin-3-yl)methylene]-2-(morpholinoamino)-4-oxo-4,5-dihydrofuran-3-carboxylate |
| 347 | 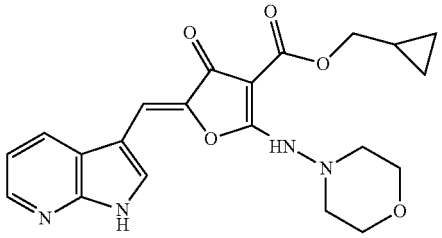 | Cyclopropylmethyl 5-[(1H-pyrrolo[2,3-b]pyridin-3-yl)methylene]-2-(morpholinoamino)-4-oxo-4,5-dihydrofuran-3-carboxylate |
| 348 | 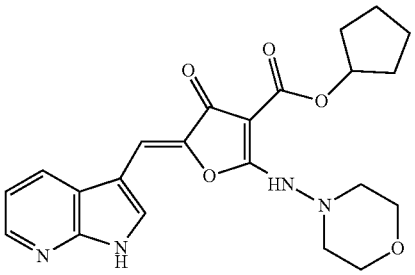 | Cyclopentyl 5-[(1H-pyrrolo[2,3-b]pyridin-3-yl)methylene]-2-(morpholinoamino)-4-oxo-4,5-dihydrofuran-3-carboxylate |

TABLE 1-9-continued

| | | |
|---|---|---|
| 349 | 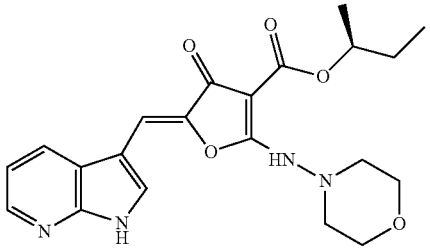 | (S)-sec-Butyl 5-[(1H-pyrrolo[2,3-b] pyridin-3-yl)methylene]-2-(morpholinoamino)-4-oxo-4,5-dihydrofuran-3-carboxylate |
| 350 | 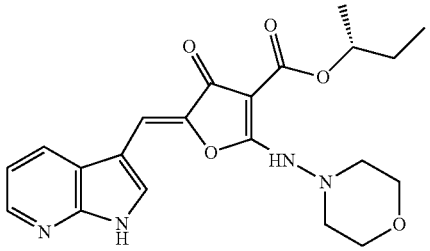 | (R)-sec-Butyl 5-[(1H-pyrrolo[2,3-b] pyridin-3-yl)methylene]-2-(morpholinoamino)-4-oxo-4,5-dihydrofuran-3-carboxylate |
| 351 | 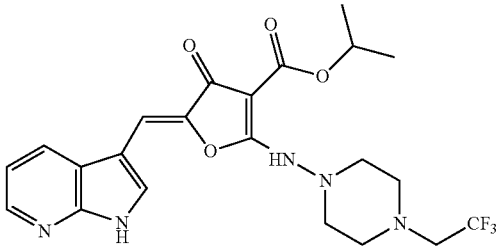 | Isopropyl 5-[(1H-pyrrolo[2,3-b]pyridin-3-yl)methylene]-4-oxo-2-{[4-(2,2,2-trifluoroethyl)piperazinyl] amino}-4,5-dihydrofuran-3-carboxylate |

TABLE 1-10

| | | |
|---|---|---|
| 352 | 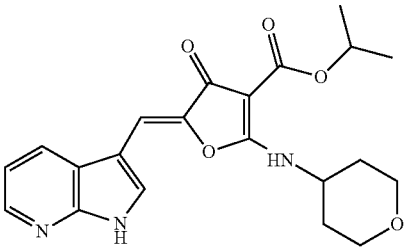 | Isopropyl 5-[(1H-pyrrolo[2,3-b]pyridin-3-yl)methylene]-4-oxo-2-[(tetrahydro-2H-pyran-4-yl)amino]-4,5-dihydrofuran-3-carboxylate |
| 353 | 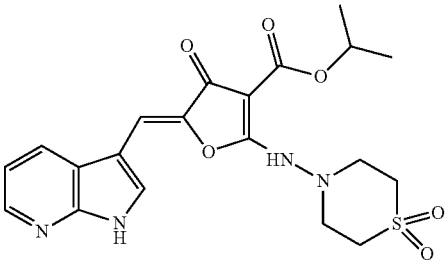 | Isopropyl 5-[(1H-pyrrolo[2,3-b]pyridin-3-yl)methylene]-4-oxo-2-[(1,1-dioxidothiomorpholino)amino]-4,5-dihydrofuran-3-carboxylate |
| 354 | 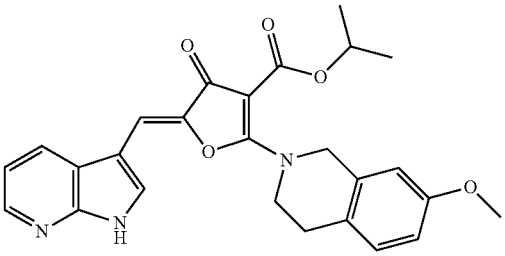 | Isopropyl 5-[(1H-pyrrolo[2,3-b]pyridin-3-yl)methylene]-2-(7-methoxy-3,4-dihydroisoquinolin-2(1H)-yl)-4-oxo-4,5-dihydrofuran-3-carboxylate |

TABLE 1-10-continued

| | | |
|---|---|---|
| 355 | 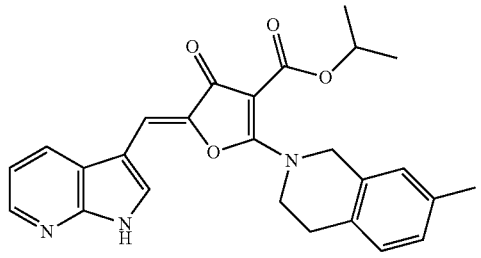 $CH_3COOH$ | Isopropyl 5-[(1H-pyrrolo[2,3-b]pyridin-3-yl)methylene]-2-(7-methyl-?3,4-dihydroisoquinolin-2 (1H)-yl)-4-oxo-4,5-dihydrofuran-3-carboxylate acetate |
| 356 | 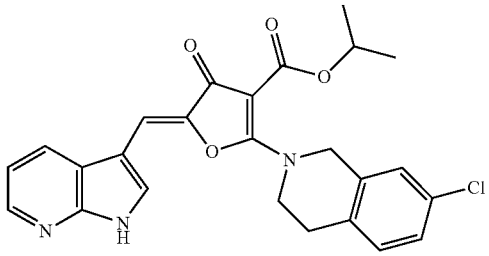 $CH_3COOH$ | Isopropyl 5-[(1H-pyrrolo[2,3-b]pyrlidin-3-yl)methylene]-2-(7-chloro-3,4-dihydroisoquinolin-2(1H)-yl)-4-oxo-4,5-dihydrofuran-3-carboxylate acetate |
| 357 | 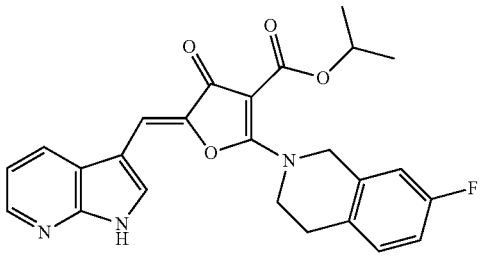 | Isopropyl 5-[(1H-pyrrolo[2,3-b]pyridin-3-yl)methylene]-2-(7-fluoro-3,4-dihydroisoquinolin-2(1H)-yl)-4-oxo-4,5-dihydrofuran-3-carboxylate |
| 358 | 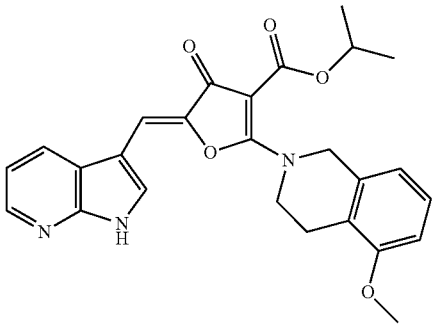 | Isopropyl 5-[(1H-pyrrolo[2,3-b]pyridin-3-yl)methylene]-2-(5-methoxy-3,4-dihydroisoquinolin-2(1H)-yl)-4-oxo-4,5-dihydrofuran-3-carboxylate |
| 359 | 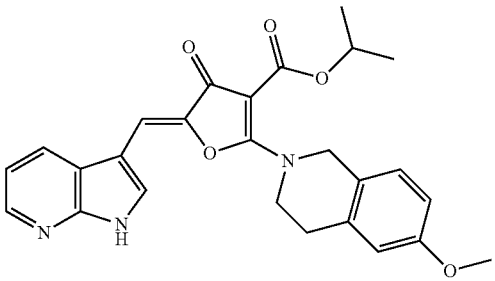 | Isopropyl 5-[(1H-pyrrolo[2,3-b]pyridin-3-yl)methylene]-2-(6-methoxy-3,4-dihydroisoquinolin-2(1H)-yl)-4-oxo-4,5-dihydrofuran-3-carboxylate |

TABLE 2-1

| Example | $^1$H-NMR δ (ppm) | LCMS m/z [M + H]$^+$ |
|---|---|---|
| 247 | (DMSO-d6): 12.17-12.43 (m, 1H), 8.18-8.41 (m, 3H), 7.94 (br. s, 1H), 7.12-7.23 (m, 1H), 6.85 (br. s, 1H), 4.10-4.23 (m, 2H), 3.65-3.93 (m, 2H), 2.93-3.13 (m, 2H), 2.77-2.93 (m, 2H), 1.80-1.98 (m, 2H), 1.10-1.35 (m, 5H). | 383.2 |
| 248 | (DMSO-d6): 12.37 (s, 1H), 8.40 (d, J = 7.6 Hz, 1H), 8.33 (d, J = 3.7 Hz, 1H), 8.09 (s, 1H), 7.47 (d, J = 4.9 Hz, 1H), 7.21 (dd, J = 7.7, 4.7 Hz, 1H), 6.87-6.98 (m, 2H), 5.07 (s, 2H), 4.21 (q, J = 6.9 Hz, 2H), 3.98-4.08 (m, 2H), 2.92-3.03 (m, 2H), 1.26 (t, J = 7.0 Hz, 3H). | 422.0 |
| 249 | (DMSO-d6): 12.37 (s, 1H), 8.28-8.39 (m, 2H), 8.02 (br. s, 1H), 7.10-7.29 (m, 5H), 6.81 (s, 1H), 5.13 (s, 2H), 4.18-4.30 (m, 2H), 4.00-4.18 (m, 2H), 2.99-3.12 (m, 2H), 1.92-2.07 (m, 2H), 1.28 (t, J = 6.6 Hz, 3H). | 430.0 |
| 250 | (DMSO-d6): 12.42 (s, 1H), 8.27-8.38 (m, 2H), 7.97 (s, 1H), 7.30-7.43 (m, 1H), 7.15-7.27 (m, 2H) 7.03-7.13 (m, 1H), 6.96 (d, J = 7.7 Hz, 1H), 6.85 (s, 1H), 5.18 (s, 2H), 4.40-4.50 (m, 2H), 4.14-4.26 (m, 2H), 4.00-4.14 (m, 2H), 1.26 (t, J = 6.6 Hz, 3H). | 432.3 |
| 251 | (DMSO-d6): 12.14 (s, 1H), 10.70-12.05 (m, 1H), 8.23 (d, J = 4.0 Hz, 1H), 8.00 (d, J = 7.8 Hz, 1H), 7.69 (s, 1H), 7.20-7.50 (m, 5H), 6.91 (dd, J = 7.7, 4.7 Hz, 1H), 4.51 (s, 2H). | 423.2 |
| 252 | (DMSO-d6): 12.33 (br. s, 1H), 8.57 (d, J = 6.02 Hz, 1H), 8.42 (dd, J = 1.38, 7.91 Hz, 1H), 8.31 (dd, J = 1.25, 4.52 Hz, 1H), 8.01 (s, 1H), 7.20 (dd, J = 4.77, 8.03 Hz, 1H), 6.90 (s, 1H), 5.20 (t, J = 5.27 Hz, 1H), 4.16-4.34 (m, 3H), 3.52-3.68 (m, 2H), 1.32 (d, J = 6.53 Hz, 3H), 1.26 (t, J = 7.15 Hz, 3H). | 358.0 |
| 253 | (DMSO-d6): 12.38 (br. s, 1H), 8.93 (br. s, 1H), 8.43 (dd, J = 1.38, 7.91 Hz, 1H), 8.31 (dd, J = 1.38, 4.64 Hz, 1H), 8.06 (s, 1H), 7.19 (dd, J = 4.64, 7.91 Hz, 1H), 6.90 (s, 1H), 4.37-4.46 (m, 1H), 4.22 (q, J = 7.03 Hz, 2H), 4.06 (dd, J = 6.53, 8.78 Hz, 1H) 3.68-3.89 (m, 3H), 1.32 (s, 3H), 1.23-1.29 (m, 6H). | 414.0 |
| 254 | (DMSO-d6): 12.35 (br. s, 1H), 8.84 (br. s, 1H), 8.46 (dd, J = 1.38, 7.91 Hz, 1H), 8.31 (dd, J = 1.38, 4.64 Hz, 1H), 8.04 (s, 1H), 7.19 (dd, J = 4.77, 8.03 Hz, 1H), 6.89 (s, 1H), 5.17 (d, J = 4.52 Hz, 1H), 4.21 (q, J = 7.03 Hz, 2H), 3.8 9-4.00 (m, 1H) 3.57-3.67 (m, 1H), 3.45-3.56 (m, 1H), 1.26 (t, J = 7.15 Hz, 3H), 1.16 (d, J = 6.27 Hz, 3H). | 358.0 |
| 255 | (DMSO-d6): 12.41 (br. s, 1H), 9.29 (br. s, 1H), 8.49 (d, J = 7.78 Hz, 1H), 8.32 (dd, J = 1.13, 4.64 Hz, 1H), 8.12 (s, 1H), 7.19 (dd, J = 4.64, 7.91 Hz, 1H), 6.96 (s, 1H), 4.43 (d, J = 1.51 Hz, 2H), 4.22 (q, J = 7.03 Hz, 2H), 3.42 (t, J = 2.26 Hz, 1H), 1.26 (t, J = 7.15 Hz, 3H). | 338.0 |
| 256 | (DMSO-d6): 12.35 (s, 1H), 11.34 (s, 1H), 10.67 (s, 1H), 8.33 (d, J = 7.3 Hz, 1H), 8.10 (d, J = 4.4 Hz, 1H), 7.94-8.05 (m, 3H), 7.68-7.76 (m, 1H), 7.58-7.68 (m, 2H), 6.93 (s, 1H), 6.29-6.36 (m, 1H), 4.26 (q, J = 7.0 Hz, 2H), 1.29 (t, J = 7.0 Hz, 3H). | 419.2 |
| 257 | (DMSO-d6): 12.20-12.50 (m, 1H), 8.26-8.40 (m, 2H), 7.89 (s, 1H), 7.15-7.59 (m, 5H), 6.84 (s, 1H), 5.03-5.30 (m, 2H), 4.12-4.31 (m, 4H), 3.10-3.50 (m, 2H), 1.22-1 .32 (m, 3H). | 448.2 |
| 258 | (DMSO-d6): 12.10-12.60 (m, 1H), 8.25-8.40 (m, 2H), 7.93 (s, 1H), 7.12-7.24 (m, 2H), 6.96-7.05 (m, 1H), 6.82 (s, 1H), 6.66-6.78 (m, 2H), 5.85 (s, 1H), 5.05 (s, 2H), 4.15-4.30 (m, 2H), 3.75-4.00 (m, 2H), 3.40-3.55 (m, 2H), 1.26 (t, J = 7.0 Hz, 3H). | 431.2 |
| 259 | (DMSO-d6): 12.33 (br. s, 1H), 8.40 (d, J = 7.8 Hz, 1H), 8.32 (d, J = 4.3 Hz, 1H), 8.07 (s, 1H), 7.17-7.29 (m, 2H), 6.80-6.95 (m 3H), 4.96 (s, 2H), 4.21 (q, J = 7.0 Hz, 2H), 3.90-4.07 (m, 2H), 3.81 (s, 3H), 2.88-3.00 (m, 2H), 1.26 (t, J = 7.1 Hz, 3H). | 446.2 |
| 260 | (DMSO-d6): 12.32 (s, 1H), 8.37 (d, J = 7.9 Hz, 1H), 8.28-8.34 (m, 1H), 8.01 (s, 1H), 7.19 (dd, J = 8.0, 4.5 Hz, 1H), 6.88 (s, 1H), 4.08-4.24 (m, 4H), 3.73-3.87 (m, 2H), 2.95-3.06 (m, 2H), 1.24 (t, J = 7.0 Hz, 3H), 1.18 (d, J = 6.0 Hz, 6H). | 398.2 |
| 261 | (DMSO-d6): 12.35 (s, 1H), 8.66 (br. s, 1H), 8.41 (d, J = 7.9 Hz, 1H), 8.32 (d, J = 3.5 Hz, 1H), 8.01 (s, 1H), 7.21 (dd, J = 7.9, 4.7 Hz, 1H), 6.90 (s, 1H), 4.18-4.30 (m, 3H), 3.89-4.00 (m, 2H), 3.40-3.53 (m, 2H), 1.82-1.96 (m, 4H), 1.25 (q, J = 7.1 Hz, 3H). | 384.2 |
| 262 | (DMSO-d6): 12.31 (s, 1H), 9.87 (s, 1H), 8.93 (d, J = 7.8 Hz, 1H), 8.30 (d, J = 3.6 Hz, 1H), 8.06 (d, J = 2.2 Hz, 1H), 7.14 (dd, J = 8.0, 4.6 Hz, 1H), 6.85 (s, 1H), 4.20 (q, J = 7.0 Hz, 2H), 3.04-3.17 (m, 4H), 1.85-1.98 (m, 4H), 1.26 (t, J = 7.1 Hz, 3H). | 369.2 |
| 263 | (DMSO-d6): 12.39 (s, 1H), 10.05 (s, 1H), 8.85 (d, J = 7.8 Hz, 1H), 8.33 (d, J = 3.8 Hz, 1H), 8.12 (s, 1H), 7.17 (dd, J = 7.8, 4.6 Hz, 1H), 6.87 (s, 1H), 4.20 (q, J = 7.0 Hz, 2H), 3.08-3.20 (m, 4H), 1.63-1.84 (m, 8H), 1.26 (t, J = 7.0 Hz, 3H). | 397.2 |
| 264 | (DMSO-d6): 12.26 (s, 1H), 8.16-8.24 (m, 2H), 7.85 (d, J = 7.9 Hz, 1H), 7.62 (s, 1H), 7.38 (d, J = 7.5 Hz, 1H), 7.31 (s, 1H), 7.25 (d, J = 7.6 Hz, 1H), 6.82 (dd, J = 7.8, 4.7 Hz, 1H), 6.75 (s, 1H), 4.20-4.30 (m, 2H), 3.57 (s, 2H), 3.10-3.60 (m, 8H), 2.68-2.77 (m, 1H), 2.24 (s, 3H), 1.29 (t, J = 7.1 Hz, 3H), 0.99 (d, J = 6.5 Hz, 6H). | 530.4 |
| 265 | (DMSO-d6): 8.21 (s, 1H), 8.17 (d, J = 3.4 Hz, 1H), 7.83 (d, J = 7.7 Hz, 1H), 7.62 (s, 1H), 7.40 (s, 1H), 7.33 (s, 2H), 6.81 (dd, J = 8.0, 4.7 Hz, 1H), 6.63 (s, 1H), 4.15-4.30 (m, 3H), 3.95 (s, 2H), 2.43-2.56 (m, 2H), 2.22 (s, 3H), 1.81-1.94 (m, 2H), 1.63-1.75 (m, 2H), 1.43-1.60 (m, 4H), 1.22-1.33 (m, 3H). | 487.2 |

TABLE 2-1-continued

| Example | $^1$H-NMR δ (ppm) | LCMS m/z [M + H]$^+$ |
|---|---|---|
| 266 | (DMSO-d6): 8.16 (d, J = 3.8 Hz, 1H), 7.83 (d, J = 7.6 Hz, 1H), 7.60 (s, 1H), 7.18-7.39 (m, 3H), 6.87 (s, 1H), 6.75-6.84 (m, 1H), 6.54 (s, 1H), 4.10-4.25 (m, 2H), 3.93 (s, 2H), 2.95-3.10 (m, 1H), 2.15-2.20 (m, 3H), 1.20-1.30 (m, 3H), 1.10-1.20 (m, 6H). | 461.2 |

TABLE 2-2

| | | |
|---|---|---|
| 267 | (DMSO-d6): 12.26 (s, 1H), 10.32 (br. s, 1H), 8.20 (d, J = 3.5 Hz, 1H), 7.71-7.82 (m, 2H), 7.46 (d, J = 8.2 Hz, 1H), 7.35 (s, 1H), 7.29 (d, J = 8.5 Hz, 1H), 6.83 (s, 1H), 6.73-6.81 (m, 1H), 4.53-4.61 (m, 1H), 4.20-4.32 (m, 2H), 3.42-3.62 (m, 3H), 2.68-2.80 (m, 2H), 2.26 (s, 3H), 2.03-2.20 (m, 2H), 1.67-1.80 (m, 2H), 1.36-1.51 (m, 2H), 1.29 (t, J = 7.0 Hz, 3H). | 503.2 |
| 268 | (DMSO-d6): 12.49 (br. s, 1H), 9.38 (br. s, 1H), 8.44 (d, J = 7.53 Hz, 1H), 8.33 (dd, J = 1.25, 4.52 Hz, 1H), 8.17 (d, J = 2.51 Hz, 1H), 7.21 (dd, J = 4.77, 8.03 Hz, 1H), 7.02 (s, 1H), 4.79 (s, 2H), 4.23 (q, J = 7.19 Hz, 2H), 1.26 (t, J = 7.03 Hz, 3H). | 339.0 |
| 269 | (DMSO-d6): 12.35 (br. s, 1H), 8.60 (d, J = 8.78 Hz, 1H), 8.45 (dd, J = 1.26, 8.03 Hz, 1H), 8.31 (dd, J = 1.25, 4.52 Hz, 1H), 8.04 (s, 1H), 7.19 (dd, J = 4.77, 8.03 Hz, 1H), 6.90 (s, 1H), 5.18 (t, J = 5.14 Hz, 2H), 4.11-4.27 (m, 3H), 3.67 (t, J = 5.40 Hz, 4H), 1.26 (t, J = 7.15 Hz, 3H). | 373.9 |
| 270 | (DMSO-d6): 12.40 (br. s, 1H), 8.84 (t, J = 5.90 Hz, 1H), 8.49 (d, J = 8.03 Hz, 1H), 8.32 (dd, J = 1.38, 4.64 Hz, 1H), 8.06 (d, J = 2.51 Hz, 1H), 7.21 (dd, J = 4.77, 8.03 Hz, 1H), 6.90 (s, 1H), 4.21 (q, J = 7.03 Hz, 2H), 3.73-3.83 (m, 2H), 3.33-3.66 (m, 5H), 1.26 (t, J = 7.03 Hz, 3H). | 374.0 |
| 271 | (DMSO-d6): 12.10-12.20 (m, 1H), 8.20-8.42 (m, 2H), 7.98 (s, 1H), 7.19 (dd, J = 7.9, 4.6 Hz, 1H), 6.85 (s, 1H), 4.10-4.40 (m, 4H), 3.85-4.05 (m, 2H), 3.25-3.40 (m, 4H), 2.35-3.45 (m, 3H), 2.65-2.80 (m, 1H), 2.15-2.25 (m, 6H), 1.80-1.95 (m, 2H), 1.53-1.72 (m, 2H), 1.20-1.28 (m, 3H). | 468.3 |
| 272 | (DMSO-d6): 12.30 (s, 1H), 8.37 (d, J = 7.9 Hz, 1H), 8.31 (d, J = 4.2 Hz, 1H), 7.98 (s, 1H), 7.19 (dd, J = 7.8, 4.6 Hz, 1H), 6.84 (s, 1H), 4.58-4.73 (m, 3H), 4.16 (q, J = 7.0 Hz, 2H), 3.93-4.01 (m, 2H), 3.68-3.77 (m, 1H), 3.40-3.56 (m, 3H), 3.31-3.39 (m, 2H), 3.16 (s, 3H), 1.74-1.90 (m, 3H), 1.58-1.72 (m, 3H), 1.24 (t, J = 7.1 Hz, 3H). | 486.2 |
| 273 | (DMSO-d6): 12.35 (s, 1H), 8.41 (d, J = 6.8 Hz, 1H), 8.32 (d, J = 3.4 Hz, 1H), 8.06 (s, 1H), 7.22 (dd, J = 7.9, 4.6 Hz, 2H), 6.83-6.93 (m, 3H), 4.90 (s, 2H), 4.20 (q, J = 7.0 Hz, 2H), 3.84-4.00 (m, 2H), 3.76 (s, 3H), 3.01-3.09 (m, 2H), 1.26 (t, J = 7.1 Hz, 3H). | 446.0 |
| 274 | (DMSO-d6): 12.24 (s, 1H), 8.26-8.48 (m, 2H), 7.95 (s, 1H), 7.10-7.17 (m, 1H), 6.84-6.94 (m, 3H), 6.59 (d, J = 8.0 Hz, 1H), 4.90 (s, 2H), 4.77 (s, 2H), 4.15 (q, J = 7.1 Hz, 2H), 3.16 (s, 3H), 2.01 (s, 3H), 1.25-1.19 (m, 3H). | 433.2 |
| 275 | (DMSO-d6): 12.31 (s, 1H), 8.37 (d, J = 8.0 Hz, 1H), 8.31 (d, J = 3.6 Hz, 1H), 7.96 (s, 1H), 7.19 (dd, J = 7.9, 4.6 Hz, 1H), 6.84 (s, 1H), 4.00-4.25 (m, 4H), 3.22-3.32 (m, 1H), 3.05-2.95 (m, 1H), 1.75-1.91 (m, 3H), 1.60-1.74 (m, 1H), 1.17-1.33 (m, 4H), 0.95 (d, J = 6.2 Hz, 3H). | 382.2 |
| 276 | (DMSO-d6): 12.32 (s, 1H), 8.37 (d, J = 7.9 Hz, 1H), 8.31 (d, J = 4.6 Hz, 1H), 8.01 (s, 1H), 7.19 (dd, J = 7.9, 4.7 Hz, 1H), 6.88 (s, 1H), 4.12-4.22 (m, 4H), 3.76-3.86 (m, 2H), 2.96-3.06 (m, 2H), 1.24 (t, J = 7.1 Hz, 3H), 1.18 (d, J = 6.2 Hz, 6H). | 398.2 |
| 277 | (DMSO-d6): 12.37 (s, 1H), 9.96 (s, 1H), 8.99 (d, J = 7.8 Hz, 1H), 8.34 (d, J = 3.3 Hz, 1H), 8.11 (d, J = 2.5 Hz, 1H), 7.23 (dd, J = 8.0, 4.7 Hz, 1H), 6.85 (s, 1H), 4.49 (t, J = 5.2 Hz, 1H), 4.21 (q, J = 7.1 Hz, 2H), 3.56 (q, J = 6.0 Hz, 2H), 2.98-3.12 (m, 4H), 2.57-2.77 (m, 4H), 2.45-2.55 (m, 2H), 1.26 (t, J = 7.1 Hz, 3H). | 428.4 |
| 278 | (DMSO-d6): 12.21 (br. s, 1H), 8.28-8.42 (m, 2H), 7.96 (s, 1H), 7.18 (dd, J = 7.9, 4.7 Hz, 1H), 6.84 (s, 1H), 4.06-4.23 (m, 4H), 2.72-2.88 (m, 2H), 1.75-1.92 (m, 3H), 1.24 (t, J = 7.0 Hz, 3H), 0.86-1.00 (m, 7H). | 396.2 |
| 279 | (DMSO-d6): 12.27 (s, 1H), 9.22 (br. s, 1H), 6.4-8.6 (m, 7H), 4.15-4.25 (m, 2H), 1.18-1.30 (m, 3H). | 367.2 |
| 280 | (DMSO-d6): 12.10-12.65 (m, 1H), 8.25-8.53 (m, 2H), 8.01 (s, 1H), 7.14-7.29 (m, 2H), 6.80-6.95 (m, 3H), 4.68-4.93 (m, 2H), 4.15-4.27 (m, 2H), 3.93-4.05 (m, 2H), 3.80-3.92 (m, 3H), 2.98-3.10 (m, 2H), 1.23-1.32 (m, 3H). | 446.0 |
| 281 | (DMSO-d6): 12.34 (s, 1H), 9.51 (br. s, 1H), 9.17 (d, J = 7.3 Hz, 1H), 8.33 (d, J = 3.3 Hz, 1H), 8.12 (s, 1H), 7.18 (dd, J = 8.0, 4.6 Hz, 1H), 6.82 (s, 1H), 4.22 (q, J = 7.0 Hz, 2H), 2.95-3.10 (m, 2H), 1.70-1.85 (m, 3H), 1.37-1.53 (m, 3H), 1.27 (t, J = 7.1 Hz, 3H), 0.98 (d, J = 6.0 Hz, 6H). | 411.2 |
| 282 | (DMSO-d6): 12.25 (br. s, 1H), 8.34-8.39 (m, 1H), 8.32 (d, J = 4.6 Hz, 1H), 7.97 (s, 1H), 7.19 (dd, J = 7.9, 4.6 Hz, 1H), 6.84 (s, 1H), 4.10-4.27 (m, 2H), 3.73 (dd, J = 13.1, 3.5 Hz, 2H), 3.43-3.59 (m, 2H), 2.06-2.20 (m, 2H), 1.54 (t, J = 5.7 Hz, 2H), 1.25 (t, J = 6.7 Hz, 3H), 0.95 (d, J = 7.3 Hz, 6H). | 396.2 |
| 283 | (DMSO-d6): 12.30 (s, 1H), 8.37 (d, J = 7.9 Hz, 1H), 8.32 (d, J = 4.7 Hz, 1H), 7.97 (s, 1H), 7.19 (dd, J = 7.8, 4.7 Hz, 1H), 6.84 (s, 1H), 4.18 (q, J = 7.1 Hz, 2H), 3.62-3.71 (m, 2H), 3.54 (s, 2H), 1.71-1.82 (m, 2H), 1.45-1.56 (m, 2H), 1.25 (t, J = 7.1 Hz, 3H), 0.97 (s, 6H). | 396.2 |

TABLE 2-2-continued

| | | |
|---|---|---|
| 284 | (DMSO-d6): 12.30 (s, 1H), 8.38 (d, J = 8.2 Hz, 1H), 8.31 (d, J = 4.2 Hz, 1H), 8.00 (s, 1H), 7.19 (dd, J = 8.0, 4.6 Hz, 1H), 6.83 (s, 1H), 4.97-5.10 (m, 1H), 4.42-4.56 (m, 1H), 4.10-4.23 (m, 2H), 3.80-3.95 (m, 2H), 3.57-3.72 (m, 2H), 1.70-1.90 (m, 3H), 1.55-1.70 (m, 3H), 1.24 (t, J = 7.0 Hz, 3H). | 398.0 |
| 285 | (DMSO-d6): 12.28 (br. s, 1H), 10.34 (br. s, 1H), 8.20 (dd, J = 1.38, 4.64 Hz, 1H), 7.73-7.79 (m, 2H), 7.42 (d, J = 7.78 Hz, 1H), 7.31 (s, 1H), 7.25 (d, J = 8.03 Hz, 1H), 6.84 (s, 1H), 6.76 (dd, J = 4.64, 7.91 Hz, 1H), 4.27 (q, J = 7.03 Hz, 2H), 3.61 (t, J = 4.52 Hz, 4H), 3.28-3.34 (m, 4H), 2.82-2.90 (m, 2H), 2.58-2.64 (m, 2H), 2.24 (s, 3H), 1.30 (t, J = 7.03 Hz, 3H). | 503.3 |
| 286 | (DMSO-d6): 12.25 (s, 1H), 10.37 (s, 1H), 8.20 (d, J = 3.7 Hz, 1H), 7.78 (d, J = 7.8 Hz, 1H), 7.72 (s, 1H), 7.42 (d, J = 8.0 Hz, 1H), 7.30 (s, 1H), 7.23 (d, J = 7.7 Hz, 1H), 6.85 (s, 1H), 6.80 (dd, J = 7.8, 4.7 Hz, 1H), 4.77 (t, J = 5.1 Hz, 1H), 4.27 (q, J = 6.9 Hz, 2H), 3.72 (q, J = 6.7 Hz, 2H), 2.85 (t, J = 6.9 Hz, 2H), 2.24 (s, 3H), 1.30 (t, J = 7.0 Hz, 3H). | 434.0 |

TABLE 2-3

| | | |
|---|---|---|
| 287 | (DMSO-d6): 12.11 (br. s, 1H), 8.15 (d, J = 3.8 Hz, 1H), 7.68-7.78 (m, 2H), 7.43 (s, 1H), 7.26-7.38 (m, 2H), 6.80 (dd, J = 7.7, 4.8 Hz, 1H), 6.60 (s, 1H), 4.15-4.25 (m, 2H), 3.66 (s, 2H), 2.60-2.70 (m, 4H), 2.19 (s, 3H), 1.91 (s, 3H), 1.70-1.82 (m, 4H), 1.27 (t, J = 7.0 Hz, 3H). | 497.2 |
| 288 | (DMSO-d6): 11.80-12.15 (m, 1H), 8.22-8.37 (m, 2H), 8.12-8.18 (m, 1H), 7.74-7.83 (m, 1H), 7.54-7.72 (m, 1H), 7.33 (s, 1H), 7.26 (d, J = 8.9 Hz, 1H), 6.9-7.05 (m, 1H), 6.77-6.84 (m, 1H), 6.27-6.39 (m, 1H), 4.04-4.23 (m, 2H), 3.60-3.70 (m, 4H), 3.56 (s, 2H), 2.53-2.62 (m, 4H), 2.10 (s, 3H), 1.20-1.30 (m, 3H). | 513.0 |
| 289 | (DMSO-d6): 8.05-8.15 (m, 1H), 7.82 (d, J = 7.4 Hz, 1H), 7.52 (s, 1H), 7.27 (s, 1H), 7.20 (d, J = 7.8 Hz, 1H), 6.91 (d, J = 7.9 Hz, 1H), 6.75-6.84 (m, 1H), 6.18 (s, 1H), 4.02-4.13 (m, 2H), 3.30-3.70 (m, 3H), 2.75-2.85 (m, 2H), 2.36-2.26 (m, 2H), 2.07 (s, 3H), 1.72-1.82 (m, 2H), 1.40-1.50 (m, 2H), 1.15-1.30 (m, 3H). | 527.0 |
| 290 | (DMSO-d6): 12.27 (br. s, 1H), 8.20 (dd, J = 1.25, 4.77 Hz, 1H), 7.72-7.80 (m, 2H), 7.40 (d, J = 8.03 Hz, 1H), 7.30 (s, 1H), 7.23 (d, J = 7.78 Hz, 1H), 6.82 (s, 1H), 6.76 (dd, J = 4.64, 7.91 Hz, 1H), 4.26 (q, J = 7.03 Hz, 2H), 3.25-3.50 (m, 4H), 2.79-2.89 (m, 2H), 2.56-2.66 (m, 2H), 2.31-3.47 (m, 4H), 2.23 (s, 3H), 2.20 (s, 3H), 1.29 (t, J = 7.15 Hz, 3H). | 516.3 |
| 291 | (DMSO-d6): 12.31 (s, 1H), 8.39 (d, J = 6.9 Hz, 1H), 8.31 (d, J = 4.6 Hz, 1H), 7.95 (s, 1H), 7.20 (dd, J = 7.9, 4.7 Hz, 1H), 6.84 (s, 1H), 4.17 (q, J = 7.1 Hz, 2H), 3.73 (q, J = 7.0 Hz, 2H), 3.26 (s, 3H), 1.20-1.33 (m, 6H). | 342.2 |
| 292 | (DMSO-d6): 8.38 (d, J = 7.9 Hz, 1H), 8.31 (d, J = 3.3 Hz, 1H), 7.95 (s, 1H), 7.19 (dd, J = 7.9, 4.7 Hz, 1H), 6.84 (s, 1H), 4.50-4.62 (m, 1H), 4.17 (d, J = 7.1 Hz, 2H), 3.09 (s, 3H), 1.36-1.20 (m, 9H). | 356.0 |
| 293 | (DMSO-d6): 12.31 (br. s, 1H), 10.01 (br. s, 1H), 8.92 (d, J = 7.8 Hz, 1H), 8.31 (d, J = 3.7 Hz, 1H), 8.08 (s, 1H), 7.18 (dd, J = 7.9, 4.7 Hz, 1H), 6.83 (s, 1H), 4.97 (br. s, 1H), 4.20 (q, J = 7.0 Hz, 2H), 3.72-3.83 (m, 1H), 3.12-3.20 (m, 1H), 2.97-3.06 (m, 1H), 2.71-2.91 (m, 2H), 1.80-1.93 (m, 2H), 1.56-1.68 (m, 1H), 1.18-1.31 (m, 4H). | 399.2 |
| 294 | (DMSO-d6): 12.29 (s, 1H), 8.29-8.38 (m, 2H), 7.96 (s, 1H), 7.19 (dd, J = 7.9, 4.7 Hz, 1H), 6.82 (s, 1H), 4.95-5.10 (m, 1H), 4.15-4.25 (m, 2H), 3,24-3.34 (m, 2H), 1.68-1.88 (m, 3H), 1.25-1.40 (m, 2H), 1.25 (d, J = 6.2 Hz, 6H), 0.97 (d, J = 6.3 Hz, 3H). | 396.4 |
| 295 | (DMSO-d6): 12.35 (s, 1H), 8.40 (d, J = 6.6 Hz, 1H), 8.33 (d, J = 4.6 Hz, 1H), 8.07 (s, 1H), 7.24-7.32 (m, 4H), 7.22 (dd, J = 7.9, 4.7 Hz, 1H), 6.87 (s, 1H), 5.00-5.12 (m, 1H), 4.97 (s, 2H), 3.90-4.02 (m, 2H), 3.03-3.13 (m, 2H), 1.27 (t, J = 8.9 Hz, 6H). | 430.2 |
| 296 | (DMSO-d6): 12.31 (s, 1H), 9.86 (s, 1H), 8.84 (d, J = 7.8 Hz, 1H), 8.30 (d, J = 3.3 Hz, 1H), 8.05 (d, J = 2.5 Hz, 1H), 7.20 (dd, J = 8.0, 4.6 Hz, 1H), 6.83 (s, 1H), 4.99-5.10 (m, 1H), 2.77 (s, 6H), 1.27 (d, J = 6.3 Hz, 6H). | 357.2 |
| 297 | (DMSO-d6): 12.26 (s, 1H), 10.07 (s, 1H), 8.17 (s, 1H), 7.85 (s, 1H), 7.69 (d, J = 7.4 Hz, 1H), 7.17 (d, J = 8.3 Hz, 1H), 6.72-6.88 (m, 2H), 6.52-6.67 (m, 2H), 5.80-5.92 (m, 1H), 5.07-5.18 (m, 1H), 4.71-4.81 (m, 1H), 3.58-3.69 (m, 2H), 3.15-3.25 (m, 2H), 2.13 (s, 3H), 1.30 (d, J = 5.9 Hz, 6H). | 462.8 |
| 298 | (MeOD): 8.15-8.24 (m, 1H), 7.86 (d, J = 7.5 Hz, 1H), 7.65 (br. s, 1H), 7.40-7.55 (m, 3H), 6.90-7.03 (m, 2H), 6.61 (s, 1H), 4.34-4.43 (m, 2H), 3.66 (s, 2H), 2.70-2.98 (m, 8H), 2.49 (s, 3H), 2.32 (s, 3H), 1.35-1.42 (m, 3H). | 526.4 |
| 299 | (DMSO-d6): 12.31 (s, 1H), 10.42 (br. s, 1H), 8.23 (dd, J = 4.6, 1.4 Hz, 1H), 7.79 (d, J = 7.3 Hz, H), 7.72 (d, J = 2.7 Hz, 1H), 7.51 (d, J = 8.0 Hz, 1H), 7.37 (s, 1H), 7.30 (d, J = 7.9 Hz, 1H), 6.87 (s, 1H), 6.78 (dd, J = 7.9, 4.8 Hz, 1H), 4.27 (q, J = 7.1 Hz, H), 3.35-3.70 (m, 4H), 3.03-3.15 (m, 4H), 2.27 (s, 3H), 1.85-2.10 (s, 4H), 1.30 (t, J = 7.1 Hz, 3H). | 487.0 |
| 300 | (DMSO-d6): 12.30 (br. s, 1H), 8.39 (d, J = 7.6 Hz, 1H), 8.31 (d, J = 4.4 Hz, 1H), 7.93 (s, 1H), 7.19 (dd, J = 7.9, 4.7 Hz, 1H), 6.85 (s, 1H), 4.16 (q, J = 7.1 Hz, 3H), 3.11 (s, 3H), 1.79-1.92 (m, 4H), 1.60-1.75 (m, 3H), 1.28-1.44 (m, 2H), 1.11-1.28 (m, 4H). | 396.0 |
| 301 | (DMSO-d6): 12.30 (br. s, 1H), 9.62 (br. s, 1H), 8.91 (d, J = 8.0 Hz, 1H), 8.31 (d, J = 3.8 Hz, 1H), 8.07 (s, 1H), 7.16 (dd, J = 8.0, 4.6 Hz, 1H), 6.84 (s, 1H), 4.21 (q, J = 7.0 Hz, 2H), 2.78-2.88 (m, 1H), 2.77 (s, 3H), 1.88-2.00 (m, 2H), 1.68-1.80 (m, 2H), 1.48-1.59 (m, 1H), 1.16-1.31 (m, 7H), 1.00-1.12 (m, 1H). | 411.0 |

TABLE 2-3-continued

| | | |
|---|---|---|
| 302 | (DMSO-d6): 12.31 (s, 1H), 10.07 (s, 1H), 8.94 (d, J = 7.5 Hz, 1H), 8.32 (d, J = 3.4 Hz, 1H), 8.12 (s, 1H), 7.21 (dd, J = 8.0, 4.7 Hz, 1H), 6.88 (s, 1H), 4.21 (q, J = 7.1 Hz, 2H), 3.57-3.76 (m, 4H), 2.97-3.12 (m, 4H), 2.08 (s, 3H), 1.26 (t, J = 7.1 Hz, 3H). | 426.0 |
| 303 | (DMSO-d6): 12.30 (br. s, 1H), 8.15-8.21 (m, 2H), 7.77 (s, 1H), 7.68 (d, J = 7.8 Hz, 1H), 7.42 (d, J = 8.7 Hz, 1H), 7.04 (s, 1H), 6.94 (d, J = 8.7 Hz, 1H), 6.73-6.81 (m, 2H), 5.08-5.19 (m, 1H), 4.19 (t, J = 5.6 Hz, 2H), 2.94 (t, J = 5.6 Hz, 2H), 2.62-2.71 (m, 4H), 2.23 (s, 3H), 1.70-1.80 (m, 4H), 1.31 (d, J = 6.2 Hz, 6H). | 517.4 |
| 304 | (DMSO-d6): 12.25 (br. s, 1H), 9.80 (br. s, 1H), 8.85 (d, J = 7.4 Hz, 1H), 8.29 (d, J = 3.6 Hz, 1H), 8.04 (s, 1H), 7.17 (dd, J = 8.0, 4.7 Hz, 1H), 6.78 (br. s, 1H), 4.19 (q, J = 6.9 Hz, 2H), 2.88-3.00 (m, 2H), 2.74 (s, 3H), 1.25 (t, J = 7.1 Hz, 3H), 1.05 (t, J = 7.1 Hz, 3H). | 357.2 |
| 305 | (DMSO-d6): 12.31 (br. s, 1H), 9.49 (br. s, 1H), 8.96 (d, J = 7.8 Hz, 1H), 8.31 (d, J = 3.3 Hz, 1H), 8.08 (s, 1H), 7.18 (dd, J = 8.0, 4.6 Hz, 1H), 6.86 (s, 1H), 4.22 (q, J = 7.1 Hz, 2H), 3.00 (q, J = 7.0 Hz, 4H), 1.27 (t, J = 7.1 Hz, 3H), 1.04 (t, J = 7.1 Hz, 6H). | 371.2 |

TABLE 2-4

| | | |
|---|---|---|
| 306 | (DMSO-d6): 12.09 (br. s, 1H), 8.98 (d, J = 7.6 Hz, 1H), 8.32 (d, J = 3.4 Hz, 1H), 8.05 (s, 1H), 7.21 (dd, J = 8.0, 4.7 Hz, 1H), 6.73 (s, 1H), 4.80 (s, 1H), 4.17 (q, J = 7.0 Hz, 2H), 3.54-3.69 (m, 1H), 3.04-3.15 (m, 2H), 2.82-2.95 (m, 2H), 1.83-1.94 (m, 2H), 1.63-1.77 (m, 2H), 1.24 (t, J = 7.0 Hz, 3H). | 399.2 |
| 307 | (DMSO-d6): 12.29 (s, 1H), 10.23 (s, 1H), 8.18 (d, J = 3.4 Hz, 1H), 7.78 (d, J = 2.5 Hz, 1H), 7.66 (d, J = 7.9 Hz, 1H), 7.42 (d, J = 8.6 Hz, 1H), 7.05 (d, J = 2.4 Hz, 1H), 6.94 (dd, J = 8.6, 2.7 Hz, 1H), 6.79 (s, 1H), 6.74 (dd, J = 7.9, 4.7 Hz, 1H), 5.09-5.18 (m, 1H), 4.19 (t, J = 5.6 Hz, 2H), 3.58-3.67 (m, 4H), 2.78 (t, J = 5.6 Hz, 2H), 2.49-2.57 (m, 4H), 2.23 (s, 3H), 1.31 (d, J = 6.3 Hz, 6H). | 533.4 |
| 308 | (DMSO-d6): 12.20 (br. s, 1H), 10.26 (br. s, 1H), 8.18 (d, J = 3.9 Hz, 1H), 7.66-7.77 (m, 2H), 7.26-7.39 (m, 1H), 7.00 (s, 1H), 6.86-6.93 (m, 1H), 6.61-6.78 (s, 2H), 5.06-5.17 (m, 1H), 4.11-4.18 (m, 2H), 2.76 (t, J = 5.5 Hz, 2H), 2.30-2.50 (m, 8H), 2.20 (s, 3H), 2.17 (s, 3H), 1.29 (d, J = 6.2 Hz, 6H). | 546.6 |
| 309 | (DMSO-d6): 12.30 (br. s, 1H), 8.42 (d, J = 8.0 Hz, 1H), 8.32 (d, J = 3.3 Hz, 1H), 7.98 (s, 1H), 7.20 (dd, J = 8.0, 4.7 Hz, 1H), 6.89 (s, 1H), 4.23-4.35 (m, 2H), 3.96-4.07 (m, 1H), 3.54-3.64 (m, 2H), 3.30 (s, 3H), 1.94-2.03 (m, 2H), 1.73-1.84 (m, 2H), 1.51-1.69 (m, 3H), 1.35-1.49 (m, 2H), 1.15-1.28 (m, 1H). | 412.2 |
| 310 | (DMSO-d6): 12.32 (s, 1H), 9.84 (s, 1H), 8.83 (d, J = 8.2 Hz, 1H), 8.30 (d, J = 3.4 Hz, 1H), 8.05 (s, 1H), 7.20 (dd, J = 8.0, 4.5 Hz, 1H), 6.88 (s, 1H), 4.25-4.32 (m, 2H), 3.57-3.63 (m, 2H), 3.30 (s, 3H), 2.78 (s, 6H). | 373.4 |
| 311 | (DMSO-d6): 12.31 (s, 1H), 10.43 (s, 1H), 8.23 (d, J = 3.8 Hz, 1H), 7.73-7.81 (m, 2H), 7.58 (d, J = 8.1 Hz, 1H), 7.53 (s, 1H), 7.44 (d, J = 7.9 Hz, 1H), 6.88 (s, 1H), 6.83 (dd, J = 7.9, 4.7 Hz, 1H), 5.42 (t, J = 5.9 Hz, 1H), 4.38 (d, J = 5.9 Hz, 2H), 4.27 (q, J = 7.0 Hz, 2H), 2.27 (s, 3H), 1.30 (t, J = 7.0 Hz, 3H). | 444.4 |
| 312 | (DMSO-d6): 12.27 (s, 1H), 10.41 (s, 1H), 8.16 (d, J = 3.4 Hz, 1H), 7.79 (d, J = 1.9 Hz, 1H), 7.64 (d, J = 7.5 Hz, 1H), 7.48-755 (m, 2H), 7.42 (d, J = 7.9 Hz, 1H), 6.82 (s, 1H), 6.79 (dd, J = 7.9, 4.6 Hz, 1H), 4.24 (q, J = 7.0 Hz, 2H), 3.53 (s, 2H), 2.30 (s, 6H), 2.23 (s, 3H), 1.27 (t, J = 7.0 Hz, 3H). | 471.1 |
| 313 | (DMSO-d6): 12.28 (s, 1H), 10.17 (br. s, 1H), 8.21 (d, J = 3.3 Hz, 1H), 7.71-7.80 (m, 2H), 7.44 (d, J = 8.1 Hz, 1H), 7.32 (s, 1H), 7.25 (d, J = 8.0 Hz, 1H), 6.84 (s, 1H), 6.75-6.81 (m, 1H), 4.23-4.32 (m, 2H), 2.85-2.95 (m, 2H), 2.75-2.85 (m, 2H), 2.42 (s, 6H), 2.24 (s, 3H), 1.30 (t, J = 7.1 Hz, 3H). | 461.1 |
| 314 | (DMSO-d6): 12.28 (s, 1H), 10.27 (br. s, 1H), 8.21 (d, J = 4.6 Hz, 1H), 7.72-7.78 (m, 2H), 7.42 (d, J = 8.0 Hz, 1H), 7.30 (s, 1H), 7.24 (d, J = 8.3 Hz, 1H), 6.84 (s, 1H), 6.76 (dd, J = 7.9, 4.6 Hz, 1H), 4.58-4.72 (m, 1H), 4.22-4.32 (m, 2H), 3.44-3.60 (m, 1H), 2.80-3.00 (m, 4H), 2.40-2.60 (m, 4H), 2.24 (s, 3H), 1.72-1.85 (m, 2H), 1.38-1.53 (m, 2H), 1.29 (t, J = 7.1 Hz, 3H). | 517.1 |
| 315 | (DMSO-d6): 12.26 (br. s, 1H), 9.72 (br. s, 1H), 8.91 (d, J = 7.6 Hz, 1H), 8.30 (d, J = 3.7 Hz, 1H), 8.05 (s, 1H), 7.16 (dd, J = 7.8, 4.6 Hz, 1H), 6.77 (br. s, 1H), 4.13-4.24 (m, 2H), 3.08-3.20 (m, 1H), 2.72 (s, 3H), 1.25 (t, J = 7.1 Hz, 3H), 1.10 (d, J = 6.3 Hz, 6H). | 371.0 |
| 316 | (DMSO-d6): 12.33 (br. s, 1H), 10.25 (br. s, 1H), 8.87-8.99 (m, 1H), 8.30 (d, J = 3.4 Hz, 1H), 8.01-8.18 (m, 2H), 7.07 (dd, J = 8.0, 4.6 Hz, 1H), 6.85 (br. s, 1H), 4.15-4.26 (m, 2H), 3.60-3.72 (m, 2H), 3.20-3.30 (m, 4H), 1.26 (t, J = 7.0 Hz, 3H). | 398.0 |
| 317 | (DMSO-d6): 12.36 (s, 1H), 8.42 (d, J = 7.3 Hz, 1H), 8.33 (d, J = 3.4 Hz, 1H), 8.07 (s, 1H), 7.24-7.32 (m, 4H), 7.22 (dd, J = 7.9, 4.7 Hz, 1H), 6.91 (s, 1H), 4.98 (br. s, 2H), 4.25-4.33 (m, 2H), 3.89-4.03 (m, 2H), 3.56-3.64 (m, 2H), 3.30 (s, 3H), 3.08 (t, J = 5.7 Hz, 2H). | 446.1 |
| 318 | (DMSO-d6): 12.26 (s, 1H), 10.09 (s, 1H), 8.18 (d, J = 3.3 Hz, 1H), 7.83 (s, 1H), 7.70 (d, J = 7.7 Hz, 1H), 7.16 (d, J = 8.5 Hz, 1H), 6.75-6.86 (m, 2H), 6.61 (s, 1H), 6.57 (d, J = 8.5 Hz, 1H), 5.81-5.89 (m, 1H), 4.76 (t, J = 5.4 Hz, 1H), 4.28-4.36 (m, 2H), 3.58-3.67 (m, 4H), 3.32 (s, 1H), 3.20 (q, J = 5.9 Hz, 2H), 2.13 (s, 3H). | 479.1 |
| 319 | (DMSO-d6): 12.24 (br. s, 1H), 8.36 (d, J = 8.0 Hz, 1H), 8.31 (d, J = 4.5 Hz, 1H), 8.00 (s, 1H), 7.20 (dd, J = 7.9, 4.6 Hz, 1H), 6.88 (s, 1H), 4.16 (q, J = 7.1 Hz, 2H), 3.76-3.86 (s, 4H), 3.26-3.32 (m, 2H), 2.82-2.90 (m, 4H), 1.25 (q, J = 7.0 Hz, 3H). | 451.2 |

TABLE 2-4-continued

| | | |
|---|---|---|
| 320 | (DMSO-d6): 12.22 (br. s, 1H), 8.19 (s, 1H), 7.83 (d, J = 7.7 Hz, 1H), 7.72 (s, 1H), 7.21-7.47 (m, 3H), 6.70-6.85 (m, 2H), 5.06-5.18 (m, 1H), 3.49 (s, 2H), 2.25 (s, 3H), 2.22 (s, 6H), 1.91 (s, 3H), 1.30 (d, J = 5.8 Hz, 6H). | 461.4 |
| 321 | (DMSO-d6): 8.27-8.35 (m, 2H), 7.95 (s, 1H), 7.24-7.18 (m, 1H), 6.84 (s, 1H), 4.21-4.27 (m, 2H), 3.54-3.62 (m, 4H), 3.23-3.32 (m, 5H), 1.70-1.85 (m, 3H), 1.23-1.37 (m, 2H), 0.94 (d, J = 6.2 Hz, 3H). | 412.1 |
| 322 | (DMSO-d6): 12.27 (s, 1H), 10.24 (s, 1H), 8.16-8.23 (m, 1H), 7.76 (s, 1H), 7.68 (d, J = 7.9 Hz, 1H), 7.42 (d, J = 8.6 Hz, 1H), 7.05 (s, 1H), 6.95 (d, J = 8.1 Hz, 1H), 6.83 (s, 1H), 6.71-6.79 (m, 1H), 4.30-4.38 (m, 2H), 4.15-4.23 (m, 2H), 3.56-3.69 (m, 6H), 3.33 (s, 3H), 2.74-2.82 (m, 2H), 2.48-2.58 (m, 4H), 2.23 (s, 3H). | 548.8 |
| 323 | (DMSO-d6): 11.18 (br. s, 1H), 8.18 (d, J = 3.4 Hz, 1H), 7.66-7.75 (m, 2H), 7.32 (d, J = 8.6 Hz, 1H), 7.00 (s, 1H), 6.91 (d, J = 8.6 Hz, 1H), 6.70-6.78 (m, 2H), 4.27-4.35 (m, 2H), 4.16 (t, J = 5.7 Hz, 2H), 3.60-3.66 (m, 2H), 3.33 (s, 3H), 2.76 (t, J = 5.6 Hz, 2H), 2.48-2.58 (s, 4H), 2.31-2.42 (m, 4H), 2.20 (s, 3H), 2.17 (s, 3H), 1.90 (s, 3H). | 562.2 |

TABLE 2-5

| | | |
|---|---|---|
| 324 | (MeOD): 8.16-8.23 (m, 1H), 7.97 (d, J = 7.7 Hz, 1H), 7.30-7.60 (m, 4H), 6.90-6.71 (m, 2H), 6.60 (s, 1H), 4.42-4.53 (m, 2H), 3.65-3.80 (m, 4H), 3.41 (s, 3H), 2.41 (s, 6H), 2.35 (s, 3H). | 477.0 |
| 325 | (DMSO-d6): 12.39 (s, 1H), 8.59 (d, J = 8.4 Hz, 1H), 8.44 (d, J = 7.8 Hz, 1H), 8.34 (d, J = 4.6 Hz, 1H), 7.98 (d, J = 2.4 Hz, 1H), 7.22 (dd, J = 7.9, 4.7 Hz, 1H), 6.89 (s, 1H), 4.21 (t, J = 6.3 Hz, 2H), 3.94-4.06 (m, 1H), 3.56 (t, J = 5.9 Hz, 3H), 1.93-2.03 (m, 2H), 1.74-1.84 (m, 4H), 1.53-1.70 (m, 3H), 1.34-1.48 (m, 2H), 1.15-1.28 (m, 1H). | 412.2 |
| 326 | (DMSO-d6): 12.35 (s, 1H), 8.50 (br. s, 1H), 8.41 (d, J = 7.0 Hz, 1H), 8.30-8.35 (m, 1H), 7.98 (s, 1H), 7.20 (dd, J = 7.9, 4.7 Hz, 1H), 6.89 (s, 1H), 4.22 (t, J = 5.8 Hz, 2H), 3.94-4.06 (m, 1H), 2.51-2.58 (m, 2H), 2.23 (s, 6H), 1.96-2.05 (m, 2H), 1.75-1.86 (m, 2H), 1.62-1.72 (m, 1H), 1.34-1.59 (m, 4H), 1.16-1.29 (m, 1H). | 425.2 |
| 327 | (DMSO-d6): 12.30 (s, 1H), 8.37 (d, J = 7.8 Hz, 1H), 8.31 (d, J = 4.2 Hz, 1H), 7.96 (s, 1H), 7.19 (dd, J = 7.9, 4.4 Hz, 1H), 6.85 (s, 1H), 4.21 (t, J = 5.7 Hz, 2H), 2.40-2.60 (m, 6H), 2.22 (s, 6H), 1.73-1.87 (m, 2H), 1.15-1.42 (m, 3H), 0.97 (d, J = 6.1 Hz, 3H). | 425.2 |
| 328 | (DMSO-d6): 8.37 (d, J = 7.8 Hz, 1H), 8.31 (d, J = 3.6 Hz, 1H), 7.93 (s, 1H), 7.20-7.27 (m, 1H), 6.85 (s, 1H), 4.17 (t, J = 6.2 Hz, 2H), 3.70-3.90 (m, 4H), 3.50-3.56 (m, 2H), 1.70-1.88 (m, 6H), 1.50-1.60 (m, 4H). | 412.2 |
| 329 | (DMSO-d6): 12.42 (s, 1H), 8.43 (d, J = 7.9 Hz, 1H), 8.34 (d, J = 4.2 Hz, 1H), 7.98 (s, 1H), 7.24 (dd, J = 7.9, 4.8 Hz, 1H), 6.88 (s, 1H), 4.35-4.13 (m, 5H), 3.56 (t, J = 6.0 Hz, 2H), 3.25-3.37 (m, 2H), 1.70-1.88 (m, 5H), 1.26-1.40 (m, 2H), 0.96 (d, J = 6.2 Hz, 3H). | 412.2 |
| 330 | (DMSO-d6): 8.12-8.17 (m, 1H), 7.72-7.79 (m, 1H), 7.65 (s, 1H), 7.14-7.22 (m, 1H), 6.94 (s, 1H), 6.82-6.88 (m, 1H), 6.73-6.80 (m, 1H), 6.55 (s, 1H), 4.21-4.30 (m, 2H), 4.09-4.16 (m, 2H), 3.55-3.66 (m, 2H), 3.32 (s, 3H), 2.85 (t, J = 5.7 Hz, 2H), 2.54-2.61 (m, 4H), 2.16 (s, 3H), 1.90 (s, 3H), 1.68-1.76 (m, 4H). | 533.6 |
| 331 | (DMSO-d6): 12.47 (s, 1H), 8.47 (d, J = 7.9 Hz, 1H), 8.36 (br. s, 1H), 8.09 (s, 1H), 7.16-7.32 (m, 6H), 6.93 (s, 1H), 5.00 (br. s, 2H), 4.22 (t, J = 6.4 Hz, 2H), 3.80-4.10 (m, 2H), 3.57 (t, J = 6.0 Hz, 2H), 3.08 (t, J = 5.6 Hz, 2H), 1.75-1.85 (m, 2H). | 446.0 |
| 332 | (DMSO-d6): 12.39 (s, 1H), 10.14 (s, 1H), 8.95 (d, J = 8.0 Hz, 1H), 8.34 (d, J = 4.5 Hz, 1H), 8.12 (d, J = 2.6 Hz, 1H), 7.24 (dd, J = 8.0, 4.7 Hz, 1H), 6.88 (s, 1H), 4.21 (t, J = 6.3 Hz, 2H), 3.76-3.86 (m, 4H), 3.53-3.61 (m, 3H), 3.02-3.12 (m, 4H), 1.87-1.74 (m, 2H). | 415.1 |
| 333 | (DMSO-d6): 12.38 (s, 1H), 9.95 (br. s, 1H), 8.87 (d, J = 7.7 Hz, 1H), 8.32 (d, J = 3.4 Hz, 1H), 8.03-8.09 (m, 1H), 7.23 (dd, J = 8.0, 4.7 Hz, 1H), 6.88 (s, 1H), 4.21 (t, J = 6.3 Hz, 2H), 3.57 (t, J = 5.8 Hz, 2H), 3.39 (s, 1H), 2.77 (s, 6H), 1.75-1.85 (m, 2H). | 373.2 |
| 334 | (DMSO-d6): 12.31 (br. s, 1H), 8.91 (d, J = 7.53 Hz, 1H), 8.33 (d, J = 3.51 Hz, 1H), 8.09 (br. s, 1H), 7.22 (dd, J = 4.64, 7.91 Hz, 1H), 6.83 (br. s, 1H), 4.27 (t, J = 4.64 Hz, 2H), 3.77-3.85 (m, 4H), 3.56-3.62 (m, 2H), 3.30 (s, 3H), 3.00-3.10 (m, 4H). | 415.2 |
| 335 | (DMSO-d6): 12.37 (br. s, 1H), 8.40 (dd, J = 1.26, 8.03 Hz, 1H), 8.33 (dd, J = 1.38, 4.64 Hz, 1H), 8.06 (s, 1H), 7.63 (d, J = 1.51 Hz, 1H), 7.21 (dd, J = 4.64, 7.91 Hz, 1H), 6.92 (s, 1H), 6.47 (d, J = 1.76 Hz, 1H), 4.90 (br. s, 2H), 4.21 (q, J = 7.19 Hz, 2H), 3.95-4.05 (m, 2H), 2.74-2.83 (m, 2H), 1.26 (t, J = 7.03 Hz, 3H). | 406.2 |
| 336 | (DMSO-d6): 12.27 (s, 1H), 10.19 (s, 1H), 8.18 (d, J = 3.5 Hz, 1H), 7.80-7.86 (m, 1H), 7.68 (d, J = 7.8 Hz, 1H), 7.16 (d, J = 8.4 Hz, 1H), 6.76-6.84 (m, 2H), 6.62 (s, 1H), 6.58 (d, J = 8.5 Hz, 1H), 4.26 (t, J = 6.3 Hz, 2H), 3.54-3.66 (m, 4H), 3.20 (t, J = 6.2 Hz, 3H), 2.13 (s, 3H), 1.78-1.87 (m, 2H). | 479.2 |
| 337 | (DMSO-d6): 12.36 (s, 1H), 10.61 (br. s, 1H), 10.54 (s, 1H), 8.24 (d, J = 3.8 Hz, 1H), 7.97 (d, J = 8.6 Hz, 1H), 7.55-7.70 (m, 4H), 6.89-6.95 (m, 2H), 4.38 (d, J = 4.8 Hz, 2H), 4.29 (t, J = 6.3 Hz, 2H), 3.62-3.55 (m, 2H), 3.39 (s, 1H), 2.76 (d, J = 4.6 Hz, 6H), 2.32 (s, 3H), 1.80-1.89 (m, 2H). | 477.4 |

TABLE 2-5-continued

| | | |
|---|---|---|
| 338 | (DMSO-d6): 12.23 (s, 1H), 8.78 (d, J = 7.5 Hz, 1H), 8.29 (d, J = 4.1 Hz, 1H), 8.01 (s, 1H), 7.19 (dd, J = 7.9, 4.7 Hz, 1H), 6.77 (s, 1H), 4.20 (t, J = 5.8 Hz, 2H), 2.73 (s, 6H), 2.53-2.58 (m, 2H), 2.24 (s, 6H), 1.90 (s, 3H). | 386.4 |
| 339 | (DMSO-d6): 8.71 (d, J = 7.1 Hz, 1H), 8.27 (d, J = 4.6 Hz, 1H), 7.89 (s, 1H), 7.15 (dd, J = 7.8, 4.6 Hz, 1H), 6.37 (s, 1H), 4.10 (t, J = 5.9 Hz, 3H), 3.76-3.82 (m, 4H), 2.81-2.88 (m, 4H), 2.45-2.55 (m, 2H), 2.24 (s, 6H), 1.88 (s, 3H). | 428.4 |
| 340 | (DMSO-d6): 12.23 (br. s, 1H), 8.17 (d, J = 3.7 Hz, 1H), 7.80 (s, 1H), 7.67-7.74 (m, 1H), 7.08-7.17 (m, 1H), 6.78-6.84 (m, 1H), 6.70-6.78 (m, 1H), 6.60 (s, 1H), 6.53-6.58 (m, 1H), 5.81 (br. s, 1H), 4.71-4.79 (m, 1H), 4.21-4.30 (m, 2H), 3.59-3.67 (m, 2H), 3.15-3.25 (m, 2H), 2.55-2.60 (m, 2H), 2.21 (s, 6H), 2.12 (s, 3H), 1.90 (s, 3H). | 492.4 |
| 341 | (DMSO-d6): 12.28 (br. s, 1H), 10.45 (s, 1H), 8.18 (dd, J = 1.38, 4.64 Hz, 1H), 7.70-7.76 (m, 2H), 7.55 (d, J = 8.03 Hz, 1H), 7.43 (s, 1H), 7.36 (d, J = 7.78 Hz, 1H), 6.85 (s, 1H), 6.77 (dd, J = 4.64, 7.91 Hz, 1H), 4.27 (q, J = 7.03 Hz, 2H), 4.17 (s, 2H), 2.28 (s, 3H), 1.30 (t, J = 7.15 Hz, 3H) | 429.1 |
| 342 | (DMSO-d6): 12.19 (br. s., 1H), 9.17 (s, 1H), 8.12-8.24 (m, 3H), 7.82 (d, J = 8.03 Hz, 1H), 7.66 (s, 1H), 7.21-7.40 (m, 3H), 6.78 (dd, J = 4.64, 7.91 Hz, 1H), 6.72 (s, 1H), 4.29 (t, J = 5.77 Hz, 2H), 3.52 (s, 2H), 2.65-2.73 (m, 2H), 2.30 (s, 6H), 2.23 (s, 9H). | 490.2 |
| 343 | (DMSO-d6): 12.39 (br. s, 1H), 9.93 (br. s, 1H), 8.28 (dd, J = 1.26, 4.52 Hz, 1H), 7.86 (s, 1H), 7.33 (d, J = 8.53 Hz, 2H), 7.10-7.19 (m, 2H), 7.00 (dd, J = 2.76, 8.53 Hz, 1H), 5.49 (br. s, 1H), 5.04-5.17 (m, 1H), 4.99 (t, J = 5.40 Hz, 1H), 4.12 (t, J = 4.89 Hz, 2H), 3.81 (q, J = 4.94 Hz, 2H), 2.23 (s, 3H), 1.28 (d, J = 6.27 Hz, 6H) | 463.9 |

TABLE 2-6

| | | |
|---|---|---|
| 344 | (DMSO-d6): 12.33 (s, 1H), 10.07 (s, 1H), 8.93 (d, J = 7.8 Hz, 1H), 8.33 (d, J = 3.6 Hz, 1H), 8.11 (s, 1H), 7.22 (dd, J = 8.0, 4.6 Hz, 1H), 6.86 (s, 1H), 4.11 (t, J = 6.7 Hz, 2H), 3.76-3.86 (s, 4H), 3.02-3.13 (s, 4H), 1.60-1.72 (m, 2H), 0.94 (t, J = 7.4 Hz, 3H). | 399.0 |
| 345 | (DMSO-d6): 12.34 (s, 1H), 10.07 (s, 1H), 8.92 (d, J = 7.5 Hz, 1H), 8.33 (d, J = 3.3 Hz, 1H), 8.11 (d, J = 2.5 Hz, 1H), 7.22 (dd, J = 8.0, 4.7 Hz, 1H), 6.86 (s, 1H), 3.94 (d, J = 6.6 Hz, 2H), 3.75-3.87 (m, 4H), 3.00-3.15 (m, 4H), 1.88-2.02 (m, 1H), 0.95 (d, J = 6.7 Hz, 6H). | 413.4 |
| 346 | (DMSO-d6): 12.02 (br. s, 1H), 8.89 (d, J = 7.7 Hz, 1H), 8.32 (d, J = 3.4 Hz, 1H), 8.07 (s, 1H), 7.21 (dd, J = 8.0, 4.7 Hz, 1H), 6.77 (s, 1H), 4.15 (t, J = 5.4 Hz, 2H), 3.73-3.87 (m, 4H), 3.63 (t, J = 5.4 Hz, 2H), 3.17 (s, 1H), 2.95-3.07 (m, 4H). | 401.4 |
| 347 | (DMSO-d6): 12.35 (s, 1H), 10.09 (s, 1H), 8.94 (d, J = 7.9 Hz, 1H), 8.33 (d, J = 3.5 Hz, 1H), 8.12 (d, J = 2.4 Hz, 1H), 7.22 (dd, J = 8.0, 4.7 Hz, 1H), 6.87 (s, 1H), 4.02 (d, J = 7.1 Hz, 2H), 3.72-3.90 (m, 4H), 3.00-3.16 (m, 4H), 1.12-1.23 (m, 1H), 0.48-0.58 (m, 2H), 0.26-0.37 (m, 2H). | 411.3 |
| 348 | (DMSO-d6): 12.34 (s, 1H), 10.08 (s, 1H), 8.93 (d, J = 7.7 Hz, 1H), 8.33 (d, J = 4.5 Hz, 1H), 8.12 (d, J = 2.6 Hz, 1H), 7.22 (dd, J = 8.0, 4.7 Hz, 1H), 6.82 (s, 1H), 5.15-5.22 (m, 1H), 3.75-3.87 (m, 4H), 3.02-3.13 (m, 4H), 1.83-1.96 (m, 2H), 1.63-1.78 (m, 4H), 1.50-1.62 (m, 2H). | 425.4 |
| 349 | (DMSO-d6): 12.24 (br. s, 1H), 10.20 (br. s, 1H), 8.88 (d, J = 7.9 Hz, 1H), 8.32 (d, J = 3.5 Hz, 1H), 8.07 (s, 1H), 7.21 (dd, J = 8.0, 4.7 Hz, 1H), 6.72 (s, 1H), 4.94-4.79 (m, 1H), 3.74-3.88 (m, 4H), 2.90-3.14 (m, 4H), 1.48-1.70 (m, 2H), 1.23 (d, J = 6.2 Hz, 3H), 0.91 (t, J = 7.4 Hz, 3H). | 413.6 |
| 350 | (DMSO-d6): 12.48-12.19 (m, 1H), 10.04 (br. s, 1H), 8.93 (s, 1H), 8.33 (d, J = 3.7 Hz, 1H), 8.10 (s, 1H), 7.22 (dd, J = 7.9, 4.7 Hz, 1H), 6.81 (s, 1H), 4.80-4.96 (m, 1H), 3.74-3.87 (m, 4H), 3.01-3.14 (m, 4H), 1.50-1.68 (m, 2H), 1.24 (d, J = 6.2 Hz, 3H), 0.91 (t, J = 7.3 Hz, 3H). | 413.4 |
| 351 | (DMSO-d6): 12.34 (br. s, 1H), 9.86 (br. s, 1H), 8.97 (d, J = 7.8 Hz, 1H), 8.33 (d, J = 3.4 Hz, 1H), 8.11 (s, 1H), 7.25 (dd, J = 8.0, 4.7 Hz, 1H), 6.80 (s, 1H), 5.00-5.09 (m, 1H), 3.30-3.40 (m, 2H), 3.01-3.13 (m, 4H), 2.81-2.94 (m, 4H), 1.27 (d, J = 6.3 Hz, 6H). | 480.2 |
| 352 | (DMSO-d6): 12.35 (br. s, 1H), 8.62 (br. s, 1H), 8.40 (dd, J = 8.0, 1.3 Hz, 1H), 8.32 (d, J = 4.6 Hz, 1H), 8.01 (s, 1H), 7.21 (dd, J = 7.9, 4.7 Hz, 1H), 6.86 (s, 1H), 4.99-5.13 (m, 1H), 4.18-4.31 (m, 1H), 3.87-3.99 (m, 2H), 3.39-3.54 (m, 2H), 1.80-1.97 (m, 4H), 1.27 (d, J = 6.3 Hz, 6H). | 398.0 |
| 353 | (DMSO-d6): 12.36 (s, 1H), 10.43 (br. s, 1H), 8.88 (d, J = 6.5 Hz, 1H), 8.35 (d, J = 3.5 Hz, 1H), 8.14 (s, 1H), 7.17 (dd, J = 8.0, 4.7 Hz, 1H), 6.86 (s, 1H), 4.99-5.11 (m, 1H), 3.47-3.62 (m, 4H), 3.35-3.42 (m, 4H), 1.27 (d, J = 6.2 Hz, 6H). | 447.2 |
| 354 | (DMSO-d6): 12.36 (br. s, 1H), 8.39 (d, J = 7.9 Hz, 1H), 8.33 (d, J = 4.7 Hz, 1H), 8.07 (s, 1H), 7.16-7.26 (m, 2H), 6.80-6.92 (m, 3H), 5.01-5.12 (m, 1H), 4.94 (br. s, 2H), 3.83-4.02 (m, 2H), 3.76 (s, 3H), 3.00 (t, J = 5.7 Hz, 2H), 1.27 (d, J = 6.2 Hz, 6H). | 460.2 |
| 355 | (DMSO-d6): 13.04 (br. s, 1H), 8.40 (dd, J = 7.9, 1.4 Hz, 1H), 8.33 (dd, J = 4.6, 1.3 Hz, 1H), 8.07 (s, 1H), 7.22 (dd, J = 7.9, 4.7 Hz, 1H), 7.16 (d, J = 7.7 Hz, 1H), 7.08 (d, J = 7.1 Hz, 2H), 6.87 (s, 1H), 5.00-5.12 (m, 1H), 4.93 (br. s, 2H), 3.88-3.98 (m, 2H), 3.03 (t, J = 5.5 Hz, 2H), 2.30 (s, 3H), 1.89 (s, 3H), 1.28 (d, J = 6.2 Hz, 6H). | 444.2 |

TABLE 2-6-continued

| | | |
|---|---|---|
| 356 | (DMSO-d6): 11.33 (br. s, 1H), 8.39 (dd, J = 7.9, 1.4 Hz, 1H), 8.33 (dd, J = 4.6, 1.3 Hz, 1H), 8.09 (s, 1H), 7.42 (s, 1H), 7.32 (s, 2H), 7.22 (dd, J = 7.9, 4.7 Hz, 1H), 6.88 (s, 1H), 4.94-5.11 (m, 3H), 3.87-4.00 (m, 2H), 3.07 (t, J = 5.7 Hz, 2H), 1.89 (s, 3H), 1.27 (t, J = 6.0 Hz, 6H). | 464.2 |
| 357 | (MeOD): 9.17 (s, 1H), 8.16-8.34 (m, 3H), 7.19-7.27 (m, 3H), 6.94-7.04 (m, 2H), 5.14-5.28 (m, 1H), 4.93 (br. s, 2H), 3.99 (t, J = 5.8 Hz, 2H), 3.05 (t, J = 5.5 Hz, 2H), 1.37 (d, J = 6.3 Hz, 6H). | 448.0 |
| 358 | (DMSO-d6): 12.36 (s, 1H), 8.39 (d, J = 7.9 Hz, 1H), 8.33 (d, J = 4.6 Hz, 1H), 8.06 (s, 1H), 7.18-7.28 (m, 2H), 6.81-6.94 (m, 3H), 5.00-5.11 (m, 1H), 4.96 (s, 2H), 3.91-4.06 (m, 2H), 3.81 (s, 3H), 2.94 (t, J = 5.7 Hz, 2H), 1.28 (d, J = 6.2 Hz, 6H). | 460.2 |
| 359 | (DMSO-d6): 12.34 (br. s, 1H), 8.39 (dd, J = 7.9, 1.1 Hz, 1H), 8.33 (dd, J = 4.6, 1.1 Hz, 1H), 8.06 (s, 1H), 7.17-7.25 (m, 2H), 6.82-6.90 (m, 3H), 5.00-5.10 (m, 1H), 4.89 (br. s, 2H), 3.84-4.00 (m, 2H), 3.76 (s, 3H), 3.05 (t, J = 5.7 Hz, 2H), 1.27 (d, J = 6.2 Hz, 6H). | 460.4 |

Biological activities of several compounds of the present invention were measured according to the methods mentioned blow.

[Preparation and Storage of Solutions of Test Compounds]

A test compound was dissolved or suspended in DMSO so as to be at 10 mM or 1 mM, thereby making a stock solution, which was stored at −20° C. in the dark before being tested.

Test Example 1

[Inhibitory Effect on Cdc7 Protein Kinase]

Measurement of kinase activity was carried out using an MSA assay kit (QuickScout Screening Assist™ Kit, Carna Biosciences, Inc.).

Assay buffer (20 mM HEPES, 0.01% Triton X-100™, 2 mM dithiothreitol, pH 7.5) was used to prepare a substrate mixture solution comprising 4 μM of a kinase-reaction substrate (FITC-labeled MCM2 peptide), 40 mM $MgCl_2$, and 20 μM ATP.

The enzyme supplied in the kit (human Cdc7/human ASK complex protein) was diluted in the assay buffer so as to be at 7 nM, thereby preparing an enzyme solution.

The stock solution of each test compound was diluted in DMSO to prepare diluted DMSO solutions of 10 concentrations (0.00003 mM, 0.0001 mM, 0.0003 mM, 0.001 mM, 0.003 mM, 0.01 mM, 0.03 mM, 0.1 mM, 0.3 mM, 1 mM), each of which was further diluted 25 times in the assay buffer to make a drug solution (a solution containing 4% DMSO).

The kinase reaction was performed in wells of a polypropylene 384-well plate in which 5 μl of each of the drug solutions or of a solvent (assay buffer containing 4% DMSO), 5 μl of the substrate mixture solution, and 10 μl of the enzyme solution were mixed. The assay buffer, instead of the enzyme solution, was added to blank wells. After the reaction at room temperature for 5 hours, 60 μl of the termination buffer supplied in the kit was added to each well to stop the reaction. The percent inhibition of each reaction was determined using a LabChip EZ Reader II system (manufactured by Caliper Life Sciences), according to the protocol provided with the assay kit. In this case, the peak heights of the separated substrate and the phosphorylated substrate were represented as S and P, respectively, and the percent inhibition (%) by a tested compound was calculated according to the following formula:

$$\text{Percent inhibition}(\%)=(1-(C-A)/(B-A))\times 100$$

wherein A denotes P/(P+S) for a blank well, B denotes P/(P+S) for a solvent well, and C denotes P/(P+S) for a compound-added well.

The $IC_{50}$ value of a tested compound was calculated by regression analysis of the percent inhibition values versus the (logarithmic) concentrations of the tested compound.

The $IC_{50}$ values of several compounds of the present invention against Cdc7 were all less than 1 μM, as shown in Table 4 below.

Test Example 2

[Inhibitory Effect on Phosphorylation Using Cells]

Cultured Cells

COLO205 cells derived from human colon adenocarcinoma (RCB2127, RIKEN BRC) were cultured in 10 cm dishes using RPMI-1640 medium (SIGMA, R8758) supplemented with 10% FCS (Equitech-bio) and 5% penicillin/streptomycin (GIBCO, 15140). After the cells were cultured to a confluence of 70 to 90%, the medium was removed, and the cells were treated with trypsin (2 mL, TrypLE Express, GIBCO, 12604-021) and then harvested using a new medium.

Addition of Drugs to Cultured Cells

COLO205 cells were seeded in 6-well plates (FALCON, 35046) to $2.5\times10^5$ cells (1 ml) per well and cultured overnight in a 5% $CO_2$ incubator. A drug solution, which was prepared by adding 1.5 μl of a 0.1-mM stock solution in DMSO of a test compound to 500 μl of medium, was added to each well (to a final drug concentration of 0.1 μM), and then cultured for another 24 hours.

Determination of Inhibitory Effect on MCM2 Phosphorylation

Cells were cultured for 24 hours in the presence of a test compound, harvested using a similar way as described above, washed with PBS, and then pelletized and stored at −80° C. The frozen cells were thawed, subsequently suspended immediately in 2×SDS-PAGE electrophoresis buffer ($1\times10^5$ cells per 10 μl), and heated at 95° C. for 10 minutes, leading to the dissolution and denaturation of the proteins. The resulting sample solutions were subjected to SDS-PAGE using a 5-20% gradient acrylamide gel (e-PAGEL (5-20%), ATTO, E-T520L). After the electrophoresis was completed, the gel was immersed in tris-glycine buffer supplemented with 20% methanol, and the proteins in the gel were transferred onto a PVDF membrane (MILLIPORE, Immobilon-P, IPVH00010) using a semi-dry transfer apparatus (TRNS-BLOT SD SEMI-DRY TRANSFER CELL, BIO RAD).

The transferred PVDF membrane was blocked with 5% skim milk (Difco Skim Milk, BD, 232100), and then subjected to reaction with an anti-MCM2 goat antibody (N-19, Santa Cruz, sc-9839) or anti-phosphorylated MCM2 rabbit antibody (S53) (Bethyl, A300-756A) as a primary antibody and additionally with an anti-α tubulin mouse antibody (Clone DM 1A, SIGMA, 9026) as an internal control. Each band was detected by chemiluminescence using an HRP-labeled anti-goat IgG donkey antibody (Santa Cruz, sc2020), anti-rabbit IgG sheep antibody (Roche, 12015218001), or anti-mouse IgG donkey antibody (Jackson ImmunoResearch, 715-035-151) as a secondary antibody. The combinations of and the diluted concentrations of the primary and secondary antibodies were as indicated below.

TABLE 3

| | Primary antibody (diluted concentration) | Secondary antibody (diluted concentration) |
|---|---|---|
| 1 | Anti-MCM2 goat antibody (1/500) | Anti-goat IgG donkey antibody (1/10000) |
| 2 | Anti-phosphorylated MCM2 rabbit antibody (S53) (1/500) | Anti-rabbit IgG sheep antibody (1/5000) |
| 3 | Anti-α-tubulin mouse antibody (1/1000) | Anti-mouse IgG donkey antibody (1/100000) |

The bands which were detected were normalized using the amount of endogenous α-tubulin as a reference, and the percent phosphorylation of MCM2 was calculated for each of the tested compounds. Their inhibitory effects on MCM2 phosphorylation were indicated by a triple asterisk (*) in the case where the percent phosphorylation of MCM2 was less than 20%, by a dual asterisk () in the case where the percent phosphorylation of MCM2 was not less than 20% and less than 50%, and by a single asterisk (*) in the case where the percent phosphorylation of MCM2 was not less than 50% and less than 70%.

It was found from this testing that as shown in Table-4, the tested compounds of the present invention inhibited the phosphorylation of MCM2 at a concentration of 0.1 μM.

TABLE 4

| Example | Test Example 1 Cdc7 $IC_{50}$ value (μM) | Test Example 2 Inhibitory effect on MCM2 phosphorylation |
|---|---|---|
| 15 | 0.002 | ** |
| 22 | 0.010 | * |
| 63 | 0.006 | *** |
| 68 | 0.004 | *** |
| 78 | 0.011 | *** |
| 81 | 0.005 | *** |
| 89 | 0.003 | *** |
| 91 | 0.004 | *** |
| 102 | 0.004 | *** |
| 126 | 0.003 | *** |
| 129 | 0.009 | *** |
| 142 | 0.003 | ** |
| 157 | 0.003 | ** |
| 173 | 0.003 | *** |
| 226 | 0.004 | *** |
| 233 | 0.002 | ** |
| 239 | 0.001 | ** |
| 242 | 0.001 | *** |
| 244 | 0.004 | *** |
| 245 | 0.008 | *** |
| 246 | 0.008 | *** |

INDUSTRIAL APPLICABILITY

The compounds provided by the present invention are capable of controlling the growth of cells through their inhibitory effects on Cdc7. Therefore, the compounds of the present invention which have an inhibitory effect on Cdc7 will be useful as a medicine, especially an agent for the treatment of diseases derived from abnormal growth of cells, such as cancers.

The invention claimed is:

[1. A furanone derivative or a pharmaceutically acceptable salt thereof, represented by the formula (I):

[Chemical Formula 1]

(I)

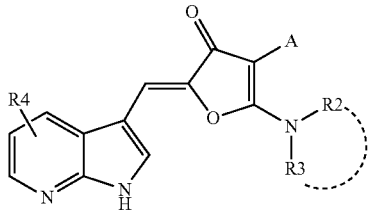

wherein A represents —COOR1 or a hydrogen atom; R1 represents a hydrogen atom, an optionally substituted hydrocarbon group, or an optionally substituted heterocycle; R2 and R3 are the same or different and each independently represent a hydrogen atom, an optionally substituted hydrocarbon group, an optionally substituted phenyl group, an optionally substituted heterocycle, an optionally substituted heterocyclic fused ring, or an optionally substituted amino group; or alternatively, R2 and R3, taken together with the nitrogen atom to which they are attached, form an optionally substituted heterocycle or an optionally substituted heterocyclic fused ring; and R4 represents a hydrogen atom or a halogen atom; with the proviso that when A represents —COOR1, R2 and R3 are not optionally substituted amino groups at the same time, and when A represents a hydrogen atom, R3 represents a hydrogen atom.]

[2. The furanone derivative or a pharmaceutically acceptable salt thereof according to claim 1, wherein A is —COOR1.]

[3. The furanone derivative or a pharmaceutically acceptable salt thereof according to claim 1, wherein A is a hydrogen atom.]

*4. A furanone derivative or pharmaceutically acceptable salt thereof, represented by the formula (III-Z) or formula (III-E):*

*(III-Z)*

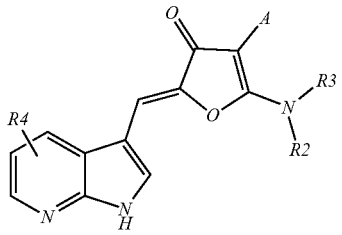

*(III-E)*

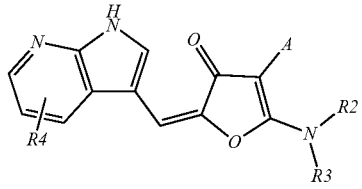

*wherein*

*A represents —COOR1 or a hydrogen atom;*

*R1 represents a hydrogen atom, an optionally substituted hydrocarbon group, or an optionally substituted heterocycle;*

*R2 and R3 are the same or different and each independently represent a hydrogen atom, an optionally substituted hydrocarbon group, an optionally substituted phenyl group, an optionally substituted heterocycle, an optionally substituted heterocyclic fused ring, or an optionally substituted amino group;*

*and R4 represents a hydrogen atom or a halogen atom;*

*with the proviso that when A represents —COOR1, R2 and R3 are not optionally substituted amino groups at the same time, and when A represents a hydrogen atom, R3 represents a hydrogen atom.*

*5. The furanone derivative or a pharmaceutically acceptable salt thereof according to claim 4, wherein the furanone derivative is:*

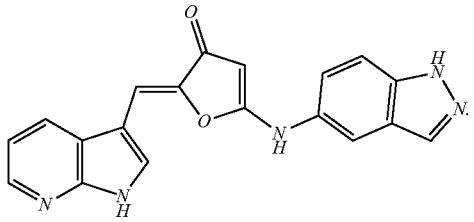

*6. The furanone derivative or a pharmaceutically acceptable salt thereof according to claim 4, wherein the furanone derivative is:*

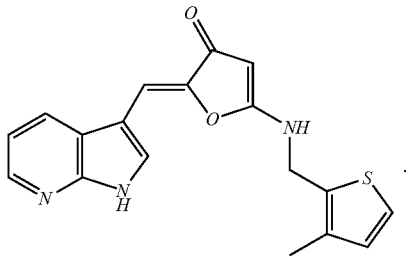

*7. The furanone derivative or a pharmaceutically acceptable salt thereof according to claim 4, wherein the furanone derivative is:*

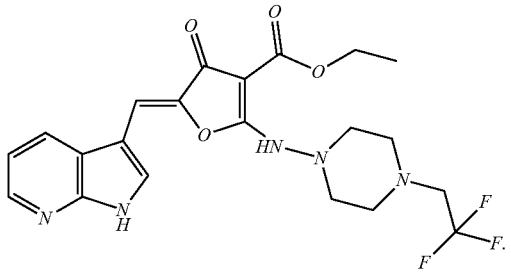

*8. The furanone derivative or a pharmaceutically acceptable salt thereof according to claim 4, wherein the furanone derivative is:*

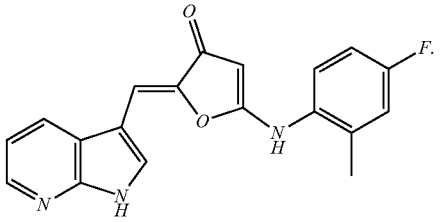

*9. The furanone derivative or a pharmaceutically acceptable salt thereof according to claim 4, wherein the furanone derivative is:*

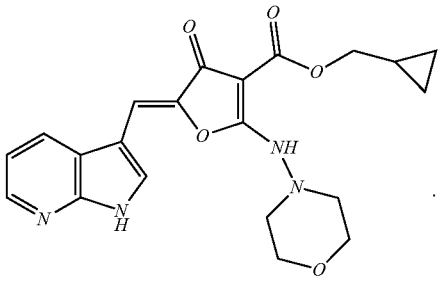

*10. The furanone derivative or a pharmaceutically acceptable salt thereof according to claim 4, wherein the furanone derivative is:*

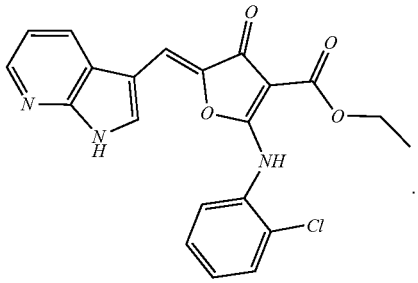

*11. The furanone derivative or a pharmaceutically acceptable salt thereof according to claim 4, wherein the furanone derivative is:*

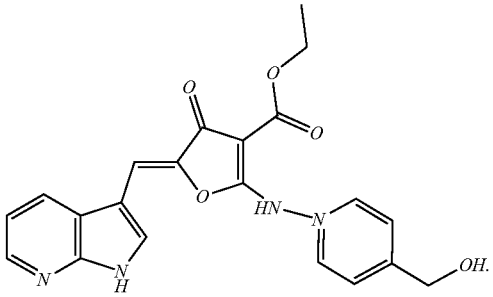

*12. The furanone derivative or a pharmaceutically acceptable salt thereof according to claim 4, wherein the furanone derivative is:*

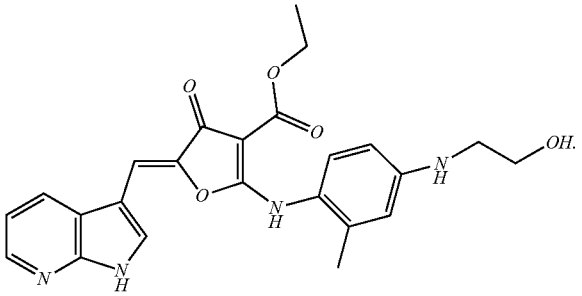

*13. The furanone derivative or a pharmaceutically acceptable salt thereof according to claim 4, wherein the furanone derivative is:*

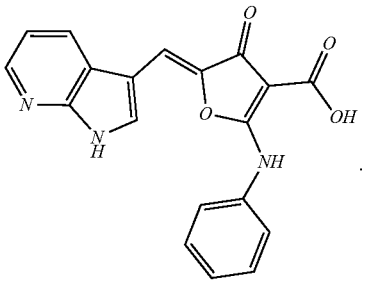

*14. The furanone derivative or a pharmaceutically acceptable salt thereof according to claim 4, wherein the furanone derivative is:*

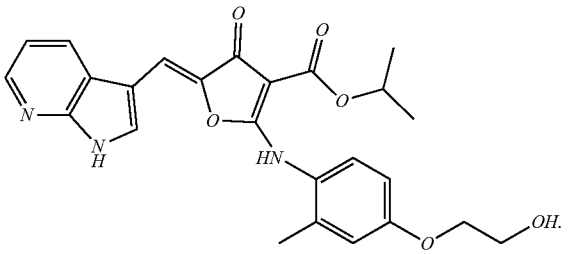

*15. The furanone derivative or a pharmaceutically acceptable salt thereof according to claim 4, wherein the furanone derivative is:*

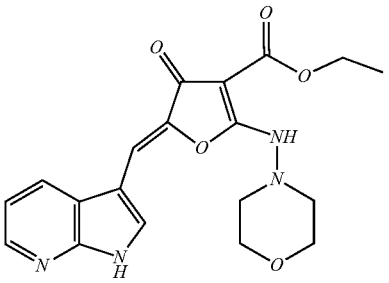

*16. The furanone derivative or a pharmaceutically acceptable salt thereof according to claim 4, wherein the furanone derivative is:*

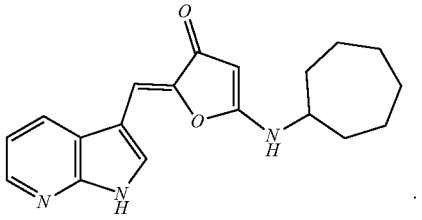

*17. The furanone derivative or a pharmaceutically acceptable salt thereof according to claim 4, wherein the furanone derivative is:*

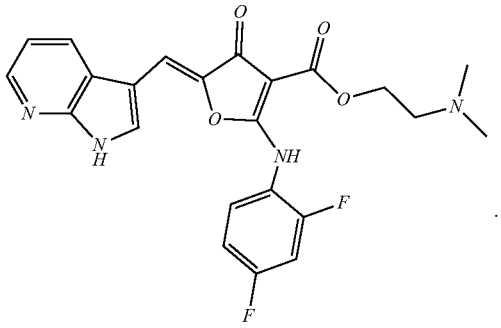

*18. The furanone derivative or a pharmaceutically acceptable salt thereof according to claim 4, wherein the furanone derivative is:*

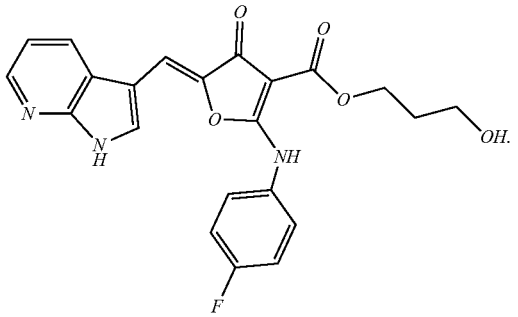

*19. The furanone derivative or a pharmaceutically acceptable salt thereof according to claim 4, wherein the furanone derivative is:*

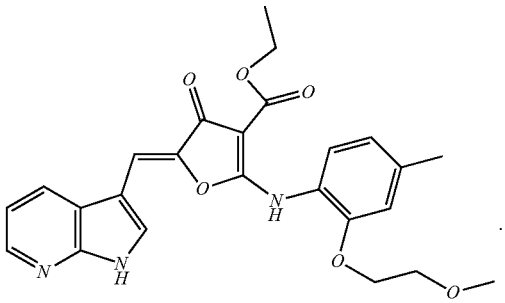

*20. The furanone derivative or a pharmaceutically acceptable salt thereof according to claim 4, wherein A is —COOR1.*

*21. The furanone derivative or a pharmaceutically acceptable salt thereof according to claim 4, wherein A is a hydrogen atom.*

* * * * *